United States Patent
Whitehead et al.

(10) Patent No.: US 10,780,092 B2
(45) Date of Patent: *Sep. 22, 2020

(54) FUSED PYRAZINE DERIVATIVES USEFUL AS SOLUBLE GUANYLATE CYCLASE STIMULATORS

(71) Applicants: Merck Sharp & Dohme Corp., Rahway, NJ (US); Alan Whitehead, Scotch Plains, NJ (US); Olga Ornoski, Teaneck, NJ (US); Subharekha Raghavan, Teaneck, NJ (US); Raphaelle Berger, New York, NY (US); Joie Garfunkle, Metuchen, NJ (US); Zhiqiang Yang, Westfield, NJ (US); Gang Ji, Beijing (CN); Falong Jiang, Beijing (CN); Jianmin Fu, Beijing (CN)

(72) Inventors: Alan Whitehead, Scotch Plains, NJ (US); Olga Ornoski, Teaneck, NJ (US); Subharekha Raghavan, Teaneck, NJ (US); Raphaelle Berger, New York, NY (US); Joie Garfunkle, Metuchen, NJ (US); Zhiqiang Yang, Westfield, NJ (US); Gang Ji, Beijing (CN); Falong Jiang, Beijing (CN); Jianmin Fu, Beijing (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/301,935

(22) PCT Filed: May 11, 2017

(86) PCT No.: PCT/US2017/032060
§ 371 (c)(1),
(2) Date: Nov. 15, 2018

(87) PCT Pub. No.: WO2017/200825
PCT Pub. Date: Nov. 23, 2017

(65) Prior Publication Data
US 2019/0307753 A1    Oct. 10, 2019

(30) Foreign Application Priority Data

May 16, 2016    (WO) ................ PCT/CN2016/082180

(51) Int. Cl.
*C07D 487/04* (2006.01)
*C07D 519/00* (2006.01)
(Continued)

(52) U.S. Cl.
CPC .............. *A61K 31/519* (2013.01); *A61P 9/12* (2018.01); *C07D 487/04* (2013.01); *C07D 519/00* (2013.01)

(58) Field of Classification Search
CPC .. C07D 487/04; C07D 519/00; A61K 31/519; A61K 31/5377; A61K 31/541; A61K 31/52; A61P 9/12
(Continued)

(56) References Cited

U.S. PATENT DOCUMENTS

| 4,845,079 A | 7/1989 | Luly et al. |
| 4,885,292 A | 12/1989 | Ryono et al. |

(Continued)

FOREIGN PATENT DOCUMENTS

| DE | 19744027 A1 | 10/1997 |
| EP | 908456 B1 | 9/1998 |

(Continued)

OTHER PUBLICATIONS

Gupta et al., Clin Pharmacol Ther. Jan. 2015; 97(1): 88-102.*
Cecil Textbook of Medicine, edited by Bennet, J.C., and Plum F., 20th edition, vol. 1, 1004-1010 1996.*
Freshney et al., Culture of Animal Cells, A Manual of Basic Technique, Alan R. Liss, Inc., 1983, New York, p. 4.*
Dermeret al., Bio/Technology, 1994, 12:320.*

(Continued)

*Primary Examiner* — Venkataraman Balasubramanian
(74) *Attorney, Agent, or Firm* — Eric Meade; John C. Todaro

(57) ABSTRACT

The invention provides certain fused pyrazine compounds of the Formula (I) or a pharmaceutically acceptable salts thereof, wherein X, Y, $R^1$, $R^3$, $R^{4a}$, $R^{5a}$, $R^{5b}$, $R^6$, and the subscript t are as described herein. The compounds or their pharmaceutically acceptable salts can modulate the body's production of cyclic guanosine monophosphate ("cGMP"), and are generally suitable for the therapy and prophylaxis of diseases or disorders which are associated with a disturbed cGMP balance. The invention also provides pharmaceutical compositions which comprise compounds of Formula (I) or pharmaceutically acceptable salts thereof. The invention also relates to methods for use of the compounds or their pharmaceutically acceptable salts in the therapy and prophylaxis of the abovementioned diseases and disorders and for preparing pharmaceuticals for this purpose.

(I)

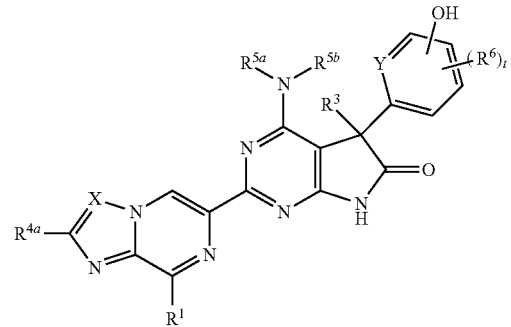

19 Claims, No Drawings

(51) Int. Cl.
*A61K 31/519* (2006.01)
*A61P 9/12* (2006.01)

(58) Field of Classification Search
USPC .......................................... 544/253; 514/249
See application file for complete search history.

(56) References Cited

U.S. PATENT DOCUMENTS

| | | |
|---|---|---|
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,075,451 A | 12/1991 | Ocain et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,114,937 A | 5/1992 | Hamby et al. |
| 5,116,835 A | 5/1992 | Ruger et al. |
| 6,054,587 A | 4/2000 | Reddy et al. |
| 6,110,903 A | 8/2000 | Kasibhatla et al. |
| 6,284,748 B1 | 9/2001 | Dang et al. |
| 6,399,782 B1 | 6/2002 | Kasibhatla et al. |
| 6,489,476 B1 | 12/2002 | Dang et al. |
| 6,743,798 B1 | 6/2004 | Straub et al. |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |
| 9,216,978 B2 | 12/2015 | Follmann et al. |
| 9,284,301 B2 | 3/2016 | Schmidt et al. |
| 9,365,574 B2 | 6/2016 | Raghavan et al. |
| 9,611,278 B2 | 4/2017 | Han et al. |
| 9,783,552 B2 | 10/2017 | Han et al. |
| 9,796,733 B2 | 10/2017 | Campbell et al. |
| 9,822,130 B2 | 11/2017 | Berger et al. |
| 10,030,027 B2 | 7/2018 | Berger et al. |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2016/0145272 A1 | 5/2016 | Berger et al. |
| 2017/0107236 A1 | 4/2017 | Campbell et al. |
| 2018/0147208 A1 | 5/2018 | Garfunkle et al. |
| 2018/0193343 A1 | 7/2018 | Garfunkle et al. |
| 2018/0305366 A1 | 10/2018 | Berger et al. |

FOREIGN PATENT DOCUMENTS

| | | |
|---|---|---|
| WO | 200208188 A1 | 1/2002 |
| WO | 2002060388 A1 | 1/2002 |
| WO | 2004019869 A2 | 3/2004 |
| WO | 2004020408 A1 | 3/2004 |
| WO | 2004020409 A1 | 3/2004 |
| WO | 2004066963 A2 | 8/2004 |
| WO | 2009001836 A1 | 12/2008 |
| WO | 2009042053 A2 | 4/2009 |
| WO | 2009000087 A1 | 12/2009 |
| WO | 2010065275 A1 | 6/2010 |
| WO | 2011149921 A1 | 12/2011 |
| WO | 2015088885 A1 | 6/2015 |
| WO | 2015088886 A1 | 6/2015 |
| WO | 2015187470 A1 | 12/2015 |
| WO | 2016081668 A1 | 5/2016 |
| WO | 2017200857 A1 | 11/2017 |

OTHER PUBLICATIONS

Belanger, D.B., et al, "Discovery of Novel Imidazo[1,2-a]Pyrazin-8-Amines As Brk/PTK6 Inhibitors", Bioorg. Med. Chem. Lett., 2011, pp. 5870-5875, vol. 21.

Vesely, D.L., et al., "Phencyclidine Stimulates Guanylate Cyclase Activity", Biochem. Biophys. Res. Comm., 1979, 88, pp. 1244-1248.

Follmann, N. et al., "The Chemistry and Biology of Soluble Guanylate Cyclase Stimulators and Activators", Angewandte Chemie-International Edition, 2013, vol. 52, No. 36, pp. 9442-9462.

Garigipati, Ravi S., "An Efficient Conversion of Nitriles to Amidines", Tetrahedron Letters, 1990, pp. 1969-1972, vol. 31, No. 14.

Ignarro, L.J. "Regulation of Cytosolic Guanylyl Cyclase by Porphirins and Metalloporphyrins", Adv. Pharmacol. 1994, vol. 26, pp. 35-65.

International Search Report and Written Opinion for PCT/CN2016/082180, dated Dec. 30, 2016, 16 pages.

Ko, F.N., et al., "YC-1 a novel activator of platelet guanylate cyclase", Blood, 1994, vol. 84, pp. 4226-4233.

Pettibone, et al., "A structurally novel stimulator of guanylate cyclase with long-lasting hypotensive activity in the dog", Eur J. Pharmacol., 1985, vol. 116, pp. 307-312.

Pinner, A., et al, "Umwandlung Der Nirile in Imide", Ber. Dtsch. Chem Ges., 1877, pp. 1889-1897, vol. 10.

Vesely, D.L., et al., "B complex vitamins activate rat guanylate cyclase and increase cyclic GMP levels", Eur. J. Clin. Invest., 1985, vol. 15, pp. 258-262.

Wu, C.C., et al., "YC-1 inhibited human platelet aggregation through NO-independent activation of soluble guyanylate cyclase", Brit J. Pharmacol., 1995, vol. 116, pp. 1973-1978.

Yu, S.M., et al., "Vasorelaxant effect of isoliquiritigenin, a novel soluble guanylate cyclase activator, in rat aorta", Brit. J. Pharmacol., 1995, vol. 114, pp. 1587-1594.

Yu, S.M.., "Mechanism of anti-proliferation caused by YC-1, an indazole derivative, in cultured rat A10 vascular smooth muscle cells", Biochem. J., 1995, vol. 306, pp. 787-792.

\* cited by examiner

US 10,780,092 B2

FUSED PYRAZINE DERIVATIVES USEFUL AS SOLUBLE GUANYLATE CYCLASE STIMULATORS

CROSS REFERENCE TO RELATED APPLICATIONS

This application is a U.S. National Phase application under 35 U.S.C. § 371 of PCT Application No. PCT/US2017/032060, filed May 11, 2017, which claims the benefit of PCT Application No. PCT/CN2016/082180, filed May 16, 2016.

FIELD OF THE INVENTION

The present invention relates to certain fused pyrazine derivatives of the Formula (I) (also referred to as "compounds of the Formula (I)", "compounds of Formula (I)", or "compounds of structural Formula (I)") pharmaceutical compositions comprising such compounds, and methods of using such compounds for treating diseases or disorders which are associated with a disturbed cyclic guanosine monophosphate (cGMP) balance.

BACKGROUND OF THE INVENTION cGMP is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are each composed of an α and a β subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore may make possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent No. 908,456 and German Patent Application No. 19,744,027.

It has now been found that the compounds of the present invention effect a strong activation of soluble guanylate cyclase and therefore may be suitable for the therapy and prophylaxis of disorders which are associated with a low cGMP level.

SUMMARY OF THE INVENTION

The present invention relates to compounds which activate soluble guanylate cyclase and may be valuable pharmaceutically active compounds for the therapy and prophylaxis of diseases, for example, for cardiovascular diseases such as hypertension, heart failure, pulmonary hypertension, angina pectoris, diabetes, cardiac insufficiency, thrombosis, chronic kidney disease, fibrosis or atherosclerosis. The compounds of Formula (I)

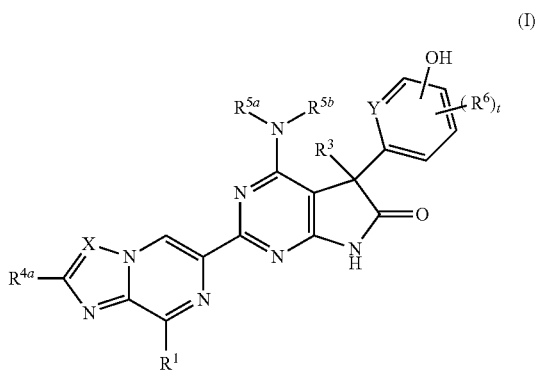

(I)

are capable of modulating the body's production of cGMP and may be suitable for the therapy and prophylaxis of diseases or disorders which are associated with a disturbed cGMP balance. The invention furthermore relates to processes for preparing compounds of Formula (I), to the use of such compounds for the therapy and prophylaxis of the above mentioned diseases and for preparing compounds for this purpose, and to pharmaceutical compositions which comprise compounds of Formula (I).

DETAILED DESCRIPTION OF THE INVENTION

In embodiment no. 1, the present invention provides a compound having structural Formula (I):

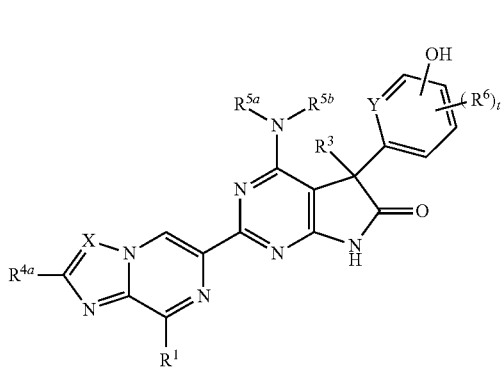

(I)

or a pharmaceutically acceptable salt thereof, wherein:
X is $C(R^{4b})$ or N;
Y is C(H) or N;
$R^1$ is:
  (a.) $(C_1-C_3)$alkyl-$R^2$,
    $R^2$ is phenyl, pyridyl, $C_3-C_8$ cycloalkyl, or $C_5-C_7$ cycloalkenyl, wherein
      $R^2$ is unsubstituted or substituted by 1 to 3 $R^{2a}$;
      each $R^{2a}$ is independently halo, $(C_1-C_3)$alkyl, or $(C_1-C_3)$fluoroalkyl; or
  (b.) $(C_1-C_6)$alkyl, wherein said alkyl is unsubstituted or substituted by 1 to 6 fluoro;
$R^3$ is $(C_1-C_3)$alkyl or $(C_3-C_6)$cycloalkyl;
$R^{4a}$ is H or $(C_1-C_3)$alkyl;
$R^{4b}$ is H or $NH_2$;
$R^{5a}$ and $R^{5b}$ are independently H or $(C_1-C_6)$alkyl, wherein said alkyl is unsubstituted or substituted by 1 to 6 substituents independently selected from fluoro or hydroxyl; or alternatively, $R^{5a}$ and $R^{5b}$ together with the nitrogen atom to which they are attached form ring $C_5$ which is an azetidinyl, pyrrolyl, piperidinyl, piperazinyl, or azepinyl ring, wherein ring $C_5$ is unsubstituted or substituted by 1 to 3 substituents which are independently halo, hydroxyl, $(C_1-C_3)$alkyl, or $(C_1-C_3)$fluoroalkyl;
each $R^6$ is independently halo, $(C_1-C_3)$alkyl, $(C_1-C_3)$ fluoroalkyl, or cyano; and
the subscript t is 0, 1, 2, or 3; and
with the proviso that the compound is not:
4-amino-5-(5-hydroxypyridin-2-yl)-5-methyl-2-(8-(3,3,4,4, 4-pentafluorobutyl)-[1,2,4]triazolo[1,5-a]pyrazin-6-yl)-5, 7-dihydro-6H-pyrrolo[2,3-d]pyrimidine-6-one;
4-amino-5-(5-hydroxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidine-6(7H)-one; or
4-amino-5-cyclopropyl-5-(5-hydroxypyridin-2-yl)-2-(8-(4, 4,4-trifluorobutyl)-[1,2,4]triazolo[1,5-a]pyrazin-6-yl)-5H-pyrrolo[2,3-d]pyrimidine-6(7H)-one (including pharmaceutically acceptable salts of said three specifically recited compounds).

In embodiment no. 2, the present invention provides the compound having structural Formula (I), wherein X is $C(R^{4b})$, and the remaining variables are as set forth in embodiment no. 1. In embodiment no. 3, the present invention provides the compound having structural Formula (I), wherein X is $C(R^{4b})$ and $R^{4b}$ is H, and the remaining variables are as set forth in embodiment no. 1.

In embodiment no. 4, the present invention provides the compound having structural Formula (I), wherein X is N; and the remaining variables are as set forth in embodiment no. 1.

In embodiment no. 5, the present invention provides the compound having structural Formula (I), wherein Y is N, and the remaining variables are as set forth in embodiment no. 1.

In embodiment no. 6, the present invention provides the compound having structural Formula (I), wherein Y is C(H), and the remaining variables are as set forth in embodiment no. 1.

In embodiment no. 7, the present invention provides the compound having structural Formula (I), wherein $R^1$ is $(C_1-C_3)$alkyl-$R^2$,
  $R^2$ is phenyl, $C_3-C_8$ cycloalkyl, or $C_5-C_7$ cycloalkenyl, wherein $R^2$ is unsubstituted or substituted by 1 to 3 $R^{2a}$; and
  each $R^{2a}$ is independently halo, $(C_1-C_3)$alkyl, or $(C_1-C_3)$ fluoroalkyl; and
the remaining variables are as set forth in embodiment no. 1.

In embodiment no. 8, the present invention provides the compound having structural Formula (I), wherein $R^1$ is —$CH_2$—$R^2$; $R^2$ is as set forth in embodiment no. 7; and the remaining variables are as set forth in embodiment no. 1.

In embodiment no. 9, the present invention provides the compound having structural Formula (I), wherein $R^1$ is —$CH_2$—$R^2$; $R^2$ is unsubstituted phenyl or phenyl substituted by 1 to 3 $R^{2a}$; and the remaining variables are as set forth in embodiment no. 1.

In embodiment no. 10, the present invention provides the compound having structural Formula (I), wherein $R^3$ is methyl, and the remaining variables are as set forth in embodiment no. 1.

In embodiment no. 11, the present invention provides the compound having structural Formula (I), wherein $R^{4a}$ is H, and the remaining variables are as set forth in embodiment no. 1.

In embodiment no. 12, the present invention provides the compound having structural Formula (I), wherein $R^{5a}$ and $R^{5b}$ are H, and the remaining variables are as set forth in embodiment no. 1.

In embodiment no. 13, the present invention provides the compound having structural Formula (I), wherein the subscript t is 0 or 1, and the remaining variables are as set forth in embodiment no. 1.

In embodiment no. 14, the present invention provides the compound having structural Formula (I),

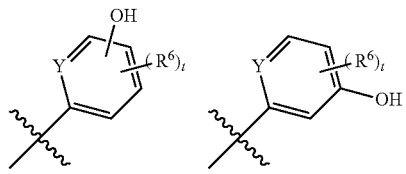

wherein the group is,
and the remaining variables are set forth in embodiment no. 1.

In embodiment no. 15, the present invention provides the compound having structural Formula (I), wherein:
$R^1$ is $(C_1-C_6)$alkyl, wherein said alkyl is unsubstituted or substituted by 1 to 6 fluoro;
Y is C(H), and the remaining variable are as set forth in embodiment no. 1.

In embodiment no. 16, the present invention provides the compound having structural Formula (I), wherein:
$R^1$ is $(C_1-C_6)$alkyl, wherein said alkyl is unsubstituted or substituted by 1 to 6 fluoro; group is,

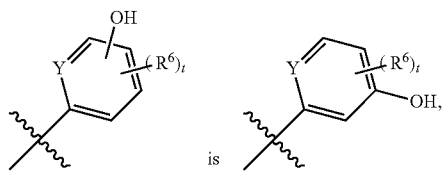

is

Y is N, and the remaining variable are as set forth in embodiment no. 1.

In embodiment no. 17, the present invention provides the compound having structural Formula (I),

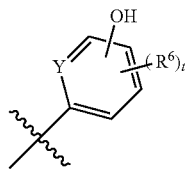

wherein the group is as set forth in embodiment no. 14,
X is C(H) or N;
Y is C(H) or N;
$R^1$ is —$CH_2$—$R^2$,
$R^2$ is unsubstituted phenyl or phenyl substituted by 1 to 3 $R^{2a}$;

each $R^{2a}$ is independently halo, $(C_1-C_3)$alkyl, or $(C_1-C_3)$ fluoroalkyl;
$R^3$ is methyl;
$R^{5a}$ and $R^{5b}$ are H; and
the subscript t is 0 or 1.

In embodiment no. 18, the present invention provides the compound having structural Formula (I) as set forth in any one of embodiment nos. 1, 2, 3, 4, 5, 6, 10, 11, 12, 13, 14, or 15, wherein $R^1$ is:
(a.) $(C_1-C_3)$alkyl-$R^2$,
$R^2$ is phenyl, $C_3-C_8$ cycloalkyl, or $C_5-C_7$ cycloalkenyl, wherein $R^2$ is unsubstituted or substituted by 1 to 3 $R^{2a}$;
each $R^{2a}$ is independently halo, $(C_1-C_3)$alkyl, or $(C_1-C_3)$fluoroalkyl; or
(b.) $(C_1-C_6)$alkyl, wherein said alkyl is unsubstituted or substituted by 1 to 6 fluoro.

In another embodiment, the present invention provides a compound selected from:
4-amino-5-(4-chloro-3-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;
4-amino-5-(4-chloro-3-fluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
4-amino-2-{8-[(2-fluorophenyl)methyl]imidazo[1,2-a]pyrazin-6-yl}-5-[3-hydroxy-4-(trifluoromethyl)phenyl]-5-methyl-5,7-dihydro-6H-pyrrolo[2,3-d]pyrimidin-6-one;
4-amino-5-(5-chloro-4-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
4-amino-5-(4-chloro-3-fluoro-5-hydroxyphenyl)-2-{8-[(3-fluorophenyl)methyl]imidazo[1,2-a]pyrazin-6-yl}-methyl-5,7-dihydro-6H-pyrrolo[2,3-d]pyrimidin-6-one;
4-amino-5-(4-chloro-3-fluoro-5-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;
4-amino-5-(4-chloro-3-fluoro-5-hydroxyphenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;
4-amino-5-(4-chloro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
4-amino-5-(3,4-difluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
4-amino-5-(4-chloro-3-fluoro-5-hydroxyphenyl)-2-{8-[(2-fluorophenyl)methyl]-[1,2,4]triazolo[1,5-a]pyrazin-6-yl}-5-methyl-5,7-dihydro-6H-pyrrolo[2,3-d]pyrimidin-6-one;
4-amino-2-{8-[(2,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;
4-amino-5-(4-chloro-3-fluoro-5-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;
4-amino-5-(4-fluoro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
4-amino-5-(4-chloro-3-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;
4-(4-amino-2-(8-(cyclohexylmethyl)-[1,2,4]triazolo[1,5-a]pyrazin-6-yl)-5-methyl-6-oxo-6,7-dihydro-5H-pyrrolo[2,3-d]pyrimidin-5-yl)-2-fluoro-6-hydroxybenzonitrile;

4-amino-5-(4-chloro-3-fluoro-5-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-2-{8-[(3-fluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;

4-(4-amino-2-(8-(cyclohexylmethyl)imidazo[1,2-a]pyrazin-6-yl)-5-methyl-6-oxo-6,7-dihydro-5H-pyrrolo[2,3-d]pyrimidin-5-yl)-2-fluoro-6-hydroxybenzonitrile;

4-amino-5-(4-chloro-3-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(3,4-difluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-fluoro-5-hydroxyphenyl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;

4-amino-2-{8-[(2,4-difluorophenyl)methyl]imidazo[1,2-a]pyrazin-6-yl}-5-(4-fluoro-3-hydroxyphenyl)-5-methyl-5,7-dihydro-6H-pyrrolo[2,3-d]pyrimidin-6-one;

4-(4-amino-2-{8-[(2-fluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

4-amino-5-(3-fluoro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-(8-isopentylimidazo[1,2-a]pyrazin-6-yl)-5-methyl-5,7-dihydro-6H-pyrrolo[2,3-d]pyrimidin-6-one;

4-amino-5-(4-chloro-3-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

4-(4-amino-2-{8-[(3,5-difluorophenyl)methyl]-[1,2,4]triazolo[1,5-a]pyrazin-6-yl}-5-methyl-6-oxo-6,7-dihydro-5H-pyrrolo[2,3-d]pyrimidin-5-yl)-2-fluoro-6-hydroxybenzonitrile;

4-amino-5-(3-chloro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

4-amino-5-(3-fluoro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

4-amino-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(4-chloro-3-fluoro-5-hydroxyphenyl)-2-(8-isopentylimidazo[1,2-a]pyrazin-6-yl)-5-methyl-5,7-dihydro-6H-pyrrolo[2,3-d]pyrimidin-6-one;

4-amino-5-(3-hydroxy-4-(trifluoromethyl)phenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

4-amino-2-{8-[(2,4-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(3-chloro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-5-(4-fluoro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

4-(4-amino-2-{8-[(3,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

4-amino-2-(8-butylimidazo[1,2-a]pyrazin-6-yl)-5-(4-chloro-3-fluoro-5-hydroxyphenyl)-5-methyl-5,7-dihydro-6H-pyrrolo[2,3-d]pyrimidin-6-one;

4-amino-5-(5-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-5-(3-fluoro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(4-chloro-3-fluoro-5-hydroxyphenyl)-5-methyl-5,7-dihydro-6H-pyrrolo[2,3-d]pyrimidin-6-one;

4-amino-2-{8-[(4-fluorophenyl)methyl]imidazo[1,2-a]pyrazin-6-yl}-5-(4-hydroxyphenyl)-5-methyl-5,7-dihydro-6H-pyrrolo[2,3-d]pyrimidin-6-one;

4-amino-5-(4-chloro-3-hydroxyphenyl)-2-{8-[(4-chlorophenyl)methyl]imidazo[1,2-a]pyrazin-6-yl}-5-methyl-5,7-dihydro-6H-pyrrolo[2,3-d]pyrimidin-6-one;

4-amino-2-{8-[(3-fluorophenyl)methyl]imidazo[1,2-a]pyrazin-6-yl}-5-(4-hydroxy-3-methylphenyl)-5-methyl-5,7-dihydro-6H-pyrrolo[2,3-d]pyrimidin-6-one;

4-amino-2-{8-[(3,5-difluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;

4-amino-5-(4-fluoro-3-hydroxyphenyl)-2-(8-isopentylimidazo[1,2-a]pyrazin-6-yl)-5-methyl-5,7-dihydro-6H-pyrrolo[2,3-d]pyrimidin-6-one;

4-amino-2-{8-[(3,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(5-chloro-6-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(4-chloro-3-hydroxyphenyl)-5-methyl-5,7-dihydro-6H-pyrrolo[2,3-d]pyrimidin-6-one;

4-amino-5-(5-chloro-4-hydroxypyridin-2-yl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

4-amino-2-(8-butylimidazo[1,2-a]pyrazin-6-yl)-5-(4-chloro-3-hydroxyphenyl)-5-methyl-5,7-dihydro-6H-pyrrolo[2,3-d]pyrimidin-6-one;

4-amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

4-amino-5-(3-fluoro-4-hydroxyphenyl)-2-(8-isopentylimidazo[1,2-a]pyrazin-6-yl)-5-methyl-5,7-dihydro-6H-pyrrolo[2,3-d]pyrimidin-6-one;

4-amino-5-(4-chloro-3-hydroxyphenyl)-5-methyl-2-(8-(4,4,4-trifluorobutyl)imidazo[1,2-a]pyrazin-6-yl)-5,7-dihydro-6H-pyrrolo[2,3-d]pyrimidin-6-one;

4-amino-2-{8-[(4-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(5-chloro-4-hydroxypyridin-2-yl)-2-(8-isopentylimidazo[1,2-a]pyrazin-6-yl)-5-methyl-5,7-dihydro-6H-pyrrolo[2,3-d]pyrimidin-6-one;

4-amino-5-(4-hydroxyphenyl)-2-(8-isopentylimidazo[1,2-a]pyrazin-6-yl)-5-methyl-5,7-dihydro-6H-pyrrolo[2,3-d]pyrimidin-6-one;

4-amino-5-(3-hydroxyphenyl)-2-(8-isopentylimidazo[1,2-a]
pyrazin-6-yl)-5-methyl-5,7-dihydro-6H-pyrrolo[2,3-d]
pyrimidin-6-one;

4-amino-5-(3-chloro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(3-hydroxy-4-(trifluoromethyl)phenyl)-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(4-fluoro-3-hydroxyphenyl)-5-methyl-5,7-dihydro-6H-pyrrolo[2,3-d]pyrimidin-6-one;

4-amino-5-(4-chloro-3-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

4-amino-5-(3-hydroxy-4-(trifluoromethyl)phenyl)-2-(8-isopentylimidazo[1,2-a]pyrazin-6-yl)-5-methyl-5,7-dihydro-6H-pyrrolo[2,3-d]pyrimidin-6-one;

4-amino-5-(4-chloro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

4-amino-5-(3-chloro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

4-amino-2-(8-(cyclohexylmethyl)-[1,2,4]triazolo[1,5-a]pyrazin-6-yl)-5-(2,4-dichloro-3-hydroxyphenyl)-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(3-hydroxyphenyl)-5-methyl-5,7-dihydro-6H-pyrrolo[2,3-d]pyrimidin-6-one;

4-amino-2-(8-(cyclohexylmethyl)imidazo[1,2-a]pyrazin-6-yl)-5-(2,4-dichloro-3-hydroxyphenyl)-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(4-hydroxyphenyl)-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(3-fluoro-4-hydroxyphenyl)-5-methyl-5,7-dihydro-6H-pyrrolo[2,3-d]pyrimidin-6-one;

4-amino-2-(8-butylimidazo[1,2-a]pyrazin-6-yl)-5-(5-chloro-4-hydroxypyridin-2-yl)-5-methyl-5,7-dihydro-6H-pyrrolo[2,3-d]pyrimidin-6-one;

4-amino-5-(3,5-dichloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-2-(8-butyl-[1,2,4]triazolo[1,5-a]pyrazin-6-yl)-5-(3-chloro-4-hydroxyphenyl)-5-methyl-5,7-dihydro-6H-pyrrolo[2,3-d]pyrimidin-6-one;

4-amino-2-(8-butylimidazo[1,2-a]pyrazin-6-yl)-5-(3-chloro-4-hydroxyphenyl)-5-methyl-5,7-dihydro-6H-pyrrolo[2,3-d]pyrimidin-6-one;

4-amino-2-(8-butylimidazo[1,2-a]pyrazin-6-yl)-5-(3-hydroxy-4-(trifluoromethyl)phenyl)-5-methyl-5,7-dihydro-6H-pyrrolo[2,3-d]pyrimidin-6-one;

4-amino-5-(3-chloro-4-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

4-amino-5-(3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

4-amino-5-(3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

4-amino-5-(4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

4-amino-5-(4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

4-amino-2-(8-(cyclohexylmethyl)imidazo[1,2-a]pyrazin-6-yl)-5-(3-hydroxyphenyl)-5-methyl-5,7-dihydro-6H-pyrrolo[2,3-d]pyrimidin-6-one;

4-amino-2-(8-(2-cyclohexylethyl)imidazo[1,2-a]pyrazin-6-yl)-5-(3-hydroxyphenyl)-5-methyl-5,7-dihydro-6H-pyrrolo[2,3-d]pyrimidin-6-one;

4-amino-2-(8-(2-cyclohexylethyl)imidazo[1,2-a]pyrazin-6-yl)-5-(3-fluoro-4-hydroxyphenyl)-5-methyl-5,7-dihydro-6H-pyrrolo[2,3-d]pyrimidin-6-one;

4-amino-2-(8-(2-cyclohexylethyl)imidazo[1,2-a]pyrazin-6-yl)-5-(4-hydroxyphenyl)-5-methyl-5,7-dihydro-6H-pyrrolo[2,3-d]pyrimidin-6-one;

4-amino-2-(8-(2-cyclohexylethyl)imidazo[1,2-a]pyrazin-6-yl)-5-(4-fluoro-3-hydroxyphenyl)-5-methyl-5,7-dihydro-6H-pyrrolo[2,3-d]pyrimidin-6-one;

4-amino-5-(4-chloro-3-hydroxyphenyl)-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one;

4-amino-5-(4-chloro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

4-amino-5-(3-chloro-4-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;

4-amino-5-(4-chloro-3-hydroxyphenyl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(2,4-difluorophenyl)methyl]imidazo[1,2-a]pyrazin-6-yl}-5-methyl-5,7-dihydro-6H-pyrrolo[2,3-d]pyrimidin-6-one;

4-amino-5-(5-chloro-4-hydroxypyridin-2-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

4-amino-5-(5-chloro-4-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

4-amino-5-(5-chloro-4-hydroxypyridin-2-yl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-(8-((4,4-difluorocyclohexyl)methyl)imidazo[1,2-a]pyrazin-6-yl)-5-methyl-5,7-dihydro-6H-pyrrolo[2,3-d]pyrimidin-6-one;

4-amino-5-(3-chloro-4-fluoro-2-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-2-(8-(cyclohexylmethyl)imidazo[1,2-a]pyrazin-6-yl)-5-(3-fluoro-5-hydroxy-4-(trifluoromethyl)phenyl)-5-methyl-5,7-dihydro-6H-pyrrolo[2,3-d]pyrimidin-6-one;

4-amino-5-(5-chloro-4-hydroxypyridin-2-yl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(3-fluorophenyl)methyl]-2-methylimidazo[1,2-a]pyrazin-6-yl}-5-methyl-5,7-dihydro-6H-pyrrolo[2,3-d]pyrimidin-6-one;

4-amino-5-(4-chloro-3-hydroxyphenyl)-2-{8-[(2-fluorophenyl)methyl]-2-methylimidazo[1,2-a]pyrazin-6-yl}-5-methyl-5,7-dihydro-6H-pyrrolo[2,3-d]pyrimidin-6-one;

4-(4-amino-2-{8-[(2,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

4-(4-amino-5-methyl-6-oxo-2-{8-[(2,3,5-trifluorophenyl)methyl]imidazo[1,2-a]pyrazin-6-yl}-6,7-dihydro-5H-pyrrolo[2,3-d]pyrimidin-5-yl)-2-fluoro-6-hydroxybenzonitrile;

4-amino-5-(5-chloro-4-hydroxypyridin-2-yl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

4-amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

4-amino-5-(5-chloro-4-hydroxypyridin-2-yl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;

4-amino-5-(4-chloro-3-hydroxyphenyl)-2-(8-(4-fluorobutyl)-[1,2,4]triazolo[1,5-a]pyrazin-6-yl)-5-methyl-5,7-dihydro-6H-pyrrolo[2,3-d]pyrimidin-6-one;

4-amino-2-{8-[(3-fluorophenyl)methyl]imidazo[1,2-a]pyrazin-6-yl}-5-(3-hydroxy-4-methylphenyl)-5-methyl-5,7-dihydro-6H-pyrrolo[2,3-d]pyrimidin-6-one;

4-amino-5-(4-chloro-3-hydroxyphenyl)-5-methyl-2-{8-[(4-methylcyclohexyl)methyl]imidazo[1,2-a]pyrazin-6-yl}-5,7-dihydro-6H-pyrrolo[2,3-d]pyrimidin-6-one;

4-amino-2-(8-(cyclohexylmethyl)-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

4-amino-2-{8-[(3-fluorophenyl)methyl]-[1,2,4]triazolo[1,5-a]pyrazin-6-yl}-5-(4-hydroxypyridin-2-yl)-5-methyl-5,7-dihydro-6H-pyrrolo[2,3-d]pyrimidin-6-one;

4-amino-5-(5-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

4-amino-2-(8-(cyclohexylmethyl)-[1,2,4]triazolo[1,5-a]pyrazin-6-yl)-5-(3,5-dichloro-4-hydroxyphenyl)-5-methyl-5,7-dihydro-6H-pyrrolo[2,3-d]pyrimidin-6-one;

4-amino-2-(8-(cyclohexylmethyl)imidazo[1,2-a]pyrazin-6-yl)-5-(3,5-dichloro-4-hydroxyphenyl)-5-methyl-5,7-dihydro-6H-pyrrolo[2,3-d]pyrimidin-6-one;

4-amino-5-(4-fluoro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

4-amino-5-(4-fluoro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

4-amino-5-(3-fluoro-4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

4-amino-5-(3-fluoro-4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

4-amino-2-(8-butyl-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

4-amino-5-(4-hydroxypyridin-2-yl)-2-(8-isopentyl-[1,2,4]triazolo[1,5-a]pyrazin-6-yl)-5-methyl-5,7-dihydro-6H-pyrrolo[2,3-d]pyrimidin-6-one;

4-amino-5-(3-chloro-4-hydroxyphenyl)-5-methyl-2-{8-[(4-methylcyclohexyl)methyl]imidazo[1,2-a]pyrazin-6-yl}-5,7-dihydro-6H-pyrrolo[2,3-d]pyrimidin-6-one;

4-amino-2-{8-[(3-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(3-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

4-amino-2-(8-benzylimidazo[1,2-a]pyrazin-6-yl)-5-(3-hydroxyphenyl)-5-methyl-5,7-dihydro-6H-pyrrolo[2,3-d]pyrimidin-6-one;

4-amino-2-{8-[(3-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

4-amino-5-(3-fluoro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

4-amino-2-{8-[(3-chlorophenyl)methyl]imidazo[1,2-a]pyrazin-6-yl}-5-(3-fluoro-4-hydroxyphenyl)-5-methyl-5,7-dihydro-6H-pyrrolo[2,3-d]pyrimidin-6-one;

4-amino-5-(3-fluoro-4-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

4-amino-2-(8-benzylimidazo[1,2-a]pyrazin-6-yl)-5-(3-fluoro-4-hydroxyphenyl)-5-methyl-5,7-dihydro-6H-pyrrolo[2,3-d]pyrimidin-6-one;

5-(4-fluoro-3-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

5-(3-fluoro-4-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

5-(4-chloro-3-hydroxyphenyl)-2-{8-[(3-fluorophenyl)methyl]imidazo[1,2-a]pyrazin-6-yl}-5-methyl-4-[(3,3,3-trifluoro-2-hydroxypropyl)amino]-5,7-dihydro-6H-pyrrolo[2,3-d]pyrimidin-6-one;

5-(4-chloro-3-hydroxyphenyl)-2-{8-[(4-fluorophenyl)methyl]imidazo[1,2-a]pyrazin-6-yl}-5-methyl-4-[(3,3,3-trifluoro-2-hydroxypropyl)amino]-5,7-dihydro-6H-pyrrolo[2,3-d]pyrimidin-6-one;

5-(4-chloro-3-hydroxyphenyl)-5-methyl-2-(8-(3,3,4,4,4-pentafluorobutyl)-[1,2,4]triazolo[1,5-a]pyrazin-6-yl)-4-[(3,3,3-trifluoro-2-hydroxypropyl)amino]-5,7-dihydro-6H-pyrrolo[2,3-d]pyrimidin-6-one;

5-(4-chloro-3-hydroxyphenyl)-2-{8-[(4-fluorophenyl)methyl]imidazo[1,2-a]pyrazin-6-yl}-5-methyl-4-(4-methylpiperazin-1-yl)-5,7-dihydro-6H-pyrrolo[2,3-d]pyrimidin-6-one;

4-(4,4-difluoropiperidin-1-yl)-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

5-(4-chloro-3-hydroxyphenyl)-4-(4,4-difluoropiperidin-1-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

5-(4-chloro-3-hydroxyphenyl)-5-methyl-2-(8-(3,3,4,4,4-pentafluorobutyl)-[1,2,4]triazolo[1,5-a]pyrazin-6-yl)-4-(4-(trifluoromethyl)piperidin-1-yl)-5,7-dihydro-6H-pyrrolo[2,3-d]pyrimidin-6-one;

5-(4-chloro-3-hydroxyphenyl)-5-methyl-2-(8-(3,3,4,4,4-pentafluorobutyl)-[1,2,4]triazolo[1,5-a]pyrazin-6-yl)-4-((3,3,3-trifluoropropyl)amino)-5,7-dihydro-6H-pyrrolo[2,3-d]pyrimidin-6-one;

5-(4-chloro-3-hydroxyphenyl)-5-methyl-2-(8-(3,3,4,4,4-pentafluorobutyl)-[1,2,4]triazolo[1,5-a]pyrazin-6-yl)-4-((4,4,4-trifluorobutyl)amino)-5,7-dihydro-6H-pyrrolo[2,3-d]pyrimidin-6-one;

4-amino-2-(3-amino-8-[(3-fluorophenyl)methyl]imidazo[1,2-a]pyrazin-6-yl)-5-(4-chloro-3-hydroxyphenyl)-5-methyl-5,7-dihydro-6H-pyrrolo[2,3-d]pyrimidin-6-one;

4-amino-5-(5-chloro-4-hydroxypyridin-2-yl)-2-(8-(cyclopentylmethyl)imidazo[1,2-a]pyrazin-6-yl)-5-methyl-5,7-dihydro-6H-pyrrolo[2,3-d]pyrimidin-6-one;

4-(4-amino-2-{8-(cyclohexylmethyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

4-(4-amino-2-{8-(2-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;
4-(4-amino-2-{8-(3-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;
4-amino-2-(8-{3-fluorobenzyl}imidazo[1,2-a]pyrazin-6-yl)-5-(4-hydroxy-5(trifluoromethyl)pyridin-2-yl)-5-methyl-5,7-dihydro-6H-pyrrolo[2,3-d]pyrimidin-6-one;
4-amino-2-(8-{2-fluorobenzyl}imidazo[1,2-a]pyrazin-6-yl)-5-(4-hydroxy-5-(trifluoromethyl)pyridin-2-yl)-5-methyl-5,7-dihydro-6H-pyrrolo[2,3-d]pyrimidin-6-one;
4-amino-2-{8-(cyclohexylmethyl)imidazo[1,2-a]pyrazin-6-yl}-5-(4-hydroxy-5-(trifluoromethyl)pyridin-2-yl)-5-methyl-5,7-dihydro-6H-pyrrolo[2,3-d]pyrimidin-6-one;
4-amino-5-(5-chloro-4-hydroxypyridin-2-yl)-2-{8-(2-fluorobenzyl)-[1,2,4]triazolo[1,5-a]pyrazin-6-yl}-5-methyl-5,7-dihydro-6H-pyrrolo[2,3-d]pyrimidin-6-one;
4-(4-amino-2-{8-(2-fluorobenzyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile;
4-(4-amino-2-{8-(cyclohexylmethyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile and;
4-amino-2-{8-(3-fluorobenzyl)imidazo[1,2-a]pyrazin-6-yl}-5-(4-hydroxy-5-methylpyridin-2-yl)-5-methyl-5,7-dihydro-6H-pyrrolo[2,3-d]pyrimidin-6-one; or a pharmaceutically acceptable salt thereof.

In another embodiment, the present invention provides a compound selected from:
(5R)-4-amino-5-(4-chloro-3-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-2-{8-[(2-fluorophenyl)methyl]imidazo[1,2-a]pyrazin-6-yl}-5-[3-hydroxy-4-(trifluoromethyl)phenyl]-5-methyl-5,7-dihydro-6H-pyrrolo[2,3-d]pyrimidin-6-one;
(5R)-4-amino-5-(5-chloro-4-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;
(5R)-4-amino-5-(4-chloro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(3,4-difluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-2-{8-[(2-fluorophenyl)methyl]-[1,2,4]triazolo[1,5-a]pyrazin-6-yl}-5-methyl-5,7-dihydro-6H-pyrrolo[2,3-d]pyrimidin-6-one;
(5R)-4-amino-2-{8-[(2,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;
(5R)-4-amino-5-(4-chloro-3-fluoro-5-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;
(5R)-4-amino-5-(4-fluoro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;
(5R)-4-(4-amino-2-(8-(cyclohexylmethyl)-[1,2,4]triazolo[1,5-a]pyrazin-6-yl)-5-methyl-6-oxo-6,7-dihydro-5H-pyrrolo[2,3-d]pyrimidin-5-yl)-2-fluoro-6-hydroxybenzonitrile;
(5R)-4-amino-5-(4-chloro-3-fluoro-5-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;
(5R)-4-amino-2-{8-[(3-fluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;
(5R)-4-(4-amino-2-(8-(cyclohexylmethyl)imidazo[1,2-a]pyrazin-6-yl)-5-methyl-6-oxo-6,7-dihydro-5H-pyrrolo[2,3-d]pyrimidin-5-yl)-2-fluoro-6-hydroxybenzonitrile;
(5R)-4-amino-5-(4-chloro-3-hydroxyphenyl)-2-{8-[(2,5-difluorophenyl)methyl]imidazo[1,2-a]pyrazin-6-yl}-5-methyl-5,7-dihydro-6H-pyrrol[2,3-d]pyrimidin-6-one;
(5R)-4-amino-5-(4-chloro-3-hydroxyphenyl)-2-{8-[(3,4-difluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-fluoro-5-hydroxyphenyl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;
(5R)-4-amino-2-{8-[(2,4-difluorophenyl)methyl]imidazo[1,2-a]pyrazin-6-yl}-5-(4-fluoro-3-hydroxyphenyl)-5-methyl-5,7-dihydro-6H-pyrrolo[2,3-d]pyrimidin-6-one;
(5R)-4-(4-amino-2-{8-[(2-fluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;
(5R)-4-amino-5-(3-fluoro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-hydroxyphenyl)-2-(8-isopentylimidazo[1,2-a]pyrazin-6-yl)-5-methyl-5,7-dihydro-6H-pyrrolo[2,3-d]pyrimidin-6-one;
(5R)-4-amino-5-(4-chloro-3-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;
(5R)-4-(4-amino-2-{8-[(3,5-difluorophenyl)methyl]-[1,2,4]triazolo[1,5-a]pyrazin-6-yl}-5-methyl-6-oxo-6,7-dihydro-5H-pyrrolo[2,3-d]pyrimidin-5-yl)-2-fluoro-6-hydroxybenzonitrile;
(5R)-4-amino-5-(3-chloro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(3-fluoro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;
(5R)-4-amino-5-(4-chloro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5R)-4-amino-2-{8-[(4-fluorophenyl)methyl]imidazo[1,2-a]pyrazin-6-yl}-5-(3-hydroxyphenyl)-S-methyl-5,7-dihydro-6H-pyrrolo[2,3-d]pyrimidin-6-one;

(5R)-4-amino-5-(4-chloro-3-fluoro-5-hydroxyphenyl)-2-(8-isopentylimidazo[1,2-a]pyrazin-6-yl)-S-methyl-5,7-dihydro-6H-pyrrolo[2,3-d]pyrimidin-6-one;

(5R)-4-amino-S-(3-hydroxy-4-(trifluoromethyl)phenyl)-S-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

(5R)-4-amino-2-{8-[1(2,4-difluorophenyl)methyl]imidazo[1,2-a]pyrazin-6-yl}-S-(3-hydroxyphenyl)-S-methyl-5,7-dihydro-6H-pyrrolo[2,3-d]pyrimidin-6-one;

(5R)-4-amino-5-(3-chloro-4-hydroxyphenyl)-2-{8-[(3-fluorophenyl)methyl]imidazo[1,2-a]pyrazin-6-yl}-S-methyl-5,7-dihydro-6H-pyrrolo[2,3-d]pyrimidin-6-one;

(5R)-4-amino-5-(4-chloro-3-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(4-fluoro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5R)-4-(4-amino-2-{8-[(3,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

(5R)-4-amino-2-(8-butylimidazo[1,2-a]pyrazin-6-yl)-5-(4-chloro-3-fluoro-5-hydroxyphenyl)-5-methyl-5,7-dihydro-6H-pyrrolo[2,3-d]pyrimidin-6-one;

(5R)-4-amino-5-(5-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(3-fluoro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(4-chloro-3-fluoro-5-hydroxyphenyl)-5-methyl-5,7-dihydro-6H-pyrrolo[2,3-d]pyrimidin-6-one;

(5R)-4-amino-2-{8-[(4-fluorophenyl)methyl]imidazo[1,2-a]pyrazin-6-yl}-5-(4-hydroxyphenyl)-5-methyl-5,7-dihydro-6H-pyrrolo[2,3-d]pyrimidin-6-one;

(5R)-4-amino-5-(4-chloro-3-hydroxyphenyl)-2-{8-[(4-chlorophenyl)methyl]imidazo[1,2-a]pyrazin-6-yl}-5-methyl-5,7-dihydro-6H-pyrrolo[2,3-d]pyrimidin-6-one;

(5R)-4-amino-2-{8-[(3-fluorophenyl)methyl]imidazo[1,2-a]pyrazin-6-yl}-5-(4-hydroxy-3-methylphenyl)-5-methyl-5,7-dihydro-6H-pyrrolo[2,3-d]pyrimidin-6-one;

(5R)-4-amino-2-{8-[(3,5-difluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;

(5R)-4-amino-5-(4-fluoro-3-hydroxyphenyl)-2-(8-isopentylimidazo[1,2-a]pyrazin-6-yl)-5-methyl-5,7-dihydro-6H-pyrrolo[2,3-d]pyrimidin-6-one;

(5R)-4-amino-2-{8-[(3,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5R)-4-amino-5-(5-chloro-6-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(4-chloro-3-hydroxyphenyl)-5-methyl-5,7-dihydro-6H-pyrrolo[2,3-d]pyrimidin-6-one;

(5R)-4-amino-5-(5-chloro-4-hydroxypyridin-2-yl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5R)-4-amino-2-(8-butylimidazo[1,2-a]pyrazin-6-yl)-5-(4-chloro-3-hydroxyphenyl)-5-methyl-5,7-dihydro-6H-pyrrolo[2,3-d]pyrimidin-6-one;

(5R)-4-amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(3-fluoro-4-hydroxyphenyl)-2-(8-isopentylimidazo[1,2-a]pyrazin-6-yl)-5-methyl-5,7-dihydro-6H-pyrrolo[2,3-d]pyrimidin-6-one;

(5R)-4-amino-5-(4-chloro-3-hydroxyphenyl)-5-methyl-2-(8-(4,4,4-trifluorobutyl)imidazo[1,2-a]pyrazin-6-yl)-5,7-dihydro-6H-pyrrolo[2,3-d]pyrimidin-6-one;

(5R)-4-amino-2-{8-[(4-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5R)-4-amino-5-(5-chloro-4-hydroxypyridin-2-yl)-2-(8-isopentylimidazo[1,2-a]pyrazin-6-yl)-5-methyl-5,7-dihydro-6H-pyrrolo[2,3-d]pyrimidin-6-one;

(5R)-4-amino-5-(4-hydroxyphenyl)-2-(8-isopentylimidazo[1,2-a]pyrazin-6-yl)-5-methyl-5,7-dihydro-6H-pyrrolo[2,3-d]pyrimidin-6-one;

(5R)-4-amino-5-(3-hydroxyphenyl)-2-(8-isopentylimidazo[1,2-a]pyrazin-6-yl)-5-methyl-5,7-dihydro-6H-pyrrolo[2,3-d]pyrimidin-6-one;

(5R)-4-amino-5-(3-chloro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(3-hydroxy-4-(trifluoromethyl)phenyl)-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(4-fluoro-3-hydroxyphenyl)-5-methyl-5,7-dihydro-6H-pyrrolo[2,3-d]pyrimidin-6-one;

(5R)-4-amino-5-(4-chloro-3-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

(5R)-4-amino-5-(3-hydroxy-4-(trifluoromethyl)phenyl)-2-(8-isopentylimidazo[1,2-a]pyrazin-6-yl)-5-methyl-5,7-dihydro-6H-pyrrolo[2,3-d]pyrimidin-6-one;

(5R)-4-amino-5-(4-chloro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-4-amino-5-(3-chloro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

(5R)-4-amino-2-(8-(cyclohexylmethyl)-[1,2,4]triazolo[1,5-a]pyrazin-6-yl)-5-(2,4-dichloro-3-hydroxyphenyl)-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(3-hydroxyphenyl)-5-methyl-5,7-dihydro-6H-pyrrolo[2,3-d]pyrimidin-6-one;

(5R)-4-amino-2-(8-(cyclohexylmethyl)imidazo[1,2-a]pyrazin-6-yl)-5-(2,4-dichloro-3-hydroxyphenyl)-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(4-hydroxyphenyl)-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(3-fluoro-4-hydroxyphenyl)-5-methyl-5,7-dihydro-6H-pyrrolo[2,3-d]pyrimidin-6-one;

(5R)-4-amino-2-(8-butylimidazo[1,2-a]pyrazin-6-yl)-5-(5-chloro-4-hydroxypyridin-2-yl)-5-methyl-5,7-dihydro-6H-pyrrolo[2,3-d]pyrimidin-6-one;

(5R)-4-amino-5-(3,5-dichloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(3-chloro-4-hydroxyphenyl)-5-methyl-5,7-dihydro-6H-pyrrolo[2,3-d]pyrimidin-6-one;

(5R)-4-amino-2-(8-butylimidazo[1,2-a]pyrazin-6-yl)-5-(3-chloro-4-hydroxyphenyl)-5-methyl-5,7-dihydro-6H-pyrrolo[2,3-d]pyrimidin-6-one;

(5R)-4-amino-2-(8-butylimidazo[1,2-a]pyrazin-6-yl)-5-(3-hydroxy-4-(trifluoromethyl)phenyl)-5-methyl-5,7-dihydro-6H-pyrrolo[2,3-d]pyrimidin-6-one;

(5R)-4-amino-5-(3-chloro-4-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

(5R)-4-amino-5-(3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5R)-4-amino-5-(3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-4-amino-5-(4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5R)-4-amino-5-(4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-4-amino-2-(8-(cyclohexylmethyl)imidazo[1,2-a]pyrazin-6-yl)-5-(3-hydroxyphenyl)-5-methyl-5,7-dihydro-6H-pyrrolo[2,3-d]pyrimidin-6-one;

(5R)-4-amino-2-(8-(2-cyclohexylethyl)imidazo[1,2-a]pyrazin-6-yl)-5-(3-hydroxyphenyl)-5-methyl-5,7-dihydro-6H-pyrrolo[2,3-d]pyrimidin-6-one;

(5R)-4-amino-2-(8-(2-cyclohexylethyl)imidazo[1,2-a]pyrazin-6-yl)-5-(3-fluoro-4-hydroxyphenyl)-5-methyl-5,7-dihydro-6H-pyrrolo[2,3-d]pyrimidin-6-one;

(5R)-4-amino-2-(8-(2-cyclohexylethyl)imidazo[1,2-a]pyrazin-6-yl)-5-(4-hydroxyphenyl)-5-methyl-5,7-dihydro-6H-pyrrolo[2,3-d]pyrimidin-6-one;

(5R)-4-amino-2-(8-(2-cyclohexylethyl)imidazo[1,2-a]pyrazin-6-yl)-5-(4-fluoro-3-hydroxyphenyl)-5-methyl-5,7-dihydro-6H-pyrrolo[2,3-d]pyrimidin-6-one;

(5R)-4-amino-5-(4-chloro-3-hydroxyphenyl)-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one;

(5R)-4-amino-5-(4-chloro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5R)-4-amino-5-(3-chloro-4-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;

(5R)-4-amino-5-(4-chloro-3-hydroxyphenyl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(4-chloro-3-hydroxyphenyl)-2-{8-[(2,4-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(5-chloro-4-hydroxypyridin-2-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(5-chloro-4-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

(5R)-4-amino-5-(5-chloro-4-hydroxypyridin-2-yl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(4-chloro-3-hydroxyphenyl)-2-(8-((4,4-difluorocyclohexyl)methyl)imidazo[1,2-a]pyrazin-6-yl)-5-methyl-5,7-dihydro-6H-pyrrolo[2,3-d]pyrimidin-6-one;

(5R)-4-amino-5-(3-chloro-4-fluoro-2-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-2-(8-(cyclohexylmethyl)imidazo[1,2-a]pyrazin-6-yl)-5-(3-fluoro-5-hydroxy-4-(trifluoromethyl)phenyl)-5-methyl-5,7-dihydro-6H-pyrrolo[2,3-d]pyrimidin-6-one;

(5R)-4-amino-5-(5-chloro-4-hydroxypyridin-2-yl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

(5R)-4-amino-5-(4-chloro-3-hydroxyphenyl)-2-{8-[(3-fluorophenyl)methyl]-2-methylimidazo[1,2-a]pyrazin-6-yl}-5-methyl-5,7-dihydro-6H-pyrrolo[2,3-d]pyrimidin-6-one;

(5R)-4-amino-5-(4-chloro-3-hydroxyphenyl)-2-{8-[(2-fluorophenyl)methyl]-2-methylimidazo[1,2-a]pyrazin-6-yl}-5-methyl-5,7-dihydro-6H-pyrrolo[2,3-d]pyrimidin-6-one;

(5R)-4-(4-amino-2-{8-[(2,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

(5R)-4-(4-amino-5-methyl-6-oxo-2-{8-[(2,3,5-trifluorophenyl)methyl]imidazo[1,2-a]pyrazin-6-yl}-6,7-dihydro-5H-pyrrolo[2,3-d]pyrimidin-5-yl)-2-fluoro-6-hydroxybenzonitrile;

(5R)-4-amino-5-(5-chloro-4-hydroxypyridin-2-yl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

(5R)-4-amino-5-(4-chloro-5-hydroxypyridin-2-yl)-2-{8-[(2-fluorophenyl)methyl]imidazo[1,2-a]pyrazin-6-yl}-5-methy-5,7-dihydro-6H-pyrrolo[2,3-d]pyrimidin-6-one;

(5R)-4-amino-5-(5-chloro-4-hydroxypyridin-2-yl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;

(5R)-4-amino-5-(4-chloro-3-hydroxyphenyl)-2-(8-(4-fluorobutyl)-[1,2,4]triazolo[1,5-a]pyrazin-6-yl)-5-methyl-5,7-dihydro-6H-pyrrolo[2,3-d]pyrimidin-6-one;

(5R)-4-amino-2-{8-[(3-fluorophenyl)methyl]imidazo[1,2-a]pyrazin-6-yl}-5-(3-hydroxy-4-methylphenyl)-5-methyl-5,7-dihydro-6H-pyrrolo[2,3-d]pyrimidin-6-one;

(5R)-4-amino-5-(4-chloro-3-hydroxyphenyl)-5-methyl-2-{8-[(trans-4-methylcyclohexyl)methyl]imidazo[1,2-a]pyrazin-6-yl}-5,7-dihydro-6H-pyrrolo[2,3-d]pyrimidin-6-one;

(5R)-4-amino-5-(4-chloro-3-hydroxyphenyl)-5-methyl-2-{8-[(cis-4-methylcyclohexyl)methyl]imidazo[1,2-a]pyrazin-6-yl}-5,7-dihydro-6H-pyrrolo[2,3-d]pyrimidin-6-one;

(5R)-4-amino-2-(8-(cyclohexylmethyl)-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

(5R)-4-amino-2-{8-[(3-fluorophenyl)methyl]-[1,2,4]triazolo[1,5-a]pyrazin-6-yl}-5-(4-hydroxypyridin-2-yl)-5-methyl-5,7-dihydro-6H-pyrrolo[2,3-d]pyrimidin-6-one;

(5R)-4-amino-5-(3-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5R)-4-amino-2-(8-(cyclohexylmethyl)-[1,2,4]triazolo[1,5-a]pyrazin-6-yl)-5-(3,5-dichloro-4-hydroxyphenyl)-5-methyl-5,7-dihydro-6H-pyrrolo[2,3-d]pyrimidin-6-one;

(5R)-4-amino-2-(8-(cyclohexylmethyl)imidazo[1,2-a]pyrazin-6-yl)-5-(3,5-dichloro-4-hydroxyphenyl)-5-methyl-5,7-dihydro-6H-pyrrolo[2,3-d]pyrimidin-6-one;

(5R)-4-amino-5-(4-fluoro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5R)-4-amino-5-(4-fluoro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-4-amino-5-(3-fluoro-4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5R)-4-amino-5-(3-fluoro-4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-4-amino-2-(8-butyl-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

(5R)-4-amino-5-(4-hydroxypyridin-2-yl)-2-(8-isopentyl-[1,2,4]triazolo[1,5-a]pyrazin-6-yl)-5-methyl-5,7-dihydro-6H-pyrrolo[2,3-d]pyrimidin-6-one;

(5R)-4-amino-5-(3-chloro-4-hydroxyphenyl)-S-methyl-2-{8-[(trans-4-methylcyclohexyl)methyl]imidazo[1,2-a]pyrazin-6-yl}-5,7-dihydro-6H-pyrrolo[2,3-d]pyrimidin-6-one;

(5R)-4-amino-5-(3-chloro-4-hydroxyphenyl)-5-methyl-2-{8-[(cis-4-methylcyclohexyl)methyl]imidazo[1,2-a]pyrazin-6-yl}-5,7-dihydro-6H-pyrrolo[2,3-d]pyrimidin-6-one;

(5R)-4-amino-2-{8-[(3-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5R)-4-amino-5-(3-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

(5R)-4-amino-2-(8-benzylimidazo[1,2-a]pyrazin-6-yl)-5-(3-hydroxyphenyl)-5-methyl-5,7-dihydro-6H-pyrrolo[2,3-d]pyrimidin-6-one;

(5R)-4-amino-2-{8-[(3-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5R)-4-amino-5-(3-fluoro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5R)-4-amino-2-{8-[(3-chlorophenyl)methyl]imidazo[1,2-a]pyrazin-6-yl}-5-(3-fluoro-4-hydroxyphenyl)-5-methyl-5,7-dihydro-6H-pyrrolo[2,3-d]pyrimidin-6-one;

(5R)-4-amino-5-(3-fluoro-4-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

(5R)-4-amino-2-(8-benzylimidazo[1,2-a]pyrazin-6-yl)-5-(3-fluoro-4-hydroxyphenyl)-5-methyl-5,7-dihydro-6H-pyrrolo[2,3-d]pyrimidin-6-one;

(5R)-5-(4-fluoro-3-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-5-(3-fluoro-4-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5R)-5-(4-Chloro-3-hydroxyphenyl)-2-{8-[(3-fluorophenyl)methyl]imidazo[1,2-a]pyrazin-6-yl}-5-methyl-4-{[(2R)-3,3,3-trifluoro-2-hydroxypropyl]amino}-5,7-dihydro-6H-pyrrolo[2,3-d]pyrimidin-6-one (5R)-5-(4-Chloro-3-hydroxyphenyl)-2-{8-[(3-fluorophenyl)methyl]imidazo[1,2-a]pyrazin-6-yl}-5-methyl-4-{[(2S)-3,3,3-trifluoro-2-hydroxypropyl]amino}-5,7-dihydro-6H-pyrrolo[2,3-d]pyrimidin-6-one (5R)-5-(4-chloro-3-hydroxyphenyl)-2-{8-[(4-fluorophenyl)methyl]imidazo[1,2-a]pyrazin-6-yl}-5-methyl-4-{[(2R)-3,3,3-trifluoro-2-hydroxypropyl]amino}-5,7-dihydro-6H-pyrrolo[2,3-d]pyrimidin-6-one;

(5R)-5-(4-chloro-3-hydroxyphenyl)-2-{8-[(4-fluorophenyl)methyl]imidazo[1,2-a]pyrazin-6-yl}-5-methyl-4-{[(2S)-3,3,3-trifluoro-2-hydroxypropyl]amino}-5,7-dihydro-6H-pyrrolo[2,3-d]pyrimidin-6-one;

(5R)-5-(4-chloro-3-hydroxyphenyl)-5-methyl-2-(8-(3,3,4,4,4-pentafluorobutyl)-[1,2,4]triazolo[1,5-a]pyrazin-6-yl)-4-{[(2R)-3,3,3-trifluoro-2-hydroxypropyl]amino}-5,7-dihydro-6H-pyrrolo[2,3-d]pyrimidin-6-one;

(5R)-5-(4-chloro-3-hydroxyphenyl)-5-methyl-2-(8-(3,3,4,4,4-pentafluorobutyl)-[1,2,4]triazolo[1,5-a]pyrazin-6-yl)-4-{[(2S)-3,3,3-trifluoro-2-hydroxypropyl]amino}-5,7-dihydro-6H-pyrrolo[2,3-d]pyrimidin-6-one;

(5R)-5-(4-chloro-3-hydroxyphenyl)-2-{8-[(4-fluorophenyl)methyl]imidazo[1,2-a]pyrazin-6-yl}-5-methyl-4-(4-methylpiperazin-1-yl)-5,7-dihydro-6H-pyrrolo[2,3-d]pyrimidin-6-one;

(5R)-4-(4,4-difluoropiperidin-1-yl)-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5R)-5-(4-chloro-3-hydroxyphenyl)-4-(4,4-difluoropiperidin-1-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5R)-5-(4-chloro-3-hydroxyphenyl)-5-methyl-2-(8-(3,3,4,4,4-pentafluorobutyl)-[1,2,4]triazolo[1,5-a]pyrazin-6-yl)-4-(4-(trifluoromethyl)piperidin-1-yl)-5,7-dihydro-6H-pyrrolo[2,3-d]pyrimidin-6-one;

(5R)-5-(4-chloro-3-hydroxyphenyl)-5-methyl-2-(8-(3,3,4,4,4-pentafluorobutyl)-[1,2,4]triazolo[1,5-a]pyrazin-6-yl)-4-((3,3,3-trifluoropropyl)amino)-5,7-dihydro-6H-pyrrolo[2,3-d]pyrimidin-6-one;

(5R)-5-(4-chloro-3-hydroxyphenyl)-5-methyl-2-(8-(3,3,4,4,4-pentafluorobutyl)-[1,2,4]triazolo[1,5-a]pyrazin-6-yl)-4-((4,4,4-trifluorobutyl)amino)-5,7-dihydro-6H-pyrrolo[2,3-d]pyrimidin-6-one;

(5R)-4-amino-2-(3-amino-8-[(3-fluorophenyl)methyl]imidazo[1,2-a]pyrazin-6-yl)-5-(4-chloro-3-hydroxyphenyl)-5-methyl-5,7-dihydro-6H-pyrrolo[2,3-d]pyrimidin-6-one;

(5R)-4-amino-5-(5-chloro-4-hydroxypyridin-2-yl)-2-(8-(cyclopentylmethyl)imidazo[1,2-a]pyrazin-6-yl)-5-methyl-5,7-dihydro-6H-pyrrolo[2,3-d]pyrimidin-6-one;

(5R)-4-(4-amino-2-{8-(cyclohexylmethyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5R)-4-(4-amino-2-{8-(2-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5R)-4-(4-amino-2-{8-(3-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5R)-4-amino-2-(8-{3-fluorobenzyl}imidazo[1,2-a]pyrazin-6-yl)-5-(4-hydroxy-5(trifluoromethyl)pyridin-2-yl)-5-methyl-5,7-dihydro-6H-pyrrolo[2,3-d]pyrimidin-6-one;

(5R)-4-amino-2-(8-{2-fluorobenzyl}imidazo[1,2-a]pyrazin-6-yl)-5-(4-hydroxy-5-(trifluoromethyl)pyridin-2-yl)-5-methyl-5,7-dihydro-6H-pyrrolo[2,3-d]pyrimidin-6-one;

(5R)-4-amino-2-{8-(cyclohexylmethyl)imidazo[1,2-a]pyrazin-6-yl}-5-(4-hydroxy-5-(trifluoromethyl)pyridin-2-yl)-5-methyl-5,7-dihydro-6H-pyrrolo[2,3-d]pyrimidin-6-one;

(5R)-4-amino-5-(5-chloro-4-hydroxypyridin-2-yl)-2-{8-(2-fluorobenzyl)-[1,2,4]triazolo[1,5-a]pyrazin-6-yl}-5-methyl-5,7-dihydro-6H-pyrrolo[2,3-d]pyrimidin-6-one;

(5R)-4-(4-amino-2-{8-(2-fluorobenzyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile;

(5R)-4-(4-amino-2-{8-(cyclohexylmethyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile; and (5R)-4-amino-2-{8-(3-fluorobenzyl)imidazo[1,2-a]pyrazin-6-yl}-5-(4-hydroxy-5-methylpyridin-2-yl)-5-methyl-5,7-dihydro-6H-pyrrolo[2,3-d]pyrimidin-6-one;

or a pharmaceutically salt thereof.

In another embodiment, the present invention provides a compound selected from:

(5S)-4-amino-5-(4-chloro-3-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-fluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-2-{8-[(2-fluorophenyl)methyl]imidazo[1,2-a]pyrazin-6-yl}-5-[3-hydroxy-4-(trifluoromethyl)phenyl]-5-methyl-5,7-dihydro-6H-pyrrolo[2,3-d]pyrimidin-6-one;

(5S)-4-amino-5-(5-chloro-4-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-fluoro-5-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-fluoro-5-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-fluoro-5-hydroxyphenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

(5S)-4-amino-5-(4-chloro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(3,4-difluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5 (4-chloro-3-fluoro-5-hydroxyphenyl)-2-{8-[(2-fluorophenyl)methyl]-[1,2,4]triazolo[1,5-a]pyrazin-6-yl}-5-methyl-5,7-dihydro-6H-pyrrolo[2,3-d]pyrimidin-6-one;

(5S)-4-amino-2-{8-[(2,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(4-chloro-3-fluoro-5-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;

(5S)-4-amino-5-(4-fluoro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;

(5S)-4-(4-amino-2-(8-(cyclohexylmethyl)-[1,2,4]triazolo[1,5-a]pyrazin-6-yl)-5-methyl-6-oxo-6,7-dihydro-5H-pyrrolo[2,3-d]pyrimidin-5-yl)-2-fluoro-6-hydroxybenzonitrile;

(5S)-4-amino-5-(4-chloro-3-fluoro-5-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-2-{8-[(3-fluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;

(5S)-4-(4-amino-2-(8-(cyclohexylmethyl)imidazo[1,2-a]pyrazin-6-yl)-5-methyl-6-oxo-6,7-dihydro-5H-pyrrolo[2,3-d]pyrimidin-5-yl)-2-fluoro-6-hydroxybenzonitrile;

(5S)-4-amino-5-(4-chloro-3-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(3,4-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-fluoro-5-hydroxyphenyl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;

(5S)-4-amino-2-{8-[(2,4-difluorophenyl)methyl]imidazo[1,2-a]pyrazin-6-yl}-5-(4-fluoro-3-hydroxyphenyl)-5-methyl-5,7-dihydro-6H-pyrrolo[2,3-d]pyrimidin-6-one;

(5S)-4-(4-amino-2-{8-[(2-fluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

(5S)-4-amino-5-(3-fluoro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(4-chloro-3-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

(5S)-4-(4-amino-2-{8-[(3,5-difluorophenyl)methyl]-[1,2,4]triazolo[1,5-a]pyrazin-6-yl}-S-methyl-6-oxo-6,7-dihydro-5H-pyrrolo[2,3-d]pyrimidin-5-yl)-2-fluoro-6-hydroxybenzonitrile;

(5S)-4-amino-5-(3-chloro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(3-fluoro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-4-amino-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(4-chloro-3-fluoro-5-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(3-hydroxy-4-(trifluoromethyl)phenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

(5S)-4-amino-2-{8-[(2,4-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(3-chloro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-fluoro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-4-(4-amino-2-{8-[(3,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

(5S)-4-amino-2-(8-butylimidazo[1,2-a]pyrazin-6-yl)-5-(4-chloro-3-fluoro-5-hydroxyphenyl)-5-methyl-5,7-dihydro-6H-pyrrolo[2,3-d]pyrimidin-6-one;

(5S)-4-amino-5-(5-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(3-fluoro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(4-chloro-3-fluoro-5-hydroxyphenyl)-5-methyl-5,7-dihydro-6H-pyrrolo[2,3-d]pyrimidin-6-one;

(5S)-4-amino-2-{8-[(4-fluorophenyl)methyl]imidazo[1,2-a]pyrazin-6-yl}-5-(4-hydroxyphenyl)-5-methyl-5,7-dihydro-6H-pyrrolo[2,3-d]pyrimidin-6-one;

(5S)-4-amino-5 (4-chloro-3-hydroxyphenyl)-2-{8-[(4-chlorophenyl)methyl]imidazo[1,2-a]pyrazin-6-yl}-5-methyl-5,7-dihydro-6H-pyrrolo[2,3-d]pyrimidin-6-one;

(5S)-4-amino-2-{8-[(3-fluorophenyl)methyl]imidazo[1,2-a]pyrazin-6-yl}-5-(4-hydroxy-3-methylphenyl)-5-methyl-5,7-dihydro-6H-pyrrolo[2,3-d]pyrimidin-6-one;

(5S)-4-amino-2-{8-[(3,5-difluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one;

(5S)-4-amino-5-(4-fluoro-3-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-2-{8-[(3,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(5-chloro-6-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(4-chloro-3-hydroxyphenyl)-5-methyl-5,7-dihydro-6H-pyrrolo[2,3-d]pyrimidin-6-one;

(5S)-4-amino-5-(5-chloro-4-hydroxypyridin-2-yl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5S)-4-amino-2-(8-butylimidazo[1,2-a]pyrazin-6-yl)-5-(4-chloro-3-hydroxyphenyl)-5-methyl-5,7-dihydro-6H-pyrrolo[2,3-d]pyrimidin-6-one;

(5S)-4-amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(3-fluoro-4-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(4-chloro-3-hydroxyphenyl)-5-methyl-2-(8-(4,4,4-trifluorobutyl)imidazo[1,2-a]pyrazin-6-yl)-5,7-dihydro-6H-pyrrolo[2,3-d]pyrimidin-6-one;

(5S)-4-amino-2-{8-[(4-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(5-chloro-4-hydroxypyridin-2-yl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(4-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(3-hydroxyphenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(3-chloro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(3-hydroxy-4-(trifluoromethyl)phenyl)-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(4-fluoro-3-hydroxyphenyl)-5-methyl-5,7-dihydro-6H-pyrrolo[2,3-d]pyrimidin-6-one;

(5S)-4-amino-5-(4-chloro-3-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

(5S)-4-amino-5-(3-hydroxy-4-(trifluoromethyl)phenyl)-2-(8-isopentylimidazo[1,2-a]pyrazin-6-yl)-5-methyl-5,7-dihydro-6H-pyrrolo[2,3-d]pyrimidin-6-one;

(5S)-4-amino-5-(4-chloro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-4-amino-5-(3-chloro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one;

(5S)-4-amino-2-(8-(cyclohexylmethyl)-[1,2,4]triazolo[1,5-a]pyrazin-6-yl)-5-(2,4-dichloro-3-hydroxyphenyl)-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(3-hydroxyphenyl)-5-methyl-5,7-dihydro-6H-pyrrolo[2,3-d]pyrimidin-6-one;

(5S)-4-amino-2-(8-(cyclohexylmethyl)imidazo[1,2-a]pyrazin-6-yl)-5-(2,4-dichloro-3-hydroxyphenyl)-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(4-hydroxyphenyl)-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(3-fluoro-4-hydroxyphenyl)-5-methyl-5,7-dihydro-6H-pyrrolo[2,3-d]pyrimidin-6-one;

(5S)-4-amino-2-(8-butylimidazo[1,2-a]pyrazin-6-yl)-5-(5-chloro-4-hydroxypyridin-2-yl)-5-methyl-5,7-dihydro-6H-pyrrolo[2,3-d]pyrimidin-6-one;

(5S)-4-amino-5-(3,5-dichloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(3-chloro-4-hydroxyphenyl)-5-methyl-5,7-dihydro-6H-pyrrolo[2,3-d]pyrimidin-6-one;

(5S)-4-amino-2-(8-butylimidazo[1,2-a]pyrazin-6-yl)-5-(3-chloro-4-hydroxyphenyl)-5-methyl-5,7-dihydro-6H-pyrrolo[2,3-d]pyrimidin-6-one;

(5S)-4-amino-2-(8-butylimidazo[1,2-a]pyrazin-6-yl)-5-(3-hydroxy-4-(trifluoromethyl)phenyl)-5-methyl-5,7-dihydro-6H-pyrrolo[2,3-d]pyrimidin-6-one;

(5S)-4-amino-5-(3-chloro-4-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one;

(5S)-4-amino-5-(3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5S)-4-amino-5-(3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-4-amino-5-(4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5S)-4-amino-5-(4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-4-amino-2-(8-(cyclohexylmethyl)imidazo[1,2-a]pyrazin-6-yl)-5-(3-hydroxyphenyl)-5-methyl-5,7-dihydro-6H-pyrrolo[2,3-d]pyrimidin-6-one;

(5S)-4-amino-2-(8-(2-cyclohexylethyl)imidazo[1,2-a]pyrazin-6-yl)-5-(3-hydroxyphenyl)-5-methyl-5,7-dihydro-6H-pyrrolo[2,3-d]pyrimidin-6-one;

(5S)-4-amino-2-(8-(2-cyclohexylethyl)imidazo[1,2-a]pyrazin-6-yl)-5-(3-fluoro-4-hydroxyphenyl)-5-methyl-5,7-dihydro-6H-pyrrolo[2,3-d]pyrimidin-6-one;

(5S)-4-amino-2-(8-(2-cyclohexylethyl)imidazo[1,2-a]pyrazin-6-yl)-5-(4-hydroxyphenyl)-5-methyl-5,7-dihydro-6H-pyrrolo[2,3-d]pyrimidin-6-one;

(5S)-4-amino-2-(8-(2-cyclohexylethyl)imidazo[1,2-a]pyrazin-6-yl)-5-(4-fluoro-3-hydroxyphenyl)-5-methyl-5,7-dihydro-6H-pyrrolo[2,3-d]pyrimidin-6-one;

(5S)-4-amino-5-(4-chloro-3-hydroxyphenyl)-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one;

(5S)-4-amino-5-(4-chloro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5S)-4-amino-5-(3-chloro-4-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one;

(5S)-4-amino-5-(4-chloro-3-hydroxyphenyl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(2,4-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(5-chloro-4-hydroxypyridin-2-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(5-chloro-4-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one;

(5S)-4-amino-5-(5-chloro-4-hydroxypyridin-2-yl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-(8-((4,4-difluorocyclohexyl)methyl)imidazo[1,2-a]pyrazin-6-yl)-5-methyl-5,7-dihydro-6H-pyrrolo[2,3-d]pyrimidin-6-one;

(5S)-4-amino-5-(3-chloro-4-fluoro-2-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-2-(8-(cyclohexylmethyl)imidazo[1,2-a]pyrazin-6-yl)-5-(3-fluoro-5-hydroxy-4-(trifluoromethyl)phenyl)-5-methyl-5,7-dihydro-6H-pyrrolo[2,3-d]pyrimidin-6-one;

(5S)-4-amino-5-(5-chloro-4-hydroxypyridin-2-yl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(3-fluorophenyl)methyl]-2-methylimidazo[1,2-a]pyrazin-6-yl}-5-methyl-5,7-dihydro-6H-pyrrolo[2,3-d]pyrimidin-6-one;

(5S)-4-amino-5-(4-chloro-3-hydroxyphenyl)-2-{8-[(2-fluorophenyl)methyl]-2-methylimidazo[1,2-a]pyrazin-6-yl}-5-methyl-5,7-dihydro-6H-pyrrolo[2,3-d]pyrimidin-6-one;

(5S)-4-(4-amino-2-{8-[(2,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile;

(5S)-4-(4-amino-5-methyl-6-oxo-2-{8-[(2,3,5-trifluorophenyl)methyl]imidazo[1,2-a]pyrazin-6-yl}-6,7-dihydro-5H-pyrrolo[2,3-d]pyrimidin-5-yl)-2-fluoro-6-hydroxybenzonitrile;

(5S)-4-amino-5-(5-chloro-4-hydroxypyridin-2-yl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one;

(5S)-4-amino-5-(4-chloro-5-hydroxypyridin-2-yl)-2-{8-[(2-fluorophenyl)methyl]imidazo[1,2-a]pyrazin-6-yl}-5-methy-5,7-dihydro-6H-pyrrolo[2,3-d]pyrimidin-6-one;

(5S)-4-amino-5-(5-chloro-4-hydroxypyridin-2-yl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one;

(5S)-4-amino-5-(4-chloro-3-hydroxyphenyl)-2-(8-(4-fluorobutyl)-[1,2,4]triazolo[1,5-a]pyrazin-6-yl)-5-methyl-5,7-dihydro-6H-pyrrolo[2,3-d]pyrimidin-6-one;

(5S)-4-amino-2-{8-[(3-fluorophenyl)methyl]imidazo[1,2-a]pyrazin-6-yl}-5-(3-hydroxy-4-methylphenyl)-5-methyl-5,7-dihydro-6H-pyrrolo[2,3-d]pyrimidin-6-one;

(5S)-4-amino-5-(4-chloro-3-hydroxyphenyl)-5-methyl-2-{8-[(trans-4-methylcyclohexyl)methyl]imidazo[1,2-a]pyrazin-6-yl}-5,7-dihydro-6H-pyrrolo[2,3-d]pyrimidin-6-one;

(5S)-4-amino-5-(4-chloro-3-hydroxyphenyl)-5-methyl-2-{8-[(cis-4-methylcyclohexyl)methyl]imidazo[1,2-a]pyrazin-6-yl}-5,7-dihydro-6H-pyrrolo[2,3-d]pyrimidin-6-one;

(5S)-4-amino-2-(8-(cyclohexylmethyl)-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

(5S)-4-amino-2-{8-[(3-fluorophenyl)methyl]-[1,2,4]triazolo[1,5-a]pyrazin-6-yl}-5-(4-hydroxypyridin-2-yl)-5-methyl-5,7-dihydro-6H-pyrrolo[2,3-d]pyrimidin-6-one;

(5S)-4-amino-5-(3-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one;

(5S)-4-amino-2-(8-(cyclohexylmethyl)-[1,2,4]triazolo[1,5-a]pyrazin-6-yl)-5-(3,5-dichloro-4-hydroxyphenyl)-5-methyl-5,7-dihydro-6H-pyrrolo[2,3-d]pyrimidin-6-one;

(5S)-4-amino-2-(8-(cyclohexylmethyl)imidazo[1,2-a]pyrazin-6-yl)-5-(3,5-dichloro-4-hydroxyphenyl)-5-methyl-5,7-dihydro-6H-pyrrolo[2,3-d]pyrimidin-6-one;

(5S)-4-amino-5-(4-fluoro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5S)-4-amino-5-(4-fluoro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-4-amino-5-(3-fluoro-4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one;

(5S)-4-amino-5-(3-fluoro-4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-4-amino-2-(8-butyl-[1,2,4]triazolo[1,5-a]pyrazin-6-yl)-5-(4-hydroxypyridin-2-yl)-5-methyl-5,7-dihydro-6H-pyrrolo[2,3-d]pyrimidin-6-one;

(5S)-4-amino-5-(4-hydroxypyridin-2-yl)-2-(8-isopentyl-[1,2,4]triazolo[1,5-a]pyrazin-6-yl)-5-methyl-5,7-dihydro-6H-pyrrolo[2,3-d]pyrimidin-6-one;

(5S)-4-amino-5-(3-chloro-4-hydroxyphenyl)-5-methyl-2-{8-[(trans-4-methylcyclohexyl)methyl]imidazo[1,2-a]pyrazin-6-yl}-5,7-dihydro-6H-pyrrolo[2,3-d]pyrimidin-6-one;

(5S)-4-amino-5-(3-chloro-4-hydroxyphenyl)-5-methyl-2-{8-[(cis-4-methylcyclohexyl)methyl]imidazo[1,2-a]pyrazin-6-yl}-5,7-dihydro-6H-pyrrolo[2,3-d]pyrimidin-6-one;

(5S)-4-amino-2-{8-[(3-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(3-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

(5S)-4-amino-2-(8-benzylimidazo[1,2-a]pyrazin-6-yl)-5-(3-hydroxyphenyl)-5-methyl-5,7-dihydro-6H-pyrrolo[2,3-d]pyrimidin-6-one;

(5S)-4-amino-2-{8-[(3-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-4-amino-5-(3-fluoro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one;

(5S)-4-amino-2-{8-[(3-chlorophenyl)methyl]imidazo[1,2-a]pyrazin-6-yl}-5-(3-fluoro-4-hydroxyphenyl)-5-methyl-5,7-dihydro-6H-pyrrolo[2,3-d]pyrimidin-6-one;

(5S)-4-amino-5-(3-fluoro-4-hydroxyphenyl)-5-methyl-2-{8-[(3-methylphenyl)methyl]imidazo[1,2-a]pyrazin-6-yl}-5,7-dihydro-6H-pyrrolo[2,3-d]pyrimidin-6-one;

(5S)-4-amino-2-(8-benzylimidazo[1,2-a]pyrazin-6-yl)-5-(3-fluoro-4-hydroxyphenyl)-5-methyl-5,7-dihydro-6H-pyrrolo[2,3-d]pyrimidin-6-one;

(5S)-5-(4-fluoro-3-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-5-(3-fluoro-4-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one;

(5S)-5-(4-chloro-3-hydroxyphenyl)-2-{8-[(3-fluorophenyl)methyl]imidazo[1,2-a]pyrazin-6-yl}-5-methyl-4-{[(2S)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-2-{8-[(3-fluorophenyl)methyl]imidazo[1,2-a]pyrazin-6-yl}-5-methyl-4-{[(2R)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-2-{8-[(4-fluorophenyl)methyl]imidazo[1,2-a]pyrazin-6-yl}-5-methyl-4-{[(2S)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-2-{8-[(4-fluorophenyl)methyl]imidazo[1,2-a]pyrazin-6-yl}-5-methyl-4-{[(2R)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-5-methyl-2-(8-(3,3,4,4,4-pentafluorobutyl)-[1,2,4]triazolo[1,5-a]pyrazin-6-yl)-4-{[(2S)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-5-methyl-2-(8-(3,3,4,4,4-pentafluorobutyl)-[1,2,4]triazolo[1,5-a]pyrazin-6-yl)-4-{[(2R)-3,3,3-trifluoro-2-hydroxypropyl]amino}-5,7-dihydro-6H-pyrrolo[2,3-d]pyrimidin-6-one;

(5S)-5-(4-chloro-3-hydroxyphenyl)-2-{8-[(4-fluorophenyl)methyl]imidazo[1,2-a]pyrazin-6-yl}-5-methyl-4-(4-methylpiperazin-1-yl)-5,7-dihydro-6H-pyrrolo[2,3-d]pyrimidin-6-one;

(5S)-4-(4,4-difluoropiperidin-1-yl)-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one;

(5S)-5-(4-chloro-3-hydroxyphenyl)-4-(4,4-difluoropiperidin-1-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one;

(5S)-5-(4-chloro-3-hydroxyphenyl)-5-methyl-2-(8-(3,3,4,4,4-pentafluorobutyl)-[1,2,4]triazolo[1,5-a]pyrazin-6-yl)-4-(4-(trifluoromethyl)piperidin-1-yl)-5,7-dihydro-6H-pyrrolo[2,3-d]pyrimidin-6-one;

(5S)-5-(4-chloro-3-hydroxyphenyl)-5-methyl-2-(8-(3,3,4,4,4-pentafluorobutyl)-[1,2,4]triazolo[1,5-a]pyrazin-6-yl)-4-((3,3,3-trifluoropropyl)amino)-5,7-dihydro-6H-pyrrolo[2,3-d]pyrimidin-6-one;

(5S)-5-(4-chloro-3-hydroxyphenyl)-5-methyl-2-(8-(3,3,4,4,4-pentafluorobutyl)-[1,2,4]triazolo[1,5-a]pyrazin-6-yl)-4-((4,4,4-trifluorobutyl)amino)-5,7-dihydro-6H-pyrrolo[2,3-d]pyrimidin-6-one;

(5S)-4-amino-2-(3-amino-8-[(3-fluorophenyl)methyl]imidazo[1,2-a]pyrazin-6-yl)-5-(4-chloro-3-hydroxyphenyl)-5-methyl-5,7-dihydro-6H-pyrrolo[2,3-d]pyrimidin-6-one;

(5S)-4-amino-5-(5-chloro-4-hydroxypyridin-2-yl)-2-(8-(cyclopentylmethyl)imidazo[1,2-a]pyrazin-6-yl)-5-methyl-5,7-dihydro-6H-pyrrolo[2,3-d]pyrimidin-6-one;

(5S)-4-(4-amino-2-{8-(cyclohexylmethyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5S)-4-(4-amino-2-{8-(2-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5S)-4-(4-amino-2-{8-(3-fluorobenzyl)imidazo[1,2-a]pyrazin-6-yl}-5-methyl-6-oxo-6,7-dihydro-5H-pyrrolo[2,3-d]pyrimidin-5-yl)-2-chloro-6-hydroxybenzonitrile;

(5S)-4-amino-2-(8-{3-fluorobenzyl}imidazo[1,2-a]pyrazin-6-yl)-5-(4-hydroxy-5(trifluoromethyl)pyridin-2-yl)-5-methyl-5,7-dihydro-6H-pyrrolo[2,3-d]pyrimidin-6-one;

(5S)-4-amino-2-(8-{2-fluorobenzyl}imidazo[1,2-a]pyrazin-6-yl)-5-(4-hydroxy-5-(trifluoromethyl)pyridin-2-yl)-5-methyl-5,7-dihydro-6H-pyrrolo[2,3-d]pyrimidin-6-one;

(5S)-4-amino-2-{8-(cyclohexylmethyl)imidazo[1,2-a]pyrazin-6-yl}-5-(4-hydroxy-5-(trifluoromethyl)pyridin-2-yl)-5-methyl-5,7-dihydro-6H-pyrrolo[2,3-d]pyrimidin-6-one;

(5S)-4-amino-5-(5-chloro-4-hydroxypyridin-2-yl)-2-{8-(2-fluorobenzyl)-[1,2,4]triazolo[1,5-a]pyrazin-6-yl}-5-methyl-5,7-dihydro-6H-pyrrolo[2,3-d]pyrimidin-6-one;

(5S)-4-(4-amino-2-{8-(2-fluorobenzyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile;

(5S)-4-(4-amino-2-{8-(cyclohexylmethyl)-[1,2,4]triazolo[1,5-a]pyrazin-6-yl}-5-methyl-6-oxo-6,7-dihydro-5H-pyrrolo[2,3-d]pyrimidin-5-yl)-2-chloro-6-hydroxybenzonitrile; and (5S)-4-amino-2-{8-(3-fluorobenzyl)imidazo[1,2-a]pyrazin-6-yl}-5-(4-hydroxy-5-methylpyridin-2-yl)-5-methyl-5,7-dihydro-6H-pyrrolo[2,3-d]pyrimidin-6-one; or a pharmaceutically acceptable salt thereof.

The present invention includes the pharmaceutically acceptable salts of the compounds defined herein, including the pharmaceutically acceptable salts of all structural formulas, embodiments and classes defined herein.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Alkyl-NH—" refers to an alkyl group linked to an NH group. Examples of alkyl-NH-include methyl-amino or methyl-NH— and ethyl-amino or ethyl-NH—.

"Aryl" means phenyl or naphthyl.

"Haloalkyl" include mono-substituted as well as multiple halo substituted alkyl groups, up to perhalo substituted alkyl. For example, halomethyl, 1,1-difluoroethyl, trifluoromethyl or 1,1,1,2,2-pentafluorobutyl are included.

"Haloalkoxy" and "haloalkyl-O" are used interchangeably and refer to halo substituted alkyl groups or "haloalkyl" linked through the oxygen atom. Haloalkoxy include mono-substituted as well as multiple halo substituted alkoxy groups, up to perhalo substituted alkoxy. For example, trifluoromethoxy is included.

"Cycloalkyl" means a saturated cyclic hydrocarbon radical having the number of carbon atoms designated if no number of atoms is specified, 3-12 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, adamantyl, decahydronaphthyl, indanyl and the like.

"Cycloalkoxy" and "cycloalkyl-O" are used interchangeably and refer to a cycloalkyl group, as defined above, linked to oxygen.

"Cycloalkenyl" means a non-aromatic monocyclic ring system comprising about 3 to about 8 carbon atoms which contains at least one carbon-carbon double bond. Preferred cycloalkenyl rings contain about 5 to about 7 ring atoms. Unless otherwise indicated, a cycloalkenyl group is unsubstituted. Non-limiting examples of suitable cycloalkenyls include cyclopentenyl, cyclohexenyl, cyclohepta-1,3-dienyl, and the like.

"Heterocyclyl" "heterocycle" or "heterocyclic" refers to nonaromatic monocyclic ring structures in which one or more atoms in the ring, the heteroatom(s), is an element other than carbon. Such nonaromatic cyclic ring structures can be saturated or unsaturated. Heteroatoms are typically O, S or N atoms. Examples of heterocyclyl groups include: piperidine, piperazinyl, morpholinyl, pyrrolidinyl, tetrahydrofuranyl, azetidinyl, oxiranyl, or aziridinyl, and the like.

"Heteroaryl" refers to an aromatic monocyclic ring structures in which one or more atoms in the ring, the heteroatom(s), is an element other than carbon. Heteroatoms are typically O, S, or N atoms. Examples of heteroaromatic groups include: pyridinyl, pyrimidinyl, pyrrolyl, pyridazinyl, isoxazolyl, indolyl, or imidazolyl.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^{2a}$, $R^6$) occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e., $R^{2a}$, $R^6$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^6$ in Formula (I), are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

Compounds of Formula (I) may contain one or more asymmetric centers and can thus occur as racemates and racemic mixtures, single enantiomers, diastereoisomeric mixtures and individual diastereoisomers. Centers of asymmetry that are present in the compounds of Formula (I) can all independently of one another have S configuration or R configuration. The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereoisomeric forms of the compounds of Formula (I). Where a structural formula or chemical name specifies a particular configuration at a stereocenter, the enantiomer or stereoisomer of the compound resulting from that specified stereocenter is intended.

Compounds of Formula (I) may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula (I) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography.

The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula (I) described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed by the compounds of Formula I of the present invention.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of Formula (I) and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule the invention also includes, in addition to the salt forms mentioned, inner salts or betaines (zwitterions). Salts can be obtained from the compounds of Formula (I) by customary methods which are known to the person skilled in the art, for example, by combination with an organic or inorganic acid or base in a solvent or dispersant, or by anion exchange or cation exchange from other salts. The present invention also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula (I), including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

The present invention also relates to processes for the preparation of the compounds of Formula (I) which are described in the following schemes and examples, and by which the compounds of the invention are obtainable.

The compounds of Formula (I) according to the invention effect an increase of cGMP concentration via the activation of the soluble guanylate cyclase (sGC), and they therefore may be useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula (I) can be examined, for example, in the cell-based sGC functional assay described in the Biological Assays below.

The compounds of Formula (I) bind with high potency to sGC to enable administration of, for example, doses of less than 10 μg. High potency compounds are preferred to enable administration of low human doses. For inhaled delivery applications, high potency compounds may enable use of low human doses, and allow for formulation within the restraints of an inhaled delivery device.

The binding potencies of the compounds of Formula (I) can be determined in a competitive binding assay that uses a labeled sGC ligand. The Biological Assays section below describes an example of a competitive binding assay used to determine the compounds' abilities to displace a radioligand that binds to purified recombinant sGC.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. In a preferred embodiment, the term "therapeutically effective amount" means an amount of a pharmaceutical drug that alleviates at least one clinical symptom in a human patient. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula (I) are, for example, cardiovascular diseases, such as endothelial dysfunction, diastolic dysfunction, atherosclerosis, hypertension, heart failure, pulmonary hypertension (WHO Groups I, II, III, IV), which includes pulmonary arterial hypertension (PAH), stable and unstable angina pectoris, thromboses, restenoses, myocardial infarction, stroke, cardiac insufficiency, fibrosis or pulmonary hypertonia, or, for example, erectile dysfunction, asthma (e.g., bronchial asthma), cirrhosis of the liver, chronic obstructive pulmonary disease (COPD), acute respiratory distress syndrome (ARDS), acute lung injury, pulmonary fibrosis, chronic kidney disease, chronic kidney insufficiency, cystic fibrosis, interstitial lung disease, sickle cell anemia, scleroderma, Raynaud's Syndrome, or diabetes.

In one embodiment of the invention, the compounds of Formula (I) may be used for treating cardiovascular disease, endothelial dysfunction, diastolic dysfunction, atherosclerosis, hypertension, heart failure, pulmonary hypertension (WHO groups I, II, III, IV), angina pectoris, thrombosis, restenosis, myocardial infarction, stroke, cardiac insufficiency, fibrosis, pulmonary hypertonia, erectile dysfunction, asthma, chronic kidney disease, diabetes, diabetic retinopathy, cirrhosis of the liver, chronic obstructive pulmonary disease (COPD), acute respiratory distress syndrome, acute lung injury, pulmonary fibrosis, cystic fibrosis, or interstitial lung disease.

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Subjects of the present invention therefore also are the compounds of Formula (I) and their pharmaceutically acceptable salts for use as pharmaceuticals, their use for activating soluble guanylate cyclase, for normalizing a disturbed cGMP balance, and in particular, their use in the therapy and prophylaxis of the above mentioned syndromes as well as their use for preparing medicaments for these purposes.

Furthermore, a subject of the present invention is pharmaceutical compositions which comprise as active component an effective dose of at least one compound of Formula (I) and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical compositions which comprise as active component an effective dose of the compound of Formula (I) and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceutical compositions according to the invention can be administered orally, for example, in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion.

The pharmaceutical compositions can also be administered by the inhaled route. Dosage forms for inhaled administration may conveniently be formulated as aerosols or dry powders. For compositions suitable and/or adapted for inhaled administration, it is preferred that the compound of Formula (I) is in a particle-size-reduced form, and more preferably the size-reduced form is obtained or obtainable by micronisation or other protocols for controlling particle size.

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

Pharmaceutical compositions suitable for inhaled administration may also take the form of a dry powder inhalable composition. Such a composition can comprise a powder base such as lactose, glucose, trehalose, mannitol or starch, the compound of Formula (I) (preferably in particle-size-reduced form, e.g., in micronised form), and optionally a performance modifier such as L-leucine or another amino acid, and/or metals salts of stearic acid such as magnesium or calcium stearate. In some embodiments, the dry powder inhalable composition comprises a dry powder blend of lactose and the compound of Formula (I) or salt thereof.

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Merck & Co., Inc.), Turbuhaler® (AstraZeneca), Ultrahaler® (Aventis), and the like.

Other suitable administration forms are, for example, percutaneous or topical administration, for example in the form of ointments, tinctures, sprays or transdermal therapeutic systems, or, for example, microcapsules, implants or rods. The preferred administration form depends, for example, on the disease to be treated and on its severity.

The amount of active compound of Formula (I) and/or its pharmaceutically acceptable salts in the pharmaceutical composition normally is from 0.1 to 200 mg, preferably from 1 to 200 mg, per dose, but depending on the type of the pharmaceutical composition it can also be higher. The pharmaceutical compositions usually comprise 0.5 to 90 percent by weight of the compound of Formula (I) and/or their pharmaceutically acceptable salts. The preparation of the pharmaceutical compositions can be carried out in a manner known per se. For this purpose, one or more compounds of Formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula (I) and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, on the selected route of administration, or on whether other active compounds are administered in addition to compounds of Formula (I). In general, a daily dose of approximately 0.0001 to 100 mg/kg, in particular, 0.0001 to 0.30 mg/kg or 0.01 to 0.03 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula (I) activate soluble guanylate cyclase. Due to this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula (I) and salts thereof can furthermore be employed, as already mentioned above, as intermediates for the preparation of other pharmaceutically active compounds.

One or more additional pharmacologically active agents may be administered in combination with a compound of Formula (I). An additional active agent (or agents) is intended to mean a pharmaceutically active agent (or agents) that is active in the body, including pro-drugs that convert to pharmaceutically active form after administration, which are different from the compound of Formula (I), and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula (I) in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZ-AAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635), endothelin receptor antagonists, phosphodiesterase-5 inhibitors (e.g., sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholytics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g., hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARU agonists such as fenofibric acid derivatives (e.g., gemfibrozil, clofibrate, ciprofibrate, fenofibrate, bezafibrate), (3) selective PPARγ modulators (SPPARyM's), (e.g., such as those disclosed in WO 02/060388, WO 02/08188, WO 2004/019869, WO 2004/020409, WO 2004/020408, and WO 2004/066963); and (4) PPARy partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); LDL cholesterol lowering agents such as (i) HMG-CoA reductase inhibitors (e.g., simvastatin, lovastatin, pravastatin, cerivastatin, fluvastatin, atorvastatin, and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe); HDL-raising drugs, (e.g., niacin and nicotinic acid receptor agonists, and extended-release versions thereof); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40; SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, ertugliflozin, canagliflozin, BI-10773, PF-04971729, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base; bronchodilators such as $\beta_2$ agonist agents (e.g., albuterol, terbutaline, salmeterol, and formoterol) and anticholinergic agents (e.g., ipratropium bromide and tiotropium bromide); corticosteroids (e.g., beclomethasone, methylprednisolone, betamethasone, prednisone, triamcinolone, dexamethasone, fluticasone, flunisolide, hydrocortisone, and corticosteroid analogs (e.g., budesonide); and pharmaceutically acceptable salt forms of the above active agents where chemically possible.

In a particular embodiment, the additional active therapeutic agent which may be administered in combination with the compound of Formula (I) is selected from an angiotensin converting enzyme inhibitor, an angiotensin II receptor antagonist, a neutral endopeptidase inhibitor, an aldosterone antagonist, a renin inhibitor, an endothelin receptor antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent, metabolic altering agent, a 132 agonist, an anticholinergic, a corticosteroid or a corticosteroid analog.

The following examples are provided so that the invention might be more fully understood. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula (I) are also described by the Schemes as follows. In some cases the order of carrying out the steps of reaction schemes may be varied to facilitate the reaction or to avoid unwanted reaction products. The "R," "X," and "Y" groups in the Schemes correspond to the variables defined in Formula (I) at the same positions on the structures.

Scheme 1, in lines A and B, illustrates the general approach to assembling compounds of structural Formula (I) when X is C(H) or N and $R^{5a}$, $R^{5b}$ are both H. Thus, coupling of the amidine S-1a to the malononitrile S-1b in an alcoholic solvent, such as t-BuOH, in the presence of a suitable inorganic base such as $NaHCO_3$, $KHCO_3$, or $Na_2CO_3$ at an elevated temperature, provides compound S-1c. Upon treatment with an appropriate deprotecting reagent such as $BBr_3$, HBr or TBAF in a solvent such as DCM or THF, S-1c can be converted into compound of Formula (I). Alternatively, compounds of structural Formula (I) can be assembled via coupling of the amidine S-1a to the lactam intermediate S-1d in the presence of an amine base such as $Et_3N$ in a suitable solvent such as dioxane or THF at elevated temperature.

Scheme 1

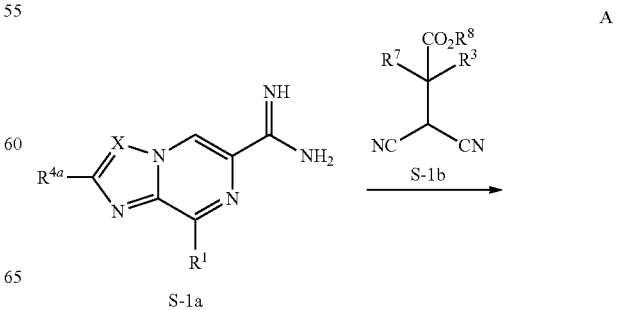

A

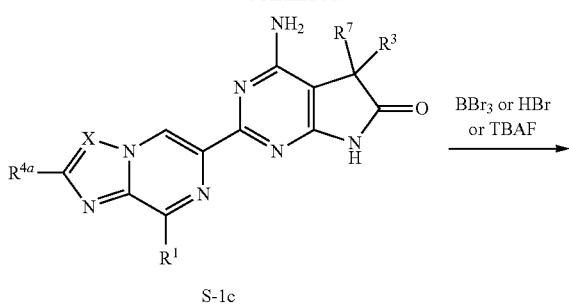

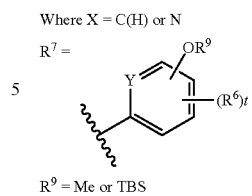

Compounds with N-alkyl substitution at $R^5$ position (when $R^{5a}$ and/or $R^{5b}$ are not H) can be prepared as outlined in Scheme 2. Treatment of the intermediate S-1c with a suitable diazotizing reagent such as tert-butyl nitrite or isopentyl nitrite in a solvent such as 1,2-DCE or DMF in a presence of excess copper(II) chloride or copper(II) bromide can provide the respective halogenated intermediate S-2a. Treatment of S-2a with an excess of amine $HN(R^{5a})(R^{5b})$ in a suitable solvent, such as 1,2-DCE, DMF, DMA, MeOH or THF, with or without a base additive at elevated temperatures may result in the conversion of S-2a to the compounds of formula S-2b. Upon treatment with an appropriate deprotecting agent such as $BBr_3$, HBr or TBAF in a solvent such as DCM or THF, the intermediate S-2b yields compounds of structural Formula (I).

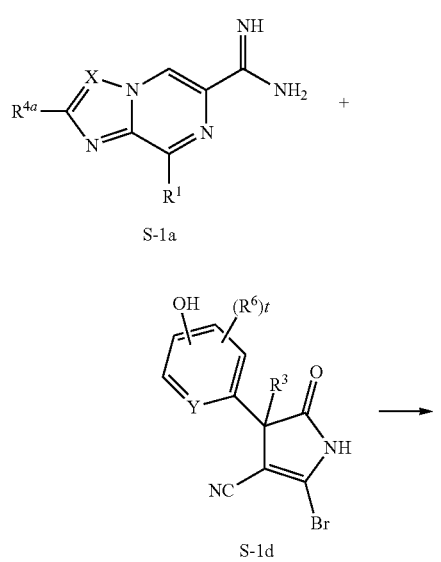

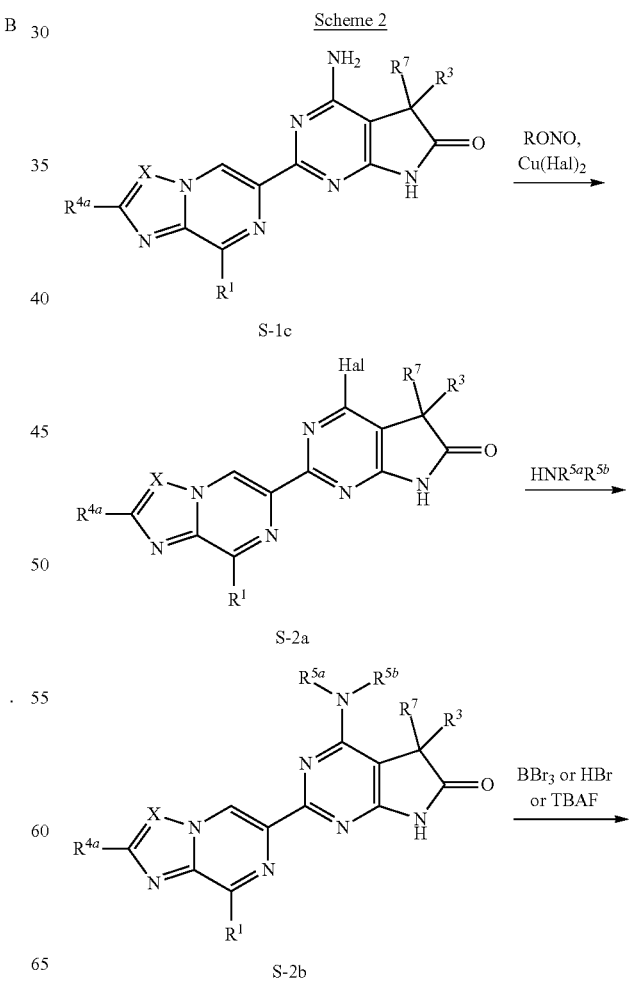

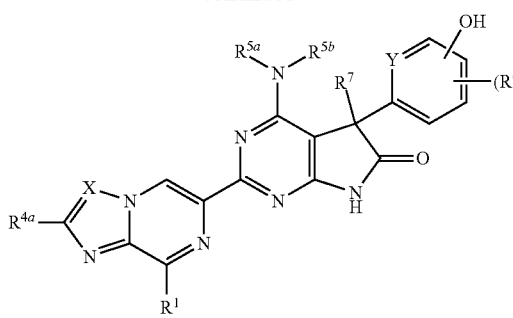

(I)

Where X = C(H) or N

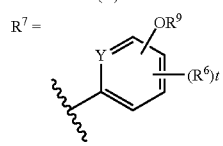

$R^9$ = Me or TBS

Compounds of Formula (I) where X is C($R^{4b}$) and $R^{4b}$ is $NH_2$ can be prepared as outlined in Scheme 3. Treatment of S-1c with a halogenating agent such as NBS in a solvent such as DMF can provide the respective halogenated intermediate S-3a. Treatment of S-3a with an imine such as diphenylmethanimine in the presence of a palladium catalyst such as $2^{nd}$ generation XantPhos precatalyst and a base in dioxane at elevated temperature results in the intermediate S-3b. Treatment of S-3b with HCl at RT in THF and water results in the conversion of S-3b to compounds of the formula S-3c, which upon deprotection with a reagent such as $BBr_3$ or HBr or TBAF in a solvent such as DCM affords compounds of structural Formula (I).

Scheme 3

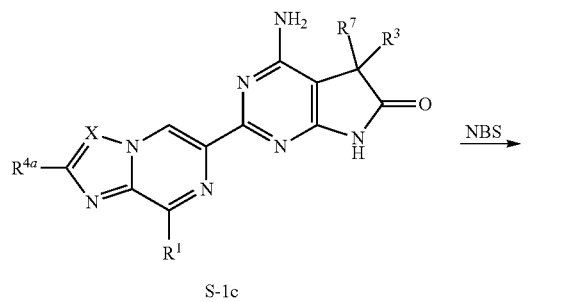

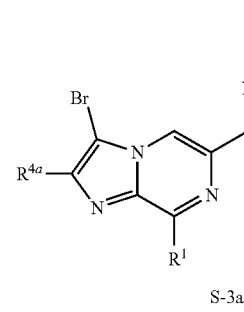

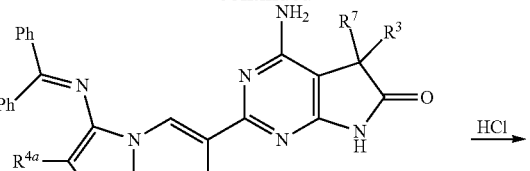

S-3b

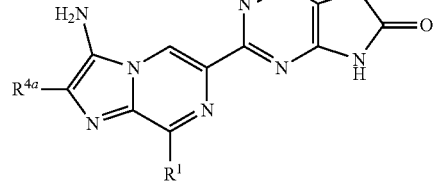

S-3c

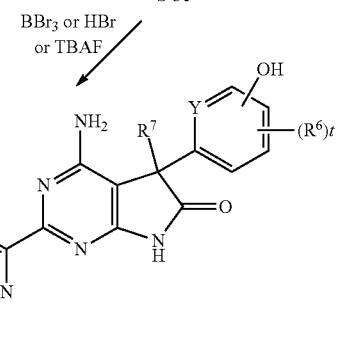

(I)

Where $R^7$ = 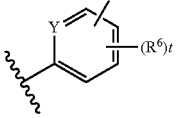

$R^9$ = Me or TBS

Advanced intermediate of the formula S-1c can be alternatively prepared as depicted in Scheme 4. The thiomethyl amidine intermediate S-4a can be cyclized with a suitable malononitrile reagent S-1b, utilizing the methods described in Scheme 1, to afford the intermediate S-4b. Treatment of S-4b with an appropriate alkylzinc reagent, $R^1$ZnHal, in the presence of a suitable palladium catalyst-ligand system such as Xantphos biaryl precatalyst, affords compounds of formula S-1c.

Scheme 4

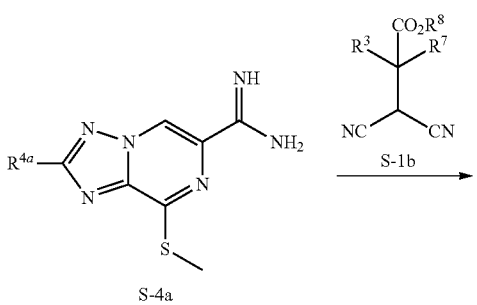

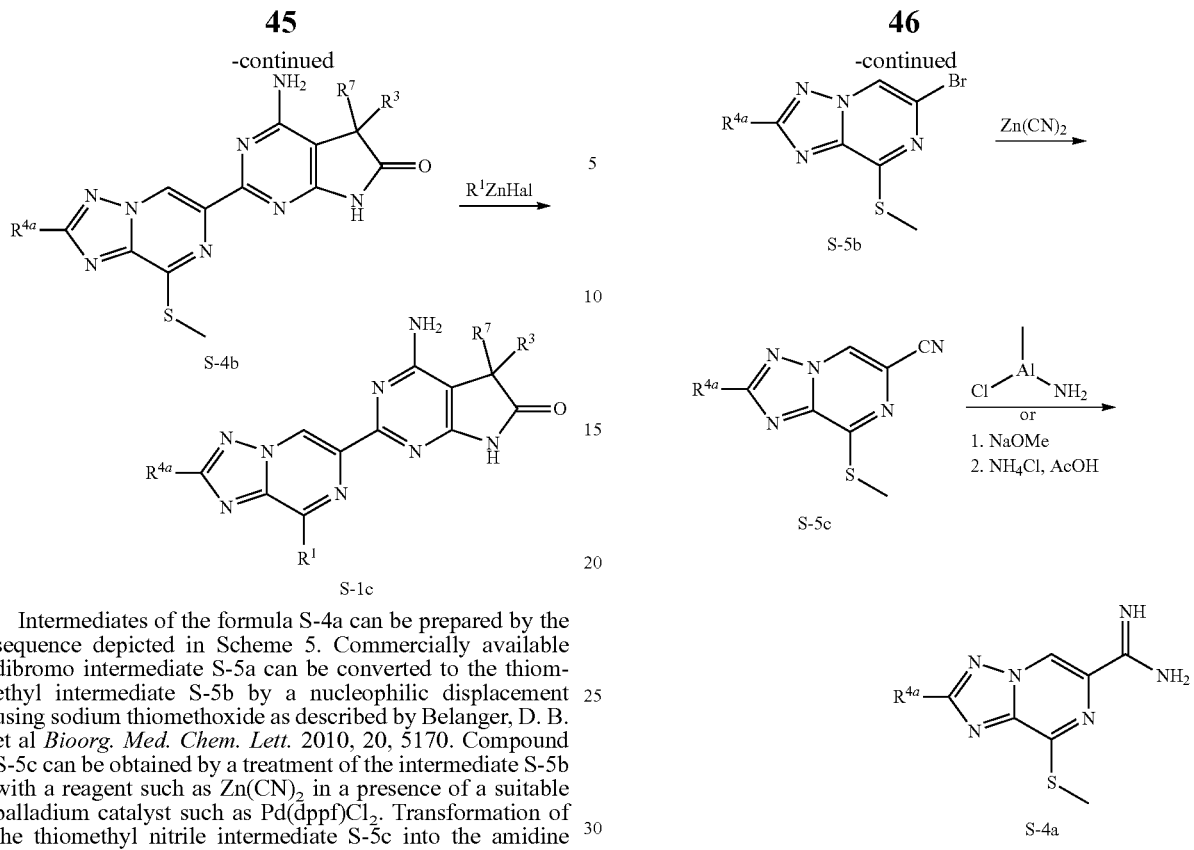

Intermediates of the formula S-4a can be prepared by the sequence depicted in Scheme 5. Commercially available dibromo intermediate S-5a can be converted to the thiomethyl intermediate S-5b by a nucleophilic displacement using sodium thiomethoxide as described by Belanger, D. B. et al *Bioorg. Med. Chem. Lett.* 2010, 20, 5170. Compound S-5c can be obtained by a treatment of the intermediate S-5b with a reagent such as $Zn(CN)_2$ in a presence of a suitable palladium catalyst such as $Pd(dppf)Cl_2$. Transformation of the thiomethyl nitrile intermediate S-5c into the amidine intermediate S-4a can be accomplished with a reagent such as amino(chloro)methylaluminum, prepared from trimethylaluminum and $NH_4Cl$, in a non-polar solvent such as toluene at elevated temperature as described by Garigipati, R. S. et al *Tetrahedron Letters* 1990, 31(14), 1969. The nitrile S-5c can also be converted to the amidine S-4a by using sodium methoxide in methanol to form the imidate, which can then be transformed to the amidine S-4a using $NH_4Cl$ and acetic acid as described by Pinner, A. et al, *O. Dtsch. Chem. Ges.* 1877, 10, 1889.

Scheme 5

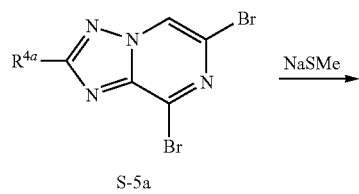

The amidine coupling partners of the formula S-1a can be prepared as outlined in Scheme 6, lines A and B. Commercially available dibromo intermediates of the formula S-5a can be selectively coupled to an alkylzinc reagent, $R^1ZnHal$, using a palladium catalyst such as $Pd(PPh_3)_2Cl_2$ to give the compound S-6a, which can be transformed into the nitrile intermediate S-6b using $Zn(CN)_2$ and a palladium catalyst such as $Pd(dppf)Cl_2$ at an elevated temperature. Transformation of the nitrile intermediate S-6b into the amidine intermediate S-1a can be accomplished with a reagent such as amino(chloro)methylaluminum or sodium methoxide, $NH_4Cl$ and acetic acid in accordance with the literature references from Scheme 5. Alternatively, intermediates of the formula S-1a can be prepared when the amidine S-4a is treated with an appropriate alkylzinc reagent, $R^1ZnHal$, in a presence of a suitable catalyst-ligand system such as Xantphos biaryl precatalyst.

Scheme 6

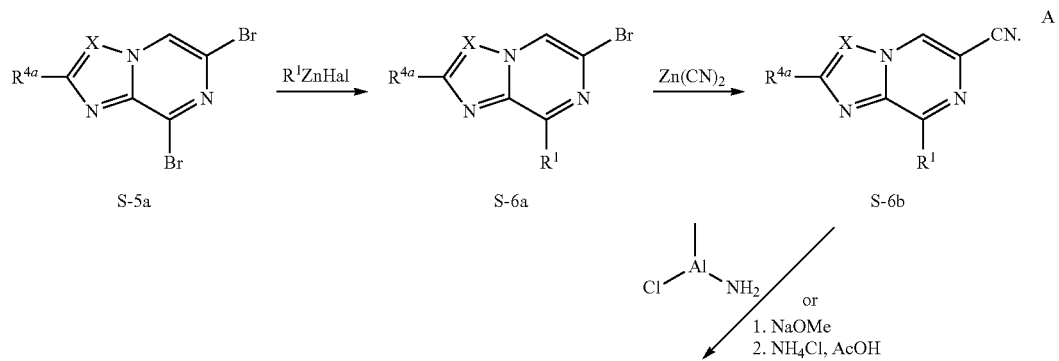

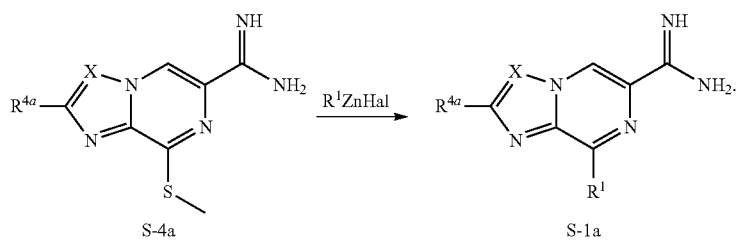

Malononitrile type coupling partners such as S-1b, depicted as the ethyl ester, may be prepared as shown in Scheme 7, lines A and B. Thus, treatment of the diethyl oxalate S-7a with a suitable aryl magnesium bromide (with or without lithium chloride additive) or the lithiate of heteroaryl reagents derived from the bromide precursor via metal-halogen exchange in a suitable solvent such as THF affords the compound S-7b. Treatment of S-7b with malononitrile and a suitable base such as piperidine in a solvent such as EtOH at an elevated temperature affords the compound S-7c which, upon reatment with a suitable alkyl magnesium bromide (with or without lithium chloride additive) in a solvent such as THF, affords the malononitrile S-1b. Alternatively, malononitrile type coupling partners can be assembled as outlined in Scheme 7, line B. Commercially available intermediate S-7d ($R^3$=Me), can undergo condensation with malononitrile, as described in the literature by Hagiwara et al. *Synthesis* 1974, 9, 669 to afford intermediate S-7e. Subsequent 1,4-addition with a Grignard reagent or lithiate in a solvent such as THF at a temperatures ranging from −78° C. to RT affords the functionalized malononitrile S-1b.

Scheme 7

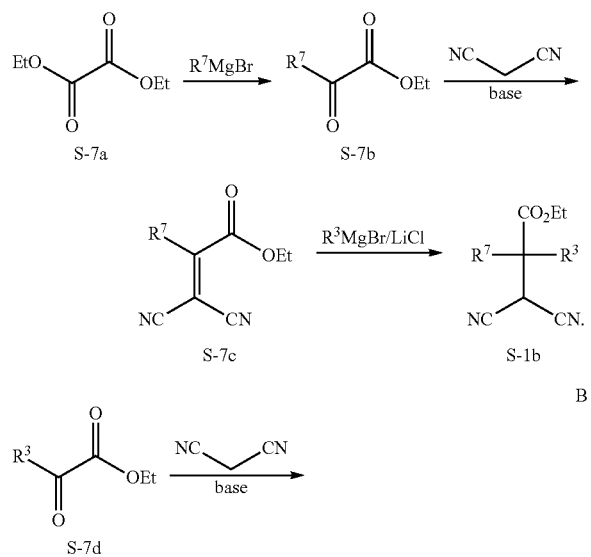

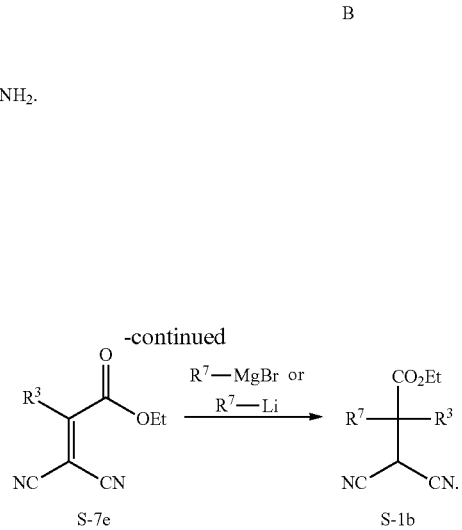

Compounds of the present invention possess an asymmetric center at the carbon bearing the $R^3$ and $R^7$ substituents which can have either the R or S configuration. These enantiomeric mixtures may be separated or resolved to single enantiomers using chiral SFC chromatography. Racemic material can be resolved to enantiomerically pure compounds at the final step, or one of the earlier steps in the route. For example, intermediates of formula S-1b can undergo chiral resolution to afford enantiopure isomers that may be carried on in the coupling with amidines to afford enantiomerically pure compounds of formula S-1c. Alternatively, enantiomeric resolution can be performed post formation of general intermediate S-1c or S-2a. Also, a chiral resolution of the intermediate S-2b may be required if a second asymmetric center is introduced to the enantiopure intermediate S-1c during its transformation into S-2b as outlined in Scheme 2. Unless otherwise noted, the examples in the present invention are enantiomerically pure isomers (R or S). Biochemical assay data is listed for the more active enantiomer if only one of the enantiomers is shown.

The independent synthesis of diastereomers and enantiomers or their chromatographic separations may be achieved using methods familiar to those skilled in the art and by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated:
AIBN=2,2'-azobisisobutyronitrile; anhydr.=anhydrous; aq.=aqueous; bp, b.p.=boiling point; br s=broad singlet; $BBr_3$=tribromoborane; Bu=butyl; t-Bu=tert-butyl; n-BuLi=n-butyllithium; t-BuOH, tert-BuOH=tert-butanol; tBuOK=potassium tert-butoxide; $CDCl_3$=deuterated chloroform; $CD_3OD$=tetradeuteromethanol; CELITE=diatomaceous earth; $CF_3$=trifluoromethyl; cGMP=cyclic guanosine monophosphate; conc, conc.=concentrated, concentrate, concentrates; DBU=1,8-Diazabicyclo[4.3.0]undec-7-ene; DCM=dichloromethane; 1,2-DCE, DCE=1,2-dichloroethane; DETA- NO=Diethylenetriamine/nitric oxide adduct; DMA, DMAC=N,N-dimethylacetamide; DMF=N,N-dimethylformamide; DMSO=dimethylsulfoxide; DMSO d-6=deuterated dimethylsulfoxide; dppf=1,1'-bis(diphenylphosphino) ferrocene; DTT=dithiothreitol; EAB=egg albumin; EBSS=Earle's balanced salt solution; equiv, eq.=equivalent(s); Et=ethyl; $Et_3N$=triethylamine; EtOAc=ethyl acetate; EtOH=Etanol; GTP=guanosine triphosphate; h, hr=hour; Hal=halogen; HCl=hydrochloric acid; HPLC=high pressure liquid chromatography; HTRF=homogeneous time resolved fluorescence; Int.=intermediate; iPr=isopropyl; IP=inflection points; IPA, i-PrOH=isopropanol; LCMS, LC/MS=liquid chromatography-mass spectrometry; LDA=lithium diisopropylamide; LiHMDS, LHMDS=lithium bis(trimethylsilyl)amide; min, min.=minute; M=Molar; Me=methyl; MeCN, ACN=acetonitrile; MeI=methyl iodide; MeOH=methanol; mp, m.p.=melting point; mpk=milligrams per kilogram; N=Normal; $N_2$=nitrogen; NaOMe=sodium methoxide; NCS=N-chloro succinimide; NBS=N-bromo succinimide; NIS=N-iodo succinimide; NaHMDS=sodium bis(trimethylsilyl)amide; $NaHCO_3$=sodium bicarbonate; $NH_4Cl$=ammonium chloride; NMR=nuclear magnetic resonance; N.D.=not determined; PDA=photodiode array; $Pd_2(dba)_3$=tris(dibenzylideneacetone)dipalladium (0); Ph=phenyl; Pr=propyl; psig=pounds per square inch gauge; PTLC, prep TLC=preparative thin layer chromatography; rac=racemic; rt=retention time; RP-HPLC=reverse phase HPLC; RT=room temperature; sat., sat'd=saturated; SFC=supercritical fluid chromatography; sGC=soluble guanylate cyclase; TBAF=tetrabutylammonium fluoride; TFA=trifluoroacetic acid; TFAA=trifluoroacetic anhydride; TLC=thin layer chromatography; THF=tetrahydrofurane; VCD=vibrational circular dichroism; v, v/v=volume, volume to volume; w, w/w=weight, weight to weight.

Columns used in the chiral resolution of stereoisomers are set forth in the examples below as follows: AD=CHIRALPAK® AD; AD-H=CHIRALPAK® AD-H; AS=CHIRALPAK® AS; AS-H=CHIRALPAK® AS-H; IA=CHIRALPAK® IA; IC=CHIRALPAK® IC; OD-H=CHIRALCEL® OD-H; and OJ-H=CHIRALCEL® OJ-H.

The following examples are provided to more fully illustrate the present invention, and shall not be construed as limiting the scope in any manner. Unless stated otherwise, the following conditions were employed. All operations were carried out at room temperature or RT (RT), that is, at a temperature in the range 18-25° C. Reactions are generally done using commercially available anhydrous solvents under an inert atmosphere, either $N_2$ or argon. Microwave reactions were done using a BIOTAGE Initiator™ or CEM EXPLORER® system. Evaporation of solvent was carried out using a rotary evaporator under reduced pressure (4.5-30 mmHg) with a bath temperature of up to 50° C. The course of reactions was followed by thin layer chromatography (TLC) and/or tandem high performance liquid chromatography (HPLC) followed by electron spray mass spectroscopy (MS), herein termed LCMS, and any reaction times are given for illustration only. The structure of all final compounds was assured by at least one of the following techniques: MS or proton nuclear magnetic resonance ($^1$H NMR) spectrometry, and the purity were assured by at least one of the following techniques: TLC or HPLC. $^1$H NMR spectra were recorded on either a Varian Unity or a Varian Inova instrument at 300, 400, 500 or 600 MHz using the indicated solvent. $^1$H NMR data are in the form of delta values for major diagnostic protons and are given in parts per million (ppm) relative to residual solvent peaks (multiplicity and number of hydrogen atoms). Conventional abbreviations used for signal shape are: s. singlet; d. doublet (apparent); t. triplet (apparent); m. multiplet; br. broad; etc. MS data were recorded on a Waters Micromass or WatersZQ unit, interfaced with a Hewlett-Packard (AGILENT 1100) HPLC instrument, and operating on MASSLYNX/OpenLynx software. Electrospray ionization was used with positive (ES+) or negative ion (ES−) detection; and diode array detection. Purification of compounds by preparative reverse phase HPLC was performed on a GILSON system using a YMC-Pack Pro C18 column (150×20 mm i.d.) eluting at 20 mL/min with a water/MeCN (0.1% TFA) gradient (typically 5% MeCN to 95% MeCN) or using a SUNFIRE Prep C18 OBD 5 μM column (100×30 mm i.d.) eluting at 50 mL/min with a water/MeCN (0.1% TFA) gradient. Purification of compounds by preparative mass triggered reverse phase HPLC was performed on Waters MS directed Preparative Scale HPLC. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm ($SiO_2$), or on a BIOTAGE $SiO_2$ cartridge system using the BIOTAGE Horizon and BIOTAGE SP-1 systems; or a Teledyne Isco $SiO_2$ cartridge using the COMBIFLASH Rf system. Chemical symbols have their usual meanings, and the following abbreviations have also been used: h or hr (hs), min (minutes), v (volume), w (weight), b.p. (boiling point), m.p. (melting point), L (litre(s)), mL (millilitres), g (gram(s)), mg (milligrams(s)), mol (moles), mmol (millimoles), eq or equiv (equivalent(s)), μM (micromolar), nM (nanomolar), ca (circa/about).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any intermediates described below may be referred to herein by their number preceded by "I-." For illustration, the racemic parent title compound would be referred to as Intermediate 15 (I-15, or rac 1-15), and the separated stereoisomers are noted as Intermediates 15A and 15B (or I-15A and I-15B). In some examples, compounds having a chiral center were derived synthetically from a single isomer intermediate; e.g., Example 13B was made using stereoisomer I-6B. In some cases intermediates or examples contain more than one chiral center. In such cases, the separation of isomers may require more than one chiral resolution. In such cases, the intermediate or example number can be followed by 2 letters (e.g. Ex-108AB). For these intermediates and examples, the first letter represents the A or B isomer from the first separation and the second letter represents the A or B isomer from the second separation. Absolute stereochemistry of separate stereoisomers in the Examples and Intermediates was not determined unless stated otherwise in an Example or Intermediate synthesis. An asterisk (*) may be used in a chemical structure drawing that indicates the location of a chiral center.

Intermediates 1, 2 and 3

2-Bromo-5-chloro-4-methoxypyridine, 2-Bromo-3-chloro-4-methoxypyridine and 2-Bromo-3,5-dichloro-4-methoxypyridine

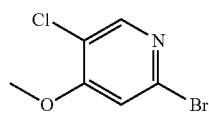

I-1

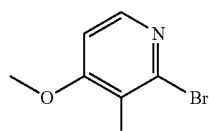

I-2

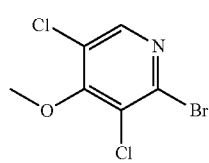

I-3

Step A—5-Chloro-4-methoxypyridin-2-amine, 3-chloro-4-methoxypyridin-2-amine and 3,5-dichloro-4-methoxypyridin-2-amine To a flask containing 4-methoxypyridin-2-amine (40.0 g, 322 mmol) in MeCN (2 L) at 0° C. was added 1-chloropyrrolidine-2,5-dione (64.6 g, 484 mmol). The resulting mixture was stirred for 1.5 h at 0° C. The reaction was quenched by the addition of sat. aq. sodium thiosulfate (1 L). The resulting mixture was extracted with EtOAc (3×500 mL) and the organic layers were combined, dried over anhydr. Na$_2$SO$_4$, filtered and the filtrate was concentrated in vacuo to dryness. The residue was purified by silica gel column chromatography with (3:1 EtOAc:EtOH)/petroleum ether (10-50%) to afford 5-chloro-4-methoxypyridin-2-amine, 3-chloro-4-methoxypyridin-2-amine and 3,5-dichloro-4-methoxypyridin-2-amine.

Step B—2-Bromo-5-chloro-4-methoxypyridine

To a flask under an inert atmosphere of N$_2$, containing 5-chloro-4-methoxypyridin-2-amine (8.0 g, 50 mmol) and hydrobromic acid (67.2 mL, 500 mmol 40%) at 0° C. was added bromine (7.6 mL, 150 mmol) dropwise, followed by the dropwise addition of sodium nitrite (8.4 g, 125 mmol) in water (67 mL). The resulting mixture was stirred at 0° C. for 1 h. To this, dropwise was added sodium hydroxide (5.9 g, 150 mmol) in water (28 mL). The mixture was extracted with EtOAc (3×200 mL). The combined organic layer was dried over anhydr. Na$_2$SO$_4$, filtered and the filtrate was concentrated in vacuo to dryness. The residue was purified by silica gel column chromatography with EtOAc/petroleum ether (0-30%) to afford the title compound, 2-bromo-5-chloro-4-methoxypyridine, I-1. MS: 222, 224 (M+1). $^1$H NMR (CDCl$_3$, 400 MHz): δ 8.24 (s, 1H), 7.05 (s, 1H), 3.99 (s, 3H).

Intermediate 2

2-Bromo-3-chloro-4-methoxypyridine was prepared via Step B using 3-chloro-4-methoxypyridin-2-amine as a starting material. 1-2: MS 222, 224 (M+1). $^1$H NMR (CDCl$_3$, 300 MHz): δ 8.18 (d, J=5.7 Hz, 1H), 6.84 (d, J=5.7 Hz, 1H), 3.98 (s, 3H).

Intermediate 3

2-Bromo-3,5-dichloro-4-methoxypyridine was prepared via Step B using 3,5-dichloro-4-methoxypyridin-2-amine as a starting material. 1-3: MS 256, 258 (M+1). $^1$H NMR (CDCl$_3$, 300 MHz): δ 8.28 (s, 1H), 4.04 (s, 3H).

Intermediate 4

2-Bromo-4-chloro-5-methoxypyridine

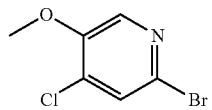

Step A—2-Bromo-5-methoxypyridine 1-oxide

Into a flask were placed 2-bromo-5-methoxypyridine (20 g, 106 mmol), 3-chlorobenzoperoxoic acid (27.5 g, 160 mmol), and DCE (250 mL). The resulting mixture was stirred at 60° C. for 16 h. The reaction mixture was cooled, quenched by the addition of diethyl amine (10 mL) and concentrated in vacuo. The residue was purified by column chromatography with EtOAc/petroleum ether (50-100%) to afford the title compound.

Step B—2-Bromo-5-methoxy-4-nitropyridine 1-oxide

To a flask, containing sulfuric acid (50 mL, 938 mmol) was added the intermediate from Step A (17 g, 83 mmol)

followed by a dropwise addition of nitric acid (10 mL, 228 mmol). The temperature was raised to 90° C. then the mixture was cooled to 60° C. and the rest of nitric acid (40 mL, 910 mmol) was added. The resulting mixture was stirred at 60° C. for 10 min, then cooled and poured into ice/water mixture (1 L). The solid was collected by filtration, washed with MeCN (2×20 mL) and EtOAc (20 mL) and dried in an oven to afford the title compound.

Step C—2-Bromo-5-methoxypyridin-4-amine

Into a flask, containing the intermediate from Step B (10 g, 40.2 mmol), were placed iron powder (22.5 g, 403 mmol) and $NH_4Cl$ (2.1 g, 39.3 mmol) in EtOH (75 mL)/water (25 mL) and the mixture was stirred at 70° C. for 1 h. The reaction mixture was filtered and the residue was washed with EtOH (3×50 mL). The combined filtrate was concentrated in vacuo to dryness. The residue was dissolved in EtOAc (100 mL), washed with water (20 mL) and brine (20 mL), dried over anhydr. $Na_2SO_4$, and filtrated. The filtrate was concentrated in vacuo to afford the title compound.

Step D—2-Bromo-4-chloro-5-methoxypyridine

To a flask containing the intermediate from Step C (5 g, 24.63 mmol) and HCl (50 mL, 37%) at 0° C. was added dropwise a solution of sodium nitrite (1.78 g, 25.9 mmol) in water (10 mL). The resulting mixture was stirred at 0° C. for 15 min, then a solution of copper (I) chloride (2.93 g, 29.6 mmol) in HCl (100 mL, 37%) was added dropwise at 0° C. The resulting mixture was stirred at RT for 2 h, then diluted with water (1 L). The solid was collected by filtration and washed with water (100 mL), then dissolved in EtOAc (100 mL), washed with sat., aq. $NaHCO_3$ (2×30 mL) and brine (100 mL), dried over anhydr. $Na_2SO_4$, and filtered through a silica gel pad. The filtrate was concentrated in vacuo to afford the title compound, 1-4. MS: 222, 224 (M+1). $^1$H NMR (400 MHz, Chloroform-d) δ 8.05 (s, 1H), 7.53 (s, 1H), 4.01 (s, 3H).

Intermediate 5, 5A and 5B

Ethyl 2-(5-chloro-4-methoxypyridin-2-yl)-3,3-dicyano-2-methylpropanoate and the S and R Isomers Thereof

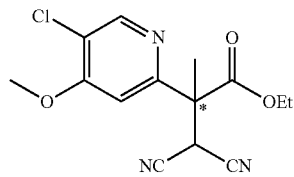 [SMILES: CCOC(=O)C(C)(c1cc(OC)c(Cl)cn1)C(C#N)C#N]

Ethyl 2-(5-chloro-4-methoxypyridin-2-yl)-3,3-dicyano-2-methylpropanoate

To a flask under an inert atmosphere of $N_2$, containing n-BuLi (12.6 mL, 31.4 mmol, 2.5 M in THF) in toluene (120 mL) at −78° C. was added dropwise 2-bromo-5-chloro-4-methoxypyridine (7.0 g, 31.4 mmol) in toluene (70 mL). The mixture was stirred at −78° C. for 30 min before a solution of ethyl 3,3-dicyano-2-methylacrylate (5.2 g, 31.4 mmol) in toluene (10 mL), prepared according to Hagiware et al. *Synthesis* 1974, 9, 669, was added. The resulting mixture was stirred at −78° C. for 30 min and then quenched by the addition of sat. aq. $NH_4Cl$ (300 mL). The resulting mixture was extracted with EtOAc (3×200 mL) and the combined organic layer was dried over anhydr. $Na_2SO_4$, filtered and the filtrate concentrated in vacuo to dryness. The residue was purified by column chromatography eluting with EtOAc/petroleum ether (5-20%) to afford the racemic title compound I-5. The racemic material was resolved using chiral Prep-SFC (CHIRALPAK AD-H) to afford isomers I-5A (faster eluting) and I-5B (slower eluting). MS: 308 (M+1). $^1$H NMR ($CDCl_3$, 300 MHz): δ 8.41 (s, 1H), 7.01 (s, 1H), 5.20 (s, 1H), 4.18-4.32 (m, 2H), 4.01 (s, 3H), 2.00 (s, 3H), 1.28 (t, J=7.2 Hz, 3H).

Intermediate 6, 6A and 6B

Ethyl 3,3-dicyano-2-(4-fluoro-3-methoxyphenyl)-2-methylpropanoate and the S and R Isomers Thereof

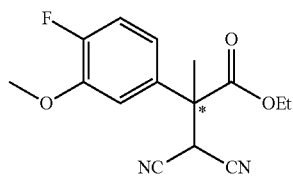 [SMILES: CCOC(=O)C(C)(c1ccc(F)c(OC)c1)C(C#N)C#N]

Into a flask under an inert atmosphere of $N_2$, were placed magnesium (0.35 g, 14.40 mmol) and iodine (0.31 g, 1.22 mmol) in THF (5 mL). A solution of 4-bromo-1-fluoro-2-methoxybenzene (2.5 g, 12.19 mmol) in THF (20 mL) was added dropwise over 10 min, maintaining the reaction temperature at reflux. The reaction mixture was stirred at reflux for 1 h, then cooled to RT. Lithium chloride (0.56 g, 13.21 mmol) was added and the mixture was stirred at RT for 30 min, then cooled to −20° C. A solution of ethyl 3,3-dicyano-2-methylprop-2-enoate (1.8 g, 10.96 mmol) in THF (25 mL), prepared according to Hagiware et al. *Synthesis* 1974, 9, 669, was added dropwise at −20° C. The resulting solution was stirred at 0° C. for 1 h, then quenched by the addition of sat. aq. $NH_4Cl$ (100 mL). The resulting solution was extracted with EtOAc (2×100 mL) and the organic layers combined, dried over anhydr. $Na_2SO_4$, and filtered. The filtrate was concentrated in vacuo to dryness and the residue was purified by column chromatography with EtOAc/petroleum ether (1/20) to afford the racemic title compound 1-6. The racemic material was resolved using chiral Prep-SFC (CHIRALPAK AS-H) to afford isomers I-6A (faster eluting) and I-6B (slower eluting). MS: 289 (M−1). $^1$H NMR ($CDCl_3$, 300 MHz): δ 7.16-7.09 (m, 1H), 6.96-6.89 (m, 2H), 4.45 (s, 1H), 4.34-4.23 (m, 2H), 3.91 (s, 3H), 1.98 (s, 3H), 1.27 (t, J=7.2 Hz, 3H).

Using a similar procedure to that described for the synthesis of intermediate I-5 or I-6, the following compounds listed in Table 1 were prepared using commercially available starting reagents or from compounds known in the literature.

TABLE 1

Structure: R⁷ and methyl on carbon bearing CO₂Et, connected to CH(CN)₂

| Int. | Chiral Resolution Column | R⁷ | MS (M − 1) or ¹H NMR |
|---|---|---|---|
| I-7A I-7B | CHIRALPAK AD-H | 3-F, 4-Cl, 5-OMe phenyl | 323 (M − 1) |
| I-8A I-8B | CHIRALPAK AD-H | 3,4-diF, 5-OMe phenyl | 307 (M − 1) |
| I-9A I-9B | CHIRALPAK AD-H | 4-CF₃, 3-OMe phenyl | 339 (M − 1) |
| I-10A I-10B | CHIRALPAK IA | 5-OMe, 4-Cl pyridin-2-yl | 306 (M − 1) |
| I-11A I-11B | CHIRALPAK IA | 4-OMe, 3-Cl phenyl | 305 (M − 1) |
| I-12A I-12B | CHIRALPAK AS-H | 4-Cl, 3-OMe phenyl | 305 (M − 1) |
| I-13 | RACEMIC | 4-OMe pyridin-2-yl (with Cl) | 372 (M − 1)<br>374 (M + 1) |
| I-14 | RACEMIC | 3-Cl, 4-OMe pyridin-2-yl | 306 (M − 1) |

TABLE 1-continued $$\text{structure: R}^7\text{-C*(CH}_3\text{)(CO}_2\text{Et)-CH(CN)}_2$$

| Int. | Chiral Resolution Column | R⁷ | MS (M − 1) or ¹H NMR |
|---|---|---|---|
| I-15A I-15B | CHIRALPAK AD-H | 3,5-dichloro-4-methoxypyridin-2-yl | 340 (M − 1) |
| I-16A I-16B | CHIRAL ART Cellulose-SB | 3-chloro-6-methoxypyridin-2-yl | 308 (M + 1) |
| I-17A I-17B | CHIRALPAK IA | 3-methoxyphenyl | 271 (M − 1) |
| I-18 | RACEMIC | 3,5-dichloro-4-methoxyphenyl | 339 (M − 1) |
| I-19A I-19B | CHIRALPAK IF | 2,4-dichloro-3-methoxyphenyl | 339 (M − 1) |
| I-20A I-20B | CHIRALPAK AD-H | 3-chloro-4-fluoro-2-methoxyphenyl | ¹H NMR (300 MHz, CDCl₃) δ 7.32 (dd, J = 8.7, 8.7 Hz, 1H), 6.84 (dd, J = 1.2, 8.7 Hz, 1H), 4.57 (s, 1H), 4.36-4.27 (m, 2H), 3.96 (s, 3H), 2.00 (s, 3H), 1.27 (t, J = 7.2 Hz, 3H); MS 323 (M − 1). |
| I-21 | RACEMIC | 4-cyano-3,5-difluorophenyl | 302 (M − 1) |
| I-22 | RACEMIC | 3,5-difluoro-4-(trifluoromethyl)phenyl | ¹H NMR (400 MHz, DMSO-d6) δ 7.55 (d, J = 11.4 Hz, 2H), 5.89 (s, 1H), 4.29 (q, J = 7.1 Hz, 2H), 1.88 (s, 3H), 1.19 (t, J = 7.1 Hz, 3H). |

Intermediate 23, 23A and 23B

Methyl 3,3-dicyano-2-(4-cyano-3-fluoro-5-methoxyphenyl)-2-methylpropanoate and the S and R Isomers Thereof

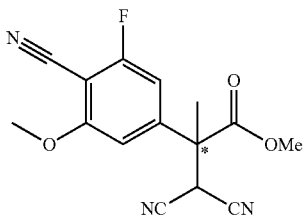 [SMILES: COC(=O)C(C)(c1cc(F)c(C#N)c(OC)c1)C(C#N)C#N]

Into a flask, containing I-21 (500 mg, 1.65 mmol) in THF (50 mL) at 0° C. was added dropwise sodium methoxide (891 mg, 4.12 mmol, 25% in MeOH). The resulting mixture was stirred at RT for 16 h, then quenched by the addition of sat. aq. NH$_4$Cl (100 mL). The resulting solution was extracted with EtOAc (3×50 mL) and the combined organic layer was dried over anhydr. Na$_2$SO$_4$, filtered and the filtrate concentrated in vacuo to dryness. The residue was purified by column chromatography with EtOAc/petroleum ether (10-50%) to afford the title compound 1-23. The racemic material was resolved using chiral SFC (CHIRALPAK AD-H) to afford isomers I-23A (faster eluting) and I-23B (slower eluting) of the title compound. MS: 300 (M−1). $^1$H NMR (CDCl$_3$, 300 MHz): δ 6.83 (dd, J=1.8, 9.3 Hz, 1H), 6.75 (dd, J=1.2, 1.2 Hz, 1H), 4.48 (s, 1H), 4.00 (s, 3H), 3.86 (s, 3H), 2.01 (s, 3H).

Intermediate 24, 24A and 24B

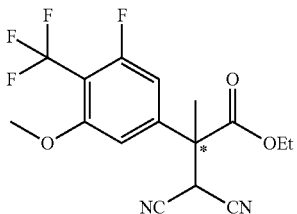

Using essentially the same procedure to that described in the synthesis of 1-23, intermediate 1-24 was prepared using 1-22 as the starting material. The racemic material was resolved using chiral SFC (CHIRALPAK AS) to afford isomers I-24A (faster eluting) and I-24B (slower eluting) of the title compound. $^1$H NMR (DMSO-d6, 400 MHz): δ 7.10 (d, J=12.8 Hz, 1H), 7.02 (s, 1H), 5.92 (s, 1H), 4.27 (q, J=7.1 Hz, 2H), 3.93 (s, 3H), 1.86 (s, 3H), 1.18 (t, J=7.1 Hz, 3H).

Intermediate 25A

2-Bromo-4-(4-chloro-3-hydroxyphenyl)-4-methyl-5-oxo-4,5-dihydro-1H-pyrrole-3-carbonitrile

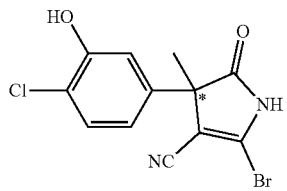 [SMILES: CC1(c2ccc(Cl)c(O)c2)C(=O)NC(Br)=C1C#N]

2-Bromo-4-(4-chloro-3-hydroxyphenyl)-4-methyl-5-oxo-4,5-dihydro-1H-pyrrole-3-carbonitrile To a flask containing I-12A (200 mg, 0.65 mmol) in DCM (6 mL) at 0° C. was added dropwise BBr$_3$ (0.6 mL, 6.52 mmol). The resulting mixture was stirred at 0° C. for 1 h and at RT for 16 h. The reaction was quenched by the addition of sat. aq. NaHCO$_3$ (100 mL). The resulting solution was extracted with EtOAc (3×100 mL), the combined organic layer was dried over anhydr. Na$_2$SO$_4$, filtered and the filtrate was concentrated in vacuo to dryness. The residue was purified by column chromatography with EtOAc/petroleum ether (20-50%) to afford the title compound I-25A. MS: 325, 327 (M−1). $^1$H NMR (CDCl$_3$, 400 MHz): δ 7.61 (br s, 1H), 7.34 (d, J=8.4 Hz, 1H), 7.05 (d, J=2.4 Hz, 1H), 6.90 (dd, J=2.0, 8.4 Hz, 1H), 5.63 (br s, 1H), 1.77 (s, 3H).

Intermediate 26, 26A and 26B

Ethyl 2-(4-(((tert-butyldimethylsilyl)oxy)-3-methylphenyl)-3,3-dicyano-2-methylpropanoate and the S and R Isomers Thereof

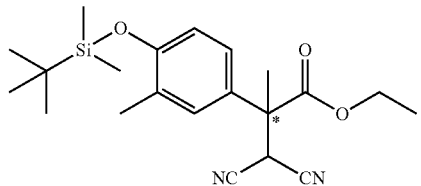 [SMILES: CCOC(=O)C(C)(c1ccc(O[Si](C)(C)C(C)(C)C)c(C)c1)C(C#N)C#N]

Step A—(4-Bromo-2-methylphenoxy)(tert-butyl)dimethylsilane

To a flask containing 4-bromo-2-methylphenol (10.0 g, 53.5 mmol), tert-butylchlorodimethylsilane (7.25 g, 48.1 mmol) in DCM (300 mL) at RT was added, in portions, 1H-imidazole (7.28 g, 107 mmol). The mixture was stirred at RT for 16 h, then quenched by the addition of water (50 mL). The organic layer was washed with sodium hydroxide (0.1N, 50 mL×3), water (50 mL) and brine (50 mL), dried over anhydr. Na$_2$SO$_4$, filtered and the filtrate was concentrated in vacuo to dryness. The residue was purified by column chromatography with petroleum ether to afford the title compound.

Step B—Ethyl 2-(4-((tert-butyldimethylsilyl)oxy)-3-methylphenyl)-2-oxoacetate To a flask under an inert atmosphere of $N_2$, containing magnesium (0.20 g, 8.63 mmol), iodine (0.10 g, 0.332 mmol) and THF (2 mL) was added dropwise to a solution of intermediate from Step A (2.00 g, 6.64 mmol) in THF (8 mL). The reaction mixture was stirred at reflux for 1 h, then allowed to cool to RT.

To a separate flask, under an inert atmosphere of $N_2$, containing diethyl oxalate (1.16 g, 7.97 mmol) in THF (10 mL) at 0° C. was added dropwise the Grignard reagent prepared above. The resulting mixture was stirred at RT for 1 h then quenched by the addition of sat. aq. $NH_4Cl$ (20 mL) and extracted with EtOAc (3×20 mL). The combined organic layer was dried over anhydr. $Na_2SO_4$, filtered and the filtrate concentrated in vacuo to dryness. The residue was purified by column chromatography with petroleum ether/EtOAc (5/1) to afford the title compound.

Step C—Ethyl 2-(4-((tert-butyldimethylsilyl)oxy)-3-methylphenyl)-3,3-dicyanoacrylate Into a flask under an inert atmosphere of $N_2$, containing the intermediate from Step B (500 mg, 1.55 mmol) and malononitrile (307 mg, 4.65 mmol) in EtOH (10 mL) was added piperidine (13.20 mg, 0.155 mmol). The resulting mixture was stirred at 90° C. for 16 h, then concentrated in vacuo to dryness and the residue was purified by column chromatography with petroleum ether/EtOAc (5/1) to afford the title compound.

Step D—Ethyl 2-(4-((tert-butyldimethylsilyl)oxy)-3-methylphenyl)-3,3-dicyano-2-methylpropanoate Into a flask under an inert atmosphere of $N_2$, were placed intermediate from Step C (570 mg, 1.54 mmol), lithium chloride (130 mg, 3.08 mmol) and THF (10 mL). The resulting mixture was stirred at RT for 0.5 h, then cooled to 0° C. and methylmagnesium bromide (2.31 mL, 2.31 mmol, 1 M in THF) was added dropwise. The resulting mixture was stirred at RT for 1 h, then quenched by the addition of sat. aq. $NH_4Cl$ (20 mL) and extracted with EtOAc (3×20 mL). The combined organic layer was dried over anhydr. $Na_2SO_4$, filtered and the filtrate concentrated in vacuo to dryness. The residue was purified by column chromatography with petroleum ether/EtOAc (5/1) to afford the title compound 1-26. The racemic material was resolved using chiral SFC ((R, R)-WHELK-O) to afford isomers I-26A (faster eluting) and I-26B (slower eluting) of the title compound. MS: 385 (M−1). $^1H$ NMR (400 MHz, $CDCl_3$): δ 7.12 (d, J=2.8 Hz, 1H), 7.07 (dd, J=2.8, 8.4 Hz, 1H), 6.80 (d, J=8.4 Hz, 1H), 4.47 (s, 1H), 4.34-4.23 (m, 2H), 2.23 (s, 3H), 1.97 (s, 3H), 1.27 (t, J=7.2 Hz, 3H), 1.03 (s, 9H), 0.25 (s, 6H).

Using a similar procedure to that described for the synthesis of intermediate 1-26, the following compounds in Table 2 were prepared using either commercial starting reagents or from compounds known in the literature. Some intermediates were commercially available at Step B and the synthesis could commence at Step C.

TABLE 2

| Int. | Chiral Resolution Column | R[7] | MS (M − 1) |
| --- | --- | --- | --- |
| I-27 | RACEMIC | (4-((tert-butyldimethylsilyl)oxy)-3-methylphenyl) | 385 (M − 1) |
| I-28A I-28B | CHIRALPAK IA | (3-fluoro-4-methoxyphenyl) | 289 (M − 1) |
| I-29A I-29B | CHIRALCEL OJ-H | (4-methoxyphenyl) | 271 (M − 1) |

Intermediate 30

2-Bromo-4-methoxy-5-(trifluoromethyl)pyridine

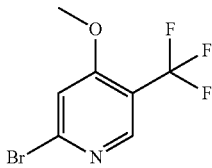

Step A—2-Bromo-5-(trifluoromethyl)isonicotinic acid

Into a flask under an inert atmosphere of $N_2$ was placed diisopropylamine (27 mL, 0.19 mol) in THF (300 mL) followed by a dropwise addition of n-BuLi (69 mL, 0.17 mol, 2.5 M in THF) at −70° C. The resulting mixture was stirred at 0° C. for 0.5 h, followed by a dropwise addition of 2-bromo-5-(trifluoromethyl)pyridine (30 g, 0.13 mol) in THF (30 mL) at −70° C. The resulting mixture was stirred at −70° C. for 1 h. Into a beaker was placed dry ice (117 g, 3.98 mol) in ether (400 mL) and the LDA solution prepared above, was poured into it. The resulting mixture was stirred for 1 h until it was equilibrated to RT. The reaction was quenched with water (300 mL), extracted with EtOAc/petroleum ether (1/1, 2×200 mL) and the pH value of the aq. phase was adjusted to 1-2 with HCl (1 N). The aq. layer was extracted with EtOAc (3×300 mL). The organic layers were combined, dried over anhydr. $Na_2SO_4$, filtered, and the filtrate was concentrated in vacuo. The crude product was washed with DCM/hexane (1/6) to afford the title compound.

Step B—tert-Butyl (2-bromo-5-(trifluoromethyl)pyridin-4-yl)carbamate

Into a flask were placed intermediate from Step A (21.0 g, 77.5 mmol) in t-BuOH (100 mL), TEA (19.6 g, 194.4 mmol) and diphenyl phosphorazidate (32.0 g, 116.5 mmol). The resulting mixture was stirred at 80° C. for 4 h, then concentrated in vacuo to dryness to afford the crude title compound, which was used directly for the next step without further purification.

Step C—2-Bromo-5-(trifluoromethyl)pyridin-4-amine

Into a flask were placed intermediate from Step B (33.4 g, 45.8 mmol) in DCM (100 mL) and TFA (100 mL). The resulting mixture was stirred at RT for 16 h. The reaction solution was concentrated in vacuo to dryness. The resultant residue was dissolved in EtOAc (300 mL), washed with sat. aq. $NaHCO_3$ (3×200 mL) and brine (2×300 mL), dried over anhydr. $Na_2SO_4$, filtered, and the filtrate was concentrated in vacuo. The residue was purified by column chromatography with EtOAc/petroleum ether (0-20%) to afford the title compound.

Step D—2-Bromo-4-chloro-5-(trifluoromethyl)pyridine

Into a flask under an inert atmosphere of $N_2$ were placed intermediate from Step C (8.0 g, 33.2 mmol) and HCl (100 mL, 37%), followed by a dropwise addition of sodium nitrite (45.8 g, 664.0 mmol) in water (50 mL) at RT. The resulting mixture was stirred for 1 h, then diluted with ice/water (400 mL), extracted with EtOAc (2×200 mL) and the organic layers were combined, dried over anhydr. $Na_2SO_4$, filtered, and the filtrate was concentrated in vacuo. The residue was purified by column chromatography with DCM/petroleum ether (0-40%) to afford the title compound.

Step E—2-Bromo-4-methoxy-5-(trifluoromethyl)pyridine

Into a flask under an inert atmosphere of $N_2$ were placed intermediate from Step D (6.4 g, 24.6 mmol) in DMA (60 mL), followed by a dropwise addition at 0° C. of NaOMe (2.0 g, 36.9 mmol) in DMA (60 mL) and MeOH (20 mL). The resulting mixture was stirred at 0° C. for 3 h, then quenched with water (500 mL), and extracted with EtOAc (2×400 mL). The organic layers were combined, washed with brine (3×500 mL), dried over anhydr. $Na_2SO_4$, filtered, and the filtrate was concentrated in vacuo. The residue was purified by column chromatography with DCM/petroleum ether (0-80%) to afford the title compound, 1-30. MS: 256, 256 (M+1). $^1$H NMR (300 MHz, Chloroform-d) δ 8.42 (d, J=1.2 Hz, 1H), 7.12 (s, 1H), 3.98 (s, 3H).

Intermediate 31

2-Bromo-4-methoxy-5-methylpyridine

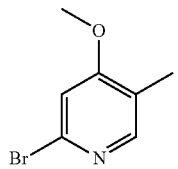

Step A—5-Iodo-4-methoxypyridin-2-amine

Into a flask under an inert atmosphere of $N_2$ was placed 4-methoxypyridin-2-amine (20 g, 161 mmol) in DMF (400 mL) and NIS (43.5 g, 193 mmol). The resulting mixture was stirred at 50° C. for 1 h, then quenched with NaOH (1 N, 2 L). The resulting mixture was extracted with EtOAc (3×500 mL), organic layers were combined, dried over anhydr. $Na_2SO_4$, filtered and the filtrate was concentrated in vacuo. The residue was purified by column chromatography with DCM/MeOH (10/1) to afford the title compound.

Step B—4-Methoxy-5-methylpyridin-2-amine

Into a flask under an inert atmosphere of $N_2$ were placed the intermediate from Step A (4.0 g, 16.0 mmol), bis(triphenylphosphine) palladium(II) dichloride (1.1 g, 1.60 mmol) and THF (150 mL). The resulting mixture was stirred for 30 min at RT, followed by the addition of dimethylzinc (64.0 mL, 64.0 mmol, 1 M in THF). The resulting solution was stirred at RT for 16 h, then quenched with brine (500 mL), and extracted with EtOAc (3×300 mL). The organic layers were combined, dried over anhydr. $Na_2SO_4$, filtered and the filtrate was concentrated in vacuo. The residue was purified by RP-HPLC with water (0.05% ammonium bicarbonate)/ACN (30-70%) to afford the title compound.

Step C—2-Bromo-4-methoxy-5-methylpyridine

Into a flask under an inert atmosphere of $N_2$ was placed intermediate from Step B (3.9 g, 28.2 mmol) and HBr (25.5 mL, 226 mmol, 48%), followed by a dropwise addition of bromine (4.4 ml, 85 mmol) and sodium nitrite (4.9 g, 70.6 mmol) in water (18 mL) at 0° C. The resulting mixture was stirred at 0° C. for 1 h, then quenched by a dropwise addition of NaOH (34.0 ml, 340 mmol, 30%) at 0° C. The reaction was extracted with EtOAc (2×100 mL). The organic layers were combined, dried over anhydr. $Na_2SO_4$, filtered, and the filtrate was concentrated in vacuo. The residue was purified by column chromatography with EtOAc/petroleum ether (0-15%) to afford the title compound, I-31. MS: 202, 204 (M+1). $^1$H NMR (300 MHz, Chloroform-d) δ 7.97 (d, J=1.0 Hz, 1H), 6.88 (s, 1H), 3.85 (s, 3H), 2.08 (d, J=0.9 Hz, 3H).

Using a similar procedure to that described for the synthesis of intermediate I-5 or I-6, the following compounds listed in Table 3 were prepared using intermediates I-30 and I-31.

Step A—4-Bromo-2-chloro-6-fluorobenzonitrile

Into a flask were placed 4-bromo-2-chloro-6-fluoroaniline (22 g, 98 mmol), DCM (200 mL) and nitrosonium tetrafluoroborate (12.6 g, 108 mmol). The resulting mixture was stirred at RT for 1 h and then cooled to 0° C. Cyanopotassium (12.8 g, 196 mmol) was added, followed by a dropwise addition of aq. solution of copper sulfate (31.3 g, 196 mmol, water 100 mL). The resultant mixture was stirred at 0° C. for 40 min, then at RT for 1 h. The mixture was diluted with DCM (100 mL), washed with sat. aq. $NaHCO_3$ (20 mL), and filtered through a pad of diatomaceous earth. The organic layer was washed with brine (2×80 mL), dried over anhydr. $Na_2SO_4$, filtered and the filtrate was concentrated in vacuo. The residue was purified by column chromatography with EtOAc/petroleum ether (1/10) to afford the title compound.

Step B—4-Bromo-2-chloro-6-methoxybenzonitrile

Into a flask were placed MeOH (20 mL) and sodium (0.91 g, 39.4 mmol). The resultant mixture was stirred at RT for

TABLE 3

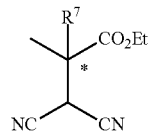

| Int. | Chiral Resolution Column | $R^7$ | $^1$H NMR and MS (M + 1) |
|---|---|---|---|
| I-32A I-32B | EnantioPak A1-5 | 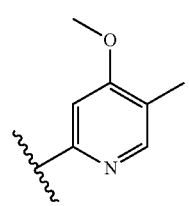 [SMILES: *c1cc(OC)c(C)cn1] | $^1$H NMR (400 MHz, CDCl$_3$): δ 8.65 (d, J = 1.2 Hz, 1H), 7.11 (s, 1H), 5.24 (s, 1H), 4.43-4.23 (m, 2H), 4.04 (s, 3H), 2.03 (s, 3H), 1.30 (t, J = 7.2 Hz, 3H); MS 342 (M + 1). |
| I-33 | RACEMIC | 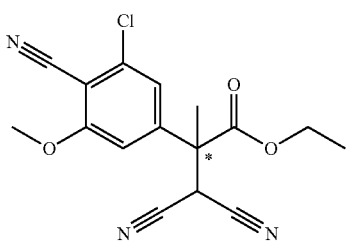 | $^1$H NMR (300 MHz, CDCl$_3$) δ 8.19 (s, 1H), 6.88 (s, 1H), 5.27 (s, 1H), 4.35-4.18 (m, 2H), 3.92 (s, 3H), 2.16 (s, 3H), 1.98 (s, 3H), 1.29-1.23 (m, 3H); MS 288 (M + 1). |

Intermediate 34, 34A and 34B

Ethyl 2-(3-chloro-4-cyano-5-methoxyphenyl)-3,3-dicyano-2-methylpropanoate and the S and R Isomers Thereof 16 h. The intermediate from Step A (7.1 g, 30.3 mmol) in THF (80 mL) was placed into a separate flask and NaOMe solution (prepared above) was added to it dropwise at 0° C. The resultant mixture was stirred at RT for 2 h. The reaction was quenched by sat. aq. $NH_4Cl$ (100 mL), and extracted with EtOAc (3×100 mL). The organic layers were combined, dried over anhydr. $Na_2SO_4$, filtered and the filtrate was concentrated in vacuo. The residue was purified by column chromatography with EtOAc/petroleum ether (1/10) to afford the title compound.

Step C—Ethyl 2-(3-chloro-4-cyano-5-methoxyphenyl)-3,3-dicyano-2-methylpropanoate Into a flask under an inert atmosphere of $N_2$, was placed the intermediate from Step B (4.83 g, 19.60 mmol) in THF (80 mL). Isopropylmagnesium chloride lithium chloride complex (16.58 mL, 21.56 mmol, 1.3 M in THF) was added dropwise to the flask at −30° C., and the reaction mixture was stirred at −10° C. for 1 h. A solution of ethyl 3,3-dicyano-2-methylprop-2-enoate (9.8 mL, 19.60 mmol, 2 M in toluene), prepared according to Hagiware et al. *Synthesis* 1974, 9, 669, was added dropwise at −50° C. The resulting solution was stirred at RT for 1 h, then quenched by the addition of sat. aq. NH$_4$Cl (150 mL), and extracted with EtOAc (3×100 mL). The organic layers were combined, dried over anhydr. Na$_2$SO$_4$, filtered and concentrated in vacuo to dryness. The residue was purified by RP-HPLC with ACN/water (10 mM ammonium bicarbonate) (30-60%) to afford the racemic title compound 1-34. The racemic material was resolved using chiral Prep-SFC (CHIRALPAK AS-H) to afford isomers I-34A (faster eluting) and I-34B (slower eluting). MS: 330 (M−1). $^1$H NMR (CDCl$_3$, 300 MHz): δ 7.09 (d, J=1.8 Hz, 1H), 6.86 (d, J=1.5 Hz, 1H), 4.47 (s, 1H), 4.39-4.27 (m, 2H), 3.99 (s, 3H), 2.00 (s, 3H), 1.28 (t, J=7.2 Hz, 3H).

Intermediate A1

8-(3-Fluorobenzyl)-[1,2,4]triazolo[1,5-a]pyrazine-6-carboximidamide

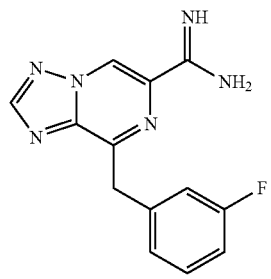 [SMILES: N=C(N)c1cn2ncnc2c(Cc2cccc(F)c2)n1]

Step A—(3-Fluorobenzyl)zinc(II) Bromide

To a flask under an inert atmosphere of N$_2$, containing zinc (2.8 g, 43.2 mmol) in THF (50 mL), was added 1,2-dibromoethane (0.2 g, 0.092 mL, 1.1 mmol), dropwise at 50° C. The mixture was stirred at 50° C. for 10 min then chlorotrimethylsilane (0.14 mL, 1.1 mmol) was added dropwise at 50° C. The mixture was allowed to cool to RT for 10 min then cooled to 0° C. for the addition of 1-(bromomethyl)-3-fluorobenzene (5.3 g, 28.1 mmol). The resulting mixture was stirred for 15 min at 0° C. then at RT for 2 h. This resulted in the zinc reagent which was used in the next step.

Step B—6-Bromo-8-(3-fluorobenzyl)-[1,2,4]triazolo[1,5-a]pyrazine

Into a flask under an inert atmosphere of N$_2$, were placed 6,8-dibromo-[1,2,4]triazolo[1,5-a]pyrazine (6.0 g, 21.6 mmol) and bis(triphenylphosphine)palladium(II) dichloride (1.5 g, 2.2 mmol). To this was added the zinc reagent from Step A, and the mixture was stirred at RT for 16 h. The mixture was quenched by the addition of sat. aq. NH$_4$Cl (200 mL), and extracted with EtOAc (3×100 mL). The combined organic layer was dried over anhydr. Na$_2$SO$_4$, filtered and the filtrate was concentrated in vacuo to dryness. The residue was purified by column chromatography with EtOAc/petroleum ether (1/5) to afford the title compound.

Step C—8-(3-Fluorobenzyl)-[1,2,4]triazolo[1,5-a]pyrazine-6-carbonitrile

Into a flask under an inert atmosphere of N$_2$, were placed the intermediate from Step B (5.2 g, 16.9 mmol), Pd$_2$(dba)$_3$ (1.5 g, 1.7 mmol), dppf (1.9 g, 3.4 mmol), zinc (0.5 g, 8.4 mmol), zinc cyanide (2.6 g, 22.0 mmol) and DMA (60 mL). The resulting mixture was stirred at 120° C. for 1 h, then diluted with EtOAc (500 mL) and washed with water (3×250 mL) and brine (2×250 mL). The combined organic layer was dried over anhydr. Na$_2$SO$_4$, filtered and the filtrate was concentrated in vacuo to dryness. The residue was purified by column chromatography with EtOAc/petroleum ether (0-50%) to afford the title compound.

Step D—8-(3-Fluorobenzyl)-[1,2,4]triazolo[1,5-a]pyrazine-6-carboximidamide

Into a flask under an inert atmosphere of N$_2$, containing NH$_4$Cl (5.5 g, 103.0 mmol) in toluene (100 mL) at 0° C. was added dropwise trimethylaluminum (41 mL, 82.4 mmol). The resulting mixture was stirred at RT for 1 h, then intermediate from Step C (2.6 g, 10.3 mmol) was added. The resulting mixture was stirred at 100° C. for 1 h, cooled to 0° C. and quenched by the addition of DCM/MeOH mixture (1:1, 500 mL). The resulting mixture was filtered and the filtrate concentrated in vacuo. The residue was dissolved in EtOAc (500 mL) and the basicity of the solution was adjusted to pH10 with sodium hydroxide (1 N). The resulting solution was extracted with EtOAc (3×200 mL) and the combined organic layer was dried over anhydr. Na$_2$SO$_4$, filtered and the filtrate concentrated in vacuo to dryness to afford the title compound, I-A1. MS: 271 (M+1). $^1$H NMR (DMSO-d$_6$, 300 MHz): δ 9.43 (s, 1H), 8.80 (s, 1H), 7.36-7.26 (m, 3H), 7.08-7.04 (m, 1H), 4.57 (s, 2H).

Intermediate A2

8-(Cyclohexylmethyl)imidazo[1,2-a]pyrazine-6-carboximidamide Hydrochloride

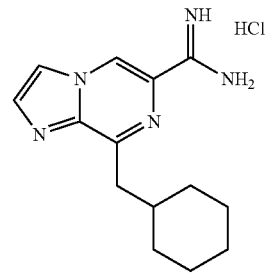 [SMILES: N=C(N)c1cn2ccnc2c(CC2CCCCC2)n1 ; Cl]

Step A—(Cyclohexylmethyl)zinc(II) Iodide

Into a flask under an inert atmosphere of N$_2$, were placed zinc (2.46 g, 37.6 mmol), DMF (35 mL) and (iodomethyl)cyclohexane (4.21 g, 18.78 mmol). To this was added a solution of diiodine (0.22 g, 0.87 mmol) in DMF (5 mL) at RT. The mixture was stirred at 80° C. for 3 h. This resulted in the zinc reagent solution which was used in the next step.

Step B—6-Bromo-8-(cyclohexylmethyl)imidazo[1,2-a]pyrazine

Into a flask under an inert atmosphere of N$_2$, were placed 6,8-dibromoimidazo[1,2-a]pyrazine (4 g, 14.44 mmol), bis (triphenylphosphine)palladium(II) dichloride (1.01 g, 1.444 mmol) and THF (120 mL). The resulting mixture was stirred at RT for 1 h before the zinc reagent solution from Step A was added dropwise at 0° C. The resulting mixture was stirred at RT for 16 h then quenched by the addition of sat. aq. NH₄Cl (400 mL). The resulting mixture was extracted with EtOAc (3×200 mL). The combined organic layer was washed with brine (2×500 mL), dried over anhydr. Na₂SO₄, filtered and the filtrate was concentrated in vacuo to dryness. The residue was purified by column chromatography with EtOAc/petroleum ether (5-45%) to afford the title compound.

Step C—8-(Cyclohexylmethyl)imidazo[1,2-a]pyrazine-6-carbonitrile

Into a flask under an inert atmosphere of N₂, were placed intermediate from Step B (2.50 g, 8.50 mmol), dicyanozinc (0.70 g, 5.95 mmol), dppf (0.47 g, 0.850 mmol), Pd₂(dba)₃ (0.440 g, 0.425 mmol), zinc (0.28 g, 4.25 mmol) and DMF (25 mL) and the resulting mixture was stirred at 120° C. for 1 h. The reaction was cooled to RT, quenched by the addition of water (250 mL) and EtOAc (250 mL). The resulting mixture was filtered and the filtrate was extracted with EtOAc (3×100 mL). The combined organic layer was washed with brine (2×200 mL), dried over anhydr. Na₂SO₄, filtered and the filtrate was concentrated in vacuo to dryness. The residue was purified by column chromatography eluting with EtOAc/petroleum ether (10-60%) to afford the title compound.

Step D—8-(Cyclohexylmethyl)imidazo[1,2-a]pyrazine-6-carboximidamide Hydrochloride Into a flask under an inert atmosphere of N₂, were placed NaOMe (1.62 g, 30.0 mmol, 25%) in MeOH (30 mL) and the intermediate from Step C (1.80 g, 7.49 mmol). The resulting mixture was stirred for at RT for 16 h then NH₄Cl (2.0 g, 37.5 mmol) was added. The resulting mixture was stirred at 70° C. for 3 h, then cooled to RT and diluted with THF (40 mL). The solid was filtered and the filtrate was concentrated in vacuo to dryness. The residue was washed with THF (2×30 mL) and dried in the air to afford the title compound, I-A2. MS: 258 (M–HCl+1). ¹H NMR (300 MHz, CD₃OD) δ 9.32 (s, 1H), 8.19 (s, 1H), 7.89 (d, J=1.2 Hz, 1H), 3.12 (d, J=7.2 Hz, 2H), 2.19-2.06 (m, 1H), 1.72-1.59 (m, 5H), 1.30-1.05 (m, 5H).

Using a similar procedure to that described for the preparation of intermediates I-A1 and I-A2, the following intermediates in the Table 4 were prepared either from a commercially available starting reagents or from compounds known in the literature. The intermediates in Table 3 might be prepared as salts or as free bases.

TABLE 4

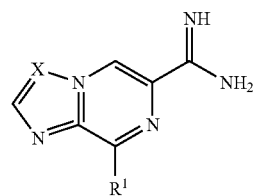

| Int. | X | R¹ | MS (M + 1) |
|---|---|---|---|
| I-A3 | C(H) | 2-F-benzyl | 270 |
| I-A4 | C(H) | 3-F-benzyl | 270 |
| I-A5 | C(H) | 4-F-benzyl | 270 |
| I-A6 | N | 2-F-benzyl | 271 |
| I-A7 | N | 4-F-benzyl | 271 |
| I-A8 | N | 3,5-di-F-benzyl | 289 |
| I-A9 | C(H) | n-butyl | 218 |
| I-A10 | C(H) | isopentyl | 232 |
| I-A11 | C(H) | 4,4,4-trifluorobutyl | 272 |

TABLE 4-continued

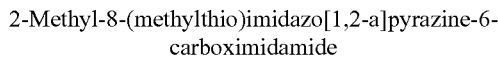

| Int. | X | R¹ | MS (M + 1) |
|---|---|---|---|
| I-A12 | C(H) | (CH₂)₃-C(F)₂-CF₃ | 308 |
| I-A13 | C(H) | -CH₂-(4,4-difluorocyclohexyl) | 294 |
| I-A14 | N | -CH₂-cyclohexyl | 259 |
| I-A15 | N | n-pentyl | 219 |
| I-A16 | N | isohexyl | 233 |
| I-A17 | N | (CH₂)₃-C(F)₂-CF₃ | 309 |
| I-A18 | N | -(CH₂)₃-CF₃ (CF₂ branch) | 273 |
| I-A19 | N | -(CH₂)₃-CHF- | 237 |

Intermediate A20

2-Methyl-8-(methylthio)imidazo[1,2-a]pyrazine-6-carboximidamide

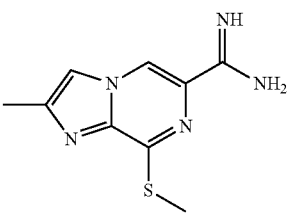

Step A—6-Bromo-2-methyl-8-(methylthio)imidazo[1,2-a]pyrazine

To a solution of 6,8-dibromo-2-methylimidazo[1,2-a]pyrazine (1.65 g, 5.67 mmol) in MeCN (17.2 mL) was slowly added sodium methanethiolate (0.48 g, 6.81 mmol) and the reaction mixture was stirred at RT overnight. The reaction mixture was concentrated in vacuo to afford the title compound that was used in the next step without purification.

Step B—2-Methyl-8-(methylthio)imidazo[1,2-a]pyrazine-6-carbonitrile

Into a flask under an inert atmosphere of $N_2$, were placed intermediate from Step A (1.3 g, 5.04 mmol) in DMA (10.1 mL), dppf (0.56 g, 1.01 mmol), $Pd_2(dba)_3$ (0.92 g, 1.01 mmol), zinc cyanide (0.65 g, 5.54 mmol) and zinc (0.17 g, 2.52 mmol). The reaction mixture was stirred at 70° C. overnight. It was cooled to RT, diluted with water (50 mL), and extracted with EtOAc (3×200 mL). The combined organic layer was dried over anhydr. $Na_2SO_4$, filtered and the filtrate concentrated in vacuo to dryness. The residue was purified by column chromatography eluting with Hexane/(EtOAc/EtOH 3:1) (0-50%) to afford the title compound.

Step C—2-Methyl-8-(methylthio)imidazo[1,2-a]pyrazine-6-carboximidamide

A solution of trimethylaluminum (9.42 mL, 18.85 mmol, 2 M toluene) was added dropwise at 0° C. to a solution of $NH_4Cl$ (1.00 g, 18.85 mmol) in toluene (18.8 mL). The reaction mixture was warmed to RT over 1 h. Intermediate from Step B (0.77 g, 3.77 mmol) in toluene (0.4 mL) was added to the above mixture and it was heated at 100° C. for 2 h. Upon completion, the reaction mixture was diluted with DCM/MeOH mixture (1:1) (50 mL) and stirred vigorously for 1 h. The resulting mixture was filtered and washed with DCM/MeOH (1:1) (2×50 mL) and the filtrate concentrated in vacuo to afford the title compound, I-A20. MS: 222 (M+1).

Intermediate A21

8-(Methylthio)imidazo[1,2-a]pyrazine-6-carboximidamide

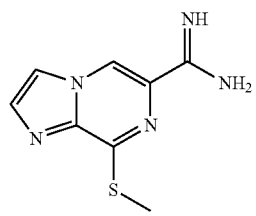

Intermediate A21 was prepared using the same procedure as one described for the preparation of Intermediate A20 using 6,8-dibromoimidazo[1,2-a]pyrazine as a starting material. MS: 208 (M+1). $^1$H NMR (400 MHz, DMSO d-6) δ 9.46 (s, 1H), 9.43 (b s, 1H), 8.28 (s, 1H), 7.82 (s, 1H), 2.70 (s, 3H).

Intermediate A22

8-(3-Fluorobenzyl)-2-methylimidazo[1,2-a]pyrazine-6-carboximidamide

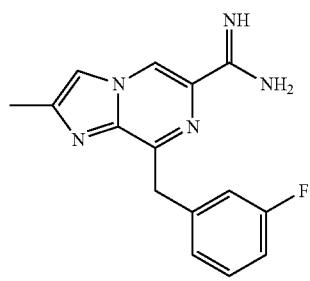 [SMILES: Cc1cn2cc(C(=N)N)nc(Cc3cccc(F)c3)c2n1]

Into a flask under an inert atmosphere of $N_2$, were placed I-A20 (200 mg, 0.90 mmol), Xantphos generation II pre-catalyst (71 mg, 0.09 mmol), and (3-fluorobenzyl)zinc(II) chloride (9.0 mL, 4.52 mmol, 0.5 M THF). The reaction was warmed at 50° C. for 4 h then cooled, diluted with EtOAc, and passed through a pad of diatomaceous earth. The filtrate was dried over anhydr. $Na_2SO_4$, and concentrated in vacuo to dryness. The crude residue was purified by column chromatography eluting with DCM/MeOH (0-10%) to afford the title compound, I-A22. MS: 284 (M+H).

Using essentially the same procedure as one described for the preparation of intermediate A22, the following intermediates in Table 4 were prepared from a commercially available starting reagents using either I-A20 or I-A21 as a starting material.

TABLE 5

| Int. | R$^1$ | R$^{4a}$ | MS (M + 1) |
|---|---|---|---|
| I-A23 | 2,6-difluorobenzyl | H | 288 |
| I-A24 | 2,4-difluorobenzyl | H | 288 |
| I-A25 | 3,4-difluorobenzyl | H | 288 |
| I-A26 | 3,5-difluorobenzyl | H | 288 |
| I-A27 | 3,4,5-trifluorobenzyl | H | 306 |
| I-A28 | 2,5-difluorobenzyl | H | 288 |
| I-A29 | 4-chlorobenzyl | H | 286 |
| I-A30 | 3-fluorobenzyl | Me | 284 |

Intermediate A31

8-[(4-Methylcyclohexyl)methyl]imidazol[1,2-a]pyrazine-6-carboximidamide

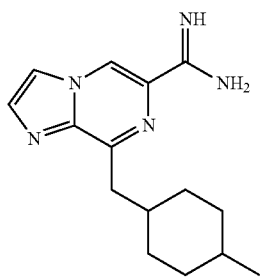 [SMILES: CC1CCC(Cc2nc(C(=N)N)cn3ccnc23)CC1]

Step A—1-(Iodomethyl)-4-methylcyclohexane

To a solution of (4-methylcyclohexyl)methyl 4-methylbenzenesulfonate (0.6 g, 2.13 mmol) in DMF (3 mL), potassium iodide (3.5 g, 21.3 mmol) was added and the reaction mixture was stirred at 60° C. for 3 h, then cooled to RT and diluted with water (100 mL). The mixture was extracted with EtOAc (3×100 mL). The combined organic layer was dried over anhydr. $Na_2SO_4$, filtered and the filtrate was concentrated in vacuo. The residue was purified by column chromatography eluting with petroleum ether to afford the title compound.

Step B—6-Bromo-8-[(4-methylcyclohexyl)methyl]imidazo[1,2-a]pyrazine

Into a flask under an inert atmosphere of argon, were placed 4,7-diphenyl-1,10-phenanthroline (108 mg, 0.33 mmol), intermediate from Step A (774 mg, 3.25 mmol), nickel(II) iodide (203 mg, 0.65 mmol), 6,8-dibromoimidazo[1,2-a]pyrazine (600 mg, 2.167 mmol), and manganese (357 mg, 6.50 mmol). The mixture was flushed with argon, then benzonitrile (45 mg, 0.43 mmol) in DMA (1 mL), chlorotrimethylsilane (47 mg, 0.43 mmol) in DMA (1 mL) were added and stirred at RT for 1 h and then diluted with water (100 mL). The mixture was extracted with EtOAc (3×200 mL), the combined organic layer was dried over anhydr. $Na_2SO_4$, filtered and concentrated in vacuo. The residue was purified by column chromatography eluting with EtOAc/petroleum ether (0-30%) to afford the title compound.

Step C—8-[(4-Methylcyclohexyl)methyl]imidazo[1,2-a]pyrazine-6-carbonitrile

Into a flask under an inert atmosphere of $N_2$, were placed intermediate from Step B (200 mg, 0.65 mmol, dicyanozinc (45.7 mg, 0.39 mmol), $Pd_2(dba)_3$-chloroform adduct (30 mg, 0.032 mmol), dppf (36 mg, 0.065 mmol), zinc (21 mg, 0.32 mmol) in DMF (1 mL), and the resulting mixture was stirred at 120° C. for 2 h then cooled to RT and diluted with water (200 mL). The mixture was extracted with EtOAc (3×200 mL), combined organic layer was dried over anhydr. $Na_2SO_4$, filtered and the filtrate was concentrated in vacuo to dryness. The residue was purified by column chromatography eluting with EtOAc/petroleum ether (0-40%) to afford the title compound.

Step D—8-[(4-Methylcyclohexyl)methyl]imidazo[1,2-a]pyrazine-6-carboximidamide Into a flask under an inert atmosphere of $N_2$, were placed intermediate from Step C (150 mg, 0.59 mmol) in MeOH (3 mL) and NaOMe (64 mg, 1.18 mmol). The reaction mixture was stirred at RT for 2 h, then $NH_4Cl$ (95 mg, 1.77 mmol) was added and the mixture was stirred at 70° C. for 3 h. Upon completion, the solution was concentrated in vacuo to dryness. The residue was poured into water (50 mL), and the acidity was adjusted to pH 1-2 with HCl (1 N). The resulting solution was extracted with diethyl ether (2×50 mL) and the basicity of the aqueous phase was adjusted to pH 11-12 with sat. aq. NaOH. The resulting solution was extracted with EtOAc (3×100 mL) and the combined organic layer was dried over anhydr. $Na_2SO_4$, filtered and concentrated in vacuo to afford the title compound, I-A31. MS: 272 (M+1). $^1$H NMR (300 MHz, $CDCl_3$) δ 9.05 (s, 1H), 7.78 (d, J=1.2 Hz, 1H), 7.72 (d, J=1.2 Hz, 1H), 5.60-4.60 (br, 3H), 3.22 (d, J=7.5 Hz, 1.5H), 3.12 (d, J=7.2 Hz, 0.5H), 2.40-2.27 (m, 1H), 1.73-1.08 (m, 9H), 0.93 (d, J=6.9 Hz, 3H).

Intermediate A32

8-(2-Cyclohexylethyl)imidazo[1,2-a]pyrazine-6-carboximidamide

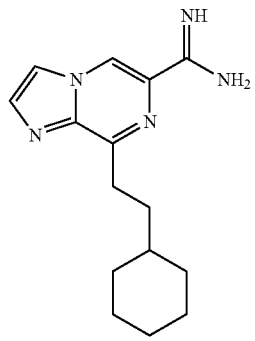 [SMILES: N=C(N)c1cn2ccnc2c(CCC2CCCCC2)n1]

Step A—6-Bromo-8-(2-cyclohexylethyl)imidazo[1,2-a]pyrazine

Into a flask under an inert atmosphere of $N_2$, were placed magnesium (0.4 g, 16.25 mmol) and iodine (0.02 g, 0.072 mmol) in THF (5 mL), then (2-bromoethyl)cyclohexane (2.1 g, 10.83 mmol) in THF (10 mL) was added dropwise at 80° C. and the reaction was stirred for 1.5 h, then cooled to RT. Into another flask under an inert atmosphere of $N_2$, was placed zinc (II) bromide (2.4 g, 10.83 mmol) in THF (35 mL), followed by the dropwise addition of the Grignard reagent (prepared above) at 0° C. The mixture was stirred at RT for 1 h, then bis(triphenylphosphine)palladium chloride (0.5 g, 0.72 mmol) and 6,8-dibromoimidazo[1,2-a]pyrazine (2 g, 7.22 mmol) were added and stirred at RT for 1.5 h. The reaction was quenched by the addition of sat. aq. $NH_4Cl$ (50 mL) and extracted with EtOAc (3×50 mL). The combined organic layer was washed with brine (2×100 mL), dried over anhydr. $Na_2SO_4$, filtered, concentrated to dryness in vacuo, and the residue purified by column chromatography with EtOAc/petroleum ether (10-45%) to afford the title compound.

Step B—8-(2-Cyclohexylethyl)imidazo[1,2-a]pyrazine-6-carbonitrile

Into a flask under an inert atmosphere of $N_2$, were placed intermediate from Step A (1 g, 3.24 mmol), dicyanozinc (0.5 g, 4.22 mmol), dppf (0.4 g, 0.649 mmol), $Pd_2(dba)_3$ (0.3 g, 0.32 mmol), and zinc (0.1 g, 1.62 mmol) in DMF (20 mL). The resulting mixture was stirred at 120° C. for 1 h then cooled, quenched by the addition of water (30 mL) and EtOAc (100 mL), and filtered through a pad of CELITE. The filtrate was extracted with EtOAc (3×20 mL) and the combined organic layer dried over anhydr. $Na_2SO_4$, filtered and concentrated in vacuo to dryness. The residue was purified by column chromatography with EtOAc/petroleum ether (1/1) to afford the title compound.

Step C—8-(2-Cyclohexylethyl)imidazo[1,2-a]pyrazine-6-carboximidamide

Into a flask under an inert atmosphere of $N_2$, was placed sodium (41 mg, 1.77 mmol) in MeOH (10 mL) and the resulting mixture was stirred at RT for 1 h until the sodium bits disappeared. The intermediate from Step B (300 mg, 1.18 mmol) was added to the mixture and it was stirred at RT for 1 h, then acetic acid (106 mg, 1.77 mmol) and $NH_4Cl$ (126 mg, 2.36 mmol) were added and the mixture was stirred at 75° C. for 2 h. It was concentrated to dryness in vacuo, diluted with water (20 mL), and washed with ether (20 mL). The basicity of the aqueous phase was adjusted to pH 11 with NaOH (1 N), and extracted with EtOAc (3×50 mL). The combined organic layer was dried over anhydr. $Na_2SO_4$, filtered, and the filtrate concentrated in vacuo to afford the title compound, I-A32. MS: 272 (M+1). $^1H$ NMR (400 MHz, $CD_3OD$) δ 9.01 (s, 1H), 8.10 (d, J=1.2 Hz, 1H), 7.83 (d, J=0.8 Hz, 1H), 3.32-3.26 (m, 2H), 1.91-1.68 (m, 7H), 1.45-1.38 (m, 1H), 1.37-1.20 (m, 3H), 1.08-0.99 (m, 2H).

Intermediate A33

8-(Cyclopentylmethyl)imidazo[1,2-a]pyrazine-6-carboximidamide

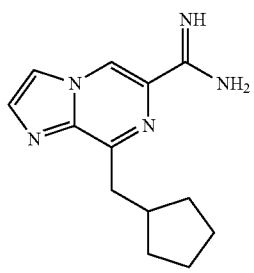 [SMILES: N=C(N)c1cn2ccnc2c(CC2CCCC2)n1]

Intermediate A33 was prepared using a similar procedure as the one described for the preparation of intermediates A1 and A2 using 6,8-dibromoimidazo[1,2-a]pyrazine as a starting material. MS: 244 (M+1).

Example 1-A

4-Amino-5-(4-chloro-3-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one

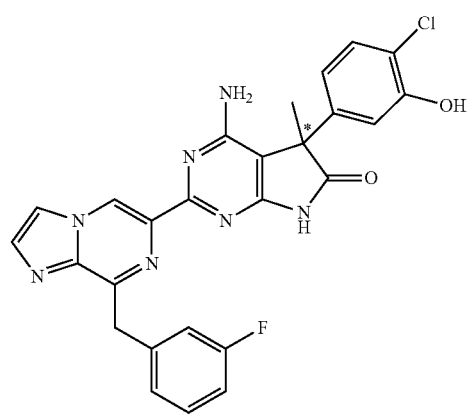 [SMILES: CC1(c2ccc(Cl)c(O)c2)C(=O)Nc2nc(-c3cn4ccnc4c(Cc4cccc(F)c4)n3)nc(N)c21]

Step A—4-Amino-5-(4-chloro-3-methoxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one Into a flask were placed amidine I-A4 (50 mg, 0.19 mmol), chiral malononitrile I-12A (63 mg, 0.20 mmol), tert-BuOH (1 mL) and potassium bicarbonate (56 mg, 0.56 mmol). The resulting mixture was stirred at 80° C. for 16 h, then concentrated to dryness in vacuo, and the residue was purified by column chromatography eluting with DCM/MeOH (10/1) to afford the title compound.

Step B—4-Amino-5-(4-chloro-3-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one Into a flask under an inert atmosphere of $N_2$, was placed intermediate from Step A (60 mg, 0.11 mmol) in DCM (1 mL), followed by a dropwise addition of $BBr_3$ (1.1 mL, 0.57 mmol, 0.5 M in DCM) at 0° C. The resulting mixture was stirred at RT for 1 h, then quenched with sat. aq. $NaHCO_3$ (10 mL), and extracted with EtOAc (3×20 mL). The combined organic layer was dried over anhydr. $Na_2SO_4$, filtered and concentrated to dryness in vacuo. The residue was purified by column chromatography eluting with (3:1 EtOAc:EtOH)/hexanes 0-70% to afford the title compound, 1-A. MS: 516 (M+1). $^1H$ NMR (DMSO-$d_6$, 300 MHz): δ 11.19 (br s, 1H), 10.11 (s, 1H), 9.25 (s, 1H), 8.33 (d, J=0.9 Hz, 1H), 7.85 (d, J=0.9 Hz, 1H), 7.36-7.21 (m, 4H), 7.06-7.00 (m, 1H), 6.86 (d, J=2.1 Hz, 1H), 6.75 (dd, J=8.1 Hz, 1.8 Hz, 1H), 6.56 (br s, 2H), 4.54 (s, 2H), 1.75 (s, 3H).

Example 2-B

4-Amino-5-(4-chloro-3-fluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one

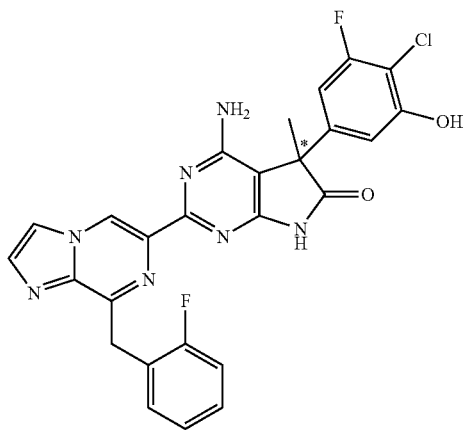

Step A—4-Amino-5-(4-chloro-3-fluoro-5-methoxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one Into a flask were placed amidine I-A3 (70 mg, 0.26 mmol), chiral malononitrile I-7B (84 mg, 0.26 mmol), potassium bicarbonate (78 mg, 0.78 mmol) and tert-BuOH (5 mL). The resulting mixture was stirred at 80° C. for 16 h, then cooled to RT, quenched by the addition of brine (20 mL), and extracted with EtOAc (3×60 mL). The combined organic layer was dried over anhydr. $Na_2SO_4$, filtered, concentrated to dryness in vacuo and the residue was purified by column chromatography eluting with MeOH/DCM (0-2%) to afford the title compound.

Step B—4-Amino-5-(4-chloro-3-fluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one Into a flask under an inert atmosphere of $N_2$, was placed intermediate from Step A (70 mg, 0.13 mmol) in DCM (10 ml), followed by a dropwise addition of $BBr_3$ (1 mL, 10.6 mmol, 1 M in DCM) at 0° C. The resulting mixture was stirred at RT for 6 h, then poured into a water/ice (50 mL) and the basicity of the solution was adjusted to pH8 with $NaHCO_3$. The aqueous was extracted with EtOAc (3×50 mL). The combined organic layer was dried over anhydr. $Na_2SO_4$, filtered and concentrated in vacuo. The residue was purified by column chromatography eluting with MeOH/DCM (1-3%) to afford the title compound, 2-B. MS: 534 (M+1). $^1H$ NMR (300 MHz, $CD_3OD$): δ 9.40 (s, 1H), 8.11 (d, J=0.9 Hz, 1H), 7.78 (d, J=0.9 Hz, 1H), 7.22-7.15 (m, 2H), 7.08-6.95 (m, 2H), 6.74 (dd, J=2.1, 10.2 Hz, 1H), 6.65 (dd, J=1.5, 1.8 Hz, 1H), 4.66 (s, 2H), 1.79 (s, 3H).

Example 3-B

4-Amino-2-{8-[(2-fluorophenyl)methyl]imidazo[1,2-a]pyrazin-6-yl}-5-[3-hydroxy-4-(trifluoromethyl)phenyl]-5-methyl-5,7-dihydro-6H-pyrrolo[2,3-d]pyrimidin-6-one

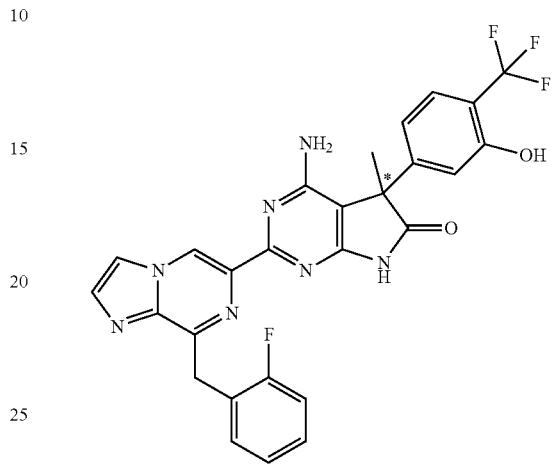

Step A—4-Amino-2-{8-[(2-fluorophenyl)methyl]imidazo[1,2-a]pyrazin-6-yl}-5-(3-methoxy-4-(trifluoromethyl)phenyl)-5-methyl-5,7-dihydro-6H-pyrrolo[2,3-d]pyrimidin-6-one Into a flask were placed amidine I-A3 (80 mg, 0.30 mmol), chiral malononitrile I-9B (101 mg, 0.30 mmol), potassium bicarbonate (60 mg, 0.60 mmol) and tert-BuOH (10 mL). The resulting mixture was stirred at 70° C. for 20 h then concentrated to dryness in vacuo, and the residue was purified by column chromatography eluting with MeOH/DCM (1-7%) to afford the title compound.

Step B—4-Amino-2-{8-[(2-fluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one Into a flask under an inert atmosphere of $N_2$, was placed intermediate from Step A (65 mg, 0.12 mmol) in DCM (7 mL), followed by a dropwise addition of $BBr_3$ (0.7 mL, 0.12 mmol) at 0° C. The resulting mixture was stirred for at RT 1 h, then poured into a water/ice (50 mL), and the acidity was adjusted to pH7-8 with solid $NaHCO_3$. The aqueous was extracted with EtOAc (3×50 mL) and the combined organic layer was washed with brine (2×50 mL), dried over anhydr. $Na_2SO_4$, filtered and concentrated in vacuo. The residue was purified by column chromatography eluting with MeOH/DCM (1-7%) to afford the title compound, 3-B. MS: 550 (M+1). $^1H$ NMR ($CD_3OD$, 300 MHz): δ 9.39 (s, 1H), 8.11 (s, 1H), 7.77 (d, J=0.9 Hz, 1H), 7.46 (d, J=8.1 Hz, 1H), 7.22-7.15 (m, 2H), 7.07-6.90 (m, 4H), 4.55 (s, 2H), 1.84 (s, 3H).

Example 4-B

4-Amino-5-(5-chloro-4-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one

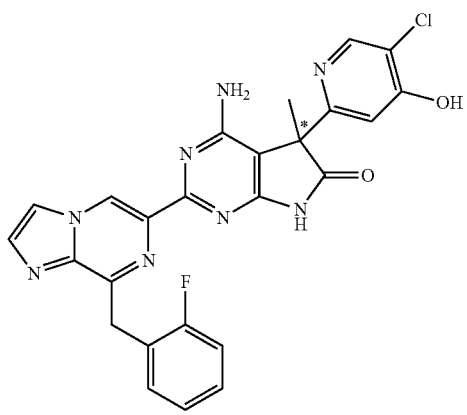

Step A—4-Amino-5-(5-chloro-4-methoxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one Into a flask were placed amidine I-A3 (95 mg, 0.35 mmol), chiral malononitrile I-5B (90 mg, 0.29 mmol), tert-BuOH (6 mL) and potassium bicarbonate (35 mg, 0.35 mmol). The resulting mixture was stirred at 75° C. for 16 h, then concentrated in vacuo to dryness and the residue was purified by column chromatography eluting with DCM/MeOH (10/1) to afford the title compound.

Step B—4-Amino-5-(5-chloro-4-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one Into a flask were placed intermediate from Step A (80 mg, 0.15 mmol) and hydrobromic acid (40%, 8 mL). The resulting mixture was stirred at 80° C. for 16 h then quenched with sat. aq. NaHCO$_3$ (150 mL), extracted with EtOAc (3×100 mL) and the combined organic layer was dried over anhydr. Na$_2$SO$_4$, filtered and concentrated to dryness in vacuo. The crude product was purified by Prep-HPLC eluting with water (0.05% ammonium bicarbonate) and MeCN (10-23%) to afford the title compound, 4-B. MS: 517 (M+1). $^1$H NMR (CD$_3$OD, 300 MHz): δ 9.42 (s, 1H), 8.14 (s, 1H), 8.10 (s, 1H), 7.81 (s, 1H), 7.26-7.18 (m, 2H), 7.11-6.99 (m, 2H), 6.64 (s, 1H), 4.69 (s, 2H), 1.87 (s, 3H).

Using essentially the same procedures described in Examples 1 through 4, the following compounds in Table 6 were prepared. The deprotection step was performed using either BBr$_3$ or HBr as a deprotecting reagent.

TABLE 6

Examples 5-B-105-B

| Ex. | Structure | Name | MS (M + 1) | Chiral starting material |
|---|---|---|---|---|
| 5-B | 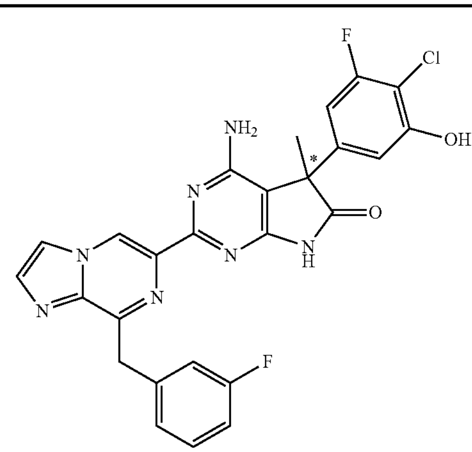 | 4-Amino-5-(4-chloro-3-fluoro-5-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one | 534 | I-7B |

TABLE 6-continued

Examples 5-B-105-B

| Ex. | Structure | Name | MS (M + 1) | Chiral starting material |
|---|---|---|---|---|
| 6-B | 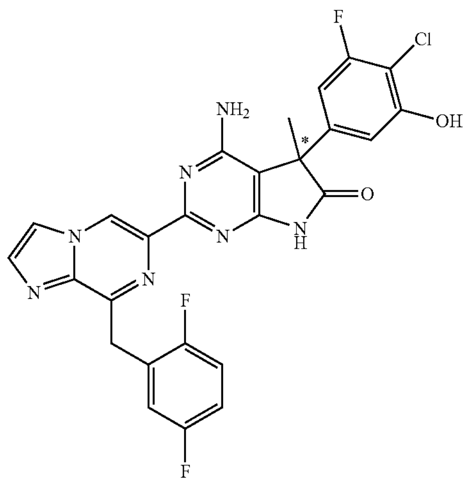 [SMILES: CC1(c2cc(O)c(Cl)c(F)c2)C(=O)Nc2nc(-c3cn4ccnc4c(Cc4cc(F)ccc4F)n3)nc(N)c21] | 4-Amino-5-(4-chloro-3-fluoro-5-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one | 552 | I-7B |
| 7-B | 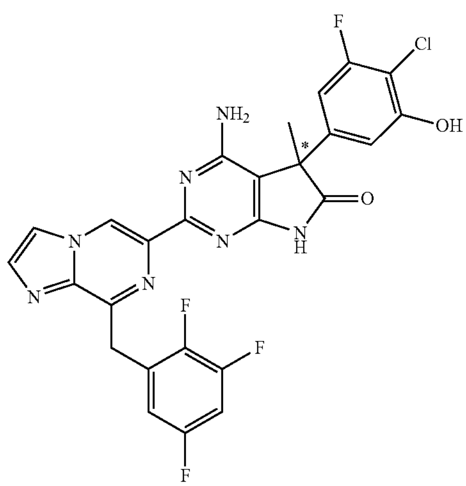 [SMILES: CC1(c2cc(O)c(Cl)c(F)c2)C(=O)Nc2nc(-c3cn4ccnc4c(Cc4cc(F)cc(F)c4F)n3)nc(N)c21] | 4-Amino-5-(4-chloro-3-fluoro-5-hydroxyphenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one | 570 | I-7B |
| 8-A | 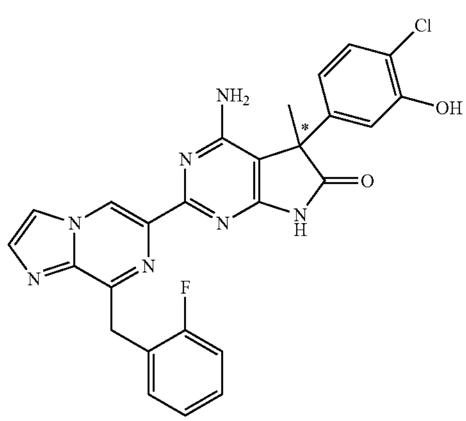 [SMILES: CC1(c2ccc(Cl)c(O)c2)C(=O)Nc2nc(-c3cn4ccnc4c(Cc4ccccc4F)n3)nc(N)c21] | 4-Amino-5-(4-chloro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 516 | I-12A |

TABLE 6-continued

Examples 5-B-105-B

| Ex. | Structure | Name | MS (M + 1) | Chiral starting material |
|---|---|---|---|---|
| 9-B | 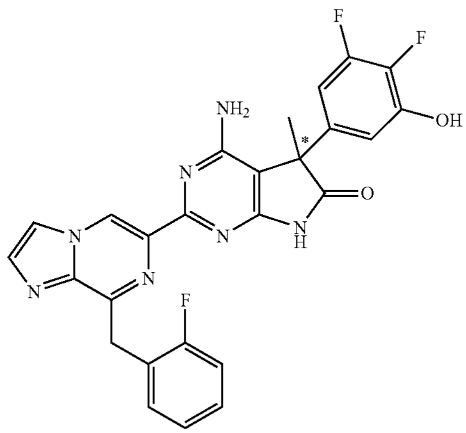 [SMILES: CC1(c2cc(O)c(F)c(F)c2)C(=O)Nc2nc(-c3cn4ccnc4c(Cc4ccccc4F)n3)nc(N)c21] | 4-Amino-5-(3,4-difluoro-5-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 518 | I-8B |
| 10-B | 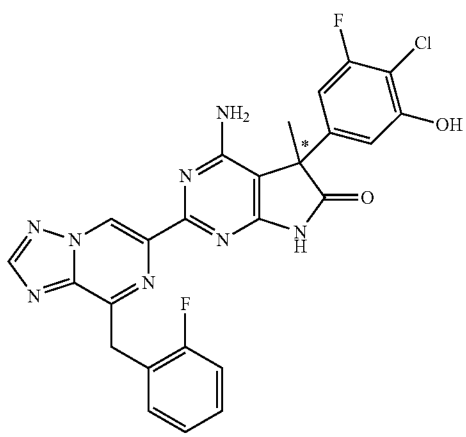 [SMILES: CC1(c2cc(O)c(Cl)c(F)c2)C(=O)Nc2nc(-c3cn4ncnc4c(Cc4ccccc4F)n3)nc(N)c21] | 4-Amino-5-(4-chloro-3-fluoro-5-hydroxyphenyl)-2-{8-[(2-fluorophenyl)methyl]-[1,2,4]triazolo[1,5-a]pyrazin-6-yl}-5-methyl-5,7-dihydro-6H-pyrrolo[2,3-d]pyrimidin-6-one | 535 | I-7B |
| 11-B | 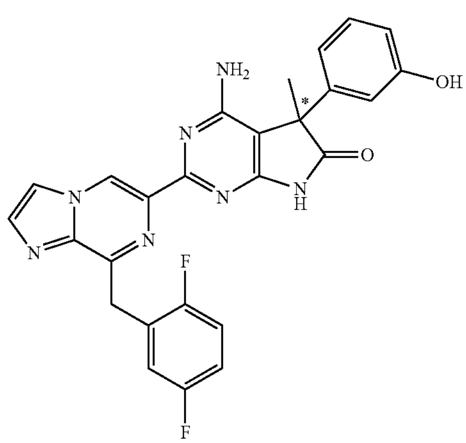 [SMILES: CC1(c2cccc(O)c2)C(=O)Nc2nc(-c3cn4ccnc4c(Cc4cc(F)ccc4F)n3)nc(N)c21] | 4-Amino-2-{8-[(2,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one | 500 | I-17B |

TABLE 6-continued

Examples 5-B-105-B

| Ex. | Structure | Name | MS (M + 1) | Chiral starting material |
|---|---|---|---|---|
| 12-B | 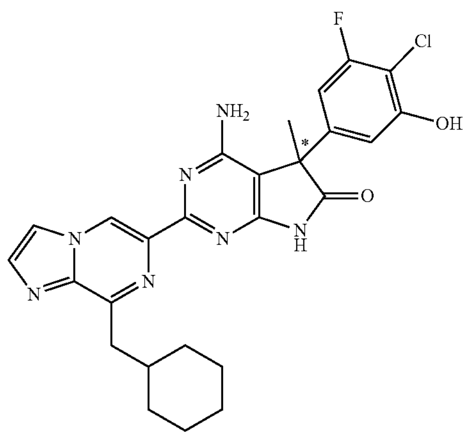 [SMILES: CC1(c2cc(O)c(Cl)c(F)c2)C(=O)Nc2nc(-c3cn4ccnc4c(CC4CCCCC4)n3)nc(N)c21] | 4-Amino-5-(4-chloro-3-fluoro-5-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one | 522 | I-7B |
| 13-B | 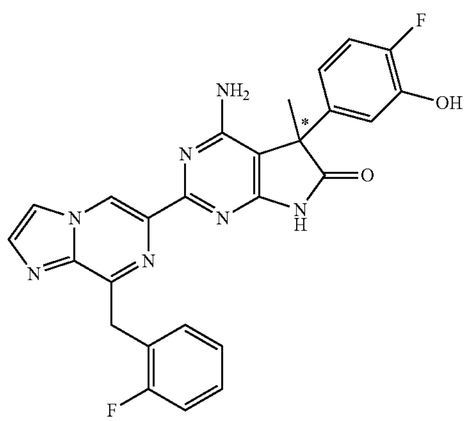 [SMILES: CC1(c2ccc(F)c(O)c2)C(=O)Nc2nc(-c3cn4ccnc4c(Cc4ccccc4F)n3)nc(N)c21] | 4-Amino-5-(4-fluoro-3-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 500 | I-6B |
| 14-A | 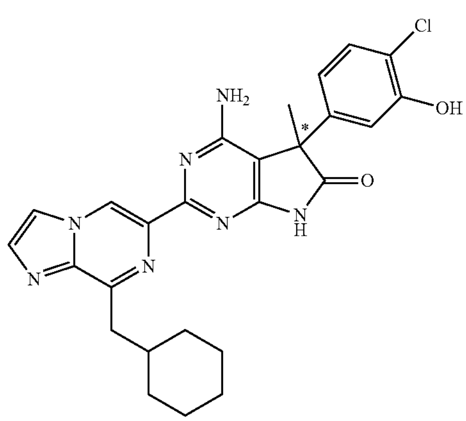 [SMILES: CC1(c2ccc(Cl)c(O)c2)C(=O)Nc2nc(-c3cn4ccnc4c(CC4CCCCC4)n3)nc(N)c21] | 4-Amino-5-(4-chloro-3-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one | 504 | I-12A |

TABLE 6-continued

Examples 5-B-105-B

| Ex. | Structure | Name | MS (M + 1) | Chiral starting material |
|---|---|---|---|---|
| 15-B | 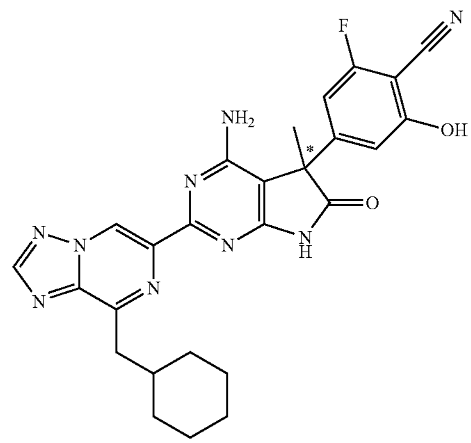 [SMILES: CC1(c2cc(O)c(C#N)c(F)c2)C(=O)Nc2nc(-c3cn4ncnc4c(CC4CCCCC4)n3)nc(N)c21] | 4-(4-Amino-2-(8-(cyclohexylmethyl)-[1,2,4]triazolo[1,5-a]pyrazin-6-yl)-5-methyl-6-oxo-6,7-dihydro-5H-pyrrolo[2,3-d]pyrimidin-5-yl)-2-fluoro-6-hydroxybenzonitrile | 514 | I-23B |
| 16-B | 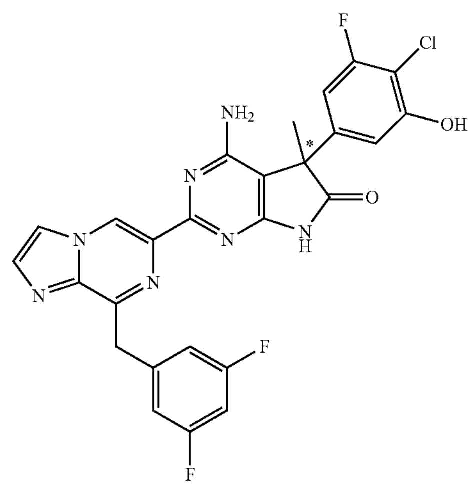 [SMILES: CC1(c2cc(O)c(Cl)c(F)c2)C(=O)Nc2nc(-c3cn4ccnc4c(Cc4cc(F)cc(F)c4)n3)nc(N)c21] | 4-Amino-5-(4-chloro-3-fluoro-5-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one | 552 | I-7B |
| 17-B | 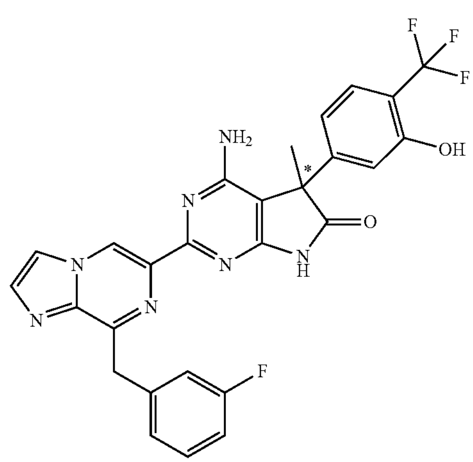 [SMILES: CC1(c2ccc(C(F)(F)F)c(O)c2)C(=O)Nc2nc(-c3cn4ccnc4c(Cc4cccc(F)c4)n3)nc(N)c21] | 4-Amino-2-{8-[(3-fluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one | 550 | I-9B |

TABLE 6-continued

Examples 5-B-105-B

| Ex. | Structure | Name | MS (M + 1) | Chiral starting material |
|---|---|---|---|---|
| 18-B | 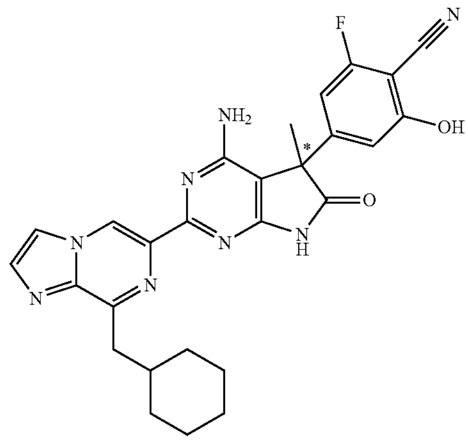 [SMILES: CC1(c2cc(O)c(C#N)c(F)c2)C(=O)Nc2nc(-c3cn4ccnc4c(CC4CCCCC4)n3)nc(N)c21] | 4-(4-Amino-2-(8-(cyclohexylmethyl)imidazo[1,2-a]pyrazin-6-yl)-5-methyl-6-oxo-6,7-dihydro-5H-pyrrolo[2,3-d]pyrimidin-5-yl)-2-fluoro-6-hydroxybenzonitrile | 513 | I-23B |
| 19-A | 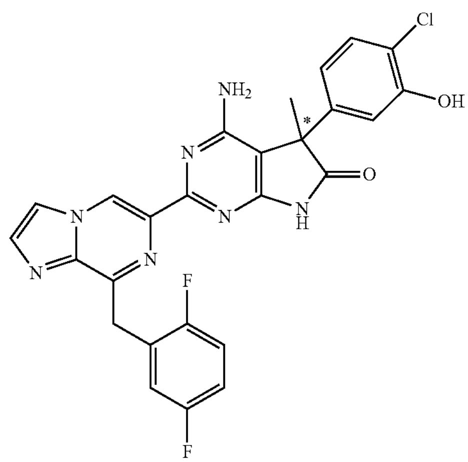 [SMILES: CC1(c2ccc(Cl)c(O)c2)C(=O)Nc2nc(-c3cn4ccnc4c(Cc4cc(F)ccc4F)n3)nc(N)c21] | 4-Amino-5-(4-chloro-3-hydroxyphenyl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one | 534 | I-12A |
| 20-A | 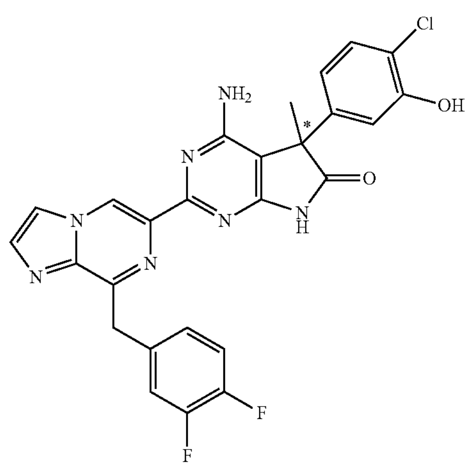 [SMILES: CC1(c2ccc(Cl)c(O)c2)C(=O)Nc2nc(-c3cn4ccnc4c(Cc4ccc(F)c(F)c4)n3)nc(N)c21] | 4-Amino-5-(4-chloro-3-hydroxyphenyl)-2-{8-[(3,4-difluorophenyl)methyl]imidazo[1,2-a]pyrazin-6-yl}-5-methyl-5,7-dihydro-6H-pyrrolo[2,3-d]pyrimidin-6-one | 534 | I-12A |

TABLE 6-continued

Examples 5-B-105-B

| Ex. | Structure | Name | MS (M + 1) | Chiral starting material |
|---|---|---|---|---|
| 21-B | 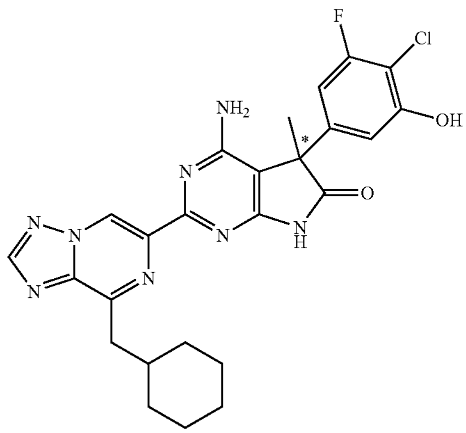 [SMILES: CC1(c2cc(O)c(Cl)c(F)c2)C(=O)Nc2nc(-c3cn4ncnc4c(CC4CCCCC4)n3)nc(N)c21] | 4-Amino-5-(4-chloro-3-fluoro-5-hydroxyphenyl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one | 523 | I-7B |
| 22-B | 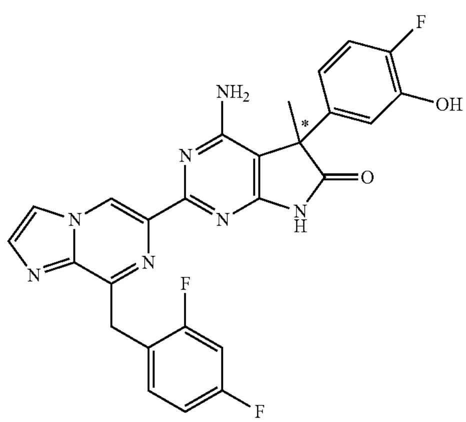 [SMILES: CC1(c2ccc(F)c(O)c2)C(=O)Nc2nc(-c3cn4ccnc4c(Cc4ccc(F)cc4F)n3)nc(N)c21] | 4-Amino-2-{8-[(2,4-difluorophenyl)methyl]imidazo[1,2-a]pyrazin-6-yl}-5-(4-fluoro-3-hydroxyphenyl)-5-methyl-5,7-dihydro-6H-pyrrolo[2,3-d]pyrimidin-6-one | 518 | I-6B |
| 23-B | 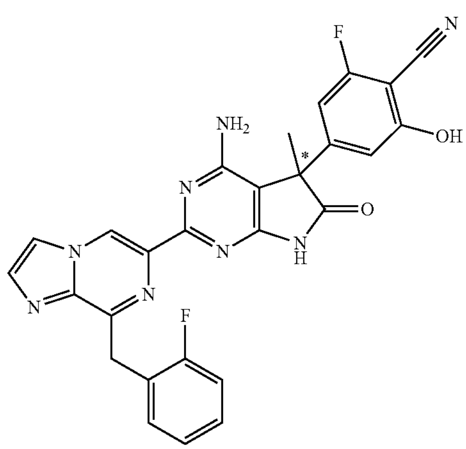 [SMILES: CC1(c2cc(O)c(C#N)c(F)c2)C(=O)Nc2nc(-c3cn4ccnc4c(Cc4ccccc4F)n3)nc(N)c21] | 4-(4-Amino-2-{8-[(2-fluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile | 525 | I-23B |

TABLE 6-continued

Examples 5-B-105-B

| Ex. | Structure | Name | MS (M + 1) | Chiral starting material |
|---|---|---|---|---|
| 24-B | 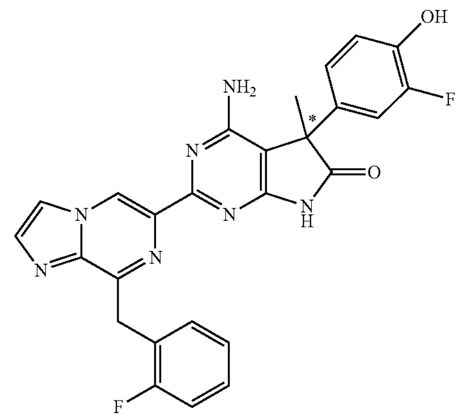 [SMILES: CC1(c2ccc(O)c(F)c2)C(=O)Nc2nc(-c3cn4ccnc4c(Cc4ccccc4F)n3)nc(N)c21] | 4-Amino-5-(3-fluoro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 500 | I-28B |
| 25-A | 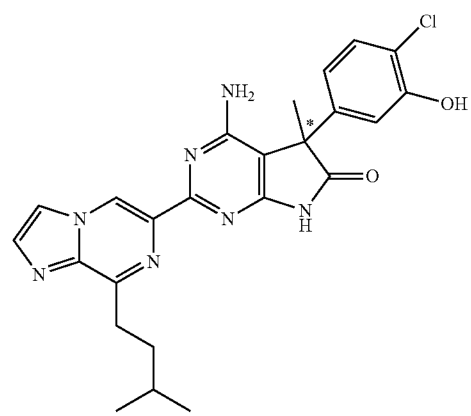 | 4-Amino-5-(4-chloro-3-hydroxyphenyl)-2-(8-isopentylimidazo[1,2-a]pyrazin-6-yl)-5-methyl-5,7-dihydro-6H-pyrrolo[2,3-d]pyrimidin-6-one | 478 | I-12A |
| 26-A | 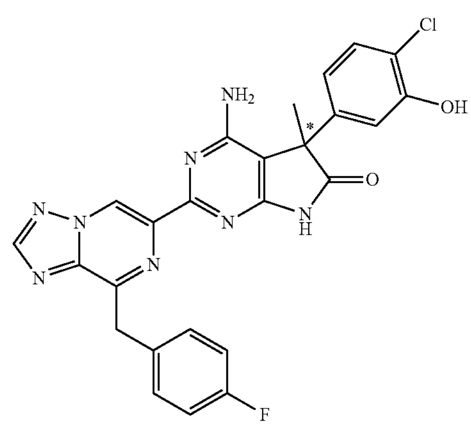 [SMILES: CC1(c2ccc(Cl)c(O)c2)C(=O)Nc2nc(-c3cn4ncnc4c(Cc4ccc(F)cc4)n3)nc(N)c21] | 4-Amino-5-(4-chloro-3-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one | 517 | I-12A |

TABLE 6-continued

Examples 5-B-105-B

| Ex. | Structure | Name | MS (M + 1) | Chiral starting material |
|---|---|---|---|---|
| 27-B | 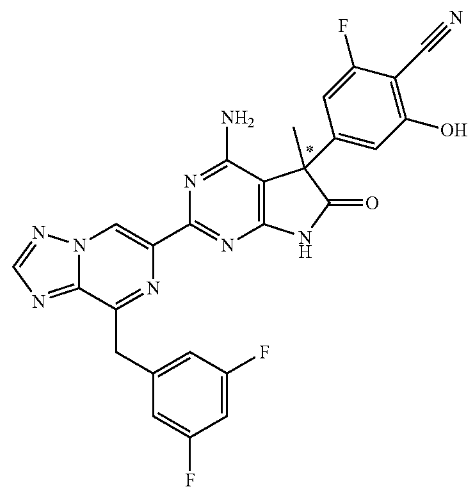 [SMILES: CC1(c2cc(O)c(C#N)c(F)c2)C(=O)Nc2nc(-c3cn4ncnc4c(Cc4cc(F)cc(F)c4)n3)nc(N)c21] | 4-(4-Amino-2-{8-[(3,5-difluorophenyl)methyl]-[1,2,4]triazolo[1,5-a]pyrazin-6-yl}-5-methyl-6-oxo-6,7-dihydro-5H-pyrrolo[2,3-d]pyrimidin-5-yl)-2-fluoro-6-hydroxybenzonitrile | 544 | I-23B |
| 28-B | 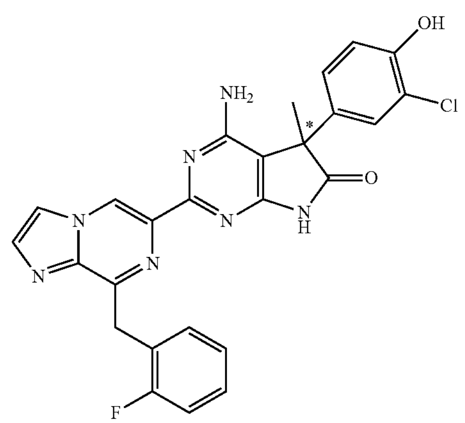 [SMILES: CC1(c2ccc(O)c(Cl)c2)C(=O)Nc2nc(-c3cn4ccnc4c(Cc4ccccc4F)n3)nc(N)c21] | 4-Amino-5-(3-chloro-4-hydroxyphenyl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 516 | I-11B |
| 29-B | 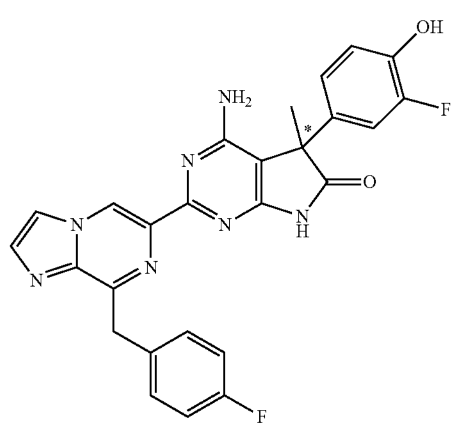 [SMILES: CC1(c2ccc(O)c(F)c2)C(=O)Nc2nc(-c3cn4ccnc4c(Cc4ccc(F)cc4)n3)nc(N)c21] | 4-Amino-5-(3-fluoro-4-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one | 501 | I-28B |

TABLE 6-continued

Examples 5-B-105-B

| Ex. | Structure | Name | MS (M + 1) | Chiral starting material |
|---|---|---|---|---|
| 30-A | 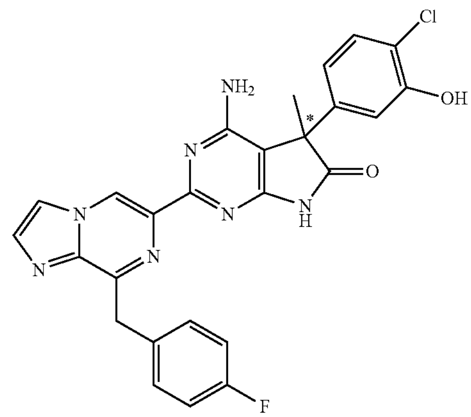 [SMILES: CC1(c2ccc(Cl)c(O)c2)C(=O)Nc2nc(-c3cn4ccnc4c(Cc4ccc(F)cc4)n3)nc(N)c21] | 4-Amino-5-(4-chloro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one | 516 | I-12A |
| 31-B | 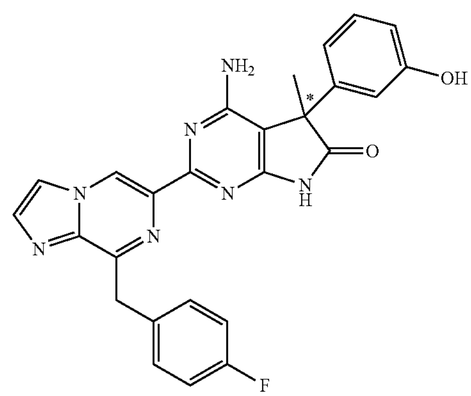 [SMILES: CC1(c2cccc(O)c2)C(=O)Nc2nc(-c3cn4ccnc4c(Cc4ccc(F)cc4)n3)nc(N)c21] | 4-Amino-2-{8-[(4-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one | 482 | I-17B |
| 32-B | 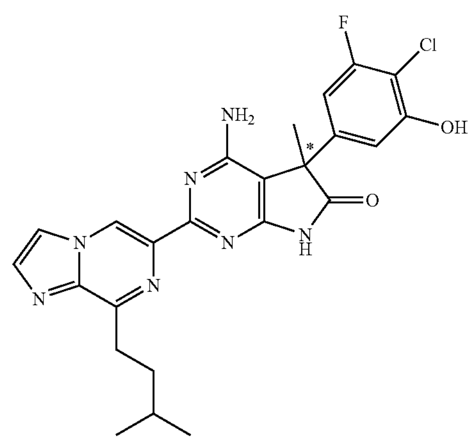 [SMILES: CC(C)CCc1nc(-c2nc(N)c3c(n2)NC(=O)C3(C)c2cc(O)c(Cl)c(F)c2)cn2ccnc12] | 4-Amino-5-(4-chloro-3-fluoro-5-hydroxyphenyl)-2-(8-isopentylimidazo[1,2-a]pyrazin-6-yl)-5-methyl-5,7-dihydro-6H-pyrrolo[2,3-d]pyrimidin-6-one | 496 | I-7B |

TABLE 6-continued

Examples 5-B-105-B

| Ex. | Structure | Name | MS (M + 1) | Chiral starting material |
|---|---|---|---|---|
| 33-B | 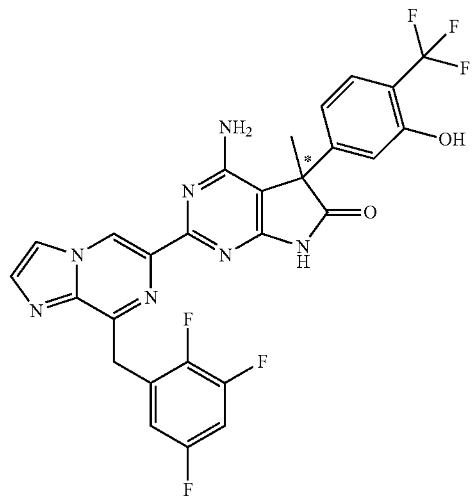 [SMILES: CC1(c2ccc(C(F)(F)F)c(O)c2)C(=O)Nc2nc(-c3cn4ccnc4c(Cc4cc(F)cc(F)c4F)n3)nc(N)c21] | 4-Amino-5-(3-hydroxy-4-(trifluoromethyl)phenyl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one | 586 | I-9B |
| 34-B | 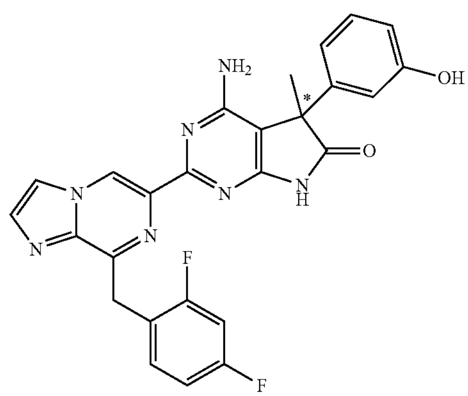 [SMILES: CC1(c2cccc(O)c2)C(=O)Nc2nc(-c3cn4ccnc4c(Cc4ccc(F)cc4F)n3)nc(N)c21] | 4-Amino-2-{8-[(2,4-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one | 500 | I-17B |
| 35-B | 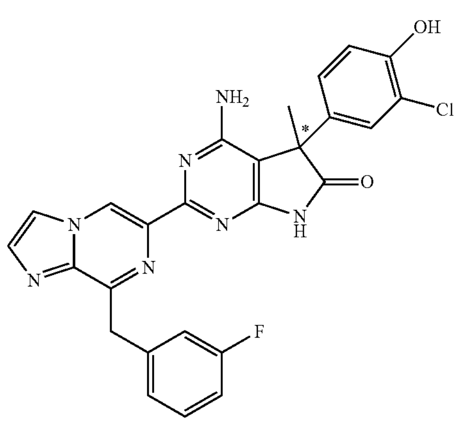 [SMILES: CC1(c2ccc(O)c(Cl)c2)C(=O)Nc2nc(-c3cn4ccnc4c(Cc4cccc(F)c4)n3)nc(N)c21] | 4-Amino-5-(3-chloro-4-hydroxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one | 516 | I-11B |

TABLE 6-continued

Examples 5-B-105-B

| Ex. | Structure | Name | MS (M + 1) | Chiral starting material |
|---|---|---|---|---|
| 36-A | 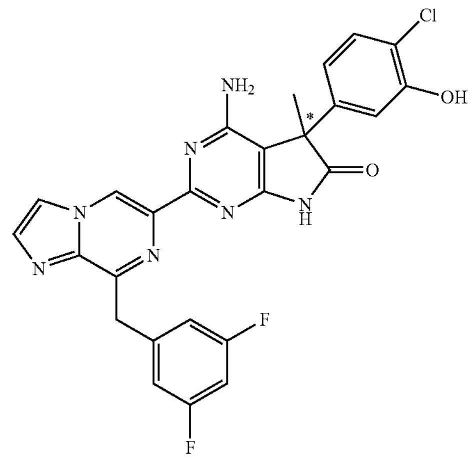 [SMILES: CC1(c2ccc(Cl)c(O)c2)C(=O)Nc2nc(-c3cn4ccnc4c(Cc4cc(F)cc(F)c4)n3)nc(N)c21] | 4-Amino-5-(4-chloro-3-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one | 534 | I-12A |
| 37-B | 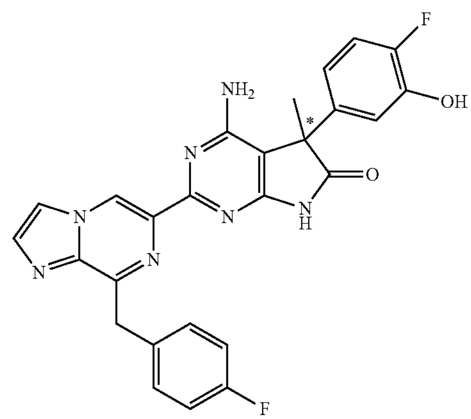 [SMILES: CC1(c2ccc(F)c(O)c2)C(=O)Nc2nc(-c3cn4ccnc4c(Cc4ccc(F)cc4)n3)nc(N)c21] | 4-Amino-5-(4-fluoro-3-hydroxyphenyl)-2-{8-[(4-fluorophenyl)methyl]imidazo[1,2-a]pyrazin-6-yl}-5-methyl-5,7-dihydro-6H-pyrrolo[2,3-d]pyrimidin-6-one | 500 | I-6B |
| 38-B | 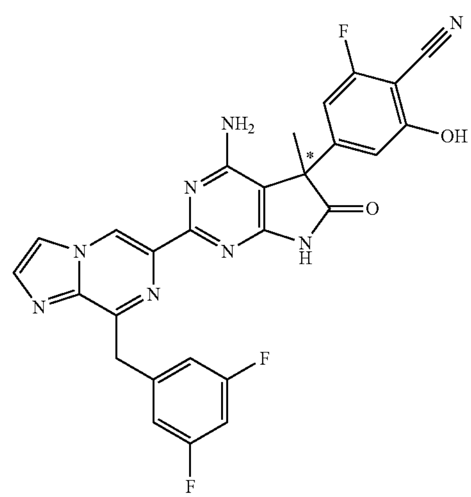 [SMILES: CC1(c2cc(O)c(C#N)c(F)c2)C(=O)Nc2nc(-c3cn4ccnc4c(Cc4cc(F)cc(F)c4)n3)nc(N)c21] | 4-(4-Amino-2-{8-[(3,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile | 543 | I-23B |

TABLE 6-continued

Examples 5-B-105-B

| Ex. | Structure | Name | MS (M + 1) | Chiral starting material |
|---|---|---|---|---|
| 39-B | 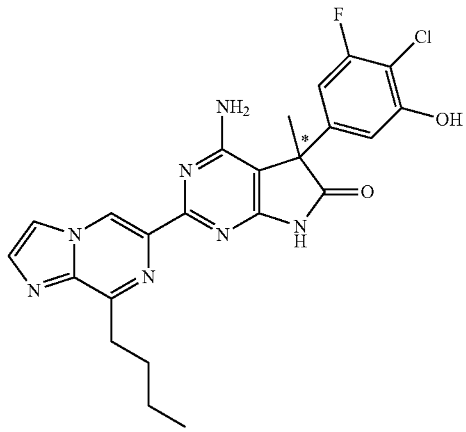 [SMILES: CCCCc1nc(-c2nc(N)c3c(n2)NC(=O)C3(C)c2cc(O)c(Cl)c(F)c2)cn2ccnc12] | 4-Amino-2-(8-butylimidazo[1,2-a]pyrazin-6-yl)-5-(4-chloro-3-fluoro-5-hydroxyphenyl)-5-methyl-5,7-dihydro-6H-pyrrolo[2,3-d]pyrimidin-6-one | 482 | I-7B |
| 40-B | 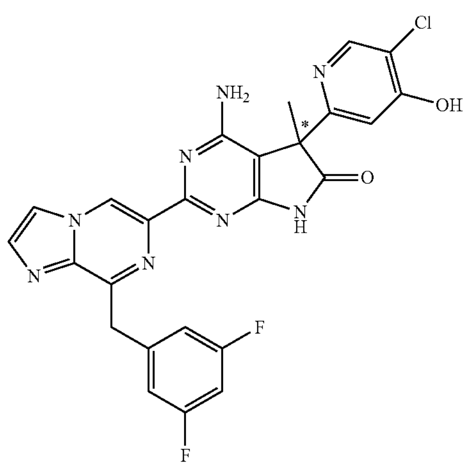 [SMILES: CC1(c2cc(O)c(Cl)cn2)C(=O)Nc2nc(-c3cn4ccnc4c(Cc4cc(F)cc(F)c4)n3)nc(N)c21] | 4-Amino-5-(5-chloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one | 535 | I-5B |
| 41-B | 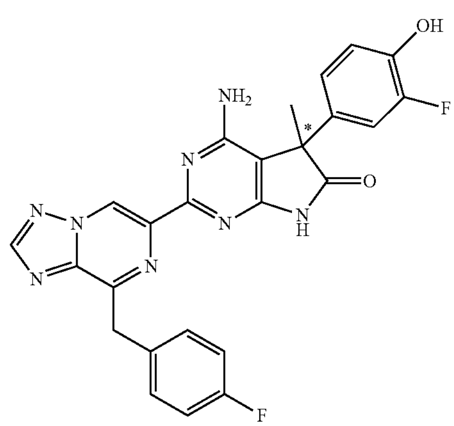 [SMILES: CC1(c2ccc(O)c(F)c2)C(=O)Nc2nc(-c3cn4ncnc4c(Cc4ccc(F)cc4)n3)nc(N)c21] | 4-Amino-5-(3-fluoro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one | 501 | I-28B |

TABLE 6-continued

Examples 5-B-105-B

| Ex. | Structure | Name | MS (M + 1) | Chiral starting material |
|---|---|---|---|---|
| 42-B | 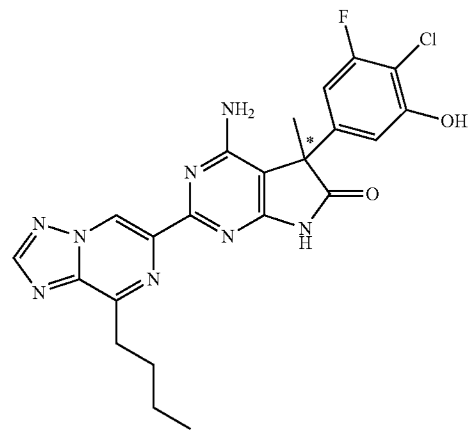 [SMILES: CCCCc1nc(-c2nc(N)c3c(n2)NC(=O)C3(C)c2cc(O)c(Cl)c(F)c2)cn2ncnc12] | 4-Amino-2-(8-butyl-[1,2,4]triazolo[1,5-a]pyrazin-6-yl)-5-(4-chloro-3-fluoro-5-hydroxyphenyl)-5-methyl-5,7-dihydro-6H-pyrrolo[2,3-d]pyrimidin-6-one | 483 | I-7B |
| 43-B | 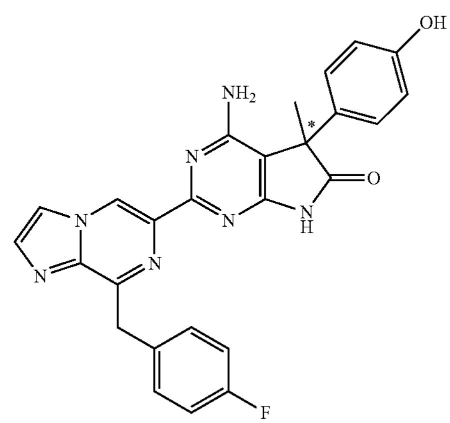 [SMILES: CC1(c2ccc(O)cc2)C(=O)Nc2nc(-c3cn4ccnc4c(Cc4ccc(F)cc4)n3)nc(N)c21] | 4-Amino-2-{8-[(4-fluorophenyl)methyl]imidazo[1,2-a]pyrazin-6-yl}-5-(4-hydroxyphenyl)-5-methyl-5,7-dihydro-6H-pyrrolo[2,3-d]pyrimidin-6-one | 482 | I-29B |
| 44-A | 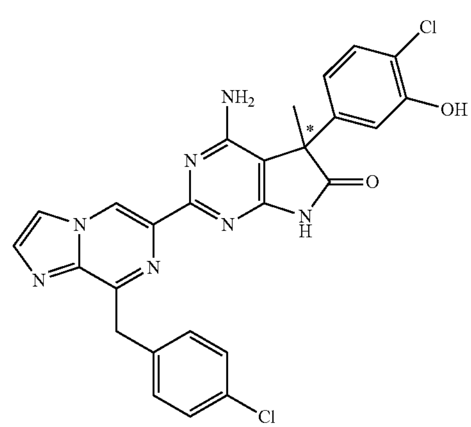 | 4-Amino-5-(4-chloro-3-hydroxyphenyl)-2-{8-[(4-chlorophenyl)methyl]imidazo[1,2-a]pyrazin-6-yl}-5-methyl-5,7-dihydro-6H-pyrrolo[2,3-d]pyrimidin-6-one | 532 | I-12A |

TABLE 6-continued

Examples 5-B-105-B

| Ex. | Structure | Name | MS (M + 1) | Chiral starting material |
|---|---|---|---|---|
| 45-A | 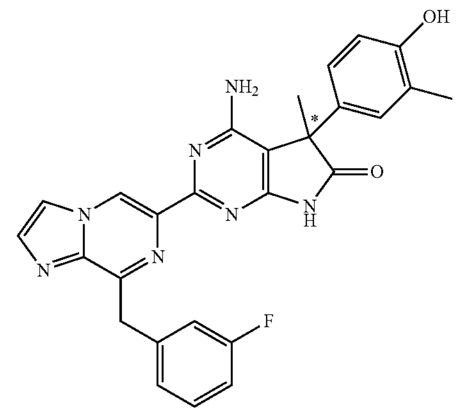 [SMILES: Cc1cc(C2(C)C(=O)Nc3nc(-c4cn5ccnc5c(Cc5cccc(F)c5)n4)nc(N)c32)ccc1O] | 4-Amino-2-{8-[(3-fluorophenyl)methyl]imidazo[1,2-a]pyrazin-6-yl}-5-(4-hydroxy-3-methylphenyl)-5-methyl-5,7-dihydro-6H-pyrrolo[2,3-d]pyrimidin-6-one | 496 | I-26A |
| 46-B | 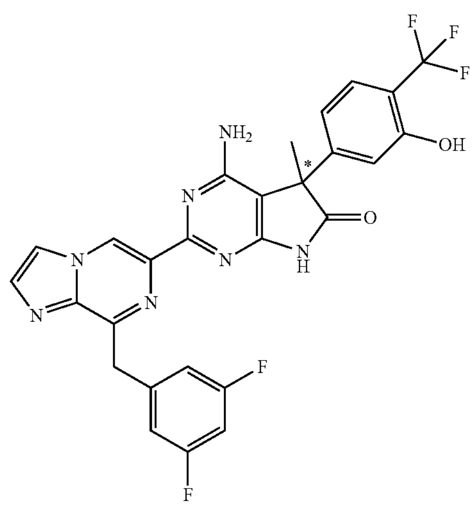 [SMILES: CC1(c2ccc(C(F)(F)F)c(O)c2)C(=O)Nc2nc(-c3cn4ccnc4c(Cc4cc(F)cc(F)c4)n3)nc(N)c21] | 4-Amino-2-{8-[(3,5-difluorophenyl)methyl]imidazo[1,2-a]pyrazin-6-yl}-5-(3-hydroxy-4-(trifluoromethyl)phenyl)-5-methyl-5,7-dihydro-6H-pyrrolo[2,3-d]pyrimidin-6-one | 568 | I-9B |
| 47-B | 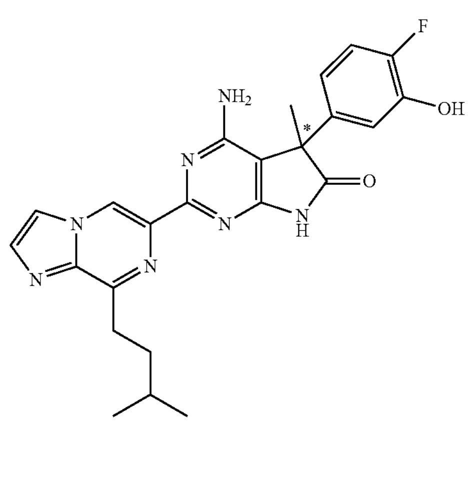 [SMILES: CC(C)CCc1nc(-c2nc(N)c3c(n2)NC(=O)C3(C)c2ccc(F)c(O)c2)cn2ccnc12] | 4-Amino-5-(4-fluoro-3-hydroxyphenyl)-2-(8-isopentylimidazo[1,2-a]pyrazin-6-yl)-5-methyl-5,7-dihydro-6H-pyrrolo[2,3-d]pyrimidin-6-one | 460 | I-6B |

TABLE 6-continued

Examples 5-B-105-B

| Ex. | Structure | Name | MS (M + 1) | Chiral starting material |
|---|---|---|---|---|
| 48-B | 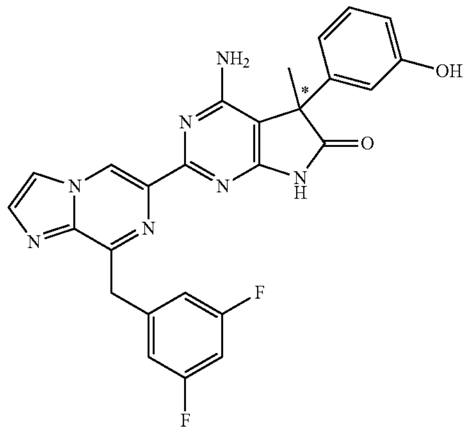 [SMILES: CC1(c2cccc(O)c2)C(=O)Nc2nc(-c3cn4ccnc4c(Cc4cc(F)cc(F)c4)n3)nc(N)c21] | 4-Amino-2-{8-[(3,5-difluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one | 500 | I-17B |
| 49-A | 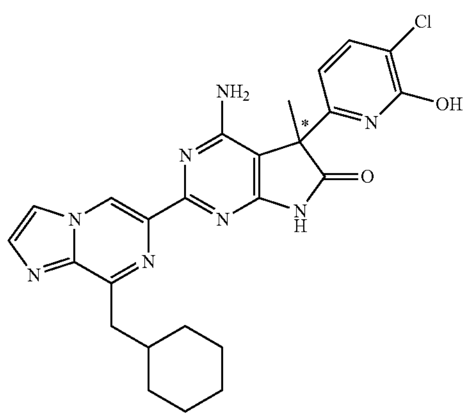 [SMILES: CC1(c2ccc(Cl)c(O)n2)C(=O)Nc2nc(-c3cn4ccnc4c(CC4CCCCC4)n3)nc(N)c21] | 4-Amino-5-(5-chloro-6-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one | 505 | I-16A |
| 50-A | 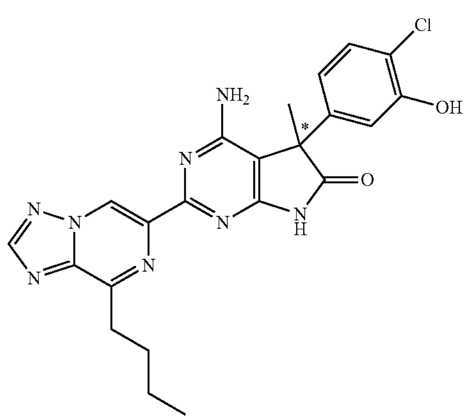 [SMILES: CCCCc1nc(-c2nc(N)c3c(n2)NC(=O)C3(C)c2ccc(Cl)c(O)c2)cn2ncnc12] | 4-Amino-2-(8-butyl-[1,2,4]triazolo[1,5-a]pyrazin-6-yl)-5-(4-chloro-3-hydroxyphenyl)-5-methyl-5,7-dihydro-6H-pyrrolo[2,3-d]pyrimidin-6-one | 465 | I-12A |

TABLE 6-continued

Examples 5-B-105-B

| Ex. | Structure | Name | MS (M + 1) | Chiral starting material |
|---|---|---|---|---|
| 51-B | 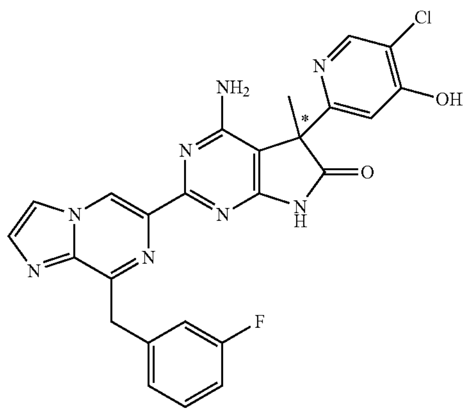 [SMILES: CC1(c2cc(O)c(Cl)cn2)C(=O)Nc2nc(-c3cn4ccnc4c(Cc4cccc(F)c4)n3)nc(N)c21] | 4-Amino-5-(5-chloro-4-hydroxypyridin-2-yl)-2-{8-[(3-fluorophenyl)methyl]imidazo[1,2-a]pyrazin-6-yl}-5-methyl-5,7-dihydro-6H-pyrrolo[2,3-d]pyrimidin-6-one | 517 | I-5B |
| 52-A | 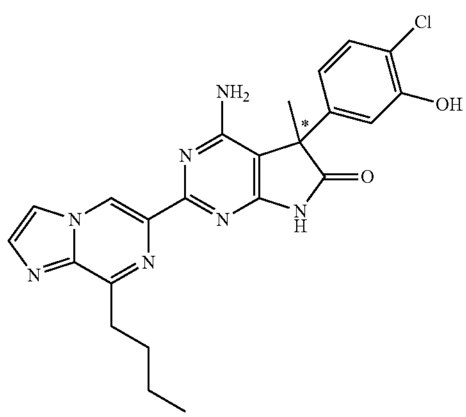 [SMILES: CCCCc1nc(-c2nc(N)c3c(n2)NC(=O)C3(C)c2ccc(Cl)c(O)c2)cn2ccnc12] | 4-Amino-2-(8-butylimidazo[1,2-a]pyrazin-6-yl)-5-(4-chloro-3-hydroxyphenyl)-5-methyl-5,7-dihydro-6H-pyrrolo[2,3-d]pyrimidin-6-one | 465 | I-12A |
| 53-B | 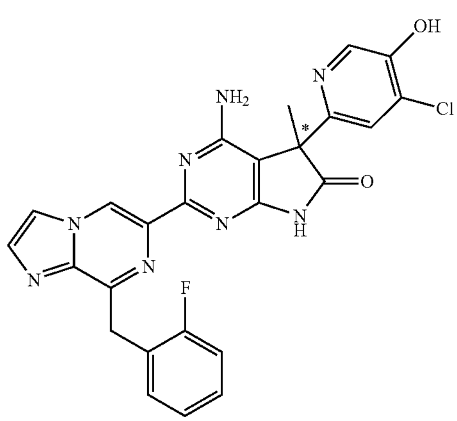 [SMILES: CC1(c2cc(Cl)c(O)cn2)C(=O)Nc2nc(-c3cn4ccnc4c(Cc4ccccc4F)n3)nc(N)c21] | 4-Amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 517 | I-5B |

TABLE 6-continued

Examples 5-B-105-B

| Ex. | Structure | Name | MS (M + 1) | Chiral starting material |
|---|---|---|---|---|
| 54-B | 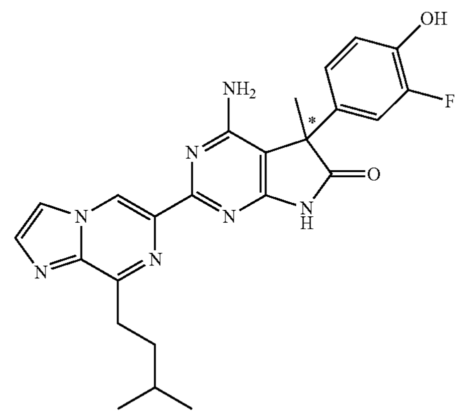 [SMILES: CC(C)CCc1nc(-c2nc(N)c3c(n2)NC(=O)C3(C)c2ccc(O)c(F)c2)cn2ccnc12] | 4-Amino-5-(3-fluoro-4-hydroxyphenyl)-2-(8-isopentylimidazo[1,2-a]pyrazin-6-yl)-5-methyl-5,7-dihydro-6H-pyrrolo[2,3-d]pyrimidin-6-one | 462 | I-28B |
| 55-A | 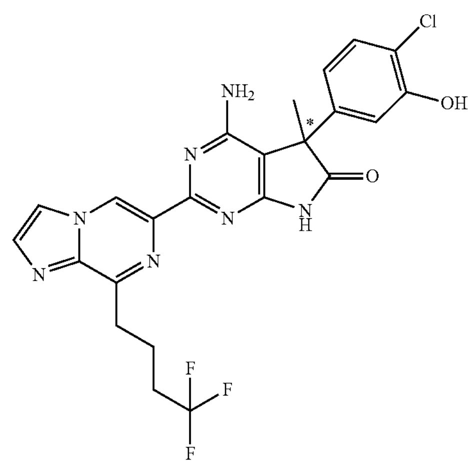 [SMILES: CC1(c2ccc(Cl)c(O)c2)C(=O)Nc2nc(-c3cn4ccnc4c(CCCC(F)(F)F)n3)nc(N)c21] | 4-Amino-5-(4-chloro-3-hydroxyphenyl)-5-methyl-2-(8-(4,4,4-trifluorobutyl)imidazo[1,2-a]pyrazin-6-yl)-5,7-dihydro-6H-pyrrolo[2,3-d]pyrimidin-6-one | 518 | I-12A |
| 56-B | 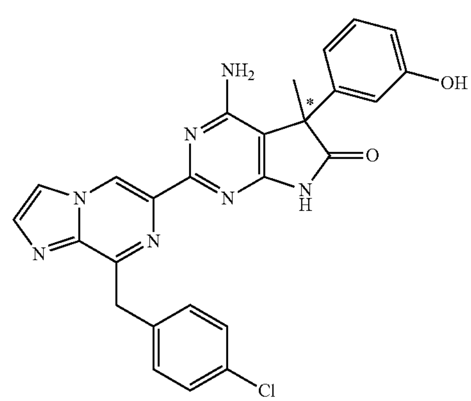 | 4-Amino-2-{8-[(4-chlorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one | 498 | I-17B |

TABLE 6-continued

Examples 5-B-105-B

| Ex. | Structure | Name | MS (M + 1) | Chiral starting material |
|---|---|---|---|---|
| 57-B | 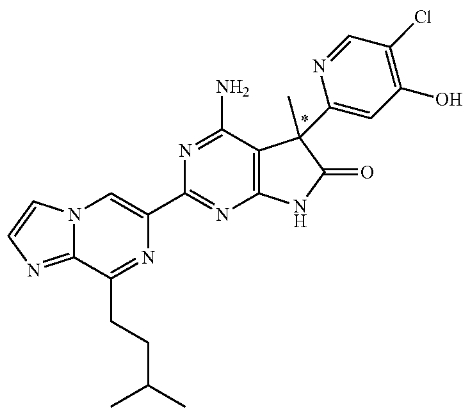 | 4-Amino-5-(5-chloro-4-hydroxypyridin-2-yl)-2-(8-isopentylimidazo[1,2-a]pyrazin-6-yl)-5-methyl-5,7-dihydro-6H-pyrrolo[2,3-d]pyrimidin-6-one | 479 | I-5B |
| 58-B | 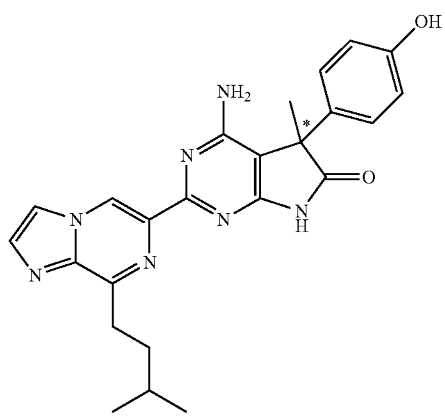 [SMILES: CC(C)CCc1nc(-c2nc(N)c3c(n2)NC(=O)C3(C)c2ccc(O)cc2)cn2ccnc12] | 4-Amino-5-(4-hydroxyphenyl)-2-(8-isopentylimidazo[1,2-a]pyrazin-6-yl)-5-methyl-5,7-dihydro-6H-pyrrolo[2,3-d]pyrimidin-6-one | 444 | I-29B |
| 59-B | 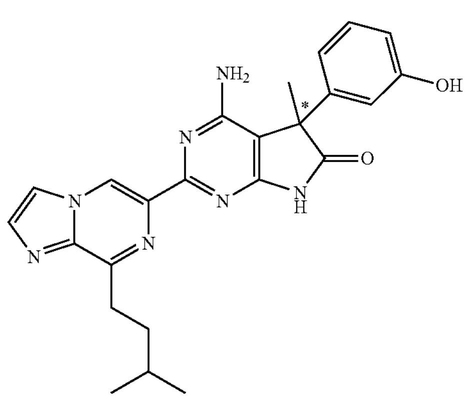 [SMILES: CC(C)CCc1nc(-c2nc(N)c3c(n2)NC(=O)C3(C)c2cccc(O)c2)cn2ccnc12] | 4-Amino-5-(3-hydroxyphenyl)-2-(8-isopentylimidazo[1,2-a]pyrazin-6-yl)-5-methyl-5,7-dihydro-6H-pyrrolo[2,3-d]pyrimidin-6-one | 444 | I-17B |

TABLE 6-continued

Examples 5-B-105-B

| Ex. | Structure | Name | MS (M + 1) | Chiral starting material |
|---|---|---|---|---|
| 60-B | 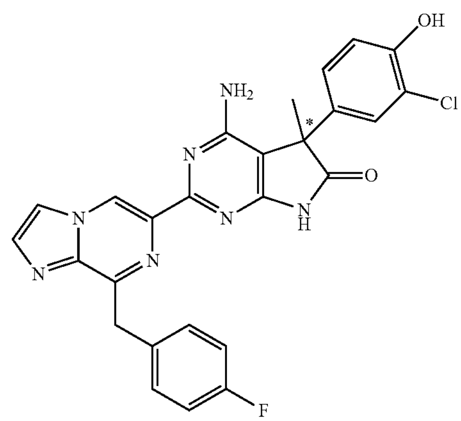 | 4-Amino-5-(3-chloro-4-hydroxyphenyl)-2-{8-[(4-fluorophenyl)methyl]imidazo[1,2-a]pyrazin-6-yl]-5-methyl-5,7-dihydro-6H-pyrrolo[2,3-d]pyrimidin-6-one | 516 | I-11B |
| 61-B | 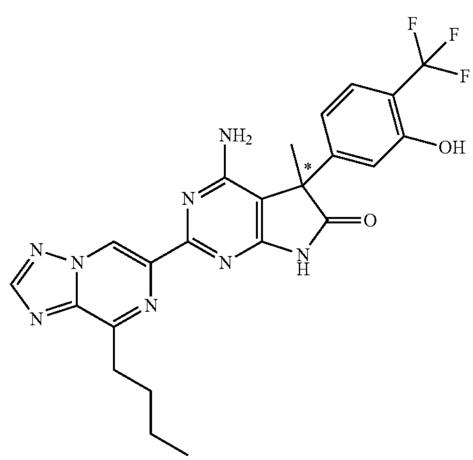 [SMILES: CCCCc1nc(-c2nc(N)c3c(n2)NC(=O)C3(C)c2ccc(C(F)(F)F)c(O)c2)cn2ncnc12] | 4-Amino-2-(8-butyl-[1,2,4]triazolo[1,5-a]pyrazin-6-yl)-5-(3-hydroxy-4-(trifluoromethyl)phenyl)-5-methyl-5,7-dihydro-6H-pyrrolo[2,3-d]pyrimidin-6-one | 499 | I-9B |
| 62-B | 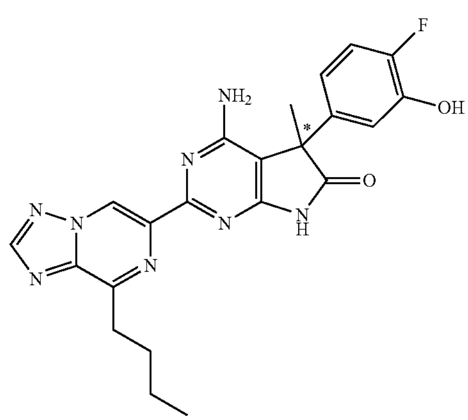 [SMILES: CCCCc1nc(-c2nc(N)c3c(n2)NC(=O)C3(C)c2ccc(F)c(O)c2)cn2ncnc12] | 4-Amino-2-(8-butyl-[1,2,4]triazolo[1,5-a]pyrazin-6-yl)-5-(4-fluoro-3-hydroxyphenyl)-5-methyl-5,7-dihydro-6H-pyrrolo[2,3-d]pyrimidin-6-one | 449 | I-6B |

TABLE 6-continued

Examples 5-B-105-B

| Ex. | Structure | Name | MS (M + 1) | Chiral starting material |
|---|---|---|---|---|
| 63-A | 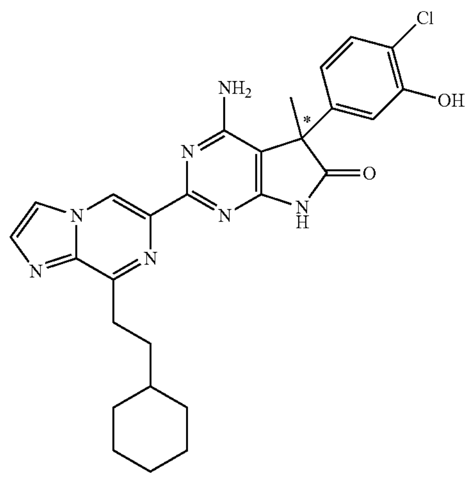 [SMILES: CC1(c2ccc(Cl)c(O)c2)C(=O)Nc2nc(-c3cn4ccnc4c(CCC4CCCCC4)n3)nc(N)c21] | 4-Amino-5-(4-chloro-3-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one | 518 | I-12A |
| 64-B | 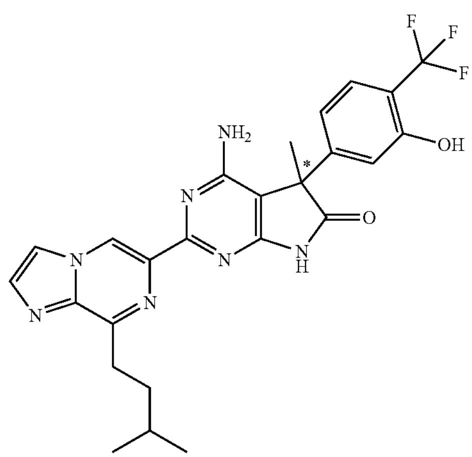 [SMILES: CC(C)CCc1nc(-c2nc(N)c3c(n2)NC(=O)C3(C)c2ccc(C(F)(F)F)c(O)c2)cn2ccnc12] | 4-Amino-5-(3-hydroxy-4-(trifluoromethyl)phenyl)-2-(8-isopentylimidazo[1,2-a]pyrazin-6-yl)-5-methyl-5,7-dihydro-6H-pyrrolo[2,3-d]pyrimidin-6-one | 512 | I-9B |
| 65-A | 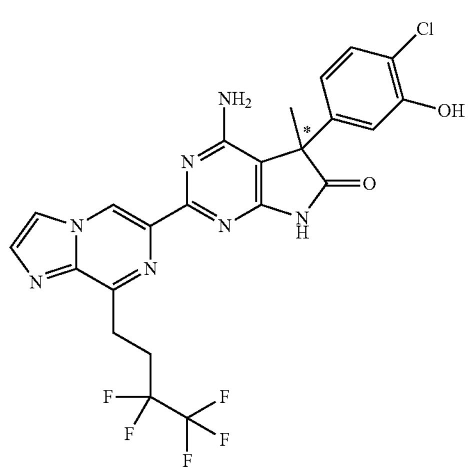 [SMILES: CC1(c2ccc(Cl)c(O)c2)C(=O)Nc2nc(-c3cn4ccnc4c(CCC(F)(F)C(F)(F)F)n3)nc(N)c21] | 4-Amino-5-(4-chloro-3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one | 554 | I-12A |

TABLE 6-continued

Examples 5-B-105-B

| Ex. | Structure | Name | MS (M + 1) | Chiral starting material |
|---|---|---|---|---|
| 66-B | 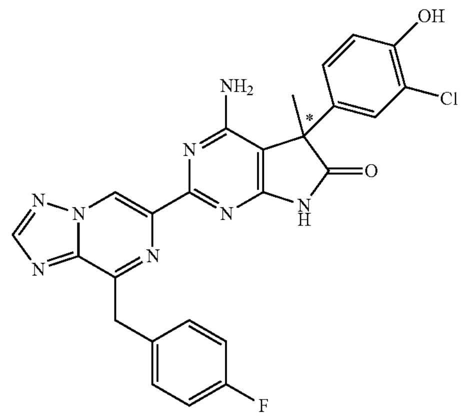 [SMILES: CC1(c2ccc(O)c(Cl)c2)C(=O)Nc2nc(-c3cn4ncnc4c(Cc4ccc(F)cc4)n3)nc(N)c21] | 4-Amino-5-(3-chloro-4-hydroxyphenyl)-2-{8-[(4-fluorophenyl)methyl]-[1,2,4]triazolo[1,5-a]pyrazin-6-yl}-5-methyl-5,7-dihydro-6H-pyrrolo[2,3-d]pyrimidin-6-one | 517 | I-11B |
| 67-A | 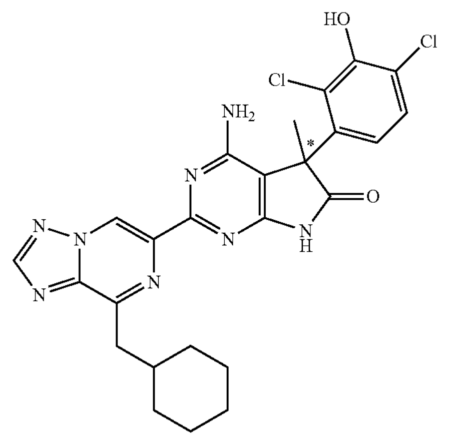 [SMILES: CC1(c2ccc(Cl)c(O)c2Cl)C(=O)Nc2nc(-c3cn4ncnc4c(CC4CCCCC4)n3)nc(N)c21] | 4-Amino-2-(8-(cyclohexylmethyl)-[1,2,4]triazolo[1,5-a]pyrazin-6-yl)-5-(2,4-dichloro-3-hydroxyphenyl)-5-methyl-5,7-dihydro-6H-pyrrolo[2,3-d]pyrimidin-6-one | 539 | I-19A |
| 68-B | 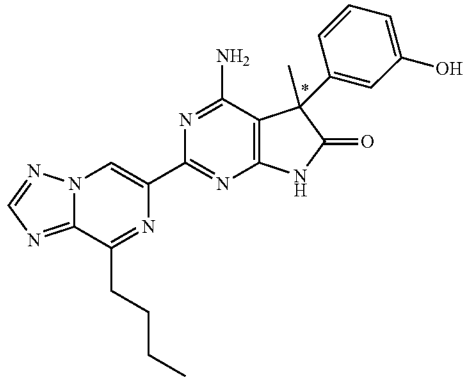 [SMILES: CCCCc1nc(-c2nc(N)c3c(n2)NC(=O)C3(C)c2cccc(O)c2)cn2ncnc12] | 4-Amino-2-(8-butyl-[1,2,4]triazolo[1,5-a]pyrazin-6-yl)-5-(3-hydroxyphenyl)-5-methyl-5,7-dihydro-6H-pyrrolo[2,3-d]pyrimidin-6-one | 431 | I-17B |

TABLE 6-continued

Examples 5-B-105-B

| Ex. | Structure | Name | MS (M + 1) | Chiral starting material |
|---|---|---|---|---|
| 69-A | 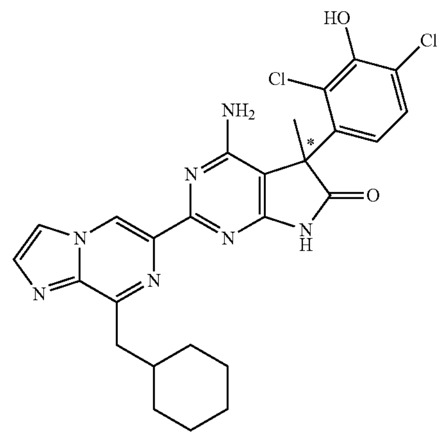 [SMILES: CC1(c2ccc(Cl)c(O)c2Cl)C(=O)Nc2nc(-c3cn4ccnc4c(CC4CCCCC4)n3)nc(N)c21] | 4-Amino-2-(8-(cyclohexylmethyl)imidazo[1,2-a]pyrazin-6-yl)-5-(2,4-dichloro-3-hydroxyphenyl)-5-methyl-5,7-dihydro-6H-pyrrolo[2,3-d]pyrimidin-6-one | 538 | I-19A |
| 70-B | 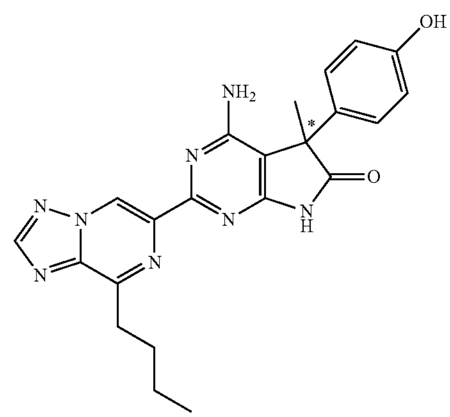 [SMILES: CCCCc1nc(-c2nc(N)c3c(n2)NC(=O)C3(C)c2ccc(O)cc2)cn2ncnc12] | 4-Amino-2-(8-butyl-[1,2,4]triazolo[1,5-a]pyrazin-6-yl)-5-(4-hydroxyphenyl)-5-methyl-5,7-dihydro-6H-pyrrolo[2,3-d]pyrimidin-6-one | 431 | I-29B |
| 71-B | 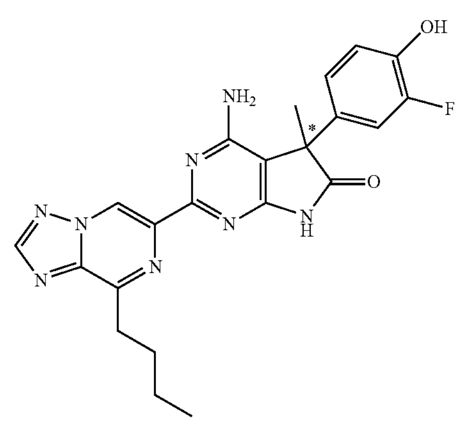 [SMILES: CCCCc1nc(-c2nc(N)c3c(n2)NC(=O)C3(C)c2ccc(O)c(F)c2)cn2ncnc12] | 4-Amino-2-(8-butyl-[1,2,4]triazolo[1,5-a]pyrazin-6-yl)-5-(3-fluoro-4-hydroxyphenyl)-5-methyl-5,7-dihydro-6H-pyrrolo[2,3-d]pyrimidin-6-one | 449 | I-28B |

TABLE 6-continued

Examples 5-B-105-B

| Ex. | Structure | Name | MS (M + 1) | Chiral starting material |
|---|---|---|---|---|
| 72-B | 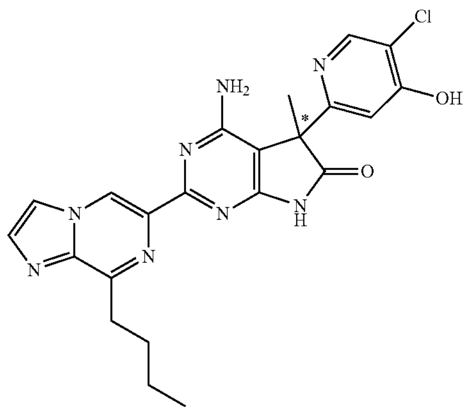 [SMILES: CCCCc1nc(-c2nc(N)c3c(n2)NC(=O)C3(C)c2cc(O)c(Cl)cn2)cn2ccnc12] | 4-Amino-2-(8-butylimidazo[1,2-a]pyrazin-6-yl)-5-(5-chloro-4-hydroxypyridin-2-yl)-5-methyl-5,7-dihydro-6H-pyrrolo[2,3-d]pyrimidin-6-one | 465 | I-5B |
| 73-A | 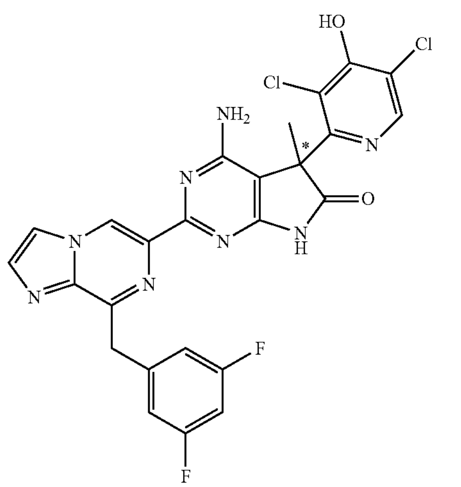 [SMILES: CC1(c2ncc(Cl)c(O)c2Cl)C(=O)Nc2nc(-c3cn4ccnc4c(Cc4cc(F)cc(F)c4)n3)nc(N)c21] | 4-Amino-5-(3,5-dichloro-4-hydroxypyridin-2-yl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one | 569 (M − 1) | I-15A |
| 74-B | 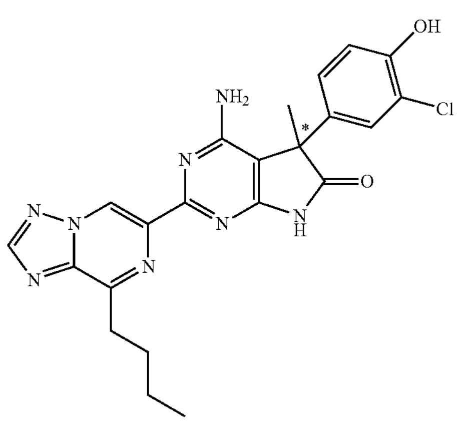 [SMILES: CCCCc1nc(-c2nc(N)c3c(n2)NC(=O)C3(C)c2ccc(O)c(Cl)c2)cn2ncnc12] | 4-Amino-2-(8-butyl-[1,2,4]triazolo[1,5-a]pyrazin-6-yl)-5-(3-chloro-4-hydroxyphenyl)-5-methyl-5,7-dihydro-6H-pyrrolo[2,3-d]pyrimidin-6-one | 465 | I-11B |

TABLE 6-continued

Examples 5-B-105-B

| Ex. | Structure | Name | MS (M + 1) | Chiral starting material |
|---|---|---|---|---|
| 75-B | 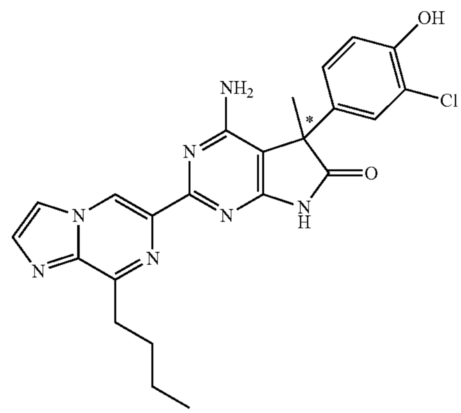 [SMILES: CCCCc1nc(-c2nc(N)c3c(n2)NC(=O)C3(C)c2ccc(O)c(Cl)c2)cn2ccnc12] | 4-Amino-2-(8-butylimidazo[1,2-a]pyrazin-6-yl)-5-(3-chloro-4-hydroxyphenyl)-5-methyl-5,7-dihydro-6H-pyrrolo[2,3-d]pyrimidin-6-one | 464 | I-11B |
| 76-B | 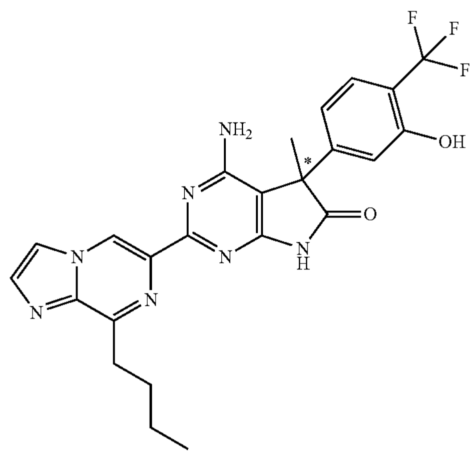 [SMILES: CCCCc1nc(-c2nc(N)c3c(n2)NC(=O)C3(C)c2ccc(C(F)(F)F)c(O)c2)cn2ccnc12] | 4-Amino-2-(8-butylimidazo[1,2-a]pyrazin-6-yl)-5-(3-hydroxy-4-(trifluoromethyl)phenyl)-5-methyl-5,7-dihydro-6H-pyrrolo[2,3-d]pyrimidin-6-one | 498 | I-9B |
| 77-B | 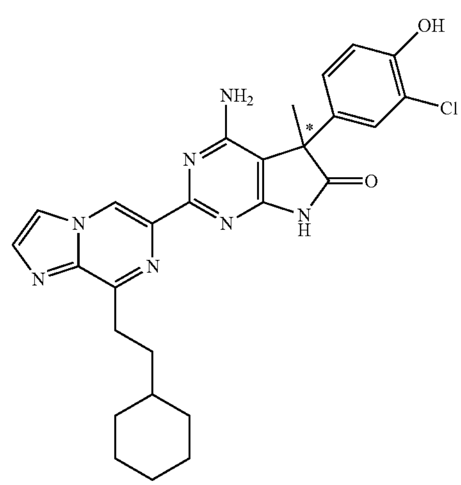 [SMILES: CC1(c2ccc(O)c(Cl)c2)C(=O)Nc2nc(-c3cn4ccnc4c(CCC4CCCCC4)n3)nc(N)c21] | 4-Amino-5-(3-chloro-4-hydroxyphenyl)-2-(8-(2-cyclohexylethyl)imidazo[1,2-a]pyrazin-6-yl)-5-methyl-5,7-dihydro-6H-pyrrolo[2,3-d]pyrimidin-6-one | 518 | I-11B |

TABLE 6-continued

Examples 5-B-105-B

| Ex. | Structure | Name | MS (M + 1) | Chiral starting material |
|---|---|---|---|---|
| 78-B | 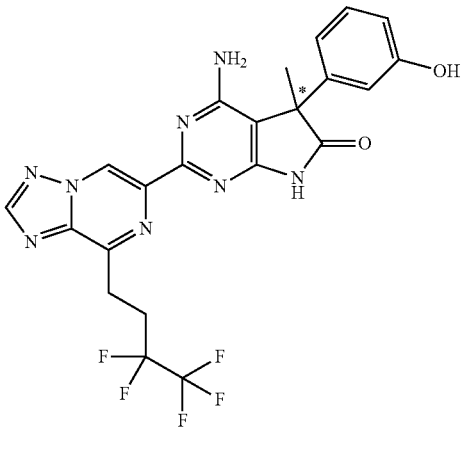 [SMILES: CC1(c2cccc(O)c2)C(=O)Nc2nc(-c3cn4ncnc4c(CCC(F)(F)C(F)(F)F)n3)nc(N)c21] | 4-Amino-5-(3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one | 521 | I-17B |
| 79-B | 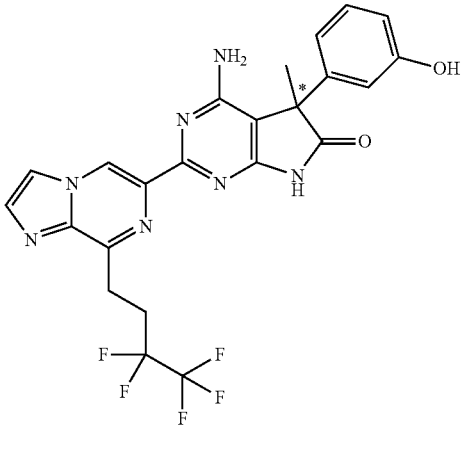 [SMILES: CC1(c2cccc(O)c2)C(=O)Nc2nc(-c3cn4ccnc4c(CCC(F)(F)C(F)(F)F)n3)nc(N)c21] | 4-Amino-5-(3-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one | 520 | I-17B |
| 80-B | 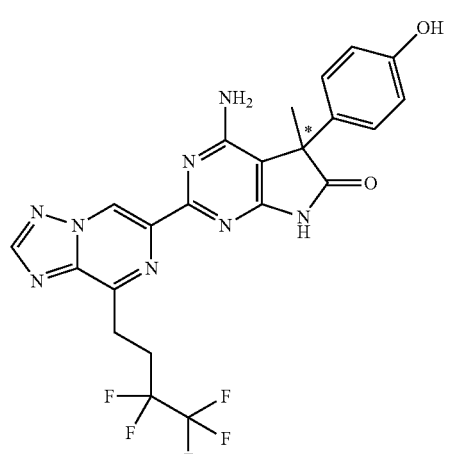 | 4-Amino-5-(4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one | 521 | I-29B |

TABLE 6-continued

Examples 5-B-105-B

| Ex. | Structure | Name | MS (M + 1) | Chiral starting material |
|---|---|---|---|---|
| 81-B | 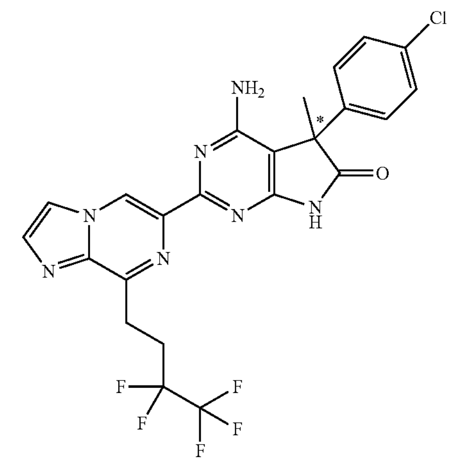 [SMILES: CC1(c2ccc(Cl)cc2)C(=O)Nc2nc(-c3cn4ccnc4c(CCC(F)(F)C(F)(F)F)n3)nc(N)c21] | 4-Amino-5-(4-hydroxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one | 520 | I-29B |
| 82-B | 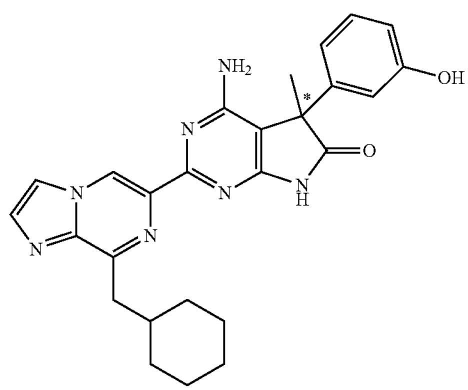 [SMILES: CC1(c2cccc(O)c2)C(=O)Nc2nc(-c3cn4ccnc4c(CC4CCCCC4)n3)nc(N)c21] | 4-Amino-2-(8-(cyclohexylmethyl)imidazo[1,2-a]pyrazin-6-yl)-5-(3-hydroxyphenyl)-5-methyl-5,7-dihydro-6H-pyrrolo[2,3-d]pyrimidin-6-one | 470 | I-17B |
| 83-B | 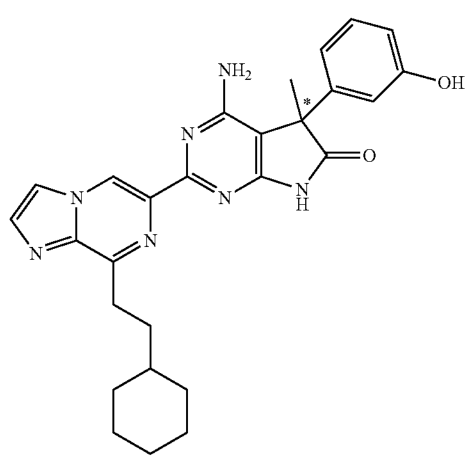 [SMILES: CC1(c2cccc(O)c2)C(=O)Nc2nc(-c3cn4ccnc4c(CCC4CCCCC4)n3)nc(N)c21] | 4-Amino-2-(8-(2-cyclohexylethyl)imidazo[1,2-a]pyrazin-6-yl)-5-(3-hydroxyphenyl)-5-methyl-5,7-dihydro-6H-pyrrolo[2,3-d]pyrimidin-6-one | 484 | I-17B |

TABLE 6-continued

Examples 5-B-105-B

| Ex. | Structure | Name | MS (M + 1) | Chiral starting material |
|---|---|---|---|---|
| 84-B | 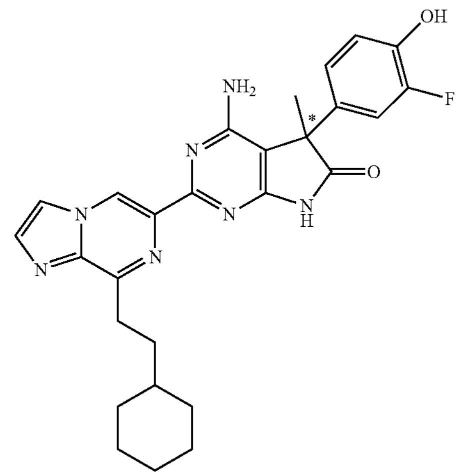 [SMILES: CC1(c2ccc(O)c(F)c2)C(=O)Nc2nc(-c3cn4ccnc4c(CCC4CCCCC4)n3)nc(N)c21] | 4-Amino-2-(8-(2-cyclohexylethyl)imidazo[1,2-a]pyrazin-6-yl)-5-(3-fluoro-4-hydroxyphenyl)-5-methyl-5,7-dihydro-6H-pyrrolo[2,3-d]pyrimidin-6-one | 502 | I-28B |
| 85-B | 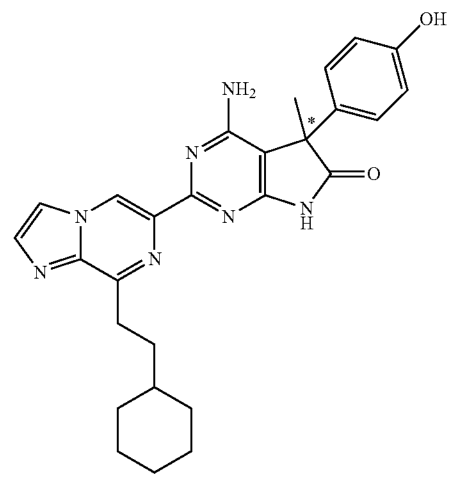 [SMILES: CC1(c2ccc(O)cc2)C(=O)Nc2nc(-c3cn4ccnc4c(CCC4CCCCC4)n3)nc(N)c21] | 4-Amino-2-(8-(2-cyclohexylethyl)imidazo[1,2-a]pyrazin-6-yl)-5-(4-hydroxyphenyl)-5-methyl-5,7-dihydro-6H-pyrrolo[2,3-d]pyrimidin-6-one | 484 | I-29B |
| 86-B | 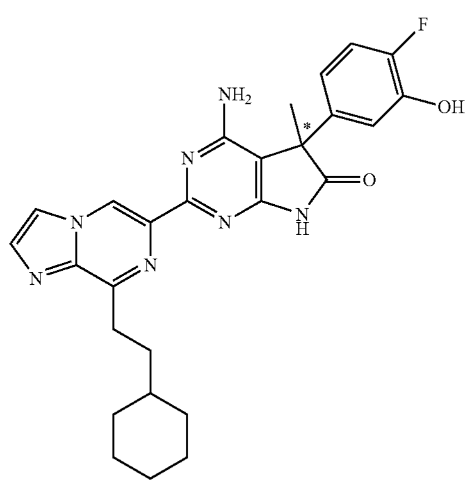 [SMILES: CC1(c2ccc(F)c(O)c2)C(=O)Nc2nc(-c3cn4ccnc4c(CCC4CCCCC4)n3)nc(N)c21] | 4-Amino-2-(8-(2-cyclohexylethyl)imidazo[1,2-a]pyrazin-6-yl)-5-(4-fluoro-3-hydroxyphenyl)-5-methyl-5,7-dihydro-6H-pyrrolo[2,3-d]pyrimidin-6-one | 502 | I-6B |

TABLE 6-continued

Examples 5-B-105-B

| Ex. | Structure | Name | MS (M + 1) | Chiral starting material |
|---|---|---|---|---|
| 87-A | 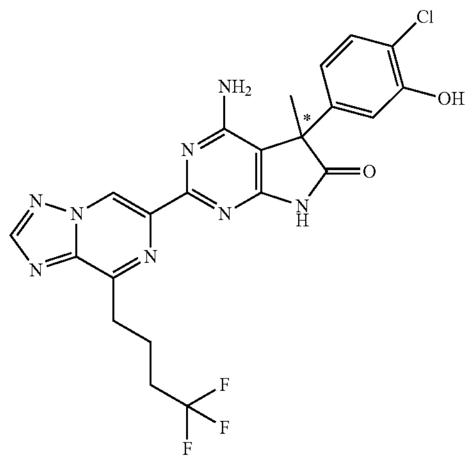 [SMILES: CC1(c2ccc(Cl)c(O)c2)C(=O)Nc2nc(-c3cn4ncnc4c(CCCC(F)(F)F)n3)nc(N)c21] | 4-Amino-5-(4-chloro-3-hydroxyphenyl)-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one | 519 | I-12A |
| 88-A | 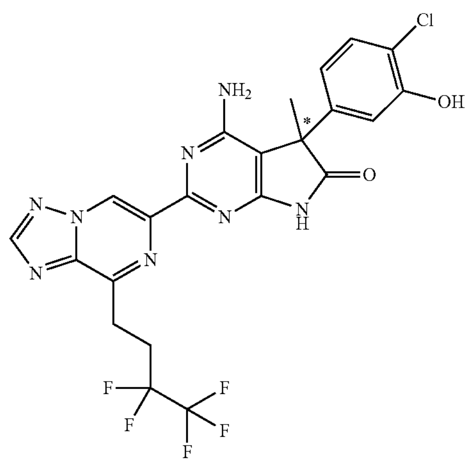 [SMILES: CC1(c2ccc(Cl)c(O)c2)C(=O)Nc2nc(-c3cn4ncnc4c(CCC(F)(F)C(F)(F)F)n3)nc(N)c21] | 4-Amino-5-(4-chloro-3-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one | 555 | I-12A |
| 89-B | 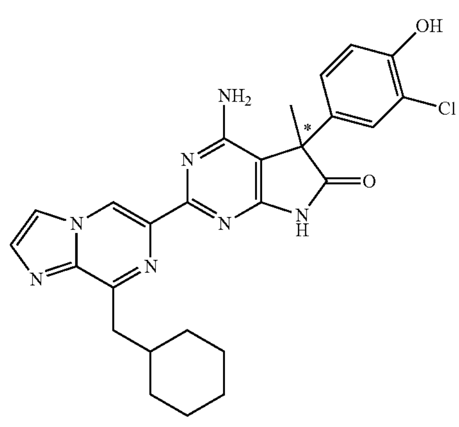 [SMILES: CC1(c2ccc(O)c(Cl)c2)C(=O)Nc2nc(-c3cn4ccnc4c(CC4CCCCC4)n3)nc(N)c21] | 4-Amino-5-(3-chloro-4-hydroxyphenyl)-2-(8-(cyclohexylmethyl)imidazo[1,2-a]pyrazin-6-yl)-5-methyl-5,7-dihydro-6H-pyrrolo[2,3-d]pyrimidin-6-one | 504 | I-11B |

TABLE 6-continued

Examples 5-B-105-B

| Ex. | Structure | Name | MS (M + 1) | Chiral starting material |
|---|---|---|---|---|
| 90-A | 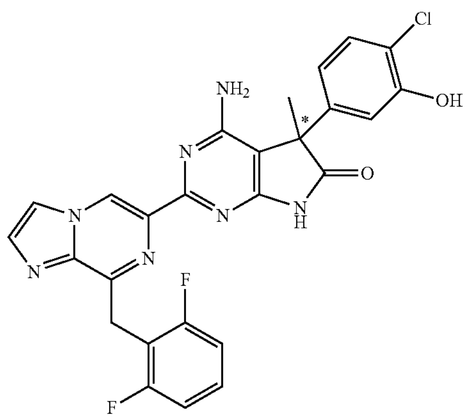 [SMILES: CC1(c2ccc(Cl)c(O)c2)C(=O)Nc2nc(-c3cn4ccnc4c(Cc4c(F)cccc4F)n3)nc(N)c21] | 4-Amino-5-(4-chloro-3-hydroxyphenyl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one | 534 | I-12A |
| 91-A | 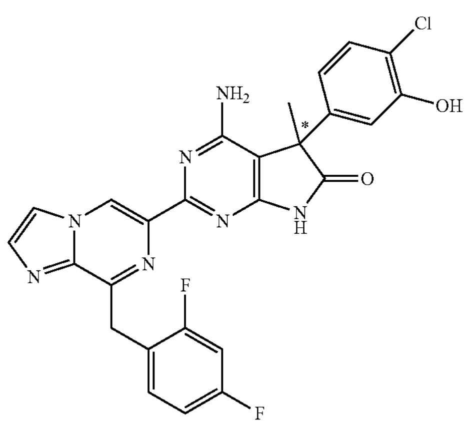 | 4-Amino-5-(4-chloro-3-hydroxyphenyl)-2-{8-[(2,4-difluorophenyl)methyl]imidazo[1,2-a]pyrazin-6-yl}-5-methyl-5,7-dihydro-6H-pyrrolo[2,3-d]pyrimidin-6-one | 534 | I-12A |
| 92-B | 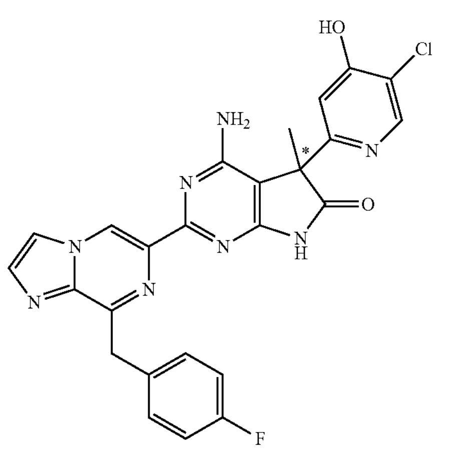 [SMILES: CC1(c2cc(O)c(Cl)cn2)C(=O)Nc2nc(-c3cn4ccnc4c(Cc4ccc(F)cc4)n3)nc(N)c21] | 4-Amino-5-(5-chloro-4-hydroxypyridin-2-yl)-2-{8-[(4-fluorophenyl)methyl]imidazo[1,2-a]pyrazin-6-yl}-5-methyl-5,7-dihydro-6H-pyrrolo[2,3-d]pyrimidin-6-one | 517 | I-5B |

TABLE 6-continued

Examples 5-B-105-B

| Ex. | Structure | Name | MS (M + 1) | Chiral starting material |
|---|---|---|---|---|
| 93-B | 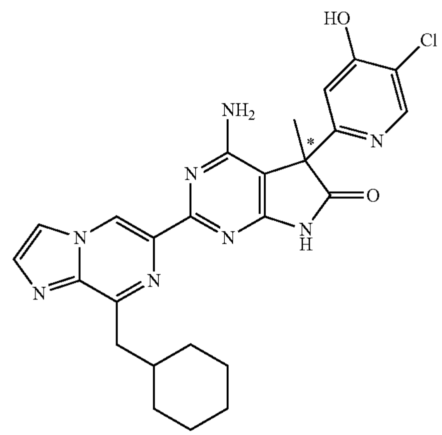 [SMILES: CC1(c2cc(O)c(Cl)cn2)C(=O)Nc2nc(-c3cn4ccnc4c(CC4CCCCC4)n3)nc(N)c21] | 4-Amino-5-(5-chloro-4-hydroxypyridin-2-yl)-2-(8-(cyclohexylmethyl)imidazo[1,2-a]pyrazin-6-yl)-5-methyl-5,7-dihydro-6H-pyrrolo[2,3-d]pyrimidin-6-one | 505 | I-5B |
| 94-B | 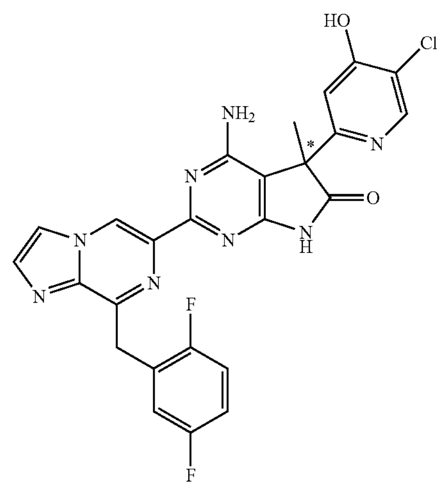 [SMILES: CC1(c2cc(O)c(Cl)cn2)C(=O)Nc2nc(-c3cn4ccnc4c(Cc4cc(F)ccc4F)n3)nc(N)c21] | 4-Amino-5-(5-chloro-4-hydroxypyridin-2-yl)-2-{8-[(2,5-difluorophenyl)methyl]imidazo[1,2-a]pyrazin-6-yl}-5-methyl-5,7-dihydro-6H-pyrrolo[2,3-d]pyrimidin-6-one | 535 | I-5B |
| 95-A | 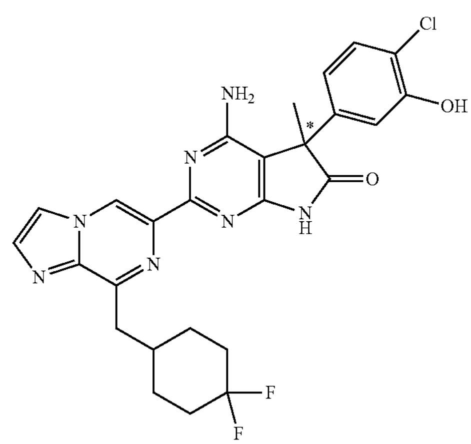 [SMILES: CC1(c2ccc(Cl)c(O)c2)C(=O)Nc2nc(-c3cn4ccnc4c(CC4CCC(F)(F)CC4)n3)nc(N)c21] | 4-Amino-5-(4-chloro-3-hydroxyphenyl)-2-(8-((4,4-difluorocyclohexyl)methyl)imidazo[1,2-a]pyrazin-6-yl)-5-methyl-5,7-dihydro-6H-pyrrolo[2,3-d]pyrimidin-6-one | 540 | I-12A |

TABLE 6-continued

Examples 5-B-105-B

| Ex. | Structure | Name | MS (M + 1) | Chiral starting material |
|---|---|---|---|---|
| 96-B | 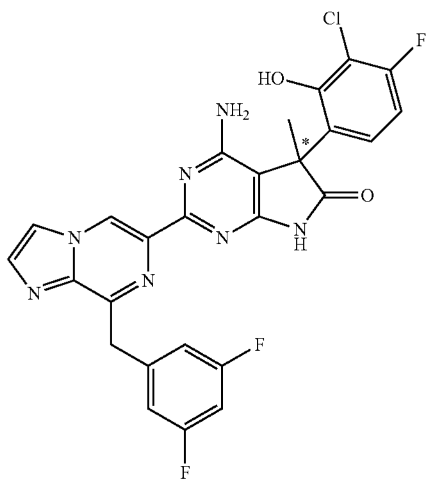 [SMILES: CC1(c2ccc(F)c(Cl)c2O)C(=O)Nc2nc(-c3cn4ccnc4c(Cc4cc(F)cc(F)c4)n3)nc(N)c21] | 4-Amino-5-(3-chloro-4-fluoro-2-hydroxyphenyl)-2-{8-[(3,5-difluorophenyl)methyl]imidazo[1,2-a]pyrazin-6-yl}-5-methyl-5,7-dihydro-6H-pyrrolo[2,3-d]pyrimidin-6-one | 552 | I-20B |
| 97-B | 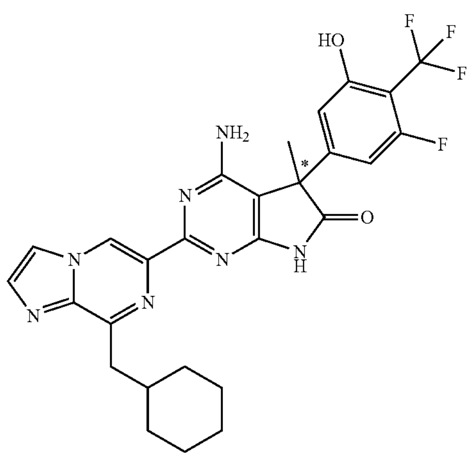 [SMILES: CC1(c2cc(O)c(C(F)(F)F)c(F)c2)C(=O)Nc2nc(-c3cn4ccnc4c(CC4CCCCC4)n3)nc(N)c21] | 4-Amino-2-(8-(cyclohexylmethyl)imidazo[1,2-a]pyrazin-6-yl)-5-(3-fluoro-5-hydroxy-4-(trifluoromethyl)phenyl)-5-methyl-5,7-dihydro-6H-pyrrolo[2,3-d]pyrimidin-6-one | 556 | I-24B |
| 98-B | 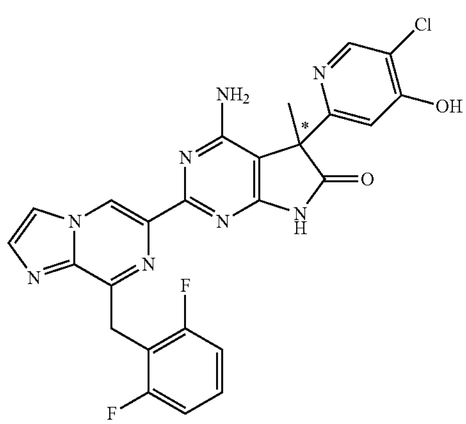 [SMILES: CC1(c2cc(O)c(Cl)cn2)C(=O)Nc2nc(-c3cn4ccnc4c(Cc4c(F)cccc4F)n3)nc(N)c21] | 4-Amino-5-(5-chloro-4-hydroxypyridin-2-yl)-2-{8-[(2,6-difluorophenyl)methyl]imidazo[1,2-a]pyrazin-6-yl}-5-methyl-5,7-dihydro-6H-pyrrolo[2,3-d]pyrimidin-6-one | 535 | I-5B |

TABLE 6-continued

Examples 5-B-105-B

| Ex. | Structure | Name | MS (M + 1) | Chiral starting material |
|---|---|---|---|---|
| 99-A | 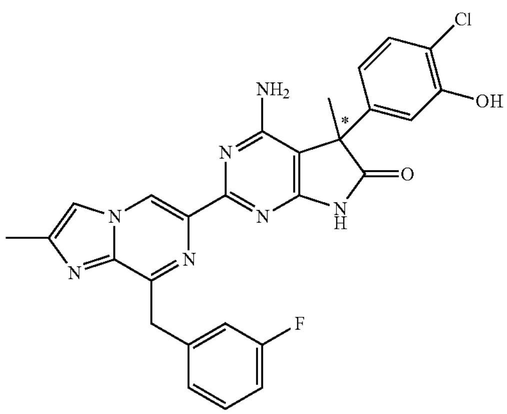 [SMILES: Cc1cn2cc(-c3nc(N)c4c(n3)NC(=O)C4(C)c3ccc(Cl)c(O)c3)nc(Cc3cccc(F)c3)c2n1] | 4-Amino-5-(4-chloro-3-hydroxyphenyl)-2-{8-[(3-fluorophenyl)methyl]-2-methylimidazo[1,2-a]pyrazin-6-yl}-5-methyl-5,7-dihydro-6H-pyrrolo[2,3-d]pyrimidin-6-one | 530 | I-12A |
| 100-A | 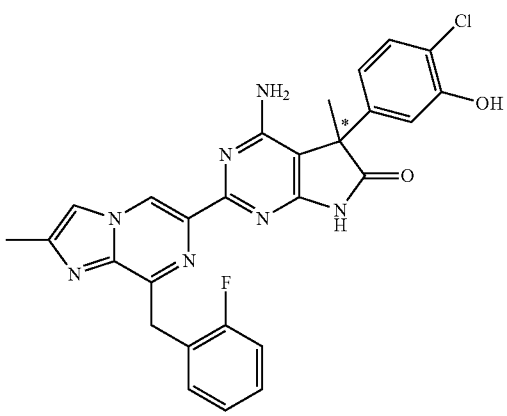 [SMILES: Cc1cn2cc(-c3nc(N)c4c(n3)NC(=O)C4(C)c3ccc(Cl)c(O)c3)nc(Cc3ccccc3F)c2n1] | 4-Amino-5-(4-chloro-3-hydroxyphenyl)-2-{8-[(2-fluorophenyl)methyl]-2-methylimidazo[1,2-a]pyrazin-6-yl}-5-methyl-5,7-dihydro-6H-pyrrolo[2,3-d]pyrimidin-6-one | 530 | I-12A |
| 101-B | 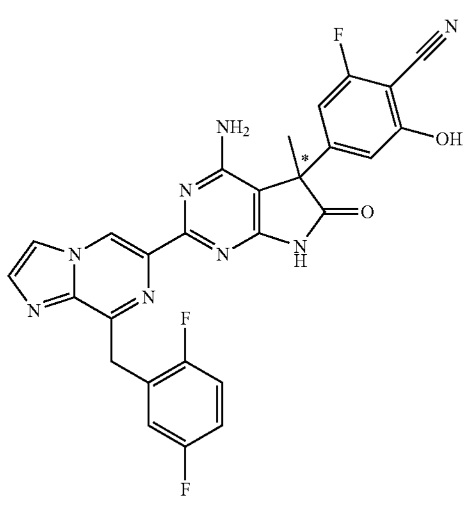 [SMILES: CC1(c2cc(O)c(C#N)c(F)c2)C(=O)Nc2nc(-c3cn4ccnc4c(Cc4cc(F)ccc4F)n3)nc(N)c21] | 4-(4-Amino-2-{8-[(2,5-difluorophenyl)methyl]imidazo[1,2-a]pyrazin-6-yl}-5-methyl-6-oxo-6,7-dihydro-5H-pyrrolo[2,3-d]pyrimidin-5-yl)-2-fluoro-6-hydroxybenzonitrile | 543 | I-23B |

TABLE 6-continued

Examples 5-B-105-B

| Ex. | Structure | Name | MS (M + 1) | Chiral starting material |
|---|---|---|---|---|
| 102-B | 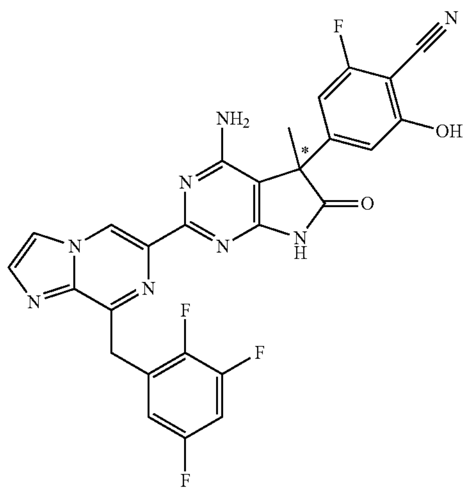 [SMILES: CC1(c2cc(O)c(C#N)c(F)c2)C(=O)Nc2nc(-c3cn4ccnc4c(Cc4cc(F)cc(F)c4F)n3)nc(N)c21] | 4-(4-Amino-5-methyl-6-oxo-2-{8-[(2,3,5-trifluorophenyl)methyl]imidazo[1,2-a]pyrazin-6-yl}-6,7-dihydro-5H-pyrrolo[2,3-d]pyrimidin-5-yl)-2-fluoro-6-hydroxybenzonitrile | 561 | I-23B |
| 103-B | 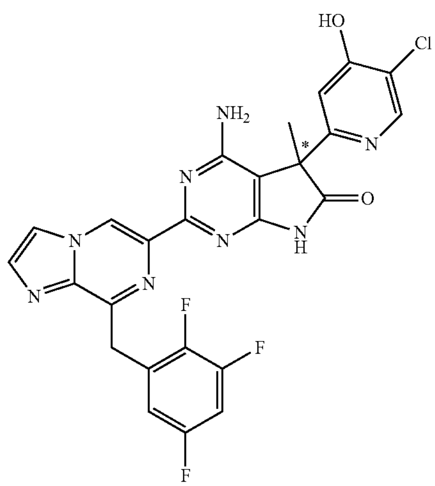 [SMILES: CC1(c2cc(O)c(Cl)cn2)C(=O)Nc2nc(-c3cn4ccnc4c(Cc4cc(F)cc(F)c4F)n3)nc(N)c21] | 4-Amino-5-(5-chloro-4-hydroxypyridin-2-yl)-5-methyl-2-{8-[(2,3,5-trifluorophenyl)methyl]imidazo[1,2-a]pyrazin-6-yl}-5,7-dihydro-6H-pyrrolo[2,3-d]pyrimidin-6-one | 553 | I-5B |
| 104-B | 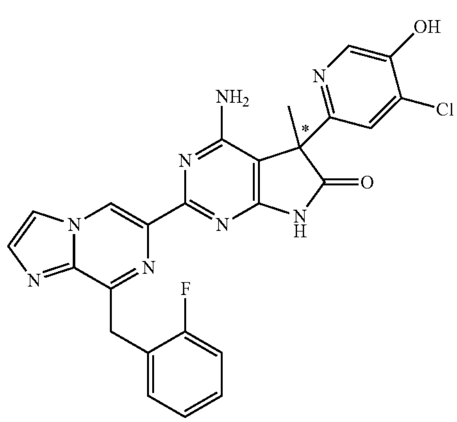 [SMILES: CC1(c2cc(Cl)c(O)cn2)C(=O)Nc2nc(-c3cn4ccnc4c(Cc4ccccc4F)n3)nc(N)c21] | 4-Amino-5-(4-chloro-5-hydroxypyridin-2-yl)-2-{8-[(2-fluorophenyl)methyl]imidazo[1,2-a]pyrazin-6-yl}-5-methyl-5,7-dihydro-6H-pyrrolo[2,3-d]pyrimidin-6-one | 517 | I-10B |

TABLE 6-continued

Examples 5-B-105-B

| Ex. | Structure | Name | MS (M + 1) | Chiral starting material |
|---|---|---|---|---|
| 105-B | 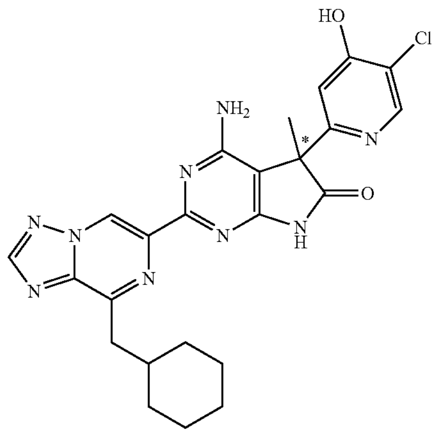 [SMILES: CC1(c2cc(O)c(Cl)cn2)C(=O)Nc2nc(-c3cn4ncnc4c(CC4CCCCC4)n3)nc(N)c21] | 4-Amino-5-(5-chloro-4-hydroxypyridin-2-yl)-2-(8-(cyclohexylmethyl)-[1,2,4]triazolo[1,5-a]pyrazin-6-yl)-5-methyl-5,7-dihydro-6H-pyrrolo[2,3-d]pyrimidin-6-one | 506 | I-5B |

Example 106-A

4-Amino-5-(4-chloro-3-hydroxyphenyl)-2-(8-(4-fluorobutyl)-[1,2,4]triazolo[1,5-a]pyrazin-6-yl)-5-methyl-5,7-dihydro-6H-pyrrolo[2,3-d]pyrimidin-6-one 4-Amino-5-(4-chloro-3-hydroxyphenyl)-2-(8-(4-fluorobutyl)-[1,2,4]triazolo[1,5-a]pyrazin-6-yl)-5-methyl-5,7-dihydro-6H-pyrrolo[2,3-d]pyrimidin-6-one Into a flask were placed amidine I-A19 (100 mg, 0.35 mmol), chiral Br-Lactam I-25A (114 mg, 0.35 mmol), 1,4-dioxane (10 mL) and Et$_3$N (0.24 mL, 1.74 mmol). The resulting mixture was stirred at 75° C. for 16 h, then quenched with water (100 mL), extracted with EtOAc (3×50 mL) and the combined organic layer was dried over anhydr. Na$_2$SO$_4$, filtered and concentrated to dryness in vacuo. The crude product was washed with MeOH (3×2 mL) to afford the title compound, 106-A. MS: 483 (M+1). $^1$H NMR (DMSO-d$_6$, 300 MHz): δ 11.25 (br s, 1H), 10.12 (s, 1H), 9.39 (s, 1H), 8.77 (s, 1H), 7.30 (d, J=8.4 Hz, 1H), 6.87 (d, J=1.8 Hz, 1H), 6.75 (dd, J=1.8 Hz, 8.1 Hz, 1H), 6.64 (br s, 2H), 4.59 (t, J=6.0 Hz, 1H), 4.43 (t, J=6.0 Hz, 1H), 3.27 (t, J=7.8 Hz, 2H), 2.03-1.93 (m, 2H), 1.87-1.75 (m, 5H).

Example 107-B

4-Amino-2-{8-[(3-fluorophenyl)methyl]imidazo[1,2-a]pyrazin-6-yl}-5-(3-hydroxy-4-methylphenyl)-5-methyl-5,7-dihydro-6H-pyrrolo[2,3-d]pyrimidin-6-one Step A—4-Amino-5-(3-((tert-butyldimethylsilyl)oxy)-4-methylphenyl)-2-{8-[(3-fluorophenyl)methyl]imidazo[1,2-a]pyrazin-6-yl}-5-methyl-5H-pyrrolo[2,3-d]pyrimidin-6(7H)-one Into a flask were placed amidine I-A4 (120 mg, 0.45 mmol), rac. malononitrile 1-27 (172 mg, 0.45 mmol), potassium bicarbonate (223 mg, 2.23 mmol) and tert-BuOH (5 mL). The resulting mixture was stirred at 75° C. for 16 h, then concentrated in vacuo and the residue was purified by column chromatography eluting with DCM/MeOH (10/1) to afford the title compound. The racemic material was resolved using chiral-prep-HPLC Column (Phenomenex Lux 5u Cellulose-4, AXIA) to afford isomers A (faster eluting) and B (slower eluting) of the title compound.

Step B—4-Amino-2-{8-[(3-fluorophenyl)methyl]imidazo[1,2-a]pyrazin-6-yl}-5-(3-hydroxy-4-methylphenyl)-5-methyl-5,7-dihydro-6H-pyrrolo[2,3-d]pyrimidin-6-one Into a flask, were placed enantiomer B from Step A (65 mg, 0.11 mmol), THF (3 mL) and TBAF (37 mg, 0.12 mmol). The resulting solution was stirred at RT for 15 min, then quenched with water (10 mL), and extracted with EtOAc (3×20 mL). The combined organic layer was washed with brine (15 mL), dried over anhydr. $Na_2SO_4$, filtered and the filtrate was concentrated in vacuo to dryness. The residue was purified by column chromatography eluting with DCM/MeOH (10/1) to afford the title compound, 107-B. MS: 496 (M+1). $^1$H NMR (400 MHz, $CD_3OD$): δ 9.40 (s, 1H), 8.13 (d, J=0.8 Hz, 1H), 7.84 (d, J=1.2 Hz, 1H), 7.32-7.22 (m, 3H), 7.07 (d, J=8.0 Hz, 1H), 6.92 (dd, J=9.2, 8.8 Hz, 1H), 6.77-6.71 (m, 2H), 4.63 (s, 2H), 2.15 (s, 3H), 1.83 (s, 3H).

Example 108-AB

4-Amino-5-(4-chloro-3-hydroxyphenyl)-5-methyl-2-{8-[(4-methylcyclohexyl)methyl]imidazo[1,2-a]pyrazin-6-yl}-5,7-dihydro-6H-pyrrolo[2,3-d]pyrimidin-6-one

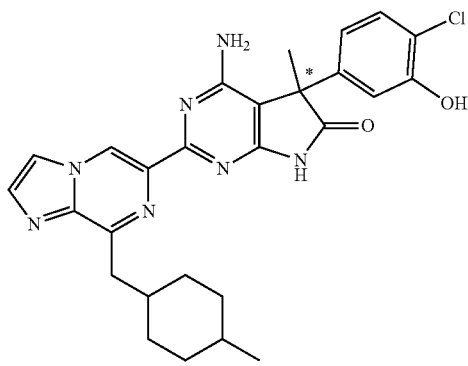 [SMILES: CC1CCC(Cc2nc(-c3nc(N)c4c(n3)NC(=O)C4(C)c3ccc(Cl)c(O)c3)cn3ccnc23)CC1]

Step A—4-Amino-5-(4-chloro-3-methoxyphenyl)-5-methyl-2-{8-[(4-methylcyclohexyl)methyl]imidazo[1,2-a]pyrazin-6-yl}-5,7-dihydro-6H-pyrrolo[2,3-d]pyrimidin-6-one Into a flask were placed amidine I-A31 (150 mg, 0.55 mmol), chiral malononitrile I-12A (170 mg, 0.55 mmol), potassium bicarbonate (111 mg, 1.11 mmol) and tert-BuOH (2 mL). The mixture was stirred at 70° C. for 16 h, then cooled to RT and concentrated in vacuo. The residue was purified by column chromatography eluting with MeOH/DCM (0-5%) to afford a cis/trans mixture of the title compound. The cis/trans diastereomers were resolved using Chiral-Prep-HPLC SFC Column (CHIRALPAK IC) to afford isomers A (faster eluting) and B (slower eluting) of the title compound.

Step B—4-Amino-5-(4-chloro-3-hydroxyphenyl)-5-methyl-2-{8-[(4-methylcyclohexyl)methyl]imidazo[1,2-a]pyrazin-6-yl}-5,7-dihydro-6H-pyrrolo[2,3-d]pyrimidin-6-one Into a flask was placed enantiomer B (slower eluting) from Step A, (50 mg, 0.094 mmol) in DCM (2 mL), followed by a dropwise addition of $BBr_3$ (235 mg, 0.940 mmol) at 0° C. The resulting mixture was stirred at RT for 1 h then poured into ice-water (10 mL) and the basicity of the solution was adjusted to pH8 with sat. aq. $NaHCO_3$. It was extracted with EtOAc (3×100 mL) and the combined organic layer was dried over anhydr. $Na_2SO_4$, filtered and the filtrate concentrated in vacuo. The residue was purified by column chromatography eluting with MeOH/DCM (0-5%) to afford the title compound, 108-AB. MS: 518 (M+1). $^1$H NMR (300 MHz, $CD_3OD$): δ 9.31 (s, 1H), 8.07 (s, 1H), 7.78 (s, 1H), 7.12 (d, J=8.4 Hz, 1H), 6.88 (d, J=2.1 Hz, 1H), 6.80 (dd, J=2.1, 8.4 Hz, 1H), 3.14 (d, J=7.2 Hz, 2H), 2.10-1.95 (m, 1H), 1.81 (s, 3H), 1.67-1.64 (m, 4H), 1.46-1.12 (m, 3H), 0.98-0.82 (m, 5H).

Using essentially the same procedures described in Example 107-B and 108-AB, the following compounds in Table 7 were prepared. The deprotection step was performed using either $BBr_3$, HBr or TBAF as a deprotecting reagent.

TABLE 7

| | Examples 108-AA-120-BB | | | |
|---|---|---|---|---|
| Ex. | Structure | Name | MS (M + 1) | Int. SM/Chiral Resolution Column |
| 108-AA | (structure shown) | 4-Amino-5-(4-chloro-3-hydroxyphenyl)-5-methyl-2-{8-[(4-methylcyclohexyl)methyl]imidazo-[1,2-a]pyrazin-6-yl}-5,7-dihydro-6H-pyrrolo-[2,3-d]pyrimidin-6-one | 518 | I-12A/ CHIRALPAK IC |

TABLE 7-continued

Examples 108-AA-120-BB

| Ex. | Structure | Name | MS (M + 1) | Int. SM/Chiral Resolution Column |
|---|---|---|---|---|
| 109-A | 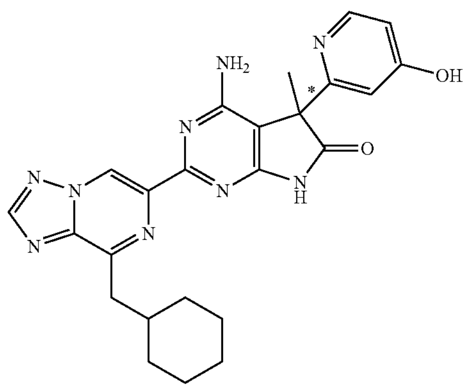 [SMILES: CC1(c2cc(O)ccn2)C(=O)Nc2nc(-c3cn4ncnc4c(CC4CCCCC4)n3)nc(N)c21] | 4-Amino-2-(8-(cyclohexylmethyl)-[1,2,4]-triazolo[1,5-a]pyrazin-6-yl)-5-(4-hydroxypyridin-2-yl)-5-methyl-5,7-dihydro-6H-pyrrolo-[2,3-d]pyrimidin-6-one | 472 | I-13/ CHIRALPAK IF |
| 110-B | 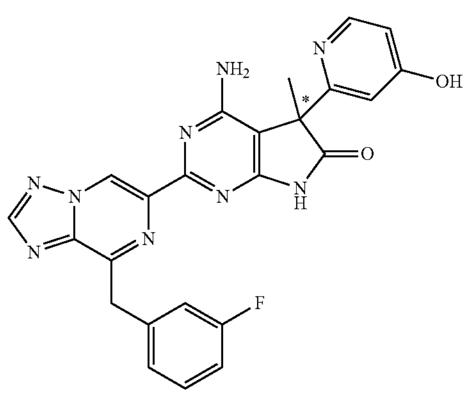 [SMILES: CC1(c2cc(O)ccn2)C(=O)Nc2nc(-c3cn4ncnc4c(Cc4cccc(F)c4)n3)nc(N)c21] | 4-Amino-2-{8-[(3-fluorophenyl)methyl]-[1,2,4]triazolo[1,5-a]pyrazin-6-yl}-5-(4-hydroxypyridin-2-yl)-5-methyl-5,7-dihydro-6H-pyrrolo[2,3-d]pyrimidin-6-one | 484 | I-13 CHIRALPAK IC |
| 111-B | 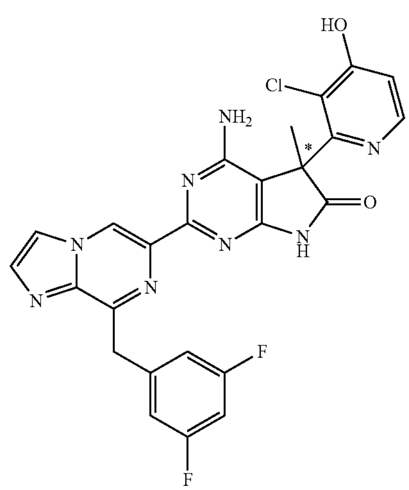 [SMILES: CC1(c2nccc(O)c2Cl)C(=O)Nc2nc(-c3cn4ccnc4c(Cc4cc(F)cc(F)c4)n3)nc(N)c21] | 4-Amino-5-(3-chloro-4-hydroxypyridin-2-yl)-2-{8-[(3,5-difluorophenyl)-methyl]imidazo[1,2-a]-pyrazin-6-yl}-5-methyl-5,7-dihydro-6H-pyrrolo-[2,3-d]pyrimidin-6-one | 535 | I-14/ CHIRAL ART Cellulose-SB |

TABLE 7-continued

Examples 108-AA-120-BB

| Ex. | Structure | Name | MS (M + 1) | Int. SM/Chiral Resolution Column |
|---|---|---|---|---|
| 112-B | 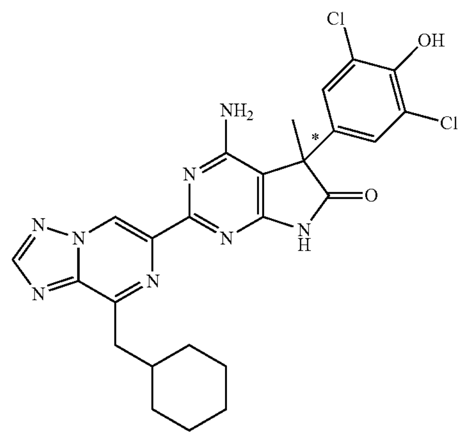 [SMILES: CC1(c2cc(Cl)c(O)c(Cl)c2)C(=O)Nc2nc(-c3cn4ncnc4c(CC4CCCCC4)n3)nc(N)c21] | 4-Amino-2-(8-(cyclo-hexylmethyl)-[1,2,4]-triazolo[1,5-a]pyrazin-6-yl)-5-(3,5-dichloro-4-hydroxyphenyl)-5-methyl-5,7-dihydro-6H-pyrrolo[2,3-d]pyrimidin-6-one | 539 | I-18/ Phenomenex Lux 5u Cellulose-4, AXIA |
| 113-A | 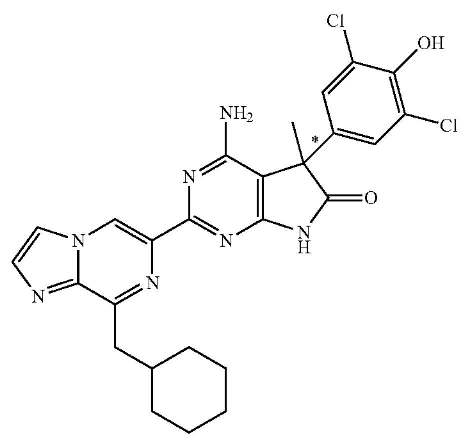 [SMILES: CC1(c2cc(Cl)c(O)c(Cl)c2)C(=O)Nc2nc(-c3cn4ccnc4c(CC4CCCCC4)n3)nc(N)c21] | 4-Amino-2-(8-(cyclo-hexylmethyl)imidazo-[1,2-a]pyrazin-6-yl)-5-(3,5-dichloro-4-hydroxy-phenyl)-5-methyl-5,7-dihydro-6H-pyrrolo-[2,3-d]-pyrimidin-6-one | 538 | I-18/ CHIRALPAK AD-H |
| 114-B | 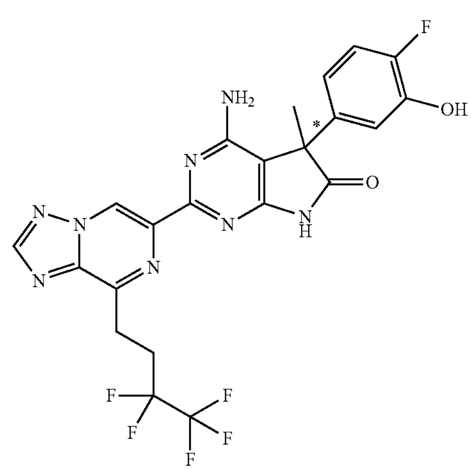 [SMILES: CC1(c2ccc(F)c(O)c2)C(=O)Nc2nc(-c3cn4ncnc4c(CCC(F)(F)C(F)(F)F)n3)nc(N)c21] | 4-Amino-5-(4-fluoro-3-hydroxyphenyl)-5-methyl-2-(8-(3,3,4,4,4-pentafluorobutyl)-[1,2,4]-triazolo[1,5-a]pyrazin-6-yl)-5,7-dihydro-6H-pyrrolo(2,3-d]pyrimidin-6-one | 539 | Rac. I-6/ CHIRALPAK IA |

TABLE 7-continued

Examples 108-AA-120-BB

| Ex. | Structure | Name | MS (M + 1) | Int. SM/Chiral Resolution Column |
|---|---|---|---|---|
| 115-B | 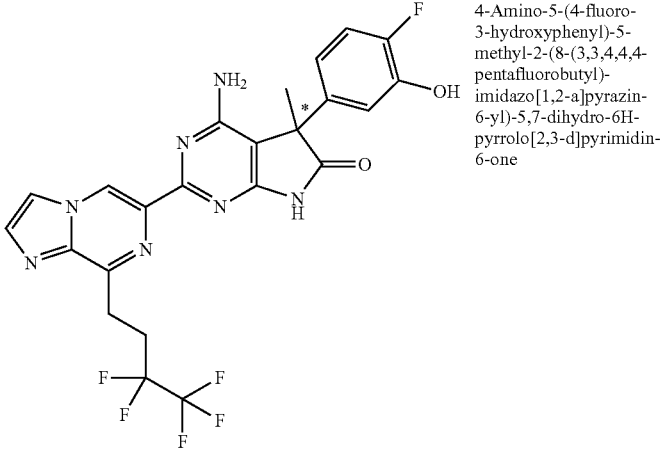 | 4-Amino-5-(4-fluoro-3-hydroxyphenyl)-5-methyl-2-(8-(3,3,4,4,4-pentafluorobutyl)-imidazo[1,2-a]pyrazin-6-yl)-5,7-dihydro-6H-pyrrolo[2,3-d]pyrimidin-6-one | 538 | Rac. I-6/ (R,R)WHELK-01 5/100 Kromasil |
| 116-B | 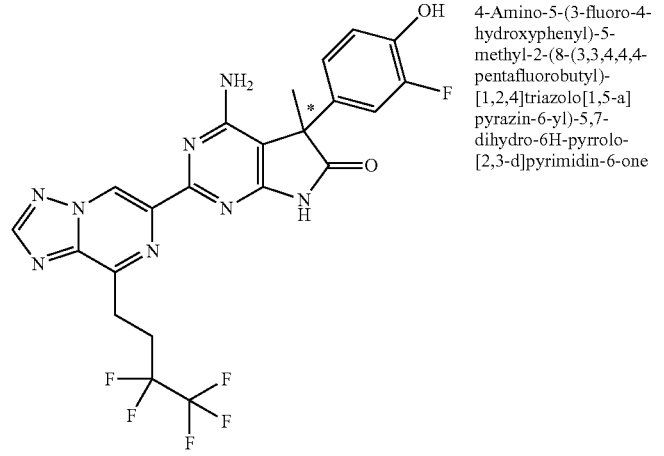 | 4-Amino-5-(3-fluoro-4-hydroxyphenyl)-5-methyl-2-(8-(3,3,4,4,4-pentafluorobutyl)-[1,2,4]triazolo[1,5-a]pyrazin-6-yl)-5,7-dihydro-6H-pyrrolo-[2,3-d]pyrimidin-6-one | 539 | Rac. I-28/ CHIRALPAK IB |
| 117-B | 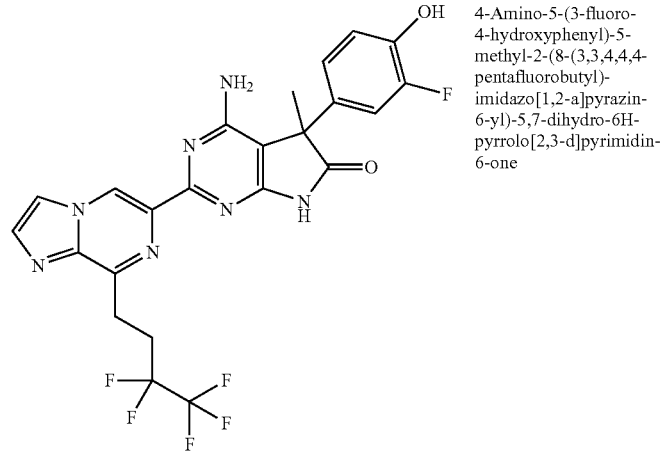 | 4-Amino-5-(3-fluoro-4-hydroxyphenyl)-5-methyl-2-(8-(3,3,4,4,4-pentafluorobutyl)-imidazo[1,2-a]pyrazin-6-yl)-5,7-dihydro-6H-pyrrolo[2,3-d]pyrimidin-6-one | 538 | Rac. I-28/ CHIRALPAK IB |

TABLE 7-continued

Examples 108-AA-120-BB

| Ex. | Structure | Name | MS (M + 1) | Int. SM/Chiral Resolution Column |
|---|---|---|---|---|
| 118-B | 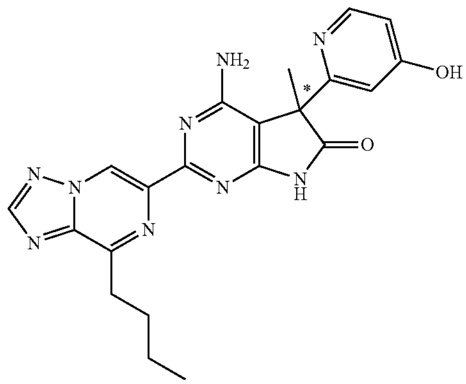 | 4-Amino-2-(8-butyl-[1,2,4]triazolo[1,5-a]-pyrazin-6-yl)-5-(4-hydroxypyridin-2-yl)-5-methyl-5,7-dihydro-6H-pyrrolo[2,3-d]-pyrimidin-6-one | 432 | I-13 CHIRALPAK IC |
| 119-B | 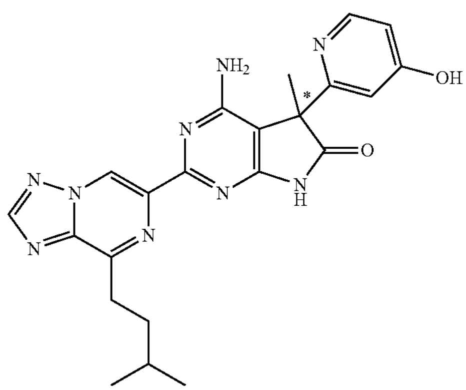 [SMILES: CC(C)CCc1nc(-c2nc(N)c3c(n2)NC(=O)C3(C)c2cc(O)ccn2)cn2ncnc12] | 4-Amino-5-(4-hydroxypyridin-2-yl)-2-(8-isopentyl-[1,2,4]-triazolo[1,5-a]pyrazin-6-yl)-5-methyl-5,7-dihydro-6H-pyrrolo-[2,3-d]pyrimidin-6-one | 446 | I-13/ CHIRALPAK IC |
| 120-BA | 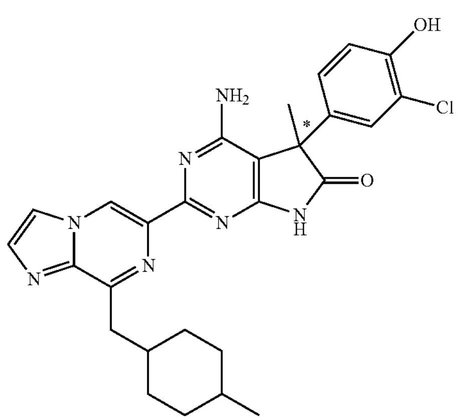 [SMILES: CC1CCC(Cc2nc(-c3nc(N)c4c(n3)NC(=O)C4(C)c3ccc(O)c(Cl)c3)cn3ccnc23)CC1] | 4-Amino-5-(3-chloro-4-hydroxyphenyl)-5-methyl-2-{8-[(4-methyl-cyclohexyl)methyl]-imidazo[1,2-a]pyrazin-6-yl}-5,7-dihydro-6H-pyrrolo[2,3-d]pyrimidin-6-one | 518 | I-11B/ CHIRAL ART Cellulose-SB |

TABLE 7-continued

Examples 108-AA-120-BB

| Ex. | Structure | Name | MS (M + 1) | Int. SM/Chiral Resolution Column |
|---|---|---|---|---|
| 120-BB | 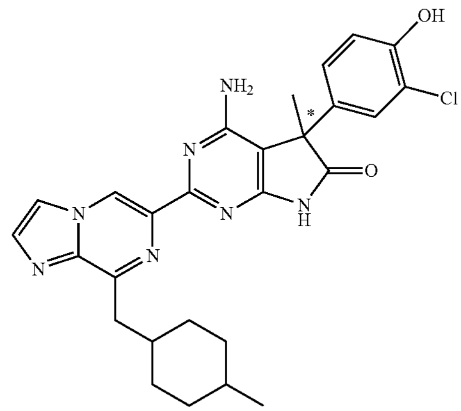 [SMILES: CC1CCC(Cc2nc(-c3nc(N)c4c(n3)NC(=O)C4(C)c3ccc(O)c(Cl)c3)cn3ccnc23)CC1] | 4-Amino-5-(3-chloro-4-hydroxyphenyl)-5-methyl-2-{8-[(4-methylcyclohexyl)methyl]imidazo-[1,2-a]pyrazin-6-yl}-5,7-dihydro-6H-pyrrolo-[2,3-d]pyrimidin-6-one | 518 | I-11B/ CHIRAL ART Cellulose-SB |

Example 121-B

4-Amino-2-{8-[(3-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one

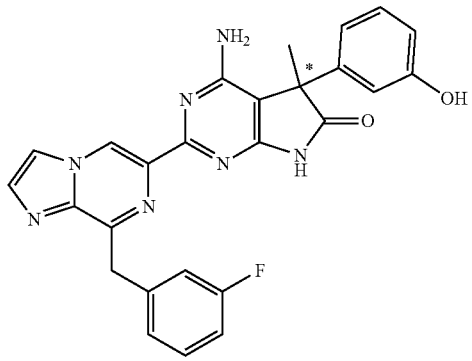 [SMILES: CC1(c2cccc(O)c2)C(=O)Nc2nc(-c3cn4ccnc4c(Cc4cccc(F)c4)n3)nc(N)c21]

Step A—4-Amino-5-(3-methoxyphenyl)-5-methyl-2-(8-(methylthio)imidazo[1,2-a]pyrazin-6-yl)-5,7-dihydro-6H-pyrrolo[2,3-d]pyrimidin-6-one Into a flask under an inert atmosphere of N₂, were placed t-BuOH (39 mL), chiral malononitrile I-17B (2.36 g, 8.65 mmol), amidine I-A21 (1.63 g, 7.86 mmol) and potassium bicarbonate (2.36 g, 23.6 mmol). The mixture was stirred at 80° C. for 16 h, then cooled to RT, quenched with water (50 mL), and extracted with EtOAc (3×100 mL). The combined organic layer was dried over anhydr. Na₂SO₄, the solid was filtered and the filtrate concentrated in vacuo to dryness. The crude was triturated with EtOAc and hexanes, and dried to afford the title compound.

Step B—4-Amino-2-{8-[(3-fluorophenyl)methyl]imidazo[1,2-a]pyrazin-6-yl}-5-(3-methoxyphenyl)-5-methyl-5,7-duhydro-6H-pyrrolo[2,3-d]pyrimidin-6-one Into a flask under an inert atmosphere of N₂ were placed intermediate from Step A (500 mg, 1.15 mmol), Xantphos generation II precatalyst (91 mg, 0.12 mmol), and (3-fluorobenzyl)zinc(II) chloride (11.5 mL, 5.77 mmol, 0.5 M in THF), and the mixture was stirred at 70° C. for 48 h. It was cooled, diluted with EtOAc (100 mL), and passed through a pad of CELITE. The filtrate was dried over anhydr. Na₂SO₄, and concentrated in vacuo to dryness. The crude residue was purified by column chromatography eluting with DCM/MeOH (0-3%) to afford the title compound.

Step C—4-Amino-2-{8-[(3-fluorophenyl)methyl]imidazo[1,2-a]pyrazin-6-yl}-5-(3-hydroxyphenyl)-5-methyl-5,7-dihydro-6H-pyrrolo[2,3-d]pyrimidin-6-one Into a flask under an inert atmosphere of N₂ was placed intermediate from Step B (140 mg, 0.28 mmol) in DCM (1.4 mL), followed by a dropwise addition of BBr₃ (1.4 mL, 1.41 mmol, 1 M in DCM) at 0° C. The reaction was stirred at RT for 48 h, then quenched with sat. aq. Na₂CO₃ (20 mL), and diluted with EtOAc (50 mL). The aqueous was extracted with EtOAc (3×20 mL), the combined organic layer was dried over anhydr. Na₂SO₄ and the filtrate concentrated in vacuo to dryness. The residue was purified by RP-HPLC eluting with MeCN/water (0.05% v/v TFA) 0-40%. The resultant residue was free-based with sat. aq. NaHCO₃ to afford the title compound, 121-B. MS: 482 (M+1). ¹H NMR (400 MHz, DMSO-d₆): δ 11.15 (1H, s), 9.35 (1H, s), 9.24 (1H, s), 8.31 (1H, s), 7.83 (1H, s), 7.30 (1H, dd, J=8.0, 8.0 Hz), 7.21 (2H, d, J=8.0 Hz), 7.14-7.09 (1H, m), 7.03-6.99 (1H, m), 6.70 (1H, d, J=8.0 Hz), 6.66-6.64 (2H, m), 4.52 (2H, s), 1.73 (3H, s).

Using essentially the same procedures described in Example 121-B, the following compounds in Table 8 were prepared using commercially available organozinc reagents.

TABLE 8

Examples 122-B-128-B

| Ex. | Structure | Name | MS (M + 1) | Chiral starting material |
|---|---|---|---|---|
| 122-B | 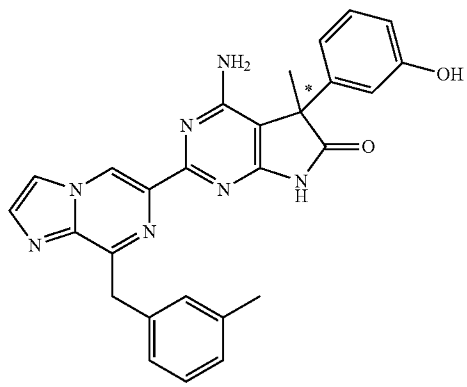 [SMILES: Cc1cccc(Cc2nc(-c3nc(N)c4c(n3)NC(=O)C4(C)c3cccc(O)c3)cn3ccnc23)c1] | 4-Amino-5-(3-hydroxy-phenyl)-5-methyl-2-{8-[(3-methylphenyl)methyl]-imidazo[1,2-a]pyrazin-6-yl}-5,7-dihydro-6H-pyrrolo-[2,3-d]pyrimidin-6-one | 478 | I-17B |
| 123-B | 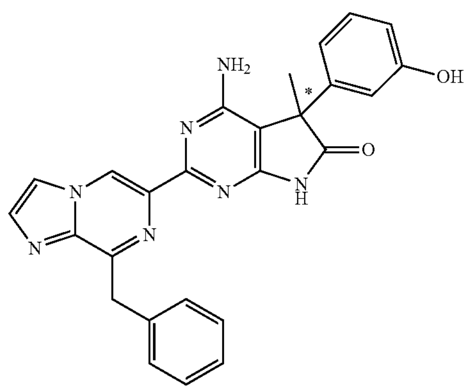 [SMILES: CC1(c2cccc(O)c2)C(=O)Nc2nc(-c3cn4ccnc4c(Cc4ccccc4)n3)nc(N)c21] | 4-Amino-2-(8-benzyl-imidazol[1,2-a]pyrazin-6-yl)-5-(3-hydroxyphenyl)-5-methyl-5,7-dihydro-6H-pyrrolo[2,3-d]pyrimidin-6-one | 464 | I-17B |
| 124-B | 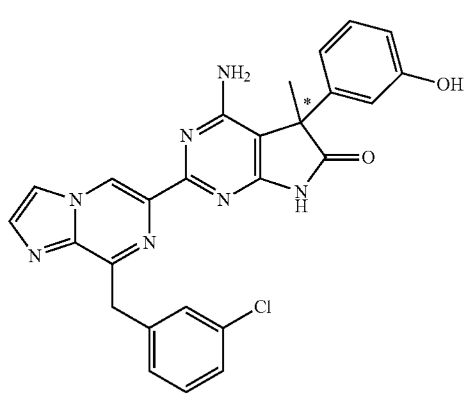 [SMILES: CC1(c2cccc(O)c2)C(=O)Nc2nc(-c3cn4ccnc4c(Cc4cccc(Cl)c4)n3)nc(N)c21] | 4-Amino-2-{8-[(3-chlorophenyl)methyl]-imidazo[1,2-a]pyrazin-6-yl}-5-(3-hydroxyphenyl)-5-methyl-5,7-dihydro-6H-pyrrolo[2,3-d]pyrimidin-6-one | 498 | I-17B |

TABLE 8-continued

Examples 122-B-128-B

| Ex. | Structure | Name | MS (M + 1) | Chiral starting material |
|---|---|---|---|---|
| 125-B | 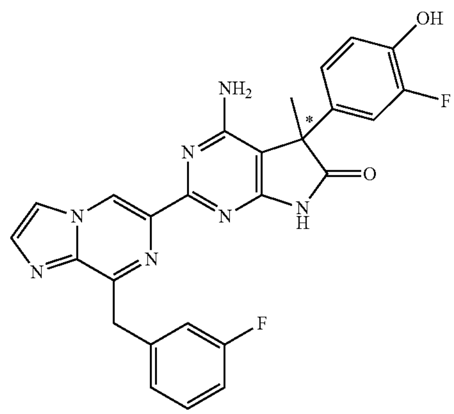 [SMILES: CC1(c2ccc(O)c(F)c2)C(=O)Nc2nc(-c3cn4ccnc4c(Cc4cccc(F)c4)n3)nc(N)c21] | 4-Amino-5-(3-fluoro-4-hydroxyphenyl)-2-{8-[(3-fluorophenyl)methyl]-imidazo[1,2-a]pyrazin-6-yl}-5-methyl-5,7-dihydro-6H-pyrrolo[2,3-d]-pyrimidin-6-one | 500 | I-28B |
| 126-B | 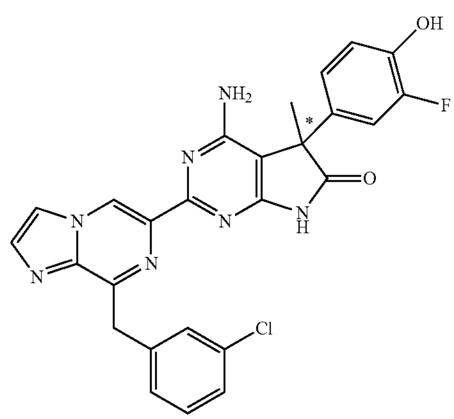 | 4-Amino-2-{8-[(3-chlorophenyl)methyl]-imidazo[1,2-a]pyrazin-6-yl}-5-(3-fluoro-4-hydroxy-phenyl)-5-methyl-5,7-dihydro-6H-pyrrolo-[2,3-d]pyrimidin-6-one | 516 | I-28B |
| 127-B | 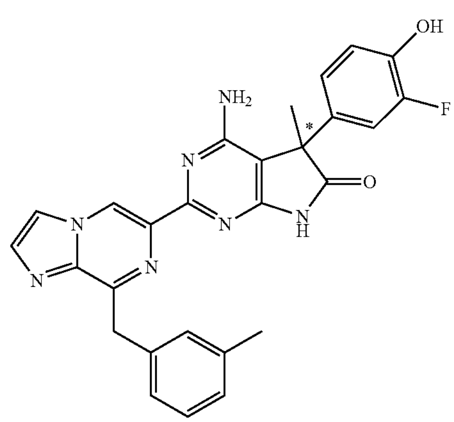 [SMILES: Cc1cccc(Cc2nc(-c3nc(N)c4c(n3)NC(=O)C4(C)c3ccc(O)c(F)c3)cn3ccnc23)c1] | 4-Amino-5-(3-fluoro-4-hydroxyphenyl)-5-methyl-2-{8-[(3-methylphenyl)-methyl]imidazo[1,2-a]-pyrazin-6-yl}-5,7-dihydro-6H-pyrrolo[2,3-d]-pyrimidin-6-one | 496 | I-28B |

TABLE 8-continued

Examples 122-B-128-B

| Ex. | Structure | Name | MS (M + 1) | Chiral starting material |
|---|---|---|---|---|
| 128-B | 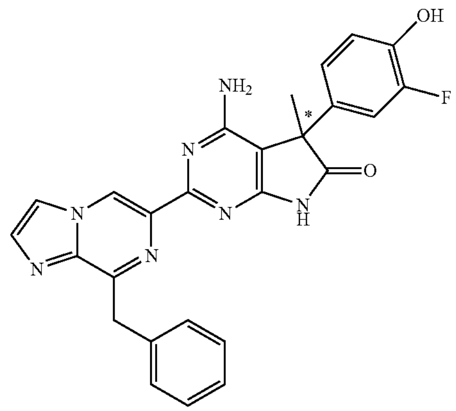 [SMILES: CC1(c2ccc(O)c(F)c2)C(=O)Nc2nc(-c3cn4ccnc4c(Cc4ccccc4)n3)nc(N)c21] | 4-Amino-2-(8-benzyl-imidazo[1,2-a]pyrazin-6-yl)-5-(3-fluoro-4-hydroxyphenyl)-5-methyl-5,7-dihydro-6H-pyrrolo[2,3-d]-pyrimidin-6-one | 482 | I-28B |

Example 129-B 5-(4-Fluoro-3-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one

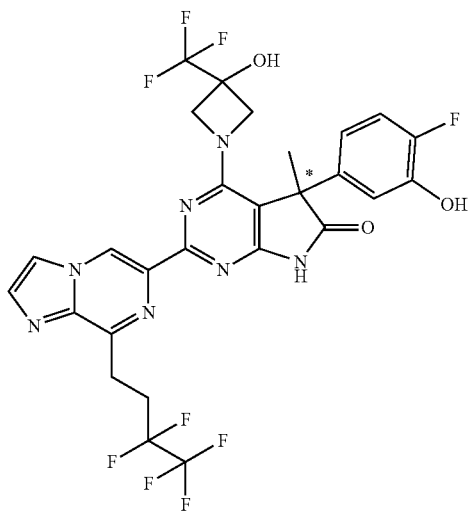 [SMILES: CC1(c2ccc(F)c(O)c2)C(=O)Nc2nc(-c3cn4ccnc4c(CCC(F)(F)C(F)(F)F)n3)nc(N3CC(O)(C(F)(F)F)C3)c21]

Step A—4-Amino-5-(4-fluoro-3-methoxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one Into a flask were placed amidine I-A12 (300 mg, 0.976 mmol), rac. malononitrile I-6 (312 mg, 1.074 mmol) and potassium bicarbonate (293 mg, 2.93 mmol) in t-BuOH (8 ml). The reaction mixture was stirred at 75° C. for 16 h, then concentrated in vacuo to dryness and the residue was purified by column chromatography with petroleum ether/EtOAc (50%) to afford the title compound.

Step B—4-Chloro-5-(4-fluoro-3-methoxyphenyl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one Into a flask under an inert atmosphere of $N_2$, were placed racemic intermediate from Step A (330 mg, 0.60 mmol), and copper(II) chloride (483 mg, 3.59 mmol) in DCE (10 mL), then tert-butyl nitrite (370 mg, 3.59 mmol) was added and the mixture was stirred at 65° C. for 4 h. The reaction was cooled to RT, quenched with $NH_4Cl$/ammonia (9/1, 100 mL) and extracted with EtOAc (3×20 mL). Combined organic layer was dried over anhydr. $Na_2SO_4$, filtered and the filtrate was concentrated in vacuo to dryness. The residue was purified by column chromatography eluting with petroleum EtOAc/ether (50-100%) to afford the title compound.

Step C—5-(4-Fluoro-3-methoxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one Into a flask were placed 3-(trifluoromethyl)azetidin-3-ol hydrochloride (154 mg, 0.87 mmol) in THF (3 mL) and $Et_3N$ (0.13 mL, 0.93 mmol) and the mixture was stirred at RT for 15 min. The solid was filtered out and the filtrate was added into a 5-mL microwave vial, followed by the addition of the intermediate from Step B (165 mg, 0.29 mmol). The mixture was irradiated with microwave radiation at 150° C. for 40 min, then concentrated in vacuo. The residue was purified by column chromatography with EtOAc/petroleum ether (50-100%) and then by Prep-HPLC with water (10% ammonium bicarbonate)/MeCN 0-50% to afford the racemic title compound. The racemic material was resolved using Prep-Chiral-HPLC Column (R,R)WHELK-01 5/100 Kromasil to afford isomers A (faster eluting) and B (slower eluting) of the title compound.

Step D—5-(4-Fluoro-3-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one Into a flask under an inert atmosphere of N₂ was placed the slower eluting enantiomer from Step C (8 mg, 0.012 mmol) in DCM (2 mL), followed by a dropwise addition of BBr₃ (0.2 mL, 2.12 mmol) at 0° C. The reaction was stirred at RT for 16 h, then quenched with sat. aq. Na₂CO₃ (20 mL), and extracted with EtOAc (3×20 mL), the combined organic layer was dried over anhydr. Na₂SO₄ and the filtrate concentrated in vacuo to dryness. The residue was purified by RP HPLC eluting with MeCN/water (0.1% NaHCO₃) 35-75% to afford the title compound, 129-B. MS: 662 (M+1). ¹H NMR (300 MHz, CD₃OD): δ 9.45 (s, 1H), 8.18 (d, J=0.9 Hz, 1H), 7.85 (d, J=0.9 Hz, 1H), 7.08 (dd, J=8.7, 10.8 Hz, 1H), 6.84 (dd, J=2.4, 8.1 Hz, 1H), 6.75 (dd, J=4.2, 6.6 Hz, 1H), 4.38 (d, J=10.2 Hz, 1H), 4.12 (d, J=10.2 Hz, 1H), 3.93 (d, J=10.2 Hz, 1H), 3.71-3.60 (m, 3H), 3.08-2.87 (m, 2H), 1.87 (s, 3H).

Example 130-A 5-(3-Fluoro-4-hydroxyphenyl)-4-(3-hydroxy-3-(trifluoromethyl)azetidin-1-yl)-5-methyl-2-(8-(3,3,4,4,4-pentafluorobutyl)imidazo[1,2-a]pyrazin-6-yl)-5,7-dihydro-6H-pyrrolo[2,3-d]pyrimidin-6-one

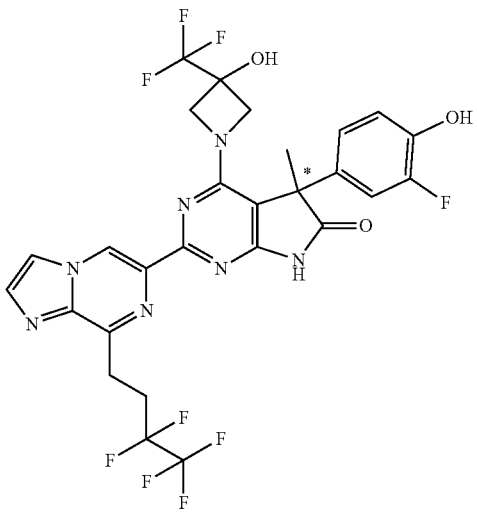 [SMILES: CC1(c2ccc(O)c(F)c2)C(=O)Nc2nc(-c3cn4ccnc4c(CCC(F)(F)C(F)(F)F)n3)nc(N3CC(O)(C(F)(F)F)C3)c21]

Example 130-A was prepared following essentially the same procedure as described in Example 129-B, using amidine I-A12 and rac. malononitrile I-28 as starting materials. The racemic material was resolved at Step C using Prep-Chiral-HPLC Column: CHIRALPAK IA. The first eluted enantiomer A was carried on to the Step D to afford the title compound, 130-A. MS: 663 (M+1). ¹H NMR (300 MHz, CD₃OD): δ 9.45 (s, 1H), 8.18 (d, J=0.9 Hz, 1H), 7.84 (d, J=0.9 Hz, 1H), 7.02 (dd, J=8.7, 10.8 Hz, 1H), 6.99-6.85 (m, 2H), 4.37 (d, J=10.2 Hz, 1H), 4.11 (d, J=10.2 Hz, 1H), 3.91 (d, J=10.2 Hz, 1H), 3.70-3.60 (m, 3H), 3.01-2.88 (m, 2H), 1.82 (s, 3H).

Example 131-AB 5-(4-Chloro-3-hydroxyphenyl)-2-{8-[(3-fluorophenyl)methyl]imidazo[1,2-a]pyrazin-6-yl}-5-methyl-4-[(3,3,3-trifluoro-2-hydroxypropyl)amino]-5,7-dihydro-6H-pyrrolo[2,3-d]pyrimidin-6-one

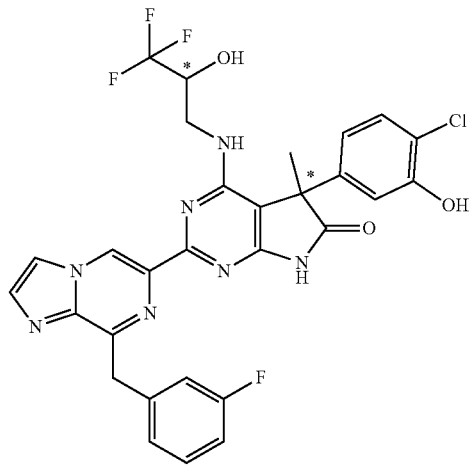 [SMILES: CC1(c2ccc(Cl)c(O)c2)C(=O)Nc2nc(-c3cn4ccnc4c(Cc4cccc(F)c4)n3)nc(NCC(O)C(F)(F)F)c21]

Step A—4-Amino-5-(4-chloro-3-methoxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one Into a flask were placed amidine I-A4 (1.3 g, 4.83 mmol), chiral malononitrile I-12A (1.5 g, 4.83 mmol), tert-BuOH (40 mL) and potassium bicarbonate (0.60 g, 5.79 mmol). The resulting mixture was stirred at 80° C. for 16 h, then concentrated to dryness in vacuo, and the residue was purified by column chromatography eluting with DCM/MeOH (10/1) to afford the title compound.

Step B—4-Chloro-5-(4-chloro-3-methoxyphenyl)-2-{8-[(3-fluorophenyl)methyl]imidazo[1,2-a]pyrazin-6-yl}-5-methyl-5,7-dihydro-6H-pyrrolo[2,3-d]pyrimidin-6-one Into a flask under an inert atmosphere of N₂, were placed copper(II) chloride (335 mg, 2.49 mmol), intermediate from Step A, (330 mg, 0.62 mmol) in DMF (1 mL) and DCE (5 mL), followed by the addition of tert-butyl nitrite (449 mg, 4.36 mmol). The mixture was stirred for at 65° C. 1 h, then quenched with NH₄Cl/ammonia (9/1, 100 mL), extracted with EtOAc (3×100 mL), and the combined organic layer was washed with water (2×100 mL), dried over anhydr. Na₂SO₄, filtered and concentrated in vacuo to dryness. The residue was purified by column chromatography with EtOAc/petroleum ether (0-60%) to afford the title compound.

Step C—5-(4-Chloro-3-methoxyphenyl)-2-(8-(3-fluorobenzyl)imidazo[1,2-a]pyrazin-6-yl)-5-methyl-4-[(3,3,3-trifluoro-2-hydroxypropyl)amino]-5,7-dihydro-6H-pyrrolo[2,3-d]pyrimidin-6-one Into a microwave vial under an inert atmosphere of N₂, were placed intermediate from Step B (220 mg, 0.40 mmol), in N-methyl-2-pyrrolidinone (3 mL) and THF (3 mL), and 3-amino-1,1,1-trifluoropropan-2-ol (207 mg, 1.60 mmol). The mixture was irradiated with microwave radiation at 180° C. for 3 h, then cooled to RT, quenched with water (100 mL), and extracted with EtOAc (3×100 mL). The combined organic layer was washed with water (2×100 mL), dried over anhydr. Na$_2$SO$_4$, filtered and concentrated in vacuo to dryness. The residue was purified by column chromatography with MeOH/DCM (0-5%) to afford the racemic title compound, which was resolved by chiral-prep-HPLC Column Phenomenex Lux 5u Cellulose-4, to afford isomers A (faster eluting) and B (slower eluting) of the title compound.

Step D—5-(4-Chloro-3-hydroxyphenyl)-2-(8-(3-fluorobenzyl)imidazo[1,2-a]pyrazin-6-yl)-5-methyl-4-[(3,3,3-trifluoro-2-hydroxypropyl)amino]-5,7-dihydro-6H-pyrrolo[2,3-d]pyrimidin-6-one Into a flask under an inert atmosphere of N$_2$ was placed the slower eluting enantiomer B from Step C (70 mg, 0.1 mmol) in DCM (2 mL), followed by a dropwise addition of BBr$_3$ (137 mg, 0.55 mmol) at 0° C. The reaction was stirred at RT for 1 h, then quenched with ice-water (10 mL) and the basicity of the solution was adjusted to pH8 with solid NaHCO$_3$. The resulting solution was extracted with EtOAc (3×100 mL), the combined organic layer was dried over anhydr. Na$_2$SO$_4$ and the filtrate concentrated in vacuo to dryness. The residue was purified by column chromatography with MeOH/DCM (0-5%) to afford the title compound, 131AB. MS: 628 (M+1). $^1$H NMR (300 MHz, CD$_3$OD): δ 9.35 (s, 1H), 8.10 (d, J=0.9 Hz, 1H), 7.82 (d, J=0.9 Hz, 1H), 7.38-7.31 (m, 2H), 7.26-7.17 (m, 2H), 6.89-6.83 (m, 2H), 6.77 (dd, J=8.4, 2.4 Hz, 1H), 4.58 (s, 2H), 4.25-4.17 (m, 1H), 3.89 (dd, J=3.3, 14.4 Hz, 1H), 3.65 (dd, J=7.2, 14.4 Hz, 1H), 1.81 (s, 3H).

Using essentially the same procedures as described in Example 131-AB, the following compounds in Table 9 were prepared. The chirality of the compounds in Table 9 results from the use of a chiral malononitrile intermediate and/or the separation of isomers performed at Step C.

TABLE 9

Examples 131-AA-139-A

| Ex. | Structure | Name | MS (M + 1) | Int. SM/ Chiral Resolution Column |
|---|---|---|---|---|
| 131-AA | 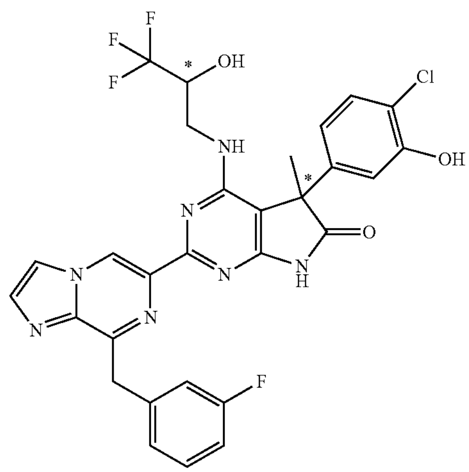 [SMILES: CC1(c2ccc(Cl)c(O)c2)C(=O)Nc2nc(-c3cn4ccnc4c(Cc4cccc(F)c4)n3)nc(NCC(O)C(F)(F)F)c21] | 5-(4-Chloro-3-hydroxyphenyl)-2-{8-[(3-fluorophenyl)methyl]imidazo[1,2-a]pyrazin-6-yl}-5-methyl-4-[(3,3,3-trifluoro-2-hydroxypropyl)amino]-5,7-dihydro-6H-pyrrolo[2,3-d]pyrimidin-6-one | 628 | I-12A/ Phenomene × Lux 5u Cellulose-4 |
| 132-AA | 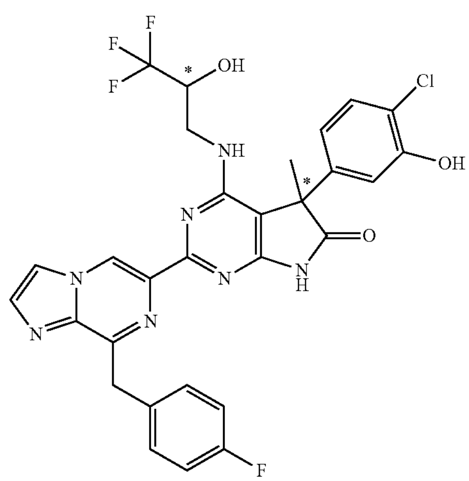 [SMILES: CC1(c2ccc(Cl)c(O)c2)C(=O)Nc2nc(-c3cn4ccnc4c(Cc4ccc(F)cc4)n3)nc(NCC(O)C(F)(F)F)c21] | 5-(4-Chloro-3-hydroxyphenyl)-2-{8-[(4-fluorophenyl)methyl]imidazo[1,2-a]pyrazin-6-yl}-5-methyl-4-[(3,3,3-trifluoro-2-hydroxypropyl)amino]-5,7-dihydro-6H-pyrrolo[2,3-d]-pyrimidin-6-one | 628 | I-12A/ Phenomene × Lux 5u Cellulose-4 |

TABLE 9-continued

Examples 131-AA-139-A

| Ex. | Structure | Name | MS (M + 1) | Int. SM/ Chiral Resolution Column |
|---|---|---|---|---|
| 132-AB | 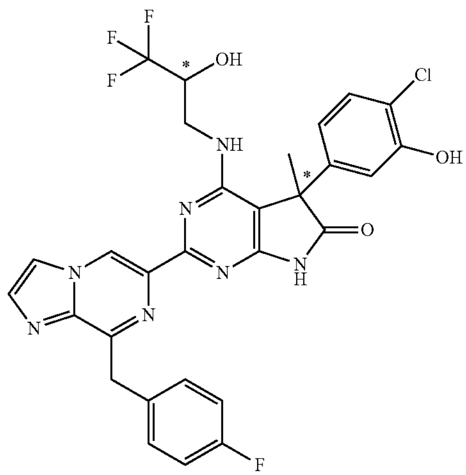 [SMILES: CC1(c2ccc(Cl)c(O)c2)C(=O)Nc2nc(-c3cn4ccnc4c(Cc4ccc(F)cc4)n3)nc(NCC(O)C(F)(F)F)c21] | 5-(4-Chloro-3-hydroxyphenyl)-2-{8-[(4-fluorophenyl)methyl]imidazo-[1,2-a]pyrazin-6-yl}-5-methyl-4-[(3,3,3-trifluoro-2-hydroxypropyl)amino]-5,7-dihydro-6H-pyrrolo-[2,3-d]pyrimidin-6-one | 628 | I-12A/ Phenomene x Lux 5u Cellulose-4 |
| 133-AA | 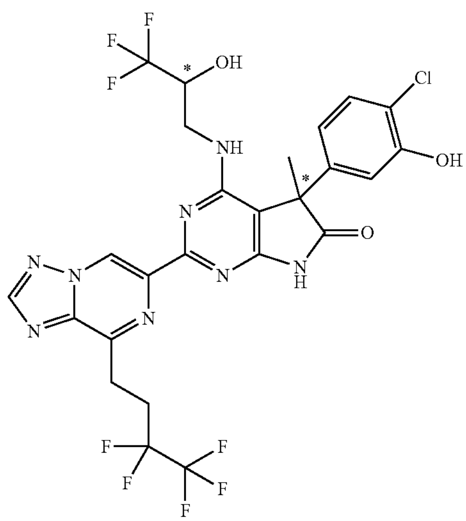 [SMILES: CC1(c2ccc(Cl)c(O)c2)C(=O)Nc2nc(-c3cn4ncnc4c(CCC(F)(F)C(F)(F)F)n3)nc(NCC(O)C(F)(F)F)c21] | 5-(4-Chloro-3-hydroxyphenyl)-5-methyl-2-(8-(3,3,4,4,4-pentafluorobutyl)-[1,2,4]triazolo-[1,5-a]pyrazin-6-yl)-4-[(3,3,3-trifluoro-2-hydroxypropyl)amino]-5,7-dihydro-6H-pyrrolo-[2,3-d]pyrimidin-6-one | 667 | I-12A/ CHIRALPAK IC |
| 133-AB | 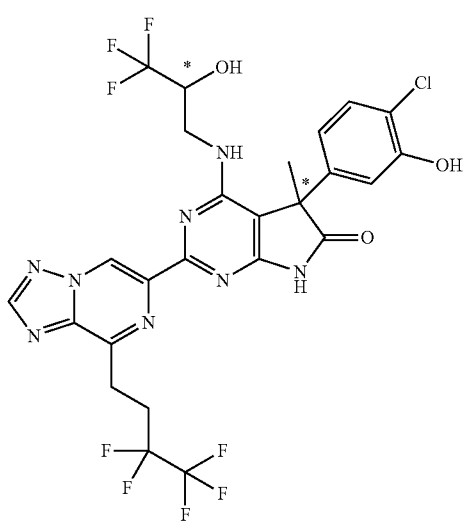 [SMILES: CC1(c2ccc(Cl)c(O)c2)C(=O)Nc2nc(-c3cn4ncnc4c(CCC(F)(F)C(F)(F)F)n3)nc(NCC(O)C(F)(F)F)c21] | 5-(4-Chloro-3-hydroxyphenyl)-5-methyl-2-(8-(3,3,4,4,4-pentafluorobutyl)-[1,2,4]triazolo-[1,5-a]pyrazin-6-yl)-4-[(3,3,3-trifluoro-2-hydroxypropyl)amino]-5,7-dihydro-6H-pyrrolo-[2,3-d]pyrimidin-6-one | 667 | I-12A/ CHIRALPAK IC |

TABLE 9-continued

Examples 131-AA-139-A

| Ex. | Structure | Name | MS (M + 1) | Int. SM/ Chiral Resolution Column |
|---|---|---|---|---|
| 134-A | 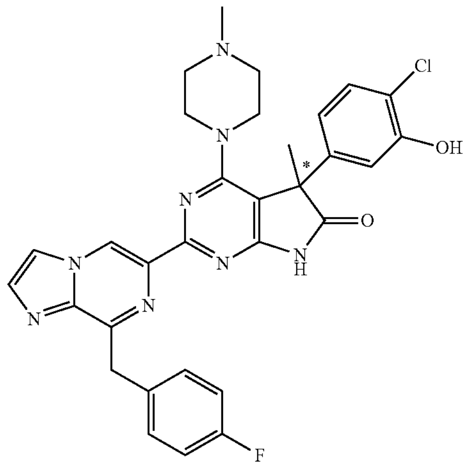 [SMILES: CN1CCN(c2nc(-c3cn4ccnc4c(Cc4ccc(F)cc4)n3)nc3c2C(C)(c2ccc(Cl)c(O)c2)C(=O)N3)CC1] | 5-(4-Chloro-3-hydroxy-phenyl)-2-{8-[(4-fluoro-phenyl)methyl]imidazo-[1,2-a]pyrazin-6-yl}-5-methyl-4-(4-methyl-piperazin-1-yl)-5,7-dihydro-6H-pyrrolo-[2,3-d]pyrimidin-6-one | 599 | I-12A |
| 135-B | 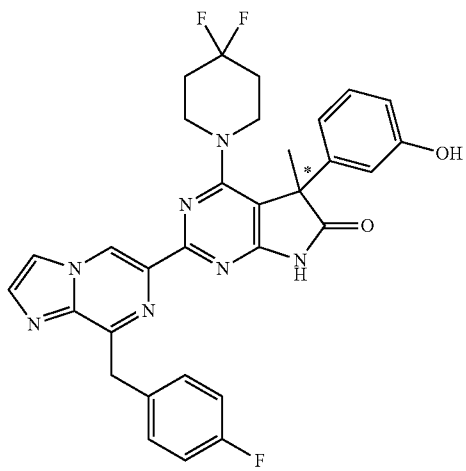 [SMILES: CC1(c2cccc(O)c2)C(=O)Nc2nc(-c3cn4ccnc4c(Cc4ccc(F)cc4)n3)nc(N3CCC(F)(F)CC3)c21] | 4-(4,4-Difluoropiperidin-1-yl)-2-{8-[(4-fluoro-phenyl)methyl]imidazo-[1,2-a]-pyrazin-6-yl}-5-(3-hydroxyphenyl)-5-methyl-5,7-dihydro-6H-pyrrolo[2,3-d]pyrimidin-6-one | 586 | I-17B |
| 136-A | 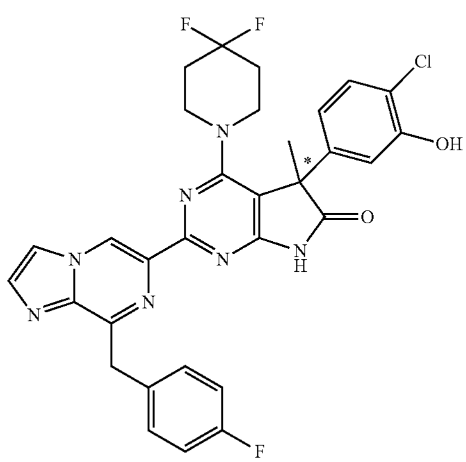 [SMILES: CC1(c2ccc(Cl)c(O)c2)C(=O)Nc2nc(-c3cn4ccnc4c(Cc4ccc(F)cc4)n3)nc(N3CCC(F)(F)CC3)c21] | 5-(4-Chloro-3-hydroxy-phenyl)-4-(4,4-difluoro-piperidin-1-yl)-2-{8-[(4-fluorophenyl)methyl]-imidazo[1,2-a]pyrazin-6-yl}-5-methyl-5,7-dihydro-6H-pyrrolo[2,3-d]-pyrimidin-6-one | 620 | I-12A |

TABLE 9-continued

Examples 131-AA-139-A

| Ex. | Structure | Name | MS (M + 1) | Int. SM/ Chiral Resolution Column |
|---|---|---|---|---|
| 137-A | 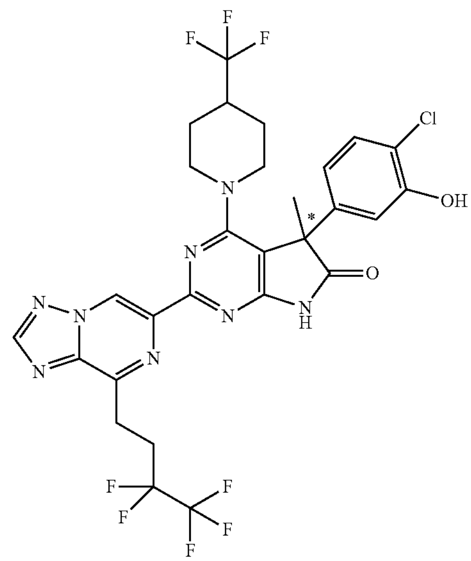 [SMILES: CC1(c2ccc(Cl)c(O)c2)C(=O)Nc2nc(-c3cn4ncnc4c(CCC(F)(F)C(F)(F)F)n3)nc(N3CCC(C(F)(F)F)CC3)c21] | 5-(4-Chloro-3-hydroxyphenyl)-5-methyl-2-(8-(3,3,4,4,4-pentafluorobutyl)-[1,2,4]triazolo-[1,5-a]pyrazin-6-yl)-4-(4-(trifluoromethyl)-piperidin-1-yl)-5,7-dihydro-6H-pyrrolo-[2,3-d]pyrimidin-6-one | 691 | I-12A |
| 138-A | 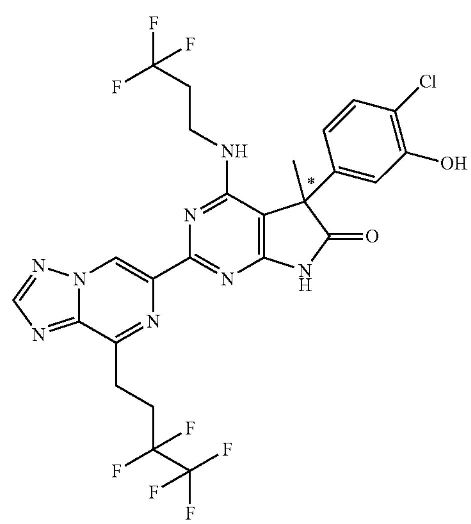 [SMILES: CC1(c2ccc(Cl)c(O)c2)C(=O)Nc2nc(-c3cn4ncnc4c(CCC(F)(F)C(F)(F)F)n3)nc(NCCC(F)(F)F)c21] | 5-(4-Chloro-3-hydroxyphenyl)-5-methyl-2-(8-(3,3,4,4,4-pentafluorobutyl)-[1,2,4]triazolo-[1,5-a]pyrazin-6-yl)-4-((3,3,3-trifluoropropyl)-amino)-5,7-dihydro-6H-pyrrolo[2,3-d]pyrimidin-6-one | 651 | I-12A |

TABLE 9-continued

Examples 131-AA-139-A

| Ex. | Structure | Name | MS (M + 1) | Int. SM/ Chiral Resolution Column |
|---|---|---|---|---|
| 139-A | 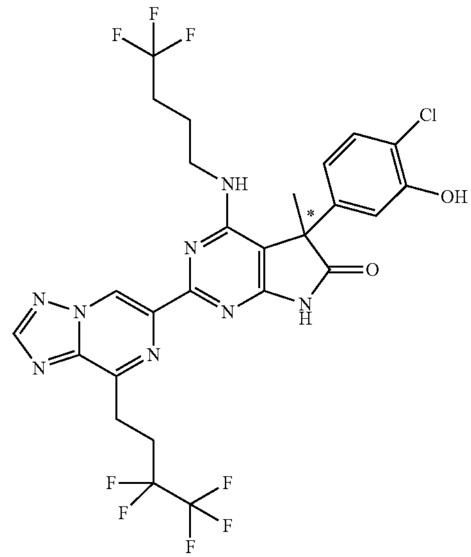 [SMILES: CC1(c2ccc(Cl)c(O)c2)C(=O)Nc2nc(-c3cn4ncnc4c(CCC(F)(F)C(F)(F)F)n3)nc(NCCCC(F)(F)F)c21] | 5-(4-Chloro-3-hydroxy-phenyl)-5-methyl-2-(8-(3,3,4,4,4-pentafluoro-butyl)-[1,2,4]triazolo-[1,5-a]pyrazin-6-yl)-4-((4,4,4-trifluorobutyl)-amino)-5,7-dihydro-6H-pyrrolo[2,3-d]pyrimidin-6-one | 665 | I-12A |

Example 140-A

4-Amino-2-(3-amino-8-[(3-fluorophenyl)methyl] imidazo[1,2-a]pyrazin-6-yl)-5-(4-chloro-3-hydroxy-phenyl)-5-methyl-5,7-dihydro-6H-pyrrolo[2,3-d] pyrimidin-6-one

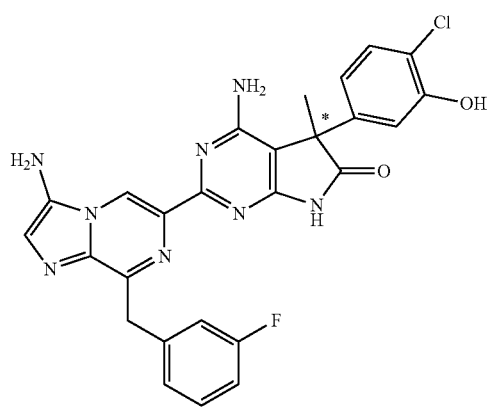 [SMILES: CC1(c2ccc(Cl)c(O)c2)C(=O)Nc2nc(-c3cn4c(N)cnc4c(Cc4cccc(F)c4)n3)nc(N)c21]

Step A—4-Amino-2-(3-bromo-8-[(3-fluorophenyl) methyl]imidazo[1,2-a]pyrazin-6-yl)-5-(4-chloro-3-methoxyphenyl)-5-methyl-5,7-dihydro-6H-pyrrolo [2,3-d]pyrimidin-6-one Into a flask were placed 4-amino-5-(4-chloro-3-methoxy-phenyl)-2-{8-[(3-fluorophenyl)methyl]imidazo[1,2-a] pyrazin-6-yl}-5-methyl-5,7-dihydro-6H-pyrrolo[2,3-d]py-rimidin-6-one (200 mg, 0.38 mmol), (prepared as in Example 1-A, Step A) in DMF (10 mL) and NBS (74 mg, 0.42 mmol) at 0° C. The mixture was stirred at RT for 1 h, then quenched with sat. aq. sodium thiosulphate (50 mL), and extracted with EtOAc (3×30 mL). The combined organic layer was washed with brine (30 mL), dried over anhydr. Na$_2$SO$_4$ and the filtrate concentrated in vacuo to dryness. The residue was purified by column chromatogra-phy with EtOAc/petroleum ether (40-90%) to afford the title compound.

Step B—4-Amino-5-(4-chloro-3-methoxyphenyl)-2-(3-((diphenylmethylene)amino)-8-[(3-fluorophenyl) methyl]imidazo[1,2-a]pyrazin-6-yl)-5-methyl-5,7-dihydro-6H-pyrrolo[2,3-d]pyrimidin-6-one Into a microwave vial under an inert atmosphere of N$_2$ were placed intermediate from Step A (200 mg, 0.33 mmol), diphenylmethanimine (119 mg, 0.66 mmol), sodium tert-butoxide (63.1 mg, 0.66 mmol), and 2nd Generation Xant-Phos precatalyst (29 mg, 0.033 mmol) in dioxane (5 mL). The reaction mixture was irradiated with microwave radia-tion at 150° C. for 1 h, then cooled, quenched with sat., aq. NH$_4$Cl (50 mL), and extracted with EtOAc (3×30 mL). The combined organic layer was washed with brine (30 mL), dried over anhydr. Na$_2$SO$_4$ and the filtrate concentrated in vacuo to dryness to afford the title compound, which was used directly.

Step C—4-Amino-2-(3-amino-8-[(3-fluorophenyl) methyl]imidazo[1,2-a]pyrazin-6-yl)-5-(4-chloro-3-methoxyphenyl)-5-methyl-5,7-dihydro-6H-pyrrolo [2,3-d]pyrimidin-6-one Into a flask were placed intermediate from Step B (250 mg, 0.35 mmol) in THF (10 mL) and water (5 mL), followed by HCl (37%, 1 mL). The reaction mixture was stirred at RT for 1 h and then the basicity of the solution was adjusted to pH8 with sat., aq. NaHCO$_3$. The mixture was extracted with EtOAc (3×20 mL) and the combined organic layer was washed with brine (20 mL), dried over anhydr. Na$_2$SO$_4$ and the filtrate concentrated in vacuo. The residue was purified by RP-HPLC with MeCN/water (0.1% v/v TFA, 50-90%) to afford the title compound.

Step D—4-Amino-2-(3-amino-8-[(3-fluorophenyl) methyl]imidazo[1,2-a]pyrazin-6-yl)-5-(4-chloro-3-hydroxyphenyl)-5-methyl-5,7-dihydro-6H-pyrrolo[2,3-d]pyrimidin-6-one Into a flask were placed intermediate from Step C (80 mg, 0.088 mmol), and hydrobromic acid (40%, 10 mL) and the mixture was stirred at 80° C. for 16 h, then at 100° C. for 6 h. It was cooled and the acidity of the solution was adjusted to pH 7 with NaHCO₃ (solid), followed by the extraction with EtOAc (3×20 mL). The combined organic layer was washed with brine (10 mL), dried over Na₂SO₄, and filtered. The filtrate was concentrated in vacuo. The residue was purified by RP-HPLC with MeCN/Water (0.1% TFA, 25-45%) followed by silica gel column chromatography with MeOH/DCM (3-5%) to afford the title compound, 140-A. MS: 531 (M+1). ¹H NMR (400 MHz, CD₃OD): δ 9.08 (s, 1H), 7.32-7.20 (m, 5H), 6.93-6.83 (m, 3H), 4.56 (s, 2H), 1.86 (s, 3H).

Using essentially the same procedures described in Examples 1 through 4, the following compounds in Table 10 were prepared. The deprotection step was performed using either BBr₃ or HBr as a deprotecting reagent.

TABLE 10

Examples 141-B-150-A

| Ex. | Structure | Name | MS (M + 1) | Chiral SM |
|---|---|---|---|---|
| 141-B | 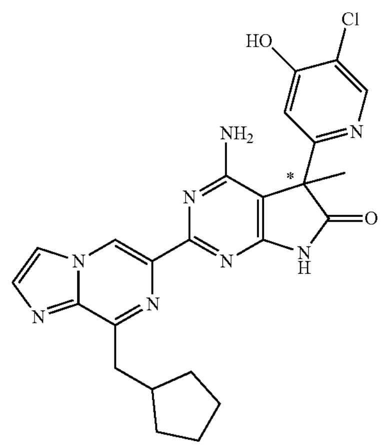 [SMILES: CC1(c2cc(O)c(Cl)cn2)C(=O)Nc2nc(-c3cn4ccnc4c(CC4CCCC4)n3)nc(N)c21] | 4-amino-5-(5-chloro-4-hydroxypyridin-2-yl)-2-(8-(cyclopentylmethyl)-imidazo[1,2-a]pyrazin-6-yl)-5-methyl-5,7-dihydro-6H-pyrrolo-[2,3-d]pyrimidin-6-one | 491 | I-5B |
| 142-A | 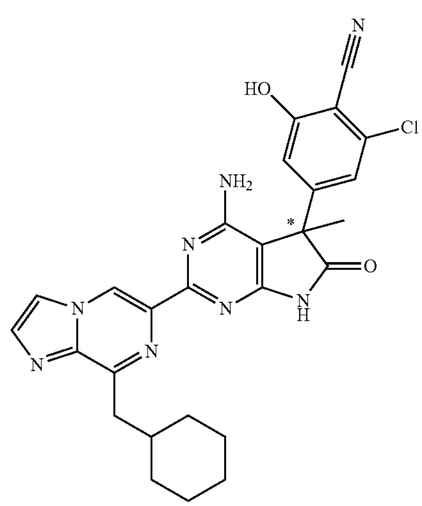 [SMILES: CC1(c2cc(O)c(C#N)c(Cl)c2)C(=O)Nc2nc(-c3cn4ccnc4c(CC4CCCCC4)n3)nc(N)c21] | 4-(4-amino-2-{8-(cyclohexylmethyl)-imidazo[1,2-a]pyrazin-6-yl}-5-methyl-6-oxo-6,7-dihydro-5H-pyrrolo-[2,3-d]pyrimidin-5-yl)-2-chloro-6-hydroxy-benzonitrile | 529 | I-34A |

TABLE 10-continued

Examples 141-B-150-A

| Ex. | Structure | Name | MS (M + 1) | Chiral SM |
|---|---|---|---|---|
| 143-A | 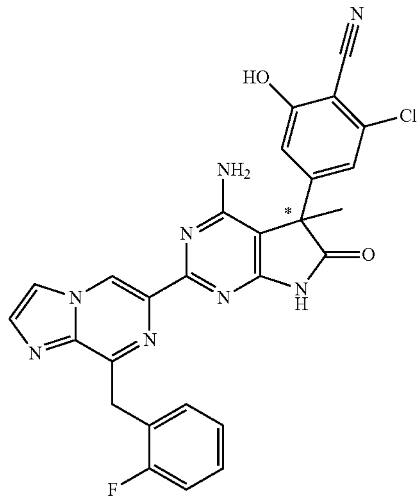 [SMILES: CC1(c2cc(O)c(C#N)c(Cl)c2)C(=O)Nc2nc(-c3cn4ccnc4c(Cc4ccccc4F)n3)nc(N)c21] | 4-(4-amino-2-{8-(2-fluorobenzyl)imidazo-[1,2-a]pyrazin-6-yl}-5-methyl-6-oxo-6,7-dihydro-5H-pyrrolo-[2,3-d]pyrimidin-5-yl)-2-chloro-6-hydroxy-benzonitrile | 541 | I-34A |
| 144-A | 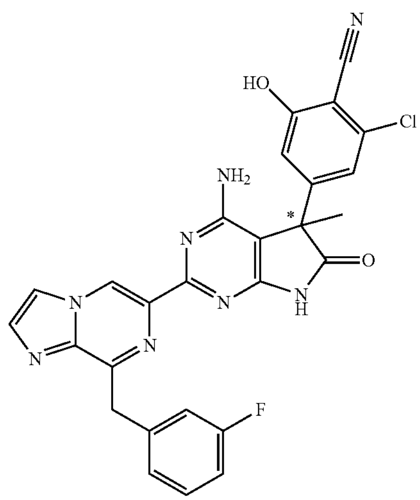 [SMILES: CC1(c2cc(O)c(C#N)c(Cl)c2)C(=O)Nc2nc(-c3cn4ccnc4c(Cc4cccc(F)c4)n3)nc(N)c21] | 4-(4-amino-2-{8-(3-fluorobenzyl)imidazo-[1,2-a]pyrazin-6-yl}-5-methyl-6-oxo-6,7-dihydro-5H-pyrrolo-[2,3-d]pyrimidin-5-yl)-2-chloro-6-hydroxy-benzonitrile | 541 | I-34A |
| 145-B | 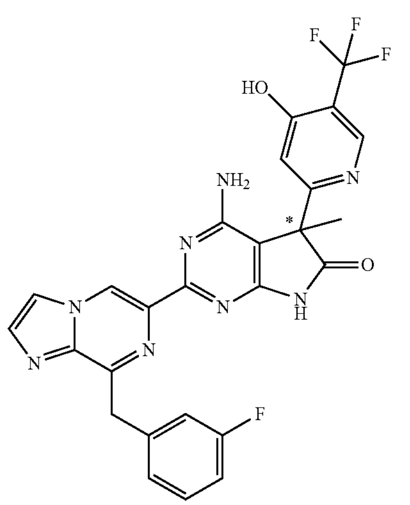 [SMILES: CC1(c2cc(O)c(C(F)(F)F)cn2)C(=O)Nc2nc(-c3cn4ccnc4c(Cc4cccc(F)c4)n3)nc(N)c21] | 4-amino-2-(8-{3-fluorobenzyl}imidazo-[1,2-a]pyrazin-6-yl)-5-(4-hydroxy-5-(trifluoromethyl)pyridin-2-yl)-5-methyl-5,7-dihydro-6H-pyrrolo-[2,3-d]pyrimidin-6-one | 551 | I-32B |

TABLE 10-continued

Examples 141-B-150-A

| Ex. | Structure | Name | MS (M + 1) | Chiral SM |
|---|---|---|---|---|
| 146-B | 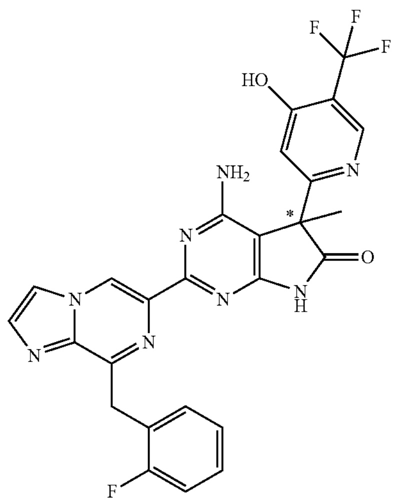 [SMILES: CC1(c2cc(O)c(C(F)(F)F)cn2)C(=O)Nc2nc(-c3cn4ccnc4c(Cc4ccccc4F)n3)nc(N)c21] | 4-amino-2-(8-{2-fluorobenzyl}imidazo-[1,2-a]pyrazin-6-yl)-5-(4-hydroxy-5-(trifluoromethyl)-pyridin-2-yl)-5-methyl-5,7-dihydro-6H-pyrrolo-[2,3-d]pyrimidin-6-one | 551 | I-32B |
| 147-B | 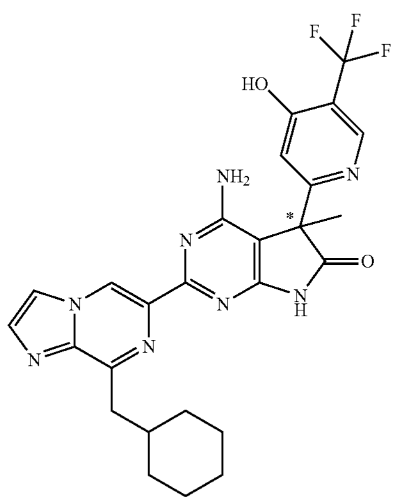 [SMILES: CC1(c2cc(O)c(C(F)(F)F)cn2)C(=O)Nc2nc(-c3cn4ccnc4c(CC4CCCCC4)n3)nc(N)c21] | 4-amino-2-{8-(cyclohexylmethyl)-imidazo[1,2-a]pyrazin-6-yl}-5-(4-hydroxy-5-(trifluoromethyl)pyridin-2-yl)-5-methyl-5,7-dihydro-6H-pyrrolo-[2,3-d]pyrimidin-6-one | 539 | I-32B |
| 148-B | 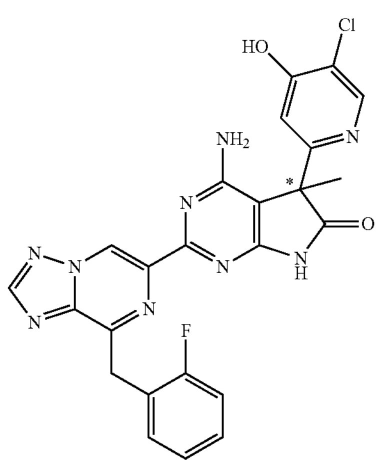 [SMILES: CC1(c2cc(O)c(Cl)cn2)C(=O)Nc2nc(-c3cn4ncnc4c(Cc4ccccc4F)n3)nc(N)c21] | 4-amino-5-(5-chloro-4-hydroxypyridin-2-yl)-2-{8-(2-fluorobenzyl)-[1,2,4]triazolo[1,5-a]-pyrazin-6-yl}-5-methyl-5,7-dihydro-6H-pyrrolo-[2,3-c]pyrimidin-6-one | 518 | I-5B |

TABLE 10-continued

Examples 141-B-150-A

| Ex. | Structure | Name | MS (M + 1) | Chiral SM |
|---|---|---|---|---|
| 149-A | 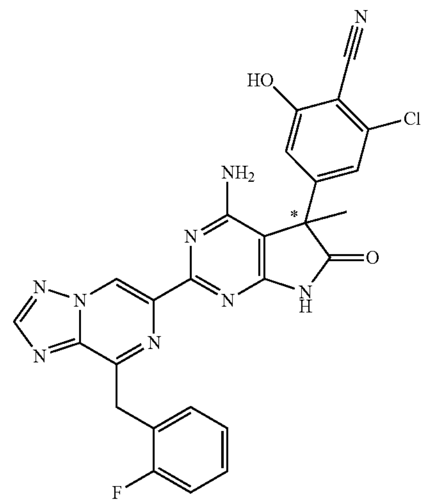 [SMILES: CC1(c2cc(O)c(C#N)c(Cl)c2)C(=O)Nc2nc(-c3cn4ncnc4c(Cc4ccccc4F)n3)nc(N)c21] | 4-(4-amino-2-{8-(2-fluorobenzyl)-[1,2,4]-triazolo[1,5-a]pyrazin-6-yl}-5-methyl-6-oxo-6,7-dihydro-5H-pyrrolo-[2,3-d]pyrimidin-5-yl)-2-chloro-6-hydroxy-benzonitrile | 542 | I-34A |
| 150-A | 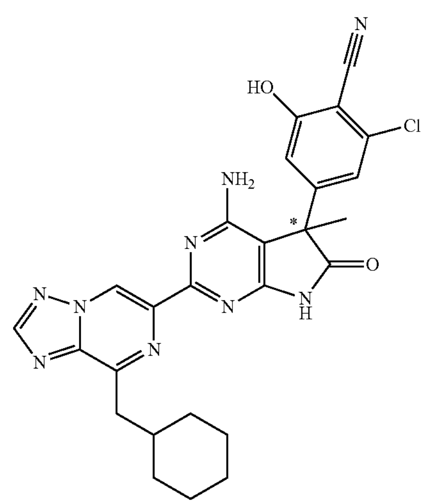 [SMILES: CC1(c2cc(O)c(C#N)c(Cl)c2)C(=O)Nc2nc(-c3cn4ncnc4c(CC4CCCCC4)n3)nc(N)c21] | 4-(4-amino-2-{8-(cyclohexylmethyl)-[1,2,4]triazolo[1,5-a]-pyrazin-6-yl}-5-methyl-6-oxo-6,7-dihydro-5H-pyrrolo-[2,3-d]pyrimidin-5-yl)-2-chloro-6-hydroxy-benzonitrile | 530 | I-34A |

Example 151-A

4-Amino-2-{8-(3-fluorobenzyl)imidazo[1,2-a]pyrazin-6-yl}-5-(4-hydroxy-5-methylpyridin-2-yl)-5-methyl-5,7-dihydro-6H-pyrrolo[2,3-d]pyrimidin-6-one

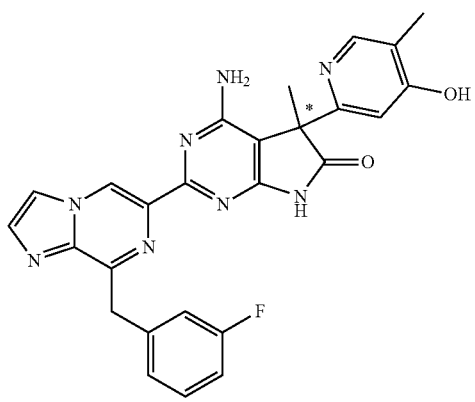 [SMILES: Cc1cnc(C2(C)C(=O)Nc3nc(-c4cn5ccnc5c(Cc5cccc(F)c5)n4)nc(N)c32)cc1O]

Step A—4-Amino-2-{8-(3-fluorobenzyl)imidazo[1,2-a]pyrazin-6-yl}-5-(4-methoxy-5-methylpyridin-2-yl)-5-methyl-5,7-dihydro-6H-pyrrolo[2,3-d]pyrimidin-6-one Into a flask were placed amidine I-A4 (257 mg, 0.74 mmol), racemic malononitrile I-33 (234 mg, 0.85 mmol), potassium bicarbonate (1.63 g, 16.3 mmol) and tert-BuOH (15 mL). The resulting mixture was stirred at 70° C. for 16 h, then concentrated in vacuo. The residue was purified by column chromatography eluting with EtOAc/petroleum ether (50-100%) to afford the title compound. The racemic material was resolved using chiral-prep-HPLC CHIRALPAK IF to afford isomers A (faster eluting) and B (slower eluting) of the title compound.

Step B—4-Amino-2-{8-(3-fluorobenzyl)imidazo[1,2-a]pyrazin-6-yl}-5-(4-hydroxy-5-methylpyridin-2-yl)-5-methyl-5,7-dihydro-6H-pyrrolo[2,3-d]pyrimidin-6-one Into a flask, were placed enantiomer A from Step A (50 mg, 0.10 mmol), and hydrobromic acid (48%, 5 mL). The mixture was stirred at 100° C. for 72 h. It was cooled, and the acidity of the solution was adjusted to pH 8 with sat. aq. NaHCO$_3$. The mixture was extracted with EtOAc (3×50 mL). The combined organic layer was washed with brine (100 mL), dried over anhydr.Na$_2$SO$_4$, and filtered. The filtrate was concentrated in vacuo. The residue was purified by RP-HPLC with MeCN/Water (10 mM, ammonium bicarbonate, 10-80%) to afford the title compound, 151-A. MS: 497 (M+1). $^1$H NMR (300 MHz, CD$_3$OD): δ 9.38 (s, 1H), 8.10 (d, J=0.9 Hz, 1H), 7.81 (d, J=0.9 Hz, 1H), 7.72-7.71 (brs, 1H), 7.18-7.29 (m, 3H), 6.90-6.84 (m, 1H), 6.43-6.42 (brs, 1H), 4.60 (s, 2H), 2.01 (s, 3H), 1.86 (s, 3H).

Reference Example—Compound B

3-(2-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic Acid This example describes the preparation of Compound B, which is radiolabeled and then used in the binding assay described in Biological Assays section below.

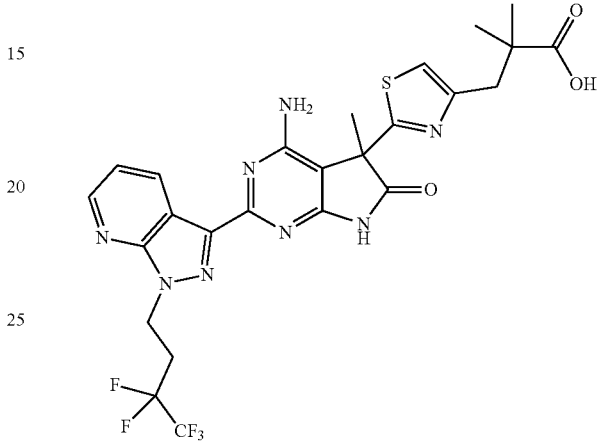

Step A—Diethyl 2-(dicyanomethyl)-2-methylmalonate

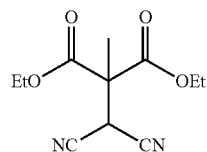 [SMILES: CCOC(=O)C(C)(C(=O)OCC)C(C#N)C#N]

Using the procedure described in WO2015/088885 diethyl 2-(dicyanomethyl)-2-methylmalonate was prepared. $^1$H NMR (500 MHz, CDCl$_3$): δ 4.55 (1H, s), 4.28-4.39 (4H, m), 1.82 (3H, s), 1.34 (6H, t, J=7.12 Hz).

Step B—Ethyl 4-cyano-5-ethoxy-3-methyl-2-oxo-2,3-dihydro-1H-pyrrole-3-carboxylate To a flask containing diethyl 2-(dicyanomethyl)-2-methylmalonate (20 g, 84 mmol) in EtOH (280 mL) at RT was added sodium ethoxide (37.6 mL, 101 mmol, 21 wt. % in EtOH) and the mixture was stirred at 65° C. overnight. The reaction was allowed to cool down to RT and concentrated in vacuo to dryness. The residue was diluted with DCM and the pH value of the solution was adjusted to 7 with AcOH. The solids were removed by filtration. The resulting mixture was concentrated under vacuum. The residue was purified by silica gel chromatography using an EtOAc:hexane gradient to afford the racemic title product. The racemic material was resolved using chiral SFC (CHIRALPAK® AS-H column) to afford isomers I-RefA (faster eluting) and I-RefB (slower eluting).

Step C—1-(3,3,4,4,4-pentafluorobutyl)-1H-pyrazolo[3,4-b]pyridine-3-carbonitrile In a flask containing 1H-pyrazolo[3,4-b]pyridine-3-carbonitrile (5 g, 34.7 mmol) in acetonitrile (75 mL) was added 1,1,1,2,2-pentafluoro-4-iodobutane (9.82 mL, 69.4 mmol) and potassium carbonate (24.0 g, 173 mmol). The reaction was stirred at 45° C. for 18 hours then cooled to RT, diluted with water and extracted with EtOAc (3×). The organic layers were combined, dried over anhydr. $Na_2SO_4$, and filtered. The filtrate was concentrated in vacuo. The residue was purified by silica gel column chromatography with EtOAc:Hex (0-100%) to afford the title compound

Step D—1-(3,3,4,4,4-pentafluorobutyl)-1H-pyrazolo[3,4-b]pyridine-3-carboximidamide In a flask containing 1-(3,3,4,4,4-pentafluorobutyl)-1H-pyrazolo[3,4-b]pyridine-3-carbonitrile (5.1 g, 17.7 mmol) in MeOH (11 mL) at RT was added NaOMe (1.34 g, 24.7 mmol). The mixture was stirred at RT for 3 h before acetic acid (4.05 mL, 70.7 mmol) was added, followed by ammonium chloride (1.23 g, 23.0 mmol). The resulting slurry was heated to 65° C. for 4 h then cooled to RT, quenched by the addition of aq. sat. $NaHCO_3$ and extracted with EtOAc (3×). The organic layers were combined, washed with brine dried over anhydr. $Na_2SO_4$, and filtered. The filtrate was concentrated in vacuo. The residue was purified by silica gel column chromatography with (EtOAc:MeOH 10:1):hexane gradient to afford the title compound. $^1$H NMR (400 MHz, DMSO-$d_6$) δ 9.45 (s, 3H), 8.77 (dd, J=4.5, 1.5 Hz, 1H), 8.56 (dd, J=8.3, 1.5 Hz, 1H), 7.53 (dd, J=8.3, 4.5 Hz, 1H), 4.93 (t, J=6.8 Hz, 2H), 3.06 (tt, J=19.1, 6.9 Hz, 2H); m/z=308 (M+1).

Step E—Ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate To a mixture of 1-(3,3,4,4,4-pentafluorobutyl)-1H-pyrazolo[3,4-b]pyridine-3-carboximidamide (1.0 g, 3.2 mmol) and I-RefB (1.16 g, 4.88 mmol) in THF (65 mL) at RT was added triethylamine (1.3 mL, 9.76 mmol). The resulting mixture was warmed at 65° C. for 16 h. The reaction was cooled to RT concentrated in vacuo to dryness. The residue was purified by silica gel chromatography using MeOH:DCM (1-10%) to afford the title compound. m/z=500 (M+1).

Step F—4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxamide In a sealed tube containing ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate (1.5 g, 3.00 mmol) was added ammonia (30 mL, 3 N in MeOH). The resulting mixture was warmed at 40° C. for 16 h. The reaction was cooled to RT concentrated in vacuo to dryness. The residue was purified by silica gel chromatography using MeOH:DCM (5%) to afford the title compound. m/z=471 (M+1).

Step G—4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carbothioamide Into a flask was placed 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxamide (1.1 g, 2.34 mmol), Lawesson's Reagent (1.1 g, 2.81 mmol) and toluene (67 mL). The resulting mixture was warmed at 80° C. for 16 h. The reaction was quenched by the addition of aq. sat. $NaHCO_3$, extracted with EtOAc (3×). The organic layer was washed with brine, dried over anhydr. $Na_2SO_4$, and filtered. The filtrate was concentrated in vacuo. The residue was purified by silica gel column chromatography with MeOH:DCM (5%) to afford the title compound. m/z=487 (M+1).

Step H—ethyl 3-(2-(4-amino-5-methyl-6-oxo-2-(1-(3,3,4,4,4-pentafluorobutyl)-1H-pyrazol[3,4-b]pyridin-3-yl)-6,7-dihydro-5H-pyrrolo[2,3-d]pyrimidin-5-yl)thiazol-4-yl)-2,2-dimethylpropanoate In a sealed tube containing 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carbothioamide (60 mg, 0.123 mmol) and ethyl 5-bromo-2,2-dimethyl-4-oxopentanoate (48.9 mg, 0.185 mmol) in EtOH (1.2 mL) was warmed at 80° C. for 16 h. The reaction was cooled to RT concentrated in vacuo to dryness. The residue was purified by silica gel chromatography using (EtOAc: EtOH 3:1): Hexane to afford the title compound. m/z=639 (M+1).

Step I—3-(2-{4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl}thiazol-4-yl)-2,2-dimethylpropanoic Acid Into a flask was placed ethyl 3-(2-(4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl)thiazol-4-yl)-2,2-dimethylpropanoate (130 mg, 0.12 mmol), LiOH (29 mg, 1.22 mmol) dioxane (2.2 mL) and water (2.2 mL) The resulting mixture was stirred at 60° C. for 16 h. The reaction was cooled to RT conc. in vacuo then diluted in EtOAc and water and acetic acid (84 μl, 1.46 mmol) was added. The resulting solution was extracted with EtOAc. The organic layer was washed with brine, dried over anhydr. $MgSO_4$, and filtered. The filtrate was concentrated in vacuo. The residue was purified by silica gel column chromatography with (EtOAc:EtOH 3:1): hexane to afford the title compound $^1$H NMR (400 MHz, DMSO-$d_6$) δ 12.23 (s, 1H), 11.45 (s, 1H), 9.02 (dd, J=8.1, 1.7 Hz, 1H), 8.63 (dd, J=4.5, 1.6 Hz, 1H), 7.37 (dd, J=8.1, 4.5 Hz, 1H), 7.24 (s, 1H), 6.96 (s, 2H), 4.87 (t, J=6.8 Hz, 2H), 3.06-2.85 (m, 4H), 1.80 (s, 3H), 1.08 (s, 6H); m/z=611 (M+1).

Biological Assays

Cell-Based sGC Functional Assay (Cyclic GMP Assay for sGC Activator: CASA Assay)

Soluble guanylate cyclase (sGC) is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially target sGC containing a ferrous heme group. To determine the effect of sGC activators on enzyme activity, the CASA assay was developed to monitor the generation of cGMP in a cell line that stably expresses the heterodimeric sGC protein.

Methods:

A CHO-K1 cell line stably expressing the sGC α1/β1 heterodimer was generated using a standard transfection protocol. The cDNA's encoding human sGC α1 and β1 were cloned in pIRES hyg and pIRES neo respectively using standard molecular biology techniques. The plasmids pIRES hyg and pIRES neo plasmids were obtained from Clontech. CHO-K1 cells were transfected with plasmids pIREShyg-hsGCα1 and pIRESneo-hsGCβ1 simultaneously using FUGENE reagent. Clones that stably express both subunits were selected with hygromycin and neomycin for ~2 weeks. The clone chosen for the assay was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in liquid nitrogen. On the day of the assay, the cells were thawed and resuspended in EBSS Assay Buffer (Sigma, E3024) supplemented with 5 mM $MgCl_2$, 10 mM HEPES (4-(2-hydroxyethyl)piperazine-1-ethanesulfonic acid) and 0.05% BSA (bovine serum albumin) and cell density was then adjusted to 2.25×105/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were pre-incubated in the presence and absence of 1 μM of Diethylenetriamine/nitric oxide adduct (DETA-NO; Sigma, 17018) for 30 min at 25° C. Compounds were subsequently added and incubated for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation) of the published sGC compound A (Example 1 in WO 2010/065275, published Jun. 10, 2010).

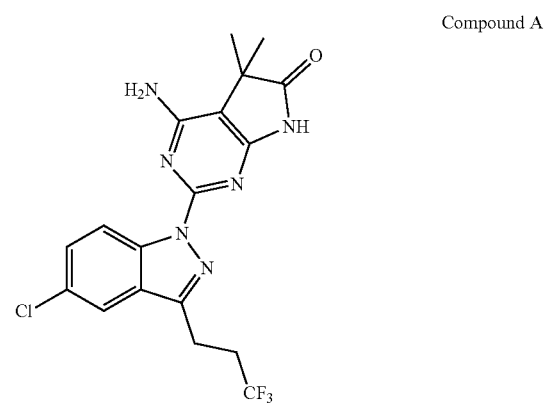 [SMILES: CC1(C)C(=O)Nc2nc(-n3nc(CCC(F)(F)F)c4cc(Cl)ccc43)nc(N)c21]

Compound A

The test compounds' activities were then expressed as a percentage of compound A, the standard in every experiment. This percent activation was calculated either in the presence or absence of DETA-NO which was then plotted. Inflection points (IP) and maximum fold induction was derived using Abase analysis software for 4P fit.

Most preferred compounds had an IP of less than or equal to about 5000 nM. Data for the compounds of the Examples is provided in Table 11.

TABLE 11

| EXAMPLE | IP (nM) | % Activation |
|---|---|---|
| 1-A | 226 | 118 |
| 2-B | 1619 | 89 |
| 3-B | 2080 | 98 |
| 4-B | 1925 | 136 |
| 5-B | 188 | 113 |
| 6-B | 94 | 113 |
| 7-B | 217 | 102 |
| 8-A | 316 | 72 |
| 9-B | 1042 | 85 |
| 10-B | 25 | 132 |
| 11-B | 503 | 137 |
| 12-B | 98 | 116 |
| 13-B | 821 | 100 |
| 14-A | 144 | 68 |
| 15-B | 771 | 107 |
| 16-B | 308 | 94 |
| 17-B | 482 | 117 |
| 18-B | 950 | 88 |
| 19-B | 78 | 152 |
| 20-A | 127 | 130 |
| 21-B | 95 | 143 |
| 22-B | 74 | 128 |
| 23-B | 3105 | 76 |
| 24-B | 752 | 88 |
| 25-A | 223 | 117 |
| 26-A | 426 | 105 |
| 27-B | 489 | 94 |
| 28-B | 433 | 141 |
| 29-B | 67 | 80 |
| 30-A | 866 | 88 |
| 31-B | 82 | 93 |
| 32-B | 648 | 107 |
| 33-B | 260 | 111 |
| 34-B | 243 | 111 |
| 35-B | 402 | 147 |
| 36-A | 381 | 116 |
| 37-B | 69 | 117 |
| 38-B | 720 | 92 |
| 39-B | 873 | 101 |
| 40-B | 368 | 88 |
| 41-B | 588 | 136 |
| 42-B | 146 | 170 |
| 43-B | 142 | 101 |
| 44-A | 460 | 100 |
| 45-A | 1571 | 120 |
| 46-B | 893 | 117 |
| 47-B | 70 | 103 |
| 48-B | 198 | 114 |
| 49-A | 363 | 111 |
| 50-A | 70 | 175 |
| 51-B | 1020 | 88 |
| 52-A | 144 | 85 |
| 53-B | 771 | 144 |
| 54-B | 42 | 72 |
| 55-A | 969 | 113 |
| 56-B | 627 | 101 |
| 57-B | 798 | 67 |
| 58-B | 164 | 121 |
| 59-B | 335 | 109 |
| 60-B | 4383 | 138 |
| 61-B | 121 | 105 |
| 62-B | 49 | 97 |
| 63-A | 600 | 121 |
| 64-B | 1323 | 125 |
| 65-A | 797 | 85 |
| 66-B | 2149 | 141 |
| 67-A | 728 | 134 |
| 68-B | 46 | 96 |
| 69-A | 1376 | 108 |
| 70-B | 32 | 81 |
| 71-B | 30 | 81 |
| 72-B | 3457 | 84 |
| 73-A | 694 | 81 |
| 74-B | 131 | 122 |
| 75-B | 770 | 153 |
| 76-B | 547 | 110 |
| 77-B | 645 | 99 |
| 78-B | 202 | 93 |

TABLE 11-continued

| EXAMPLE | IP (nM) | % Activation |
|---|---|---|
| 79-B | 96 | 108 |
| 80-B | 19 | 70 |
| 81-B | 352 | 131 |
| 82-B | 207 | 111 |
| 83-B | 222 | 109 |
| 84-B | 313 | 121 |
| 85-B | 605 | 130 |
| 86-B | 166 | 122 |
| 87-A | 935 | 111 |
| 88-A | 279 | 95 |
| 89-B | 809 | 127 |
| 90-A | 94 | 138 |
| 91-A | 75 | 141 |
| 92-B | 2862 | 104 |
| 93-B | 683 | 98 |
| 94-B | 1257 | 125 |
| 95-A | 1812 | 96 |
| 96-B | 138 | 169 |
| 97-B | 1078 | 138 |
| 98-B | 3301 | 73 |
| 99-A | 553 | 97 |
| 100-A | 652 | 106 |
| 101-B | 282 | 53 |
| 102-B | 382 | 73 |
| 103-B | 231 | 78 |
| 104-B | 813 | 144 |
| 105-B | 138 | 108 |
| 106-A | 902 | 81 |
| 107-B | 198 | 135 |
| 108-AA | 198 | 118 |
| 108-AB | 210 | 127 |
| 109-A | 221 | 97 |
| 110-B | 437 | 159 |
| 111-B | 1545 | 86 |
| 112-B | 16 | 112 |
| 113-A | 125 | 91 |
| 114-B | 137 | 112 |
| 115-B | 63 | 79 |
| 116-B | 95 | 137 |
| 117-B | 109 | 94 |
| 118-B | 457 | 103 |
| 119-B | 681 | 75 |
| 120-BA | 85 | 133 |
| 120-BB | 39 | 121 |
| 121-B | 369 | 120 |
| 122-B | 1818 | 106 |
| 123-B | 768 | 107 |
| 124-B | 224 | 113 |
| 125-B | 601 | 164 |
| 126-B | 391 | 206 |
| 127-B | 9980 | 118 |
| 128-B | 1205 | 137 |
| 129-B | 1885 | 84 |
| 130-A | 1923 | 81 |
| 131-AA | 427 | 89 |
| 131-AB | 292 | 96 |
| 132-AA | 746 | 99 |
| 132-AB | 736 | 95 |
| 133-AA | 1286 | 38 |
| 133-AB | 3376 | 48 |
| 134-A | 333 | 102 |
| 135-B | 966 | 103 |
| 136-A | 511 | 66 |
| 137-A | 744 | 99 |
| 138-A | 169 | 65 |
| 139-A | 349 | 68 |
| 140-A | 816 | 101 |
| 141-B | 1349 | 99 |
| 142-A | 3529 | 74 |
| 143-A | 2971 | 79 |
| 144-A | 2679 | 91 |
| 145-B | 2442 | 91 |
| 146-B | 2345 | 96 |
| 147-B | 1199 | 102 |
| 148-B | 242 | 105 |
| 149-A | 583 | 54 |

TABLE 11-continued

| EXAMPLE | IP (nM) | % Activation |
|---|---|---|
| 150-A | 4125 | 96 |
| 151-A | 1791 | 84 |

Binding Assay:

The binding potencies of sGC compounds to the human recombinant sGC enzyme were determined in a Size Exclusion Chromatography (SEC) competition binding assay using [$^3$H] Compound B as the radioligand. [$^3$H] Compound B was prepared using a standardardized tritium exchange procedure. The parent (non-labeled) molecule was first iodinated then a Pd-catalyzed iodine to tritium exchange provided the labeled compound.

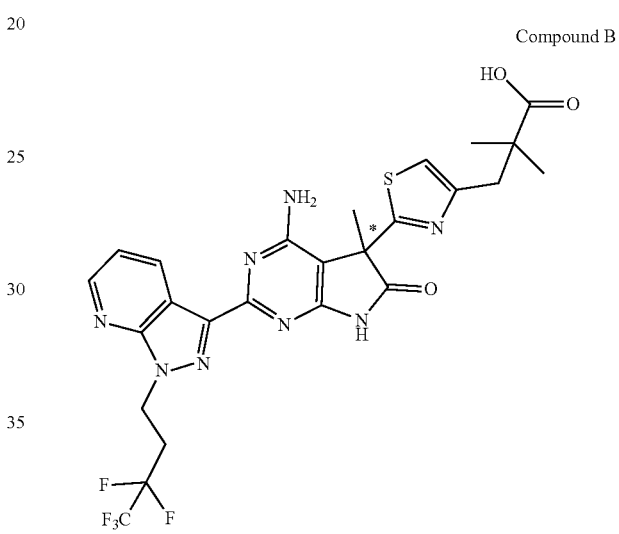

Compound B

Method: The binding buffer was composed of 50 mM triethanolamine pH 7.4, 3 mM MgCl$_2$, 0.025% BSA, 2 mM dithiothreitol (DTT), 300 μM DETA/NO and 400 μM GTP. Assays were conducted in 96-well plates in a total volume of 200 μL. Recombinant human sGC protein (40 ng) was incubated with 1.6 nM [$^3$H] Compound B for 24 h at 37° C. in the presence and absence of various concentrations of sGC testing compounds delivered as DMSO solutions to give a total of 1% organic solvent content. Non-specific binding was defined by competition with 1 μM of Compound B. After the incubation period, the binding mixtures were loaded onto the gel-filtration plate (ThermoFischer Cat. No. 89808) pre-equilibrated with binding buffer and spun at 1000×g for 3 min at 4° C. on a Bench top centrifuge. The collected eluates in White Frame Clear Well Isoplates (Perkin Elmer Cat #6005040) received 100 μl of UltimaGold scintillation cocktail. The sealed plates were shaken vigorously and span, and counted after 6 hs with a Wallac Microbeta TriLux 1450 LSC & Luminescence Counter (Perkin Elmer). Data from competition experiments were analyzed to determine K$_i$ values using one site—fit K$_i$ equation.

Most preferred compounds had an Ki of less than or equal to about 15 nM. Data for the compounds of the Examples is provided in Table 12.

TABLE 12

| EXAMPLE | Ki (nM) |
|---|---|
| 1-A | 0.095 |
| 2-B | 0.095 |
| 3-B | 0.219 |
| 4-B | 0.259 |
| 5-B | 0.091 |
| 6-B | 0.094 |
| 7-B | 0.098 |
| 8-A | 0.117 |
| 9-B | 0.126 |
| 10-B | 0.128 |
| 11-B | 0.135 |
| 12-B | 0.153 |
| 13-B | 0.154 |
| 14-A | 0.156 |
| 15-B | 0.158 |
| 16-B | 0.158 |
| 17-B | 0.163 |
| 18-B | 0.168 |
| 19-A | 0.170 |
| 20-A | 0.173 |
| 21-B | 0.206 |
| 22-B | 0.214 |
| 23-B | 0.216 |
| 24-B | 0.241 |
| 25-A | 0.252 |
| 26-A | 0.276 |
| 27-B | 0.280 |
| 28-B | 0.283 |
| 29-B | 0.291 |
| 30-A | 0.292 |
| 31-B | 0.274 |
| 32-B | 0.306 |
| 33-B | 0.312 |
| 34-B | 0.317 |
| 35-B | 0.333 |
| 36-A | 0.393 |
| 37-B | 0.427 |
| 38-B | 0.410 |
| 39-B | 0.446 |
| 40-B | 0.479 |
| 41-B | 0.490 |
| 42-B | 0.496 |
| 43-B | 0.457 |
| 44-A | 0.507 |
| 45-A | 0.565 |
| 46-B | 0.691 |
| 47-B | 0.676 |
| 48-B | 0.723 |
| 49-A | 0.746 |
| 50-A | 0.775 |
| 51-B | 0.874 |
| 52-A | 0.864 |
| 53-B | 1.076 |
| 54-B | 1.082 |
| 55-A | 1.211 |
| 56-B | 1.237 |
| 57-B | 1.242 |
| 58-B | 1.539 |
| 59-B | 1.716 |
| 60-B | 1.915 |
| 61-B | 2.085 |
| 62-B | 2.208 |
| 63-A | 2.200 |
| 64-B | 2.222 |
| 65-A | 2.257 |
| 66-B | 2.569 |
| 67-A | 2.652 |
| 68-B | 2.920 |
| 69-A | 3.471 |
| 70-B | 3.957 |
| 71-B | 4.076 |
| 72-B | 4.615 |
| 73-A | 6.014 |
| 74-B | 6.174 |
| 75-B | 6.553 |
| 76-B | 7.888 |
| 77-B | 8.795 |
| 78-B | 8.877 |
| 79-B | 9.413 |
| 80-B | 9.985 |
| 81-B | 13.95 |
| 82-B | 0.402 |
| 83-B | 5.122 |
| 84-B | 3.460 |
| 85-B | 4.817 |
| 86-B | 2.222 |
| 87-A | 2.799 |
| 88-A | 2.500 |
| 89-B | 0.823 |
| 90-A | 2.434 |
| 91-A | 0.199 |
| 92-B | 0.729 |
| 93-B | 0.374 |
| 94-B | 0.149 |
| 95-A | 14.39 |
| 96-B | 0.862 |
| 97-B | 0.587 |
| 98-B | 8.309 |
| 99-A | 0.803 |
| 100-A | 0.544 |
| 101-B | 0.162 |
| 102-B | 0.118 |
| 103-B | 0.175 |
| 104-B | 1.100 |
| 105-B | 0.213 |
| 106-A | 1.837 |
| 107-B | 0.221 |
| 108-AA | 0.924 |
| 108-AB | 0.524 |
| 109-A | 0.634 |
| 110-B | 1.625 |
| 111-B | 1.740 |
| 112-B | 1.776 |
| 113-A | 2.897 |
| 114-B | 4.950 |
| 115-B | 5.026 |
| 116-B | 6.375 |
| 117-B | 8.552 |
| 118-B | 7.952 |
| 119-B | 2.764 |
| 120-BA | 10.86 |
| 120-BB | 3.786 |
| 121-B | 0.382 |
| 122-B | 15.61 |
| 123-B | 0.372 |
| 124-B | 2.632 |
| 125-B | 0.508 |
| 126-B | 1.099 |
| 127-B | 9.721 |
| 128-B | 0.646 |
| 129-B | 1.995 |
| 130-A | 7.149 |
| 131-AA | 0.884 |
| 131-AB | 0.347 |
| 132-AA | 1.209 |
| 132-AB | 1.459 |
| 133-AA | 2.336 |
| 133-AB | 9.245 |
| 134-A | 0.592 |
| 135-B | 4.011 |
| 136-A | 1.566 |
| 137-A | 2.629 |
| 138-A | 4.622 |
| 139-A | 3.544 |
| 140-A | 0.827 |
| 141-B | 0.706 |
| 142-A | 1.138 |
| 143-A | 1.086 |
| 144-A | 0.333 |
| 145-B | 0.416 |
| 146-B | 0.378 |
| 147-B | 0.905 |
| 148-B | 0.261 |
| 149-A | 0.509 |

TABLE 12-continued

| EXAMPLE | Ki (nM) |
|---------|---------|
| 150-A | 0.989 |
| 151-A | 0.155 |

Acute Efficacy in Hypoxia-Induced Pulmonary Hypertension in Rat Following Intratracheal (IT) Administration Charles River Sprague-Dawley (CD) male rats weighing approximately 350 g were implanted with HD-S21 dual pressure telemetry transmitters (Data Sciences International (DSI)) into the pulmonary artery and femoral artery. This transmitter enables simultaneous measurement of both pulmonary and systemic hemodynamic parameters in the same animal. After a 7-10 day post-operative recovery period, animals were subjected to a normobaric hypoxic (10% oxygen) environment using a Higher Peak Mountain Air Generator (MAG-10) connected to a modified rodent cage via a fitted inlet port. Oxygen (at 10%), temperature, humidity, and $CO_2$ were controlled within normal range and animals were maintained on a 12 hour light-dark cycle with ad libitum access to food and water. After two weeks exposure to 10% $O_2$ hypoxic environment, systolic pulmonary arterial pressure readings increased from ~25 mmHg to greater than 50 mmHg. Using a 48 hour baseline average, animals with readings between 50-110 mmHg (standard deviation of less than 10 mmHg) and minimal changes in systolic systemic blood pressure were enrolled for study. Animals were utilized for up to 2 studies per week for 4 weeks with a minimum of 2 days washout between doses of test agent.

Compound or vehicle was administered intra-tracheally under light isoflurane anesthesia (5% in oxygen; flow rate 2.0 L/min for 3 minutes). Once anesthetized, rats were placed on an angled intubation stand in supine position and the trachea visualized using a small laryngoscope. Animals then received either 0.5 mL/kg of vehicle or 0.5 mL/kg vehicle containing compound intra-tracheally delivered via microsprayer by use of a Penn-Century Microsprayer® needle 3" (Model IA-1B-GP) attached to a 1 mL high pressure syringe (Penn Century-Model B—SYR-PL1000) (Penn-Century, Philadelphia, Pa.). The Microsprayer® tip was inserted into the trachea up to the point at which the bend in the needle is close to the tip of the snout, which positions the tip of the Microsprayer® in front of the carina (bifurcation of trachea at the bronchi). After dose delivery the animal is placed on its back in the home cage for recovery.

Hemodynamic measurements were continuously recorded and readings consolidated to hourly moving averages. Each animal received a vehicle on Day 1 followed by vehicle or test agent on Day 2. Change from vehicle baseline was calculated by subtracting the hourly Day 1 vehicle response from the hourly Day 2 response and treatment group data was expressed as mean±SEM.

Decreases of systolic blood pressure (SBP) and systolic pulmonary arterial pressure (PAP) were measured at a particular IT dose (mpk milligrams per kilogram) for the following Example compounds. Compounds in the Table 13 achieved a minimum decrease in PAP of ≥15 mmHg for the corresponding decrease in SBP listed.
Category A=decrease in SBP 0-5 mmHg;
Category B=decrease in SBP 5-10 mmHg;
Category C=decrease in SBP >10 mmHg.

TABLE 13

| EXAMPLE | Dose (IT mpk) | Category |
|---------|---------------|----------|
| 1-A | 0.01 | A |
| 2-B | 0.01 | A |
| 3-B | 0.03 | A |
| 4-B | 0.03 | A |
| 8-A | 0.01 | B |
| 11-B | 0.01 | B |
| 13-B | 0.01 | A |
| 14-A | 0.01 | A |
| 18-B | 0.03 | B |
| 23-B | 0.03 | A |
| 25-A | 0.03 | B |
| 28-B | 0.01 | B |
| 29-B | 0.03 | C |
| 38-B | 0.03 | A |
| 51-B | 0.03 | A |
| 78-B | 0.3 | C |
| 88-A | 0.03 | A |
| 93-B | 0.03 | A |
| 94-B | 0.03 | B |
| 97-B | 0.03 | A |
| 105-B | 0.03 | B |
| 107-B | 0.01 | A |
| 109-A | 0.03 | C |
| 115-B | 0.3 | C |
| 117-B | 0.3 | C |

What is claimed is:

1. A compound of the Formula (I)

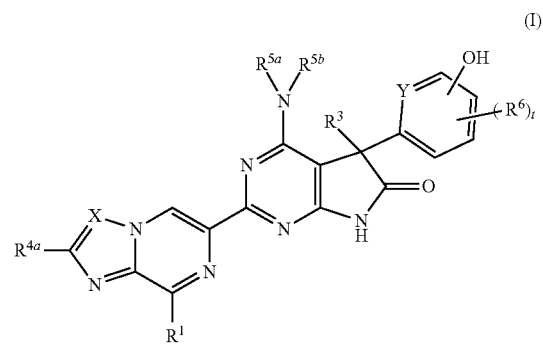

or a pharmaceutically acceptable salt thereof, wherein:
X is $C(R^{4b})$ or N;
Y is C(H) or N;
$R^1$ is:
(a.) $(C_1-C_3)$alkyl-$R^2$;
$R^2$ is phenyl, pyridyl, $C_3-C_8$ cycloalkyl, or $C_5-C_7$ cycloalkenyl, wherein $R^2$ is unsubstituted or substituted by 1 to 3 $R^{2a}$;
each $R^{2a}$ is independently halo, $(C_1-C_3)$alkyl, or $(C_1-C_3)$fluoroalkyl; or
(b.)$(C_1-C_6)$alkyl, wherein said alkyl is unsubstituted or substituted by 1 to 6 fluoro;
$R^3$ is $(C_1-C_3)$alkyl or $(C_3-C_6)$cycloalkyl;
$R^{4a}$ is H or $(C_1-C_3)$alkyl;
$R^{4b}$ is H or $NH_2$;
$R^{5a}$ and $R^{5b}$ are independently H or $(C_1-C_6)$alkyl, wherein said alkyl is unsubstituted or substituted by 1 to 6 substituents independently selected from fluoro or hydroxyl; or
alternatively, $R^{5a}$ and $R^{5b}$ together with the nitrogen atom to which they are attached form ring $C^5$ which is an azetidinyl, pyrrolyl, piperidinyl, piperazinyl, or azepinyl ring, wherein ring $C^5$ is unsubstituted or substituted by 1 to 3 substituents which are independently halo, hydroxyl, $(C_1-C_3)$alkyl, or $(C_1-C_3)$fluoroalkyl;

each $R^6$ is independently halo, $(C_1-C_3)$alkyl, $(C_1-C_3)$fluoroalkyl, or cyano; and the subscript t is 0, 1, 2, or 3; and with the proviso that the compound is not:
- 4-amino-5-(5-hydroxypyridin-2-yl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidine-6-one;
- 4-amino-5-(5-hydroxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidine-6(7H)-one; or
- 4-amino-5-cyclopropyl-5-(5-hydroxypyridin-2-yl)-2-(8-(4,4,4-trifluorobutyl)-[1,2,4]triazolo[1,5-a]pyrazin-6-yl)-5H-pyrrolo[2,3-d]pyrimidine-6(7H)-one.

2. The compound of claim 1 or a pharmaceutically acceptable salt thereof, wherein X is $C(R^{4b})$.

3. The compound of claim 2 or a pharmaceutically acceptable salt thereof, wherein $R^{4b}$ is H.

4. The compound of claim 1 or a pharmaceutically acceptable salt thereof, wherein X is N.

5. The compound of claim 1 or a pharmaceutically acceptable salt thereof, wherein Y is C(H).

6. The compound of claim 1 or a pharmaceutically acceptable salt thereof, wherein Y is N.

7. The compound of claim 1 or a pharmaceutically acceptable salt thereof, wherein $R^1$ is $(C_1-C_3)$alkyl-$R^2$,
$R^2$ is phenyl, $C_3-C_8$ cycloalkyl, or $C_5-C_7$ cycloalkenyl, wherein $R^2$ is unsubstituted or substituted by 1 to 3 $R^{2a}$; and
each $R^{2a}$ is independently halo, $(C_1-C_3)$alkyl, or $(C_1-C_3)$fluoroalkyl.

8. The compound of claim 7 or a pharmaceutically acceptable salt thereof, wherein $R^1$ is $CH_2-R^2$.

9. The compound of claim 8 or a pharmaceutically acceptable salt thereof, wherein $R^2$ is unsubstituted phenyl or phenyl substituted by 1 to 3 $R^{2a}$.

10. The compound of claim 1 or a pharmaceutically acceptable salt thereof, wherein $R^3$ is methyl.

11. The compound of claim 1 or a pharmaceutically acceptable salt thereof, wherein $R^{4a}$ is H.

12. The compound of claim 1 or a pharmaceutically acceptable salt thereof, wherein $R^{5a}$ and $R^{5b}$ are H.

13. The compound of claim 1 or a pharmaceutically acceptable salt thereof, wherein the subscript t is 0 or 1.

14. The compound of claim 1 or a pharmaceutically acceptable salt thereof, wherein
the group

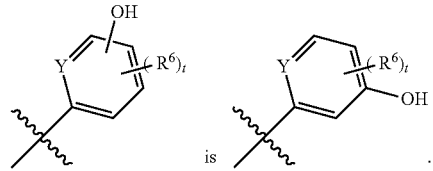

is .

15. The compound of claim 14 or a pharmaceutically acceptable salt thereof, wherein:
X is C(H) or N;
Y is C(H) or N;
$R^1$ is —$CH^2$—$R^2$;
$R^2$ is unsubstituted phenyl or phenyl substituted by 1 to 3 $R^{2a}$;
each $R^{2a}$ is independently halo, $(C_1-C_3)$alkyl, or $(C_1-C_3)$fluoroalkyl;
$R^3$ is methyl;
$R^{5a}$ and $R^{5b}$ are H; and
the subscript t is 0 or 1.

16. A pharmaceutical composition comprising a compound of claim 1 or a pharmaceutically acceptable salt thereof, and a pharmaceutically acceptable carrier.

17. The pharmaceutical composition of claim 16, further comprising one or more additional active agents selected from an angiotensin converting enzyme inhibitor, an angiotensin II receptor antagonist, a neutral endopeptidase inhibitor, an aldosterone antagonist, a renin inhibitor, an endothelin receptor antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent, metabolic altering agent, a $\beta_2$ agonist, an anticholinergic, a corticosteroid or a corticosteroid analog.

18. A method for treating pulmonary hypertension comprising administering a therapeutically effective amount of the compound of claim 1, or a pharmaceutically acceptable salt thereof, to a patient in need thereof.

19. The compound of claim 1, wherein the compound is

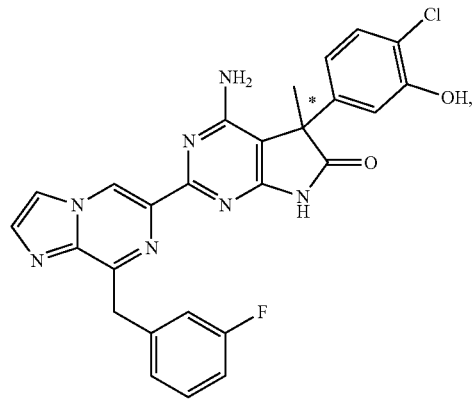

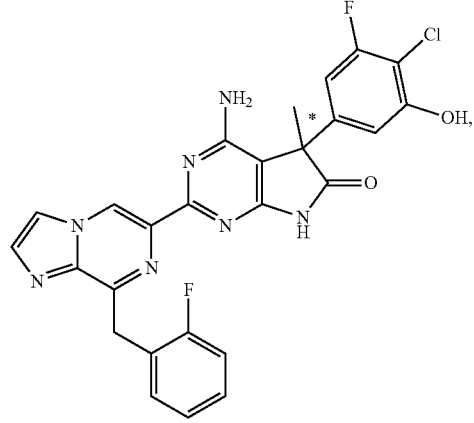

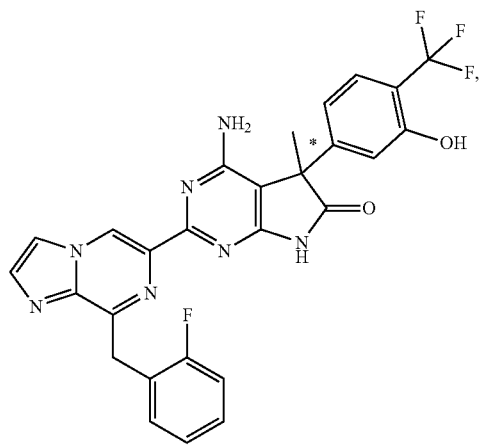
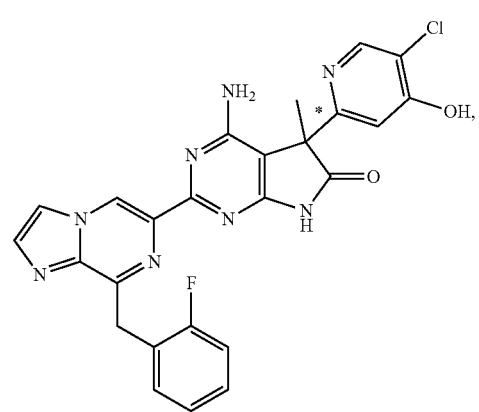
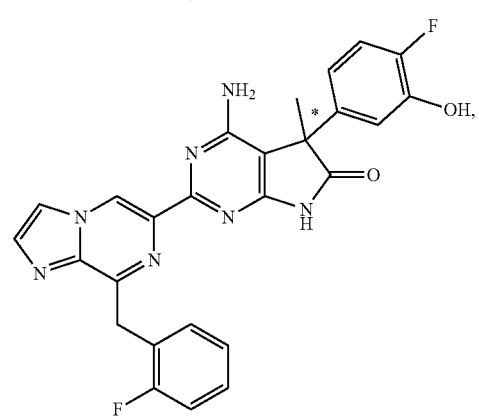
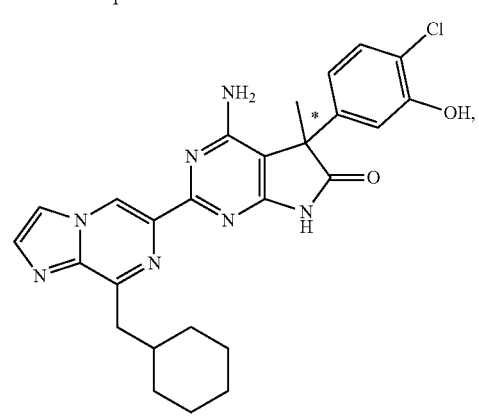
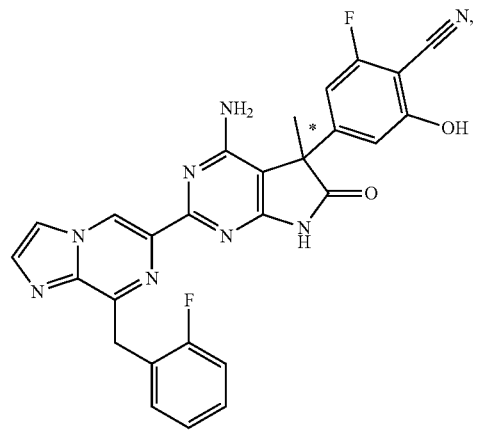
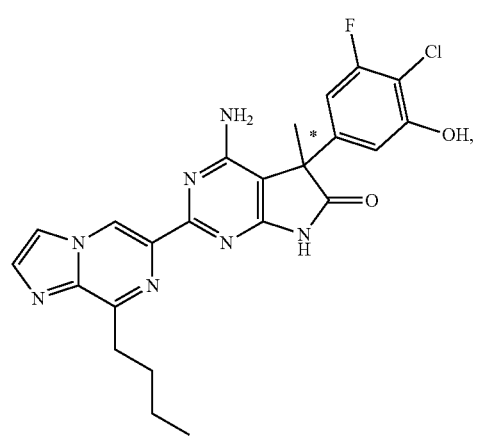
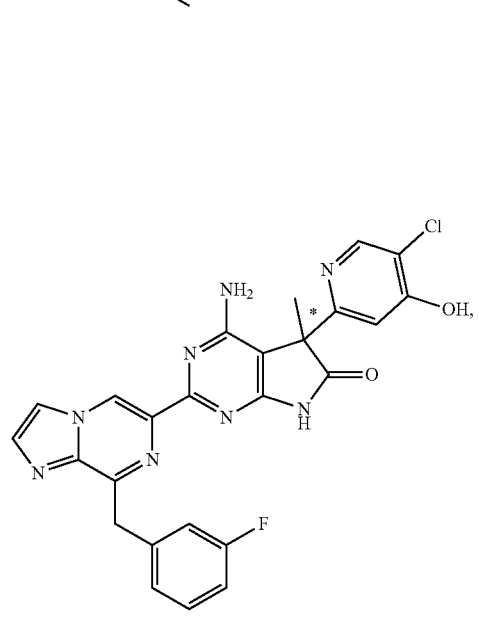

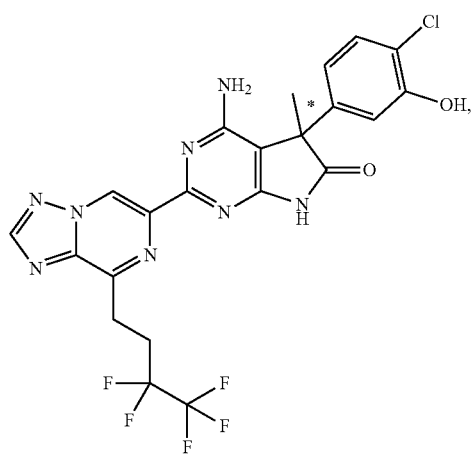
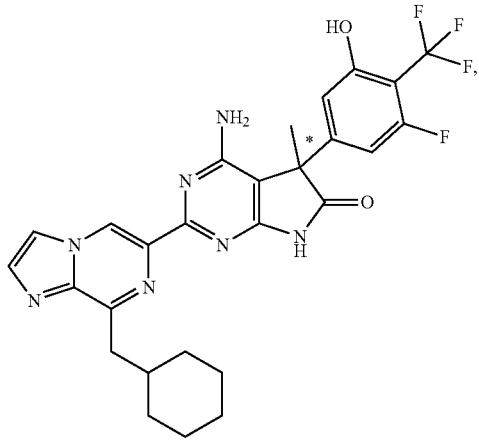
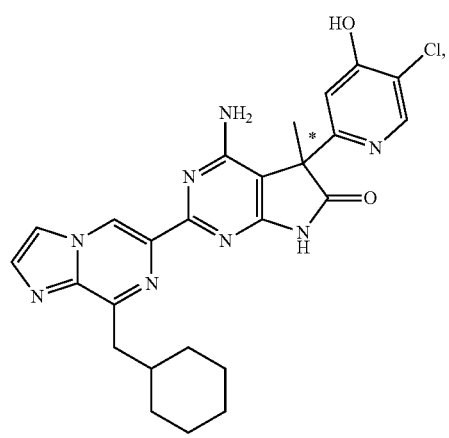
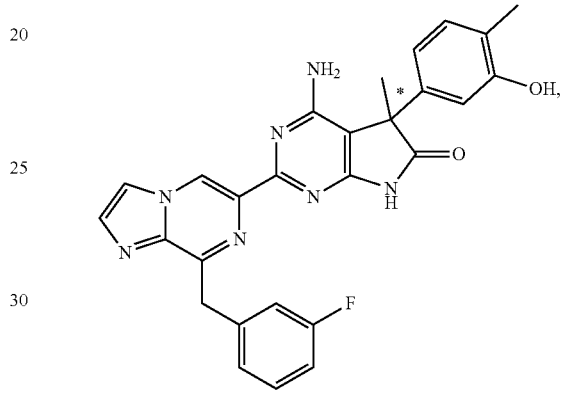
or a pharmaceutically acceptable salt thereof.
* * * * *